US011951121B2

(12) United States Patent
Sah et al.

(10) Patent No.: US 11,951,121 B2
(45) Date of Patent: **\*Apr. 9, 2024**

(54) COMPOSITIONS AND METHODS FOR TREATING HUNTINGTON'S DISEASE

(71) Applicant: VOYAGER THERAPEUTICS, INC., Lexington, MA (US)

(72) Inventors: Dinah Wen-Yee Sah, Hopkinton, MA (US); Jinzhao Hou, Lexington, MA (US); Pengcheng Zhou, Lexington, MA (US); Xin Wang, Arlington, MA (US); Jochen Deckert, Bayreuth (DE); Markus Hossbach, Kulmbach (DE)

(73) Assignee: VOYAGER THERAPEUTICS, INC., Lexington, MA (US)

( \* ) Notice: Subject to any disclaimer, the term of this patent is extended or adjusted under 35 U.S.C. 154(b) by 577 days.

This patent is subject to a terminal disclaimer.

(21) Appl. No.: 16/302,140

(22) PCT Filed: May 18, 2017

(86) PCT No.: PCT/US2017/033281
§ 371 (c)(1),
(2) Date: Nov. 16, 2018

(87) PCT Pub. No.: WO2017/201258
PCT Pub. Date: Nov. 23, 2017

(65) Prior Publication Data
US 2019/0160091 A1    May 30, 2019

Related U.S. Application Data

(60) Provisional application No. 62/485,049, filed on Apr. 13, 2017, provisional application No. 62/338,113, filed on May 18, 2016.

(51) Int. Cl.
| | | |
|---|---|---|
| *C12N 15/11* | (2006.01) | |
| *A61K 31/7105* | (2006.01) | |
| *A61K 31/713* | (2006.01) | |
| *A61K 48/00* | (2006.01) | |
| *A61P 25/14* | (2006.01) | |
| *C12N 15/113* | (2010.01) | |
| *C12N 15/63* | (2006.01) | |

(52) U.S. Cl.
CPC ........ *A61K 31/713* (2013.01); *A61K 31/7105* (2013.01); *A61K 48/0025* (2013.01); *A61K 48/005* (2013.01); *A61P 25/14* (2018.01); *C12N 15/113* (2013.01); *C12N 15/63* (2013.01); *C12N 2310/14* (2013.01); *C12N 2310/141* (2013.01); *C12N 2320/32* (2013.01); *C12N 2330/51* (2013.01); *C12N 2750/14143* (2013.01)

(58) Field of Classification Search
CPC ...... C12N 2310/14; C12N 2750/14143; C12N 15/86; C12N 2750/14122; C12N 15/8645; C12N 15/113; C12N 15/111
See application file for complete search history.

(56) References Cited

U.S. PATENT DOCUMENTS

| | | |
|---|---|---|
| 5,064,764 A | 11/1991 | Besnainon |
| 5,474,935 A | 12/1995 | Chatterjee |
| 5,587,308 A | 12/1996 | Carter |
| 5,652,224 A | 7/1997 | Wilson |
| 5,658,785 A | 8/1997 | Johnson |
| 5,688,676 A | 11/1997 | Zhou |
| 5,691,176 A | 11/1997 | Lebkowski |
| 5,693,531 A | 12/1997 | Chiorini |
| 5,741,683 A | 4/1998 | Zhou |
| 5,756,283 A | 5/1998 | Wilson |
| 5,856,152 A | 1/1999 | Wilson |
| 5,858,351 A | 1/1999 | Podsakoff |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,143,548 A | 11/2000 | ORiordan |
| 6,143,567 A | 11/2000 | Van Agthoven |
| 6,146,874 A | 11/2000 | Zolotukhin |
| 6,156,303 A | 12/2000 | Russell |
| 6,174,527 B1 | 1/2001 | Wilson |
| 6,180,613 B1 | 1/2001 | Kaplitt |

(Continued)

FOREIGN PATENT DOCUMENTS

| | | |
|---|---|---|
| EP | 1015619 | 7/2000 |
| EP | 1046711 | 10/2000 |

(Continued)

OTHER PUBLICATIONS

Auyeung et al. "Beyond secondary structure: primary-sequence determinants license primiRNA hairpins for processing." Cell 152.4 (2013): 844-858.
International Search Report & Written Opinion dated Oct. 30, 2017 in co-pending application No. PCT/US2017/033281, entitled Compositions and Methods of Treating Huntington's Disease.
Maniatis T. et al.,Molecular Cloning. CSH Laboratory, NY, N.Y. (1982).
Merten OW, et al. Viral vectors for gene therapy and gene modification approaches. Biochem Eng J. Apr. 2016;108:98-115.
Muzyczka N, et al. AAV's Golden Jubilee. Mol Ther. May 2015:23(5):807-8.

(Continued)

*Primary Examiner* — Dana H Shin
(74) *Attorney, Agent, or Firm* — K&L Gates LLP

(57) ABSTRACT

The present invention relates to small interfering RNA (siRNA) molecules against the HTT gene, adeno-associated viral (AAV) vectors encoding siRNA molecules and methods for treating Huntington's Disease (HD) using the siRNA molecules and AAV vectors.

29 Claims, No Drawings
Specification includes a Sequence Listing.

(56) References Cited

U.S. PATENT DOCUMENTS

| | | |
|---|---|---|
| 6,194,191 B1 | 2/2001 | Zhang |
| 6,200,560 B1 | 3/2001 | Couto |
| 6,204,059 B1 | 3/2001 | Samulski |
| 6,211,163 B1 | 4/2001 | Podsakoff |
| 6,251,677 B1 | 6/2001 | Wilson |
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |
| 6,274,354 B1 | 8/2001 | Wilson |
| 6,281,010 B1 | 8/2001 | Gao |
| 6,325,998 B1 | 12/2001 | Podsakoff |
| 6,335,011 B1 | 1/2002 | Podsakoff |
| 6,365,394 B1 | 4/2002 | Gao |
| 6,387,368 B1 | 5/2002 | Wilson |
| 6,399,385 B1 | 6/2002 | Croyle |
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,943,019 B2 | 9/2005 | Wilson |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | ORiordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,169,612 B2 | 1/2007 | Kostenis |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,319,002 B2 | 1/2008 | Wilson |
| 7,326,555 B2 | 2/2008 | Konz |
| 7,344,872 B2 | 3/2008 | Gao |
| 7,419,817 B2 | 9/2008 | Chiorini |
| 7,419,956 B2 | 9/2008 | Ohtaki |
| 7,445,930 B2 | 11/2008 | Zhang |
| 7,479,554 B2 | 1/2009 | Chiorini |
| 7,491,508 B2 | 2/2009 | Roy |
| 7,510,872 B2 | 3/2009 | Clark |
| 7,510,875 B2 | 3/2009 | Zhang |
| 7,579,181 B2 | 8/2009 | ORiordan |
| 7,625,570 B1 | 12/2009 | Schaffer |
| 7,638,120 B2 | 12/2009 | Liu |
| 7,662,627 B2 | 2/2010 | Johnson |
| 7,704,492 B2 | 4/2010 | Podsakoff |
| 7,704,721 B2 | 4/2010 | Wright |
| 7,732,129 B1 | 6/2010 | Zhang |
| 7,790,449 B2 | 9/2010 | Gao |
| 7,803,622 B2 | 9/2010 | Engelhardt |
| 7,838,277 B2 | 11/2010 | Gao |
| 7,888,096 B2 | 2/2011 | Wu |
| 7,901,921 B2 | 3/2011 | Coffey |
| 7,906,111 B2 | 3/2011 | Wilson |
| 7,968,333 B2 | 6/2011 | Yu |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,231,880 B2 | 7/2012 | Roy |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,318,480 B2 | 11/2012 | Gao |
| 8,318,687 B2 | 11/2012 | Tabira |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Hermens |
| 8,524,219 B2 | 9/2013 | Roy |
| 8,524,446 B2 | 9/2013 | Gao |
| 8,603,459 B2 | 12/2013 | Wilson |
| 8,614,101 B2 | 12/2013 | VanDine |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Rom |
| 8,834,863 B2 | 9/2014 | Roy |
| 8,846,030 B2 | 9/2014 | Engelhardt |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,051,542 B2 | 6/2015 | Wright |
| 9,056,892 B2 | 6/2015 | Pun |
| 9,080,183 B2 | 7/2015 | Klein |
| 9,089,667 B2 | 7/2015 | Bankiewicz |
| 9,101,645 B2 | 8/2015 | Watts |
| 9,102,943 B2 | 8/2015 | Shinmura |
| 9,115,373 B2 | 8/2015 | Hermens |
| 9,163,260 B2 | 10/2015 | Wilson |
| 9,169,483 B2 | 10/2015 | Davidson |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,415,121 B2 | 8/2016 | Kaspar |
| 9,434,776 B2 | 9/2016 | Ando |
| 9,439,979 B2 | 9/2016 | Chiorini |
| 9,441,206 B2 | 9/2016 | Grieger |

(56) References Cited

U.S. PATENT DOCUMENTS

| | | |
|---|---|---|
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,487,779 B2 | 11/2016 | Davidson |
| 9,493,788 B2 | 11/2016 | Gao |
| 9,499,597 B2 | 11/2016 | Miller |
| 9,506,083 B2 | 11/2016 | Arbetman |
| 9,523,093 B2 | 12/2016 | Davidson |
| 9,528,126 B2 | 12/2016 | Qu |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,636,370 B2 | 5/2017 | McCown |
| 9,650,631 B2 | 5/2017 | Davidson |
| 9,670,507 B2 | 6/2017 | Xiao |
| 9,677,088 B2 | 6/2017 | Nakai |
| 9,677,089 B2 | 6/2017 | Gao |
| 9,719,106 B2 | 8/2017 | Wilson |
| 10,093,927 B2 | 10/2018 | Davidson |
| 10,174,321 B2 | 1/2019 | Konstantinova |
| 10,208,318 B2 | 2/2019 | Barkats |
| 10,570,395 B2 | 2/2020 | Hou et al. |
| 10,584,337 B2 | 3/2020 | Sah et al. |
| 11,193,129 B2 | 12/2021 | Sah et al. |
| 11,198,873 B2 | 12/2021 | Hou et al. |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0100115 A1 | 5/2003 | Raj |
| 2003/0119191 A1 | 6/2003 | Gao |
| 2003/0138772 A1 | 7/2003 | Gao |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0059005 A1 | 3/2005 | Tuschl et al. |
| 2005/0181382 A1* | 8/2005 | Zamore ............... C12N 15/111 435/6.11 |
| 2005/0255086 A1 | 11/2005 | Davidson et al. |
| 2005/0261218 A1 | 11/2005 | Esau |
| 2006/0003451 A1 | 1/2006 | Gao |
| 2006/0204479 A1 | 9/2006 | Wilson |
| 2006/0217331 A1* | 9/2006 | Vargeese ............... C07H 21/04 514/44 A |
| 2007/0004042 A1 | 1/2007 | Gao |
| 2008/0008684 A1 | 1/2008 | Wilson |
| 2008/0015158 A1 | 1/2008 | Ichiro |
| 2008/0019946 A1 | 1/2008 | Nenoi et al. |
| 2008/0020992 A1 | 1/2008 | Rao |
| 2008/0050343 A1 | 2/2008 | Wilson |
| 2008/0050345 A1 | 2/2008 | Wilson |
| 2008/0075737 A1 | 3/2008 | Gao |
| 2009/0118206 A1 | 5/2009 | Aronin et al. |
| 2009/0215871 A1 | 8/2009 | Wilson |
| 2009/0275107 A1 | 11/2009 | Lock |
| 2009/0317417 A1 | 12/2009 | Vandenberghe |
| 2010/0004320 A1 | 1/2010 | Elmen |
| 2010/0036107 A1 | 2/2010 | Clawson |
| 2010/0247490 A1 | 9/2010 | Roy |
| 2010/0278791 A1 | 11/2010 | Wilson |
| 2010/0286378 A1 | 11/2010 | Li et al. |
| 2011/0020816 A1 | 1/2011 | Chen et al. |
| 2011/0136227 A1 | 6/2011 | Bakker |
| 2011/0171262 A1 | 7/2011 | Bakker |
| 2011/0212520 A1 | 9/2011 | Davidson et al. |
| 2011/0223135 A1 | 9/2011 | Roy |
| 2011/0229971 A1 | 9/2011 | Knop |
| 2012/0046349 A1 | 2/2012 | Bell |
| 2012/0058102 A1 | 3/2012 | Wilson |
| 2012/0093853 A1 | 4/2012 | Wilson |
| 2012/0093916 A1 | 4/2012 | Kaemmerer |
| 2012/0137379 A1 | 5/2012 | Gao |
| 2012/0258046 A1 | 10/2012 | Mutzke |
| 2012/0309050 A1 | 12/2012 | Kumon |
| 2013/0023033 A1 | 1/2013 | Wilson |
| 2013/0045186 A1 | 2/2013 | Gao |
| 2013/0101558 A1 | 4/2013 | Gao |
| 2013/0195801 A1 | 8/2013 | Gao |
| 2013/0296532 A1 | 11/2013 | Hermens |
| 2013/0323226 A1 | 12/2013 | Wilson |
| 2013/0323302 A1 | 12/2013 | Constable |
| 2014/0004565 A1 | 1/2014 | Rossomando et al. |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0336245 A1 | 11/2014 | Mingozzi |
| 2014/0341852 A1 | 11/2014 | Srivastava |
| 2014/0342434 A1 | 11/2014 | Hermens |
| 2015/0005369 A1 | 1/2015 | Muzyczka |
| 2015/0023924 A1 | 1/2015 | High |
| 2015/0065562 A1 | 3/2015 | Yazicioglu |
| 2015/0118287 A1 | 4/2015 | Hammond |
| 2015/0139952 A1 | 5/2015 | Webster |
| 2015/0152127 A1 | 6/2015 | Selnick |
| 2015/0159173 A1 | 6/2015 | Vandenberghe |
| 2015/0197751 A1 | 7/2015 | Roelvink |
| 2015/0232840 A1 | 8/2015 | Aronin |
| 2015/0238610 A1 | 8/2015 | Sista |
| 2015/0307898 A2 | 10/2015 | Hermens |
| 2015/0315610 A1 | 11/2015 | Nishie |
| 2015/0335708 A1 | 11/2015 | Froelich |
| 2015/0374803 A1 | 12/2015 | Wolfe |
| 2016/0032319 A1 | 2/2016 | Wright |
| 2016/0060624 A1 | 3/2016 | Davidson et al. |
| 2016/0108373 A1 | 4/2016 | Bennett |
| 2016/0153992 A1 | 6/2016 | Buening |
| 2016/0166709 A1 | 6/2016 | Davidson |
| 2016/0251653 A1 | 9/2016 | Davidson |
| 2016/0264994 A1 | 9/2016 | Lawrence |
| 2016/0271192 A1 | 9/2016 | Roy |
| 2016/0273058 A1 | 9/2016 | Akashika |
| 2016/0281084 A1 | 9/2016 | Davidson |
| 2016/0289275 A1 | 10/2016 | Chiorini |
| 2016/0296605 A1 | 10/2016 | Zhang |
| 2016/0296694 A1 | 10/2016 | Bankiewicz |
| 2016/0319278 A1 | 11/2016 | Khvorova |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0340393 A1 | 11/2016 | Schaffer |
| 2016/0340692 A1 | 11/2016 | Wang |
| 2016/0348106 A1 | 12/2016 | Harper |
| 2016/0355808 A1 | 12/2016 | Khvorova et al. |
| 2016/0361439 A1 | 12/2016 | Agbandje-McKenna |

(56) References Cited

U.S. PATENT DOCUMENTS

| | | |
|---|---|---|
| 2016/0369298 A1 | 12/2016 | Marsic |
| 2016/0369299 A1 | 12/2016 | Boye |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0007645 A1 | 1/2017 | Handa |
| 2017/0007669 A1 | 1/2017 | Sarkar |
| 2017/0007720 A1 | 1/2017 | Boye |
| 2017/0022498 A1 | 1/2017 | Cullen |
| 2017/0028082 A1 | 2/2017 | Wilson |
| 2017/0035839 A1 | 2/2017 | Miller |
| 2017/0044504 A1 | 2/2017 | Schaffer |
| 2017/0044530 A1 | 2/2017 | Kay |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088819 A1 | 3/2017 | Vandendriessche |
| 2017/0088858 A1 | 3/2017 | Gao |
| 2017/0096460 A1 | 4/2017 | Froelich |
| 2017/0096646 A1 | 4/2017 | Roy |
| 2017/0105927 A1 | 4/2017 | Thorne |
| 2017/0112946 A1 | 4/2017 | Ikeda |
| 2017/0121734 A1 | 5/2017 | Cairns |
| 2017/0128594 A1 | 5/2017 | Wright |
| 2017/0130208 A1 | 5/2017 | Potter |
| 2017/0130245 A1 | 5/2017 | Kotin |
| 2017/0145440 A1 | 5/2017 | Hermens |
| 2017/0151348 A1 | 6/2017 | Kaspar |
| 2017/0151416 A1 | 6/2017 | Kutikov |
| 2017/0152525 A1 | 6/2017 | Hermens |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0198304 A1 | 7/2017 | Wilson |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0240921 A1 | 8/2017 | Gao |
| 2017/0298323 A1 | 10/2017 | Vandenberghe |
| 2017/0304464 A1 | 10/2017 | Kügler |
| 2017/0314028 A1 | 11/2017 | Hou et al. |
| 2018/0094263 A1* | 4/2018 | Khvorova ............ A61K 9/0085 |
| 2018/0094264 A1 | 4/2018 | Mueller et al. |
| 2018/0237772 A1 | 8/2018 | Yu |
| 2018/0298380 A1 | 10/2018 | Gao |
| 2018/0339065 A1 | 11/2018 | Wilson |
| 2019/0169616 A1 | 6/2019 | Sah et al. |
| 2020/0149045 A1 | 5/2020 | Sah et al. |
| 2020/0155624 A1 | 5/2020 | Sah et al. |
| 2020/0199597 A1 | 6/2020 | Hou et al. |
| 2021/0355454 A1 | 11/2021 | Cardinal et al. |
| 2022/0127619 A1 | 4/2022 | Hou et al. |
| 2022/0162609 A1 | 5/2022 | Sah et al. |
| 2022/0275367 A1 | 9/2022 | Sah et al. |
| 2022/0333131 A1 | 10/2022 | Hou et al. |

FOREIGN PATENT DOCUMENTS

| | | |
|---|---|---|
| EP | 1078096 | 2/2001 |
| EP | 1164195 | 12/2001 |
| EP | 1183380 | 3/2002 |
| EP | 1218035 | 7/2002 |
| EP | 1240345 | 9/2002 |
| EP | 1279740 | 1/2003 |
| EP | 1453547 | 9/2004 |
| EP | 1692262 B1 | 8/2006 |
| EP | 1696036 | 8/2006 |
| EP | 1847614 | 10/2007 |
| EP | 1849872 | 10/2007 |
| EP | 1857552 | 11/2007 |
| EP | 1900815 | 3/2008 |
| EP | 1944043 | 7/2008 |
| EP | 2007795 | 12/2008 |
| EP | 2164967 | 3/2010 |
| EP | 2172549 | 4/2010 |
| EP | 2198016 | 6/2010 |
| EP | 2220241 | 8/2010 |
| EP | 2220242 | 8/2010 |
| EP | 2292779 | 3/2011 |
| EP | 2292780 | 3/2011 |
| EP | 2325298 | 5/2011 |
| EP | 2359866 | 8/2011 |
| EP | 2360251 | 8/2011 |
| EP | 2383346 | 11/2011 |
| EP | 2453735 | 5/2012 |
| EP | 2524037 | 11/2012 |
| EP | 2531604 | 12/2012 |
| EP | 2660325 | 11/2013 |
| EP | 2699270 | 2/2014 |
| EP | 2737071 | 6/2014 |
| EP | 2814958 | 12/2014 |
| EP | 2871239 | 5/2015 |
| EP | 2879719 | 6/2015 |
| EP | 2933336 | 10/2015 |
| EP | 3058959 | 8/2016 |
| EP | 3067417 | 9/2016 |
| EP | 2176283 | 11/2016 |
| EP | 3108000 | 12/2016 |
| EP | 3117005 | 1/2017 |
| EP | 3134431 | 3/2017 |
| EP | 3168298 | 5/2017 |
| EP | 3209311 | 8/2017 |
| EP | 3221456 | 9/2017 |
| EP | 3235827 | 10/2017 |
| EP | 3237618 | 11/2017 |
| JP | 2008-503590 A | 2/2008 |
| JP | 2009-513144 A | 4/2009 |
| WO | 1993009239 | 5/1993 |
| WO | 1995034670 | 12/1995 |
| WO | 1996017947 | 6/1996 |
| WO | 1996023810 | 8/1996 |
| WO | 1996030540 | 10/1996 |
| WO | 1998010088 | 3/1998 |
| WO | 1999027110 | 6/1999 |
| WO | 1999043360 | 9/1999 |
| WO | 1999058700 | 11/1999 |
| WO | 1999061595 | 12/1999 |
| WO | 1999060146 | 5/2000 |
| WO | 2000024916 | 5/2000 |
| WO | 2000066780 | 11/2000 |
| WO | 2000075353 | 12/2000 |
| WO | 2001014539 | 3/2001 |
| WO | 2001023001 | 4/2001 |
| WO | 2001025465 | 4/2001 |
| WO | 2001032711 | 5/2001 |
| WO | 2001036623 | 5/2001 |
| WO | 2001042444 | 6/2001 |
| WO | 2001068888 | 9/2001 |
| WO | 2001075164 A1 | 10/2001 |
| WO | 2001096587 | 12/2001 |
| WO | 2002012525 | 2/2002 |
| WO | 2002014487 | 2/2002 |
| WO | 2002020748 | 3/2002 |
| WO | 2002070700 A1 | 9/2002 |
| WO | 2002070719 | 9/2002 |
| WO | 2002071843 | 9/2002 |
| WO | 2003010320 | 2/2003 |
| WO | 2003024502 | 3/2003 |
| WO | 2003042397 | 5/2003 |
| WO | 2003087382 | 10/2003 |
| WO | 2003087383 | 10/2003 |
| WO | 2004027030 A2 | 4/2004 |
| WO | 2004044003 | 5/2004 |
| WO | 2004083441 | 9/2004 |
| WO | 2004108922 | 12/2004 |
| WO | 2004111248 | 12/2004 |

(56) References Cited

FOREIGN PATENT DOCUMENTS

| | | |
|---|---|---|
| WO | 2005005610 | 1/2005 |
| WO | 2005012537 | 2/2005 |
| WO | 2005111220 | 11/2005 |
| WO | 2006/002283 A1 | 1/2006 |
| WO | 2006031267 A2 | 3/2006 |
| WO | 2006083800 A2 | 8/2006 |
| WO | 2006102072 | 9/2006 |
| WO | 2007051045 A2 | 5/2007 |
| WO | 2007130519 | 11/2007 |
| WO | 2007148971 | 7/2009 |
| WO | 2009134681 | 11/2009 |
| WO | 2009137818 A1 | 11/2009 |
| WO | 2011038187 | 3/2011 |
| WO | 2011054976 | 5/2011 |
| WO | 2011122950 | 10/2011 |
| WO | 2010109053 | 11/2011 |
| WO | 2012057363 | 5/2012 |
| WO | 2012114090 | 8/2012 |
| WO | 2012144446 | 10/2012 |
| WO | 2012149646 A1 | 11/2012 |
| WO | 2012177906 A1 | 12/2012 |
| WO | 2013078199 | 5/2013 |
| WO | 2013164793 | 11/2013 |
| WO | 2013170078 | 11/2013 |
| WO | 2014016817 A2 | 1/2014 |
| WO | 2014107763 A1 | 7/2014 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015013148 | 1/2015 |
| WO | 2015018503 | 2/2015 |
| WO | 2014186746 | 3/2015 |
| WO | 2015031686 | 4/2015 |
| WO | 2015044292 | 4/2015 |
| WO | 2015060722 | 4/2015 |
| WO | 2015084254 A1 | 6/2015 |
| WO | 2015106273 | 7/2015 |
| WO | 2015108610 | 7/2015 |
| WO | 2015114365 | 8/2015 |
| WO | 2015121501 | 8/2015 |
| WO | 2015124546 | 8/2015 |
| WO | 2015/143078 A1 | 9/2015 |
| WO | 2015137802 | 9/2015 |
| WO | 2015127128 | 11/2015 |
| WO | 2015168666 A2 | 11/2015 |
| WO | 2015179525 A1 | 11/2015 |
| WO | 2015191508 A1 | 12/2015 |
| WO | 2015196179 | 12/2015 |
| WO | 2016019364 | 2/2016 |
| WO | 2016054554 | 4/2016 |
| WO | 2016054557 | 4/2016 |
| WO | 2016065001 | 4/2016 |
| WO | 2016073693 A2 | 5/2016 |
| WO | 2016077687 A1 | 5/2016 |
| WO | 2016077689 A1 | 5/2016 |
| WO | 2016081811 | 5/2016 |
| WO | 2016081927 | 5/2016 |
| WO | 2016102664 | 6/2016 |
| WO | 2016109649 | 7/2016 |
| WO | 2016115382 | 7/2016 |
| WO | 2016115503 A1 | 7/2016 |
| WO | 2016122791 | 8/2016 |
| WO | 2016126857 | 8/2016 |
| WO | 2016130589 | 8/2016 |
| WO | 2016130591 | 8/2016 |
| WO | 2016137949 | 9/2016 |
| WO | 2016154055 | 9/2016 |
| WO | 2016154344 | 9/2016 |
| WO | 2016161374 | 10/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 | 11/2016 |
| WO | 2016191418 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017024111 | 2/2017 |
| WO | 2017058892 | 4/2017 |
| WO | 2017062983 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017106236 | 6/2017 |
| WO | 2017136536 | 8/2017 |
| WO | 2017155973 | 9/2017 |
| WO | 2017161273 | 9/2017 |
| WO | 2017189963 A1 | 11/2017 |
| WO | 2017192699 | 11/2017 |
| WO | 2017192750 | 11/2017 |
| WO | 2017201248 A1 | 11/2017 |
| WO | 2018204803 A1 | 11/2018 |
| WO | 2018220211 A1 | 12/2018 |
| WO | 2018057855 A1 | 3/2019 |
| WO | 2019043027 A1 | 3/2019 |
| WO | 2019060726 A1 | 3/2019 |
| WO | 2019079240 A1 | 4/2019 |
| WO | 2020023612 A1 | 1/2020 |

OTHER PUBLICATIONS

Philiport, et al. Liposomes as tools in Basic Research and Industry. CRC Press, Ann Arbor, Mich. (1995).

Kailasan S, et al. Parvovirus Family Conundrum: What makes a killer? Annu Rev Virol. Nov. 2015;2(1):425-50.

Rutledge EA, et al. Infectious clones and vectors derived from adeno-associated virus (AAV) serotypes other than AAV type 2. J Virol. Jan. 1998;72(1):309-19.

Pillay S, et al. An essential receptor for adeno-associated virus infection. Nature. Nov. 17, 2016;539(7629):456.

Platt MP, et al. Embryonic disruption of the candidate dyslexia susceptibility gene homolog Kiaa0319-like results in neuronal migration disorders. Neuroscience. Sep. 17, 2013;248:585-93.

Poon MW, et al. Distribution of Kiaa0319-like immunoreactivity in the adult mouse brain—a novel protein encoded by the putative dyslexia susceptibility gene KIAA0319-like. Histol Histopathol. Aug. 2011;26(8):953-63.

Poon MW, et al. Dyslexia-associated kiaa0319-like protein interacts with axon guidance receptor nogo receptor 1. Cell Mol Neurobiol. Jan. 2011;31(1):27-35.

Myers EW, et al. Optimal alignments in linear space. Comput Appl Biosci. Mar. 1988;4(1):11-7.

Smith DW, et al. Biocomputing: Informatics and Genome Projects. Academic Press, New York, 1993.

Kozak M. Interpreting cDNA sequences: some insights from studies on translation. Mamm Genome. Aug. 1996;7(8):563-74.

Kozak M. Point mutations define a sequence flanking the AUG initiator codon that modulates translation by eukaryotic ribosomes. Cell. Jan. 31, 1986;44(2):283-92.

Kozak M. The scanning model for translation: an update. J Cell Biol. Feb. 1989;108(2):229-41.

(56) References Cited

OTHER PUBLICATIONS

Heim R, et al. Engineering green fluorescent protein for improved brightness, longer wavelengths and fluorescence resonance energy transfer. Curr Biol. Feb. 1, 1996;6(2):178-82.
Heim R,et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8(342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
O'Reilly DR, et al. Baculovirus expression vectors: a laboratory manual. Oxford University Press, 1994.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice. Hum Gene Ther. Aug. 10, 2016.
Hordeaux J., et al. Efficient central nervous system AAVrh10-mediated intrathecal gene transfers in adult and heonate rats. Gene Ther.Apr. 2015, 22(4):316-24.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.
Miyanohara A et al. Potent Spinal Parenchymal AAV9-mediated Gene Delivery by Subpial Injection in Adult Rats and Pigs. Mol Ther Methods Clin Dev. Jul. 13, 2016;3:16046.
Muralidharan G , et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Saraiva J et al. Gene Therapy for the CNS Using AAVs: The Impact of Systemic Delivery by AAV9. J Control Release. Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.
Hinderer C, et al. Neonatal Systemic AAV Induces Tolerance to CNS Gene Therapy in MPS I Dogs and Nonhuman Primates. Mol Ther. Aug. 2015, 23(8):1298-307.
Ojala DS, et al. Adeno-associated virus vectors and neurological gene therapy. Neuroscientist. Feb. 2015;21(1):84-98.
Katz ML, et al. AAV gene transfer delays disease onset in a TPP1-deficient canine model of the late infantile form of Batten Disease. Sci Transl Med. Nov. 2015;7(313):313ra180.
Kothari P, et al. Iodine-124 Labeled Adeno-Associated Virus: A Promising Tool for Tracking Gene Therapy. Journal of Nuclear Medicine. May 2015, 56 (supplement 3), 494-494.
Landegger LD, et al. A synthetic AAV vector enables safe and efficient gene transfer to the mammalian inner ear. Nat Biotechnol. Mar. 2017;35(3):280-284.

Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016;67(13):1556-68.
Knezevic T, et al. Adeno-associated Virus Serotype 9-Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Li SY, et al. Efficient and targeted transduction of nonhuman primate liver with systemically delivered optimized AAV3B vectors. Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(10):647-56.
Mendell JR, et al. Follistatin Gene Therapy for Sporadic Inclusion Body Myositis Improves Functional Outcomes. Mol Ther. Apr. 2017;25(4):870-879.
Schnepp BC, et al. Recombinant adeno-associated virus vector genomes take the form of long-lived transcriptionally competent episomes in human muscle. Hum Gene Ther. Jan. 2016;27(1):32-42.
Murlidharan G et al. Glymphatic Fluid Transport Controls Paravascular Clearance of AAV Vectors from the Brain. JCI Insight. Sep. 8, 2016;1(14).
Neuberger EWI, et al. Establishment of two quantitative nested qPCR assays targeting the human EPO transgene. Gene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
Gombash SE, et al. Systemic gene delivery transduces the enteric nervous system of guinea pigs and cynomolgus macaques. Gene Ther. Aug. 3, 2017. doi: 10.1038/gt.2017.72.
Hinderer C, et al. Evaluation of intrathecal routes of administration for adeno-associated virus vectors in large animals. Hum Gene Ther . Aug. 15, 2017. doi: 10.1089/hum.2017.026.
Yazdan-Shahmorad A, et al. Widespread Optogenetic Expression in Macaque Cortex Obtained with MR-Guided, Convection Enhanced Delivery (CED) of AAV vector to the Thalamus. J Neurosci Methods. Oct. 14, 2017 Epub ahead of print.
Gaura V, et al. Association between motor symptoms and brain metabolism in early huntington disease. JAMA Neurol. Sep. 1, 2017;74(9):1088-1096.
Dietrich P, et al. Elimination of huntingtin in the adult mouse leads to progressive behavioral deficits, bilateral thalamic calcification, and altered brain iron homeostasis. PLoS Genet. Jul. 17, 2017;13(7):e1006846.
Miniarikova J, et al. AAV5-miHTT gene therapy demonstrates suppression of mutant huntingtin aggregation and neuronal dysfunction in a rat model of Huntington's disease. Gene Ther. Aug. 3, 2017. doi: 10.1038/gt.2017.71.
Yang S, et al. CRISPR/Cas9-mediated gene editing ameliorates neurotoxicity in mouse model of Huntington's disease. J Clin Invest. Jun. 19, 2017. Epub ahead of print.
Pfister EL, et al. Safe and Efficient Silencing with a Pol II, but Not a Pol III, Promoter Expressing an Artificial miRNA Targeting Human Huntingtin. Mol Ther Nucleic Acids. Jun. 16, 2017;7:324-334.
Iwamoto N, et al. Control of phosphorothioate stereochemistry substantially increases the efficacy of antisense oligonucleotides. Nat Biotechnol. Aug. 21, 2017.
Kanaan NM, et al. Rationally Engineered AAV Capsids Improve Transduction and Volumetric Spread in the CNS. Molecular Therapy-Nucleic Acids 8: 184-197 Sep. 15, 2017.
Chan KY, et al. Engineered AAVs for efficient noninvasive gene delivery to the central and peripheral nervous systems. Nat Neurosci. Jun. 26, 2017. Epub ahead of print.
Herrera-Carrillo E, et al. Improving miRNA delivery by optimizing miRNA expression cassettes in viral vectors. Hum Gene Ther Methods. Jul. 16, 2017.

(56) References Cited

OTHER PUBLICATIONS

Evers MM, et al. AAV5-miHTT Gene Therapy Demonstrates Broad Distribution and Strong Human Mutant Huntingtin Lowering in a Huntington's Disease Minipig Model. Mol Ther. Jun. 25, 2018 Epub ahead of print.
Fukuoka M, et al. Supplemental Treatment for Huntington's Disease with miR-132 that Is Deficient in Huntington's Disease Brain. Mol. Ther. Nucleic Acids. Jun. 1, 2018;11:79-90.
Pfister EL, et al. Artificial miRNAs Reduce Human Mutant Huntingtin Throughout the Striatum in a Transgenic Sheep Model of Huntington's Disease. Hum Gene Ther. Jun. 2018;29(6):663-673.
Hudry E, et al. Efficient gene transfer to the central nervous system by single stranded Anc80L65. Mol Ther Meth Clin Dev. Jul. 15, 2018.
Koyuncu S, et al. The ubiquitin ligase UBR5 suppresses proteostasis collapse in pluripotent stem cells from Huntington's disease patients. Nat Commun Jul. 23, 2018;9(1):2886.
Marco S, et al. RNAi-Based GluN3A Silencing Prevents and Reverses Disease Phenotypes Induced by Mutant huntingtin. Mol Ther Aug. 1, 2018;26(8):1965-1972.
Chandran JS, et al. Gene therapy in the nervous system: failures and successes. Adv Exp Med Biol. 2017;1007:241-257.
Tse LV, et al. Mapping and engineering function domains of the assembly-activating protein of adeno-associated viruses. J. Virol. Jun. 29, 2018;92(14).
Auyeung VC, et al. Beyond secondary structure: primary sequence determinants license pri-miRNA hairpins for processing. Cell. Feb. 2013;152(4):844-858.
Fellman C, et al. An optimized microRNA backbone for effective single-copy RNAi. Cell Rep. Dec. 2013;5(6):1704-1713.
Gowanlock D, et al. A designer AAV variant permits efficient retrograde access to projection neurons. Neuron. Oct. 19, 2016;92(2):372-382.
Ha et al., Regulation of microRNA biogenesis. Nat Rev Mol Cell Bio, Aug. 2014, vol. 15, No. 8, pp. 509-524.
Boudreau RL, et al. Artificial microRNAs as siRNA shuttles: improved safety as compared to shRNAs in vitro and in vivo. The American Society of Gene Therapy. 2009; 17(1):169-175.
Kawaoka et al. Bombyx small RNAs: genomic defense system against transposons in the silkworm, *Bombyx mori*. Insect Biochem Mol Biol. Dec. 2008;38(12):1058-65. Epub Mar. 27, 2008.
Mestre TA .Recent advances in the therapeutic development for Huntington disease.Parkinsonism Relat Disord. Dec. 12, 2018. [Epub ahead of print].
Wang D, et al. Adeno-associated virus vector as a platform for gene therapy delivery. Nat Rev Drug Discov. Feb. 1, 2019. doi: 10.1038/s41573-019-0012-9. [Epub ahead of print] Review.
Chen YH etl a., Viral vectors for Gene Transfer. Curr Protoc Mouse Biol. Dec. 2018;8(4):e58.
Miniarikova et al., Translation of MicroRNA-Based Huntingtin-Lowering Therapies from Preclinical Studies to the Clinic. Mol Ther. Apr. 4, 2018;26(4):947-962.
Büning and Srivastava. Capsid Modifications for Targeting and Improving the Efficacy of AAV Vectors. vol. 12, p. 248-265, Mar. 15, 2019.
Hudry E, Vandenberghe LH. Therapeutic AAV Gene Transfer to the Nervous System: A Clinical Reality. Neuron. Mar. 6, 2019;101(5):839-862.
Betancur JG et al., miRNA-like duplexes as RNAi triggers with improved specificity. Front Genet. Jul. 12, 2012;3:127.
Chung et al., Polycystronic RNA polymerase II expression vectors for RNA interference based on BIC/miR-155. Nucleic Acids Res. Apr. 13, 2006;34(7):e53.
Cullen BR. Induction of stable RNA interference in mammalian cells. Gene Ther. Mar. 2006;13(6):503-8.
Dow LE et al., A pipeline for the generation of shRNA transgenic mice. Nat Protoc. Feb. 2, 2012;7(2):374-93.
Fellmann C. et al., Functional identification of optimized RNAi triggers using a massivelyparallel sensor assay. Mol Cell. Mar. 18, 2011;41(6):733-46.

Gu S et al., The loop position of shRNAs and pre-miRNAs is critical for the accuracy of dicer processing in vivo. Cell. Nov. 9, 2012;151(4):900-911.
Han J. et al., Molecular basis for the recognition of primary microRNAs by the Drosha-DGCR8 complex. Cell. Jun. 2, 2006;125(5):887-901.
Ketley A. et al., The miR-20 microRNA family targets smoothened to regulate hedgehog signalling in zebrafish early muscle development. PLoS One. Jun. 5, 2013;8(6):e65170.
Liu YP et al., Inhibition of HIV-1 by multiple siRNAs expressed from a single microRNApolycistron. Nucleic Acids Res. May 2008;36(9):2811-24.
Park JE et al., Dicer recognizes the 5' end of RNA for efficient and accurate processing. Nature. Jul. 13, 2011;475(7355):201-5.
Schwarz DS et al., Asymmetry in the assembly of the RNAi enzyme complex. Cell. Oct. 17, 2003;115(2):199-208.
Seitz H et al., A 5'-uridine amplifies miRNA/miRNA* asymmetry in *Drosophila* by promoting RNA-induced silencing complex formation. Silence. Jun. 7, 2011;2:4.
Wang D et al., Adeno-associated virus vector as a platform for gene therapy delivery. Nat Rev Drug Discov. Feb. 1, 2019.
Long et al., Validation of a prognostic index for Huntington's disease. Mov Disord. Feb. 2017;32(2):256-263. Epub Nov. 28, 2016.
Ross et al., Huntington's disease: from molecular pathogenesis to clinical treatment. Lancet Neurol. Jan. 2011;10(1):83-98.
Stanek et al., Silencing mutant huntingtin by adeno-associated virus-mediated RNA interference ameliorates disease manifestations in the YAC128 mouse model of Huntington's disease. Hum Gene Ther. May 2014;25(5):461-74. Epub Mar. 21, 2014.
Walker, Huntington's disease. Lancet. Jan. 20, 2007;369(9557):218-28.
Borel F et al., Recombinant AAV as a platform for translating the therapeutic potential of RNA interference .Mol Ther. Apr. 2014;22(4):692-701.
De Leeuw CN et al. rAAV-compatible MiniPromoters for Restricted Expression in the Brain and Eye. Mol Brain. May 10, 2016;9(1):52.
Hirsch ML, et al. Delivering Transgenic DNA Exceeding the Carrying Capacity of AAV Vectors. Methods Mol Biol. 2016;1382:21-39.
Lu J, et al. A 5'non-coding exon containing engineered intron enhances transgene expression from recombinant AAV vectors in vivo. Hum Gene Ther. Jan. 2017;28(1):125-134.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP.B. Front Mol Neurosci. Nov. 2016;6:116.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Med. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep. Jun. 13, 2016;6:27758.

(56) References Cited

OTHER PUBLICATIONS

Lukashcuk V et al. AAV9-mediated central nervous system-targeted gene delivery via cisterna magna route in mice. Mol Ther Methods Clin Dev. Feb. 17, 2016;3:15055.

Tarantal AF, et al. Systemic and Persistent Muscle Gene Expression in Rhesus Monkeys with a Liver De-targeted Adeno-Associated Virus (AAV) Vector. Hum Gene Ther. May 2017;28(5):385-391.

Huang LY, et al. Characterization of the Adeno-Associated Virus 1 and 6 Sialic Acid Binding Site. J Virol. May 12, 2016;90(11):5219-30.

Siu JJ, et al. Improved gene delivery to adult mouse spinal cord through the use of engineered hybrid adeno-associated viral serotypes. Gene Ther. Apr. 25, 2017. Epub ahead of print.

Deng XF, et al. Replication of an autonomous human parvovirus in non-dividing human airway epithelium is facilitated through the DNA damage and repair pathways. PLoS Pathog. Jan. 2016;12(1):e1005399.

Kailasan S, et al. Structure of an Enteric Pathogen, Bovine Parvovirus. J Virol. Mar. 2015, 89(5):2603-14.

Alton EW, et al. Repeated nebulisation of non-viral CFTR gene therapy in patients with cystic fibrosis: a randomised, double-blind, placebo-controlled, phase 2b trial. Lancet Respir Med. Sep. 2015;3(9):684-91.

Baum BJ, et al. Early responses to adenoviral-mediated transfer of the aquaporin-1 cDNA for radiation-induced salivary hypofunction. Proc Natl Acad Sci U S A. Nov. 20, 2012;109(47):19403-7.

Shen W, et al. Analysis of the Cis and Trans Requirements for DNA Replication at the Right End Hairpin of the Human Bocavirus 1 Genome. J Virol. Aug. 2016;90(17):7761-77.

Ferrand M, et al. Serotype-specific Binding Properties and Nanoparticle Characteristics Contribute to the Immunogenicity of rAAV1 Vectors. Mol Ther.Jun. 2015, 23(6):1022-33.

Loring HS, et al. Development of rAAV2-CFTR: History of the First rAAV Vector Product to be Used in Humans. Hum Gene Ther Methods. Apr. 2016;27(2):49-58.

Valdmanis P, et al. Future of rAAV gene therapy: Platform for RNAi, Gene Editing and Beyond. Hum Gene Ther. Apr. 2017;28(4):361-372.

Hocquemiller M et al. Adeno-Associated Virus-Based Gene Therapy for CNS Diseases. Hum Gene Ther. Jul. 2016;27(7):478-96.

Vodicka P, et al. Autophagy Activation by Transcription Factor EB (TFEB) in Striatum of HDQ175/Q7 Mice. J Huntingtons Dis. Oct. 2016;5(3):249-260.

Vodicka P, et al. Effects of Exogenous NUB1 Expression in the Striatum of HDQ175/Q7 Mice. J Huntingtons Dis. Jun. 2016;5(2):163-74.

Amaro IA et al. An Intrabody Drug (rAAV6-INT41) Reduces the Binding of N-Terminal Huntingtin Fragment(s) to DNA to Basal Levels in PC12 Cells and Delays Cognitive Loss in the R6/2 Animal Model. J Neurodegener Dis. 2016;2016:7120753.

Monteys AM, et al. CRISPR/Cas9 Editing of the Mutant Huntingtin Allele In Vitro and In Vivo. Mol Ther. Jan. 2017;25(1):12-23.

Hadaczek P et al. Widespread AAV1- and AAV2-mediated Transgene Expression in the Nonhuman Primate Brain: Implications for Huntington's Disease. Mol Ther Methods Clin Dev. Jun. 29, 2016;3:16037.

Miniarikova J et al. Design, Characterization, and Lead Selection of Therapeutic miRNAs Targeting Huntingtin for Development of Gene Therapy for Huntington's Disease.Mol Ther Nucleic Acids. Mar. 22, 2016;5:e297.

Keeler AM et al. Cellular Analysis of Silencing the Huntington's Disease Gene Using AAV9 Mediated Delivery of Artificial Micro RNA into the Striatum of Q140/Q140 Mice. J Huntingtons Dis. Oct. 1, 2016;5(3):239-248.

Green F, et al. Axonal transport of AAV9 in nonhuman primate brain. Gene Ther. Jun. 2016;23(6):520-6.

Bisset DR, et al. Therapeutic impact of systemic AAV-mediated RNA interference in a mouse model of myotonic dystrophy. Hum Mol Genet. Sep. 2015;24(17):4971-83.

He X, et al. Recombinant adeno-associated virus-mediated inhibition of microRNA-21 protects mice against the lethal schistosome infection by repressing both IL-13 and transforming growth factor beta 1 pathways. Hepatology. Jun. 2015, 61(6):2008-17. d.

Xie J et al. Adeno-Associated Virus-Mediated MicroRNA Delivery and Therapeutics. Semin Liver Dis. Feb. 2015, 35(1):81-8.

Keiser MS et al. Broad distribution of ataxin 1 silencing in rhesus cerebella for spinocerebellar ataxia type 1 therapy. Brain. Dec. 2015;138(Pt 12):3555-66.

Enomoto M, et al. Efficient Gene Suppression in Dorsal Root Ganglia and Spinal Cord Using Adeno-Associated Virus Vectors Encoding Short-Hairpin RNA. Methods Mol Biol. 2016;1364:77-90.

Tse LV, et al. Structure-guided evolution of antigenically distinct adeno-associated virus variants for immune evasion. Proc Natl Acad Sci U S A. May 30, 2017. Epub ahead of print.

Vandamme C, et al. Unraveling the complex story of immune responses to AAV vectors trial after trial. Hum Gene Ther. Aug. 23, 2017.

Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.

Kim Y, et al. Mutagenic Analysis of an Adeno-Associated Virus Variant Capable of Simultaneously Promoting Immune Resistance and Robust Gene Delivery. Hum Gene Ther. Jun. 24, 2017. Epub ahead of print.

Pillay S, et al. AAV serotypes have distinctive interactions with domains of the cellular receptor AAVR. J Virol. Jul. 5, 2017. Epub ahead of print.

Wang M, Sun J, Crosby A, Woodard K, Hirsch ML, Samulski RJ, Li C. Direct interaction of human serum proteins with AAV virions to enhance AAV transduction: immediate impact on clinical applications. Gene Ther. Jan. 2017;24(1):49-59. doi: 10.1038/gt.2016.75. Epub Nov. 11, 2016.

Bennett A, et al. Understanding capsid assembly and genome packaging for adeno-associated viruses. Future Virology Jun. 2017; 12(6): 283-297.

Grimm et al. Small but increasingly mightly—latest advances in AAV vector research, design and evolution. Hum Gene Ther. Nov. 2017 (Epub Aug. 23, 2017); 28(11):1075-1086.

Pillay S, et al. Host determinants of adeno-associated viral vector entry. Curr Opin Virol. Jun. 30, 2017;24:124-131. Epub ahead of print.

Merkel SF, et al. Trafficking of adeno-associated virus vectors across a model of the blood-brain barrier; a comparative study of transcytosis and transduction using primary human brain endothelial cells. J Neurochem. Jan. 2017;140(2):216-230. doi: 10.1111/jnc.13861.

Hinderer C, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.

Nicolson SC, et al. Identification and validation of small molecules that enhance recombinant Adeno-associated virus transduction following high throughput screen. J Virol. Jul. 2016;90(16):7019-31.

Wang M, et al. Direct interaction of human serum proteins with AAV virions to enhance AAV transduction: Immediate impact on clinical applications. Gene Ther. Jan. 2017;24(1):49-59.

Watakabe A, et al. Comparative analyses of adeno-associated viral vector serotypes 1 2 5 8 and 9 in marmoset mouse and macaque cerebral cortex. Neurosci Res.Apr. 2015, 93:144-57.

Xiao P, et al. Disruption of microtubules post virus entry enhances adeno-associated virus vector transduction. Hum Gene Ther. Apr. 2016;27(4):309-24.

Hudry EM, et al. Exosome-associated AAV vector as a robust and convenient neuroscience tool. Gene Ther. Apr. 2016;23(4):380-92.

Nery FC, et al. New methods for investigation of neuronal migration in embryonic brain explants J Neurosci Methods.Jan. 2015, 239:80-4.

Su W et al. Recombinant adeno-associated viral (rAAV) vectors mediate efficient gene transduction in cultured heonatal and adult microglia. J Neurochem. Jan. 2016;136 Suppl 1:49-62.

(56) References Cited

OTHER PUBLICATIONS

Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate In Vivo Non-Invasive Tracking of Adeno-Associated Gene Transfer Vectors. Sci Rep. Jan. 2017;7:39594.
Xie Q, et al. The 2.8 Å Electron Microscopy Structure of Adeno-Associated Virus-DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Thorne B, et al. Gene Therapy. Adv Biochem Eng Biotechnol. Mar. 14, 2017 Epub ahead of print.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Von Heinje G. Sequence Analysis in Molecular Biology. Academic Press, 1987.
Stahl PH, et al. Pharmaceutical Salts: Properties, Selection, and Use. Wiley-VCH, 2008.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28(4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.
Wang S, et al. Direct brain infusion can be enhanced with focused ultrasound and microbubbles. J Cereb Blood Flow Metab. Feb. 2017;37(2):706-714.
Wang et al., Noninvasive, neuron-specific gene therapy can be facilitated by focused ultrasound and recombinant adeno-associated virus. Gene Therapy. Nov. 22, 2014. 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48(5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017;7:45524.
Woodard KT et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016;90(21):9878-9888.
Wang LL, et al. Comparative study of liver gene transfer with AAV vectors based on endogenous and engineered AAV capsids. Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.
Adamson-Small L, et al. Sodium chloride enhances rAAV production in a serum-free suspension manufacturing platform using the Herpes Simplex Virus System. Hum Gene Ther Methods. Feb. 2017;28(1):1-14.
Ai J, et al. A Scalable and Accurate Method for Quantifying Vector Genomes of Recombinant Adeno-Associated Viruses in Crude Lysate. Hum Gene Ther Methods. Apr. 13, 2017. Epub ahead of print.
Buclez PO, et al. Rapid, scalable, and low-cost purification of recombinant adeno-associated virus produced by paculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.
Clement N, et al. Manufacturing of recombinant adeno-associated viral vectors for clinical trials. Mol Ther Methods Clin Dev. Mar. 2016;3:16002.
D'Costa S, et al. Practical utilization of recombinant AAV vector reference standards: focus on vector genome titration by free ITR qPCR. Mol Ther Methods Clin Dev. Mar. 2016;5:16019.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24(2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.
Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.
Kirnbauer R, et al. Virus-like particles of bovine papillomavirus type 4 in prophylactic and therapeutic immunization. Virology. May 1, 1996;219(1):37-44.
Kohlbrenner E, et al. Production and Characterization of Vectors Based on the Cardiotropic AAV Serotype 9. Methods Mol Biol. 2017;1521:91-107.
Kotin RM, et al. Large-scale recombinant adeno-associated virus production. Hum Mol Genet. Apr. 15, 2011;20(R1):R2-6. doi: 10.1093/hmg/ddr141. Epub Apr. 29, 2011.
Kotin RM, et al. Manufacturing clinical grade recombinant adeno-associated virus using invertebrate cell lines. Hum Gene Ther. Mar. 28, 2017. Epub ahead of print.
Kotterman MA, et al. Enhanced cellular secretion of AAV2 by expression of foreign viral envelope proteins. Biochemical Engineering Journal, vol. 93, Jan. 15, 2015, pp. 108-114.
Methods in Molecular Biology, ed. Richard, Humana Press, NJ (1995).
Carter BJ. Adeno-associated virus and the development of adeno-associated virus vectors: a historical perspective. Mol Ther. Dec. 2004;10(6):981-9.
G. S. Banker, Modern Pharmaceutics, Drugs and the Pharmaceutical Sciences, v. 72, Marcel Dekker, New York, Inc., 1996.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.

(56) References Cited

OTHER PUBLICATIONS

Hastie E, et al. Adeno-Associated Virus at 50: A Golden Anniversary of Discovery, Research, and Gene Therapy Success-A Personal Perspective. Hum Gene Ther. May 2015, 26(5):257-65.
Aydemir F, et al. Mutants at the 2-fold interface of AAV2 structural proteins suggest a role in viral transcription for AAV capsids. J Virol. Jul. 2016;90(16):7196-204.
Bantel-Schaal U, et al. Human adeno-associated virus type 5 is only distantly related to other known primate helper-dependent parvoviruses. J Virol. Feb. 1999;73(2):939-47.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Earley LF, et al. Adeno-Associated Virus Assembly-Activating Protein Is Not an Essential Requirement for Capsid Assembly of AAV Serotypes 4, 5 and 11. J Virol. Jan. 2017;91(3):pii:e0198-16.
Ding C, et al., Biochemical Characterization of Junonia Coenia Densovirus Nonstructural Protein NS-1. J. Virol., 76(1):338-345 2002.
Adachi K, et al. Drawing a high-resolution functional map of adeno-associated virus capsid by massively parallel sequencing. Nat Commun. 2014;5:3075. doi: 10.1038/ncomms4075.
Altschul SF, et al. Basic local alignment search tool. J Mol Biol. Oct. 5, 1990;215(3):403-10.
Carillo H, et al. The Multiple Sequence Alignment Problem in Biology. SIAM J. Appl. Math. 48-5 (1988), pp. 1073-1082.
Devereux J A comprehensive set of sequence analysis programs for the VAX. Nucleic Acids Res. Jan. 11, 1984;12(1Pt 1):387-95.
Gribskov M, et al. Sequence Analysis Primer. M Stockton Press, New York, 1991.
Griffin AM, et al. Computer Analysis of Sequence Data, Part I. Humana Press, New Jersey, 1994.
Berge SM Pharmaceutical salts. J Pharm Sci. Jan. 1977;66(1):1-19.
Bell P, et al. Effects of self-complementarity, codon optimization, transgene, and dose on liver transduction with AAV8. Hum Gene Ther Methods. Dec. 2016;27(6):228-237.
Heim et al., Wavelength mutations and posttranslational autoxidation of green fluorescent protein. Proc. Natl. Acad. Sci. USA (1994).
Hastie E, et al. Recombinant adeno-associated virus vectors in the treatment of rare diseases. Expert Opin Orphan Drugs. 2015;3(6):675-689.
Fargnoli AS, et al. Liquid jet delivery method featuring S100A1 gene therapy in the rodent model following acute myocardial infarction. Gene Ther. Feb. 2016;23(2):151-7.
Aubourg P. Gene therapy for rare central nervous system diseases comes to age. Endocr Dev. 2016;30:141-6.
Bankiewicz KS et al. AAV Viral Vector Delivery to the Brain by Shape-conforming MR-guided Infusions. J Control Release. Oct. 28, 2016;240:434-442.
Bey K, et al. Efficient CNS targeting in adult mice by intrathecal infusion of single-stranded AAV9-GFP for gene therapy of neurological disorders. Gene Ther. Apr. 20, 2017. Epub ahead of print.
Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Chandler RJ, et al. Systemic AAV9 gene therapy improves the lifespan of mice with Niemann-Pick disease, type C1. Hum Mol Genet. Jan. 2017;26(1):52-64.

Dang CH, et al. In vivo dynamics of AAV-mediated gene delivery to sensory neurons of the trigeminal ganglia. Sci Rep. Apr. 19, 2017;7(1):927.
Dimidschstein J, et al. A viral strategy for targeting and manipulating interneurons across vertebrate species. Nat Neurosci. Dec. 2016;19(12):1743-1749.
Donsante A et al. Intracerebroventricular delivery of self-complementary adeno-associated virus serotype 9 to the adult rat brain. Gene Ther. May 2016;23(5):401-7.
El-Shamayleh Y, et al. Strategies for targeting primate neural circuits with viral vectors. J Neurophysiol. Jul. 2016;116(1):122-34.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gessler DJ et al. Gene Therapy for the Treatment of Neurological Disorders: Metabolic Disorders. Methods Mol Biol. 2016;1382:429-65.
Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Gurda BL, et al. Evaluation of AAV-mediated gene therapy for central nervous system disease in canine mucopolysaccharidosis VII. Mol Ther. Feb. 2016;24(2):206-16.
Ahmed SS, et al. rAAV gene therapy in a Canavan's disease mouse model reveals immune impairments and an extended pathology beyond the central nervous system. Mol Ther. Jun. 2016;24(6):1030-41.
Dashkoff J, et al. Tailored transgene expression to specific cell types in the central nervous system after peripheral injection with AAV9. Mol Ther Methods Clin Dev. Dec. 2016;3:16081.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Greig JA, et al. Impact of intravenous infusion time on AAV8 vector pharmacokinetics, safety, and liver transduction in cynomolgus macaques. Mol Ther Methods Clin Dev. Dec. 2016;3:16079.
Gruntman AM, et al. Delivery of Adeno-associated virus gene therapy by intravascular limb infusion methods. Hum Gene Ther Clin Dev Sep. 2015;26(3):159-64.
Hagg A, et al. Using AAV vectors expressing the beta 2-adrenoceptor or associated G alpha proteins to modulate skeletal muscle mass and muscle fiber size. Sci Rep. Mar. 2016;6:23042.
Greig JA, et al. Intramuscular administration of AAV overcomes pre-existing neutralizing antibodies in rhesus macaques. Vaccine. Dec. 2016;34(50):6323-6329.
Ai J, et al. Adeno-associated virus serotype rh. 10 displays strong muscle tropism following intraperitoneal delivery. Sci Rep. Jan. 2017;7:40336.
Baum BJ, et al. Advances in salivary gland gene therapy—oral and systemic implications. Expert Opinion on Biological Therapy. 2015;15(10):1443-54.
Hai B, et al. Long-term transduction of miniature pig parotid glands using serotype 2 adeno-associated viral vectors. J Gene Med. Jun. 2009;11(6):506-14.
Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.
Mietzsch M, et al. OneBac 2.0: Sf9 cell lines for production of AAV5 vectors with enhanced infectivity and minimal encapsidation of foreign DNA. Hum Gene Ther. Oct. 201526(10):688-97.
Nambiar B, et al. Characteristics of minimally oversized adeno-associated virus vectors encoding human Factor VIII generated using producer cell lines and triple transfection. Hum Gene Ther Methods. Feb. 2017;28(1):23-38.

(56) References Cited

OTHER PUBLICATIONS

Pacouret S, et al. AAV-ID: A Rapid and Robust Assay for Batch-to-Batch Consistency Evaluation of AAV Preparations. Mol Ther. Apr. 17, 2017. Epub ahead of print.

Penaud-Budloo M, et al. Accurate identification and quantification of DNA species by next-generation sequencing in adeno-associated viral vectors produced in insect cells. Hum Gene Ther Methods. May 2, 2017. Epub ahead of print.

Ruffing M, et al. Assembly of viruslike particles by recombinant structural proteins of adeno-associated virus type 2 in insect cells. J Virol. Dec. 1992;66(12):6922-30.

Samulski RJ, et al. Helper-free stocks of recombinant adeno-associated viruses: normal integration does not require viral gene expression. J Virol. Sep. 1989;63(9):3822-8.

Smith RH, et al. A simplified baculovirus-AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.

Urabe M, et al. Scalable generation of high-titer recombinant adeno-associated virus type 5 in insect cells. J Virol. Feb. 2006;80(4):1874-85.

Van Der Loo JCM, et al. Progress and challenges in viral vector manufacturing. Hum Mol Genet. Apr. 2016;25(R1):R42-52.

Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.

Zhao KN, et al. BPV1 E2 protein enhances packaging of full-length plasmid DNA in BPV1 pseudovirions. Virology. Jul. 5, 2000;272(2):382-93.

Pierson EE, et al. Resolving adeno-associated viral particle diversity with charge detection mass spectrometry. Anal Chem. Jul. 2016;88(13):6718-25.

Rashnonejad A, et al. Large-Scale Production of Adeno-Associated Viral Vector Serotype-9 Carrying the Human Survival Motor Neuron Gene. Mol Biotechnol. Jan. 2016;58(1):30-6.

Ling C, et al. Strategies to generate high-titer, high-potency recombinant AAV3 serotype vectors. Mol Ther Methods Clin Dev. May 2016;3:16029.

Afione S, et al. Identification and Mutagenesis of the Adeno-Associated Virus 5 Sialic Acid Binding Region.J Virol. Feb. 2015, 89(3):1660-72.

Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.

Halder S, et al. Structure of neurotropic adeno-associated virus AAVrh.8. J Struct Biol. Oct. 2015;192(1):21-36.

Huang LY, et al. Characterization of the adeno-associated virus 1 and 6 sialic acid binding site. J Virol. May 2016;90(11):5219-30.

Mao Y, et al. Single point mutation in adeno-associated viral vectors—DJ capsid leads to improvement for gene delivery in vivo. BMC Biotechnol. Jan. 2016;16:1.

Marsic D et al. Altering Tropism of rAAV by Directed Evolution. Methods of Mol Biol. 2016;1382:151-73.

Tu MY, et al. Role of capsid proteins in parvoviruses infection. Virol J. Aug. 2015, 4;12:114.

Zeng C, et al. Probing the Link between Genomic Cargo, Contact Mechanics and Nanoindentation in Recombinant Adeno-Associated Virus 2. J Phys Chem B. Mar. 2017;121(8):1843-1853.

Zinn E, et al. In Silico Reconstruction of the Viral Evolutionary Lineage Yields a Potent Gene Therapy Vector. Cell Rep. Aug. 2015, 12(6):1056-68.

Grimm D, et al. E Pluribus Unum: 50 years of research, millions of viruses and one goal—tailored acceleration of AAV evolution. Mol Ther. Dec. 2015;23(12):1819-1831.

Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.

Ling C, et al. Development of Optimized AAV Serotype Vectors for High-Efficiency Transduction at Further Reduced Doses. Hum Gene Ther Methods. Aug. 2016;27(4):143-9.

Pillay S, et al. An essential receptor for adeno-associated virus infection. Nature. Feb. 2016;530(7588):108-12.

Li BZ, et al. Site directed mutagenesis of surface-exposed lysine residues leads to improved transduction by AAV2 but hot AAV8 vectors in murine hepatocytes in vivo. Hum Gene Ther Methods. Dec. 2015;26(6):211-20.

Shen S, et al. Functional Analysis of the Putative Integrin Recognition Motif on Adeno-associated virus 9. J Biol Chem. Jan. 2015, 290(3):1496-504.

Steines B, et al. CFTR gene transfer with AAV improves early cystic fibrosis pig phenotypes. JCI Insight. Sep. 2016;1(14):e88728.

Bensky MJ, et al. Targeted gene delivery to the enteric nervous system using AAV: a comparison across serotypes and capsid mutants.Mol Ther. Mar. 2015;23(3):488-500.

Castle MJ, et al. Controlling AAV Tropism in the Nervous System with Natural and Engineered Capsids. Methods Mol Biol. 2016;1382:133-49.

Choudhury SR, et al. Widespread CNS gene transfer and silencing after systemic delivery of novel AAV-AS vectors. Mol Ther. Apr. 2016;24(4):726-35.

Davis AS, et al. Rational design and engineering of a modified adeno-associated virus (AAV1)-based vector system for enhanced retrograde gene delivery. Neurosurgery. Feb. 2015;76(2):216-25.

Deverman BE et al. Cre-dependent selection yields AAV variants for widespread gene transfer to the adult brain. Nat Biotechnol. Feb. 2016;34(2):204-9.

Powell SK et al. Characterization of a novel adeno-associated viral vector with preferential oligodendrocyte tropism. Gene Ther. Sep. 15, 2016.

Tervo et al. A Designer AAV Variant Permits Efficient Retrograde Access to Projection Neurons. Neuron. Oct. 19, 2016;92(2):372-382.

Choudhury et al. In Vivo Selection Yields AAV-B1 Capsid for Central Nervous System and Muscle Gene Therapy. Mol Ther. Aug. 2016;24(7):1247-57.

Keravala A, et al. Evaluating AAV Hybrid Variants for Improved Tropism after Intravitreal Gene Delivery to the Retina. Molecular Therapy, vol. 23, Supplement 1, May 2015, pp. S127-S128.

Vercauteren K, et al. Superior in vivo Transduction of Human Hepatocytes Using Engineered AAV3 Capsid. Mol Ther. Jun. 2016;24(6):1042-9.

Chen M, et al. Efficient Gene Delivery and Expression in Pancreas and Pancreatic Tumors by Capsid-optimized AAV8 Vectors. Hum Gene Ther Methods. Feb. 2017;28(1):49-59.

Ling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495.

Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.

Zou W, et al. Nonstructural protein NP1 of human bocavirus 1 plays a critical role in the expression of viral capsid proteins. J Virol. Apr. 2016;90(9):4658-69.

Mingozzi F, et al. Adeno-associated viral vectors at the frontier between tolerance and immunity. Front Immunol.Mar. 2015, 6:120.

Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.

Xie J, et al. Short DNA Hairpins Compromise Recombinant Adeno-Associated Virus Genome Homogeneity. Mol Ther. Jun. 7, 2017;25(6):1363-1374.

Davidsson M, et al. A novel process of viral vector barcoding and library preparation enables high-diversity library generation and recombination-free paired-end sequencing. Sci Rep. Nov. 2016;6:3563.

(56) References Cited

OTHER PUBLICATIONS

Chamberlain K, et al. Expressing transgenes that exceed the packaging capacity of AAV capsids. Hum Gene Ther Methods. Feb. 2016;27(1):1-12.
Pfeifer A et al., Pharmacological potential of RNAi—focus on miRNA. Pharmacol Ther. Jun. 2010;126(3):217-27.
Tereshchenko A et al., Brain structure in juvenile-onset Huntington disease. Neurology. Apr. 10, 2019.
Miniarikova J et al., Translation of MicroRNA-Based Huntingtin-Lowering Therapies from Preclinical Studies to the Clinic. Molecular Therapy. vol. 26 No. 4, Apr. 2018. p. 1-16.
Spronck et al., AAV5-miHTT Gene Therapy Demonstrates Sustained Huntingtin Lowering and Functional Improvement in Huntington Disease Mouse Models. Mol Ther Methods Clin Dev. Mar. 16, 2019;13:334-343.
Challis et al., Systemic AAV vectors for widespread and targeted gene delivery in rodents. Nat Protoc. Feb. 2019;14(2):379-414.
Elbashir et al., Functional anatomy of siRNAs for mediating efficient RNAi in *Drosophila melanogaster* embryo lysate. EMBO J. Dec. 3, 2001; 20(23):6877-88.
Powell et al., Viral Expression Cassette Elements to Enhance Transgene Target Specificity and Expression in Gene Therapy. Discov Med. Jan. 2015;19(102):49-57.
Swarup V et al. Identification of evolutionarily conserved gene networks mediating neurodegenerative dementia. Nat Med. Jan. 2019;25(1):152-164.
Extended European Search Report issued in corresponding EP Application No. 17800155.8 dated Dec. 4, 2019.
Lisa M. Stanek et al: "Silencing Mutant Huntingtin by Adeno-Associated Virus-Mediated RNA Interference Ameliorates Disease Manifestations in the YAC128 Mouse Model of Huntington's Disease", Human Gene Therpay, vol. 25, No. 5, May 1, 2014, pp. 461-474.
Brett D. Dufour et al: "Intrajugular Vein Delivery of AAV9-RNAi Prevents Neuropathological Changes and Weight Loss in Huntington's Disease Mice", Molecular Therapy, vol. 22, No. 4, Jan. 6, 2014, pp. 797-810.
R. Grondin et al: "Six-month partial suppression of Huntingtin is well tolerated in the adult rhesus striatum", Brain, vol. 135, No. 4, Apr. 1, 2012, pp. 1197-1209.
Nicholas R. Franich et al: "AAV Vector-mediated RNAi of Mutant Huntingtin Expression Is Neuroprotective in a Novel Genetic Rat Model of Huntington's Disease", Molecular Therapy, vol. 16, No. 5, Mar. 25, 2008, pp. 947-956.
Wang et al., "Efficient and Precise Processing of the Optimized Primary Artificial MicroRNA in a Huntingtin-Lowering Adeno-Associated Viral Gene Therapy In Vitro and in Mice and Nonhuman Primates," Human Gene Therapy (2021) vol. 33, Nos. 1-2, pp. 37-60.
Abstracts from HSG 2017, Neurotherapeutics (2018) 15:233-269.
Bennett, A. et al. "Thermal Stability as a Determinant of AAV Serotype Identity." Molecular Therapy. Methods & Clinical Development vol. 6 171-182. Jul. 24, 2017.
Bofill-De Ros, X. & Gu, S. "Guidelines for the optimal design of miRNA-based shRNAs." Methods (San Diego, Calif.) vol. 103 (2016): 157-66.
Calloni, R. & Bonatto, D. "Scaffolds for Artificial miRNA Expression in Animal Cells." Human Gene Therapy Methods vol. 26,5 (2015): 162-74.
Du, G. et al. "Design of expression vectors for RNA interference based on miRNAs and RNA splicing." The FEBS Journal vol. 273,23 (2006): 5421-7.
Extended European Search Report issued in European Application No. 18794572.0, dated Jan. 11, 2021, 11 pages.
Franich, N.R. et al., "AAV Vector-mediated RNAi of Mutant Huntingtin Expression is Neuroprotective in a Novel Genetic Rat Model of Huntington's Disease," Molecular Therapy (2008) vol. 16, No. 5, pp. 947-956.
International Preliminary Report on Patentability dated Nov. 7, 2019, in International Patent Application No. PCT/US2018/031117.
International Search Report & Written Opinion dated Sep. 13, 2018, in International Patent Application No. PCT/US2018/031117.
Keskin, S. et al. "AAV5-miHTT Lowers Huntingtin mRNA and Protein without Off-Target Effects in Patient-Derived Neuronal Cultures and Astrocytes." Molecular Therapy. Methods & Clinical Development vol. 15 275-284. Oct. 4, 2019.
Kotowska-Zimmer, A. et al. "Universal RNAi Triggers for the Specific Inhibition of Mutant Huntingtin, Atrophin-1, Ataxin-3, and Ataxin-7 Expression." Molecular Therapy. Nucleic Acids vol. 19 (2020): 562-571.
Miyagishi, M. et al. "Optimization of an siRNA-expression system with an improved hairpin and its significant suppressive effects in mammalian cells." The Journal of Gene Medicine vol. 6,7 (2004): 715-23.
Schopman, N. C. T. et al. "Optimization of shRNA inhibitors by variation of the terminal loop sequence." Antiviral Research vol. 86,2 (2010): 204-11.
Tabrizi, S. J. et al. "Targeting Huntingtin Expression in Patients with Huntington's Disease." The New England Journal of Medicine vol. 380,24 (2019): 2307-2316.

\* cited by examiner

COMPOSITIONS AND METHODS FOR TREATING HUNTINGTON'S DISEASE

CROSS REFERENCE TO RELATED APPLICATIONS

This application claims priority to U.S. Provisional Patent Application No. 62/338,113, filed on May 18, 2016, entitled Compositions and Methods of Treating Huntington's Disease, and U.S. Provisional Patent Application No. 62/485,049, filed on Apr. 13, 2017, entitled Compositions and Methods of Treating Huntington's Disease, the contents each of which are herein incorporated by reference in their entireties.

REFERENCE TO THE SEQUENCE LISTING

The present application is being filed along with a Sequence Listing in electronic format. The Sequence Listing is provided as a file entitled 20571035PCT.txt, created on May 18, 2017, which is 4,448,026 bytes in size. The information in the electronic format of the sequence listing is incorporated herein by reference in its entirety.

FIELD OF THE INVENTION

The present invention relates to compositions, methods and processes for the design, preparation, manufacture, use and/or formulation of modulatory polynucleotides, e.g., polynucleotides encoding small interfering RNA (siRNA) molecules which target the Huntingtin (HTT) gene (e.g., the wild-type or the mutated CAG-expanded HTT gene). Targeting of the mutated HTT gene may interfere with the HTT gene expression and the resultant HTT protein production. The modulatory polynucleotides encoding the siRNA molecules may be inserted into recombinant adeno-associated virus (AAV) vectors. Methods for using the siRNA molecules to inhibit the HTT gene expression in a subject with a neurodegenerative disease (e.g., Huntington's Disease (HD)) are also disclosed.

BACKGROUND OF THE INVENTION

Huntington's Disease (HD) is a monogenic fatal neurodegenerative disease characterized by progressive chorea, neuropsychiatric and cognitive dysfunction. Huntington's Disease is known to be caused by an autosomal dominant triplet (CAG) repeat expansion in exon 1 of the huntingtin (htt) gene, which encodes a huntington protein (HTT) bearing a poly-glutamine expanded tract at its N-terminus. This repeat expansion results in a toxic gain of function of HTT and ultimately leads to striatal neurodegeneration which progresses to widespread brain atrophy. Symptoms typically appear between the ages of 35-44 and the average life expectancy subsequent to disease onset is 10-25 years. Interestingly, the length of the CAG expansion correlates with both age of onset and rate of disease progression, with longer expansions linked to greater severity of disease and shorter survival. In a small percentage of the HD population (~6%), disease onset occurs from 2-20 years of age with appearance of an akinetic-rigid syndrome. These cases tend to progress faster than those of the later onset variety and have been classified as juvenile or Westphal variant HD. It is estimated that approximately 35,000-70,000 patients are currently suffering from HD in the US and Europe. Currently, only symptomatic relief and supportive therapies are available for treatment of HD, with a cure yet to be identified. Ultimately, individuals with HD succumb to other diseases (e.g., pneumonia, heart failure), choking, suffocation or other complications such as physical injury from falls.

The mechanisms by which CAG repeat-expanded htt results in neurotoxicity are not well understood. Huntingtin protein is expressed in all cells, though its concentration is highest in the brain. The normal function of HTT is unknown, but in the brains of HD patients, HTT aggregates into abnormal nuclear inclusions. It is now believed that it is this process of misfolding and aggregating along with the associated protein intermediates (i.e. the soluble species and toxic N-terminal fragments) that result in neurotoxicity.

Studies in animal models of HD have suggested that phenotypic reversal is feasible, for example, subsequent to gene shut off in regulated-expression models. Further, animal models in which silencing of HTT was tested, demonstrated promising results with the therapy being both well tolerated and showing potential therapeutic benefit. These findings indicate that HTT silencing may serve as a potential therapeutic target for treatment of HD.

The present invention develops an RNA interference based approach, novel double stranded RNA (dsRNA) constructs and siRNA constructs and methods of their design, to inhibit or prevent the expression of polyglutamine expanded HTT in HD patients for treatment of the disease. In addition, these novel siRNA constructs may be synthetic molecules or be encoded in an expression vector (one or both strands) for delivery into cells. Such vectors include, but are not limited to adeno-associated viral vectors such as vector genomes of any of the AAV serotypes or other viral delivery vehicles such as lentivirus, etc.

SUMMARY OF THE INVENTION

The present invention relates to RNA molecule-mediated gene specific interference with gene expression and protein production. Methods for treating neurodegenerative diseases such as Huntington's Disease are also included in the present invention. The siRNAs included in the compositions featured herein encompass a dsRNA having an antisense strand (that is 30 nucleotides or less, generally 19-24 nucleotides in length), that is substantially complementary to at least part of an mRNA transcript of the mutated HTT gene.

The present invention provides short double stranded RNA molecules such as small interfering RNA (siRNA) duplexes that target HTT mRNA to interfere with HTT gene expression and/or HTT protein production. The siRNA duplexes of the present invention may interfere with the HTT gene, and may particularly interact with the HTT gene which has mutations to cause Huntington's Disease.

In some embodiments, such siRNA molecules, or a single strand of the siRNA molecules, are inserted into (AAV) adeno-associated viral vectors to be introduced into cells, specifically striatal or cortical neurons and/or other surrounding cells in the central nervous system. The AAV vector may comprise sequences encoding 1, 2, 3, 4, or more than 4 siRNA duplexes.

The siRNA duplex of the present invention comprises an antisense strand and a sense strand hybridized together forming a duplex structure, wherein the antisense strand is complementary to the nucleic acid sequence of the HTT gene, and wherein the sense strand is homologous to the nucleic acid sequence of the HTT gene. In some aspects, the 5' end of the antisense strand has a 5' phosphate group and the 3' end of the sense strand contains a 3' hydroxyl group.

In other aspects, there are none, one or 2 nucleotide overhangs at the 3' end of each strand.

According to the present invention, each strand of the siRNA duplex targeting the HTT gene is about 19-25 nucleotides in length, preferably about 19 nucleotides, 20 nucleotides, 21 nucleotides, 22 nucleotides, 23 nucleotides, 24 nucleotides, or 25 nucleotides in length. In some aspects, the siRNAs may be unmodified RNA molecules.

In other aspects, the siRNAs may contain at least one modified nucleotide, such as base, sugar or backbone modification.

In one embodiment, a siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding the HTT protein, and the region of complementarity is 30 nucleotides or less, and at least 15 nucleotides in length. Generally, the dsRNA is 19 to 24, e.g., 19 to 21 nucleotides in length. In some embodiments the dsRNA is from about 15 to about 25 nucleotides in length, and in other embodiments the dsRNA is from about 25 to about 30 nucleotides in length.

The dsRNA, either upon contacting with a cell expressing HTT protein or upon transcription within a cell expressing HTT protein, inhibits or suppresses the expression of a HTT gene by at least 10%, at least 20%, at least 25%, at least 30%, at least 35% or at least 40% or more, such as when assayed by a method as described herein.

According to the present invention, AAV vectors comprising the nucleic acids encoding the siRNA duplexes, one strand of the siRNA duplex or the dsRNA targeting the HTT gene are produced, the AAV vector serotype may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A (PHP.A), and/or AAV-PHP.B (PHP.B), and variants thereof. As a non-limiting example, the AAV vector serotype is AAV1. As another non-limiting example, the AAV serotype is AAV-DJ8. As another non-limiting example, the AAV serotype is AAV-PHP.A (PHP.A). As another non-limiting example, the AAV serotype is AAV-PHP.B (PHP.B).

In one embodiment, the AAV vectors comprising the nucleic acids encoding the siRNA duplexes, one strand of the siRNA duplex or the dsRNA targeting the HTT gene are produced may be selected based on the tropism for medium spiny striatal neurons, cortical neurons and/or astrocytes. As a non-limiting example, the AAV vector is selected based on the expression level in a desired cell type such as, but not limited to, medium spiny striatal neurons, cortical neurons and/or astrocytes.

According to the present invention, siRNA duplexes or dsRNA targeting the HTT gene in HD are selected from the siRNA duplexes listed in Tables 3, 4, or 5. Preferably, the siRNA duplexes or dsRNA targeting HTT gene in HD are selected from the group consisting of siRNA duplexes: D-3500 to D-3570.

The present invention also provides pharmaceutical compositions comprising at least one siRNA duplex targeting the HTT gene and a pharmaceutically acceptable carrier. In some aspects, a nucleic acid sequence encoding the siRNA duplex is inserted into an AAV vector.

In some embodiments, the present invention provides methods for inhibiting/silencing HTT gene expression in a cell. Accordingly, the siRNA duplexes or dsRNA can be used to substantially inhibit HTT gene expression in a cell. The cell may be a neuron (e.g., medium spiny neurons of the putamen, caudate or striatum, and cortical neurons in the cerebral cortex), an astrocyte (e.g., astrocyte in the striatum, cortical astrocytes in the cerebral cortex) and/or oligodendrocytes. As a non-limiting example, the inhibition (or lowering) of the HTT gene expression in the putamen, caudate and cortex reduces the effect of Huntington's Disease in a subject. As another non-limiting example, the inhibition (or lowering) of the HTT gene expression in the medium spiny neurons in the striatum reduces the effect of Huntington's Disease in a subject. As yet another non-limiting example, the inhibition (or lowering) of the HTT gene expression in the astrocytes in the striatum reduces the effect of Huntington's Disease in a subject. In some aspects, the inhibition of the HTT gene expression refers to an inhibition or lowering by at least about 20%, preferably by at least about 30%, 40%, 50%, 60%, 70%, 80%, 85%, 90%, 95% and 100%. Accordingly, the protein product of the targeted gene may be inhibited by at least about 20%, preferably by at least about 30%, 40%, 50%, 60%, 70%, 80%, 85%, 90%, 95% and 100%.

In one embodiment, the present invention provides methods for inhibiting/silencing HTT gene expression by at least about 40% in a cell using siRNA duplexes or dsRNA. The cell may be a neuron (e.g., medium spiny neurons of the putamen or striatum, and cortical neurons in the cerebral cortex), an astrocyte (e.g., astrocyte in the striatum, cortical astrocytes in the cerebral cortex) and/or oligodendrocytes. As a non-limiting example, the at least 40% inhibition (or lowering) of the HTT gene expression in the putamen and cortex reduces the effect of Huntington's Disease in a subject. As another non-limiting example, the at least 40% inhibition (or lowering) of the HTT gene expression in the medium spiny neurons in the striatum reduces the effect of Huntington's Disease in a subject. As another non-limiting example, the at least 40% inhibition (or lowering) of the HTT gene expression in the putamen and the at least 20% inhibition (or lowering) of the HTT gene expression in the cortex reduces the effect of Huntington's Disease in a subject. As yet another non-limiting example, the at least 40% inhibition (or lowering) of the HTT gene expression in the astrocytes in the striatum reduces the effect of Huntington's Disease in a subject.

In some embodiments, the present invention provides methods for treating, or ameliorating Huntington's Disease associated with the HTT gene (e.g., CAG-expanded HTT gene) and the resultant HTT protein (e.g., poly-Q protein) in a subject in need of treatment, the method comprising administering to the subject a pharmaceutically effective amount of at least one siRNA duplex targeting the HTT gene (e.g., CAG-expanded HTT gene), delivering said siRNA duplex into targeted cells, inhibiting the HTT gene (e.g., CAG-expanded HTT gene) expression and resultant protein production, and ameliorating symptoms of HD in the subject.

In some embodiments, an AAV vector comprising the nucleic acid sequence encoding at least one siRNA duplex targeting the HTT gene is administered to the subject in need for treating and/or ameliorating HD. The AAV vector serotype may be selected from the group consisting of AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A (PHP.A), and/or AAV-PHP.B (PHP.B) and variants thereof.

In some embodiments, the siRNA duplexes or dsRNA targeting HTT gene or the AAV vectors comprising such siRNA-encoding molecules may be introduced directly into the central nervous system of the subject, for example, by intracranial injection.

In some embodiments, the pharmaceutical composition of the present invention is used as a solo therapy. In other embodiments, the pharmaceutical composition of the present invention is used in combination therapy. The combination therapy may be in combination with one or more neuroprotective agents such as small molecule compounds, growth factors and hormones which have been tested for their neuroprotective effect on neuron degeneration.

In some embodiments, the present invention provides methods for treating, or ameliorating Huntington's Disease by administering to a subject in need thereof a therapeutically effective amount of a plasmid or AAV vector described herein.

In some embodiments, the present invention provides a method for inhibiting the expression of the HTT gene in a region of the central nervous system of a subject by administering to the subject a composition with at least one adeno-associated viral (AAV) vector with a nucleic acid sequence positioned between two inverted terminal repeats (ITRs). The nucleic acid sequence position between two inverted terminal repeats (ITRs) may include an antisense strand and a sense strand which may form a siRNA duplex that when expressed inhibits or suppresses the expression of HTT in the subject. The expression may be reduced in a region of the subject such as, but not limited to, the forebrain of a subject or a region of the forebrain such as, but not limited to, the putamen. The expression of HTT in the forebrain or region of the forebrain (e.g., putamen) may be reduced by 40-70%, 40-60%, 50-70%, 50-60%, or it may be reduced by 50%, 51%, 52%, 53%, 54%, 55%, 56%, 57%, 58%, 59%, or 60%.

In some embodiments, the present invention provides a method for treating Huntington's Disease (HD) in a subject in need of treatment. The method may inhibit the expression of the HTT gene in a region of the central nervous system of a subject comprising administering to the subject a composition comprising at least one adeno-associated viral (AAV) vector comprising a nucleic acid sequence positioned between two inverted terminal repeats (ITRs). The nucleic acid sequence may comprise an antisense strand and a sense strand which can form a siRNA duplex that when expressed inhibits or suppresses the expression of HTT in a said subject. The expression may be reduced in a region of the subject such as, but not limited to, the forebrain of a subject or a region of the forebrain such as, but not limited to, the putamen. The expression of HTT in the forebrain or region of the forebrain (e.g., putamen) may be reduced by 40-70%, 40-60%, 50-70%, 50-60%, or it may be reduced by 50%, 51%, 52%, 53%, 54%, 55%, 56%, 57%, 58%, 59%, or 60%.

DETAILED DESCRIPTION OF THE INVENTION

The present invention relates to modulatory polynucleotides, e.g., RNA or DNA molecules as therapeutic agents. RNA interference mediated gene silencing can specifically inhibit targeted gene expression. As used herein, a "modulatory polynucleotide" is any nucleic acid sequence(s) which functions to modulate (either increase or decrease) the level or amount of a target gene, e.g., mRNA or protein levels. The present invention then provides small double stranded RNA (dsRNA) molecules (small interfering RNA, siRNA) targeting the HTT gene, pharmaceutical compositions comprising such siRNAs, as well as processes of their design.

The present invention also provides methods of their use for inhibiting HTT gene expression and protein production, for treating neurodegenerative disease, in particular, Huntington's Disease (HD).

The present invention provides small interfering RNA (siRNA) duplexes (and modulatory polynucleotides encoding them) that target HTT mRNA to interfere with HTT gene expression and/or HTT protein production.

In some embodiments, a nucleic acid sequence encoding such siRNA molecules, or a single strand of the siRNA molecules, is inserted into adeno-associated viral vectors and introduced into cells, specifically neurons and/or other surrounding cells in the central nervous system.

The encoded siRNA duplex of the present invention contains an antisense strand and a sense strand hybridized together forming a duplex structure, wherein the antisense strand is complementary to the nucleic acid sequence of the targeted HTT gene, and wherein the sense strand is homologous to the nucleic acid sequence of the targeted HTT gene. In some aspects, the 5' end of the antisense strand has a 5' phosphate group and the 3' end of the sense strand contains a 3' hydroxyl group. In other aspects, there are none, one or 2 nucleotide overhangs at the 3' end of each strand.

According to the present invention, each strand of the siRNA duplex targeting the HTT gene is about 19 to 25, 19 to 24 or 19 to 21 nucleotides in length, preferably about 19 nucleotides, 20 nucleotides, 21 nucleotides, 22 nucleotides, 23 nucleotides, 24 nucleotides, or 25 nucleotides in length. In some aspects, the siRNAs may be unmodified RNA molecules.

In other aspects, the siRNAs may contain at least one modified nucleotide, such as base, sugar or backbone modification.

In one embodiment, a siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding HTT, and the region of complementarity is 30 nucleotides or less, and at least 15 nucleotides in length. Generally, the dsRNA is 19 to 25, 19 to 24 or 19 to 21 nucleotides in length. In some embodiments the dsRNA is from about 15 to about 25 nucleotides in length, and in other embodiments the dsRNA is from about 25 to about 30 nucleotides in length.

The dsRNA, whether directly administered or encoded in an expression vector upon contacting with a cell expressing HTT protein, inhibits the expression of HTT protein by at least 10%, at least 20%, at least 25%, at least 30%, at least 35% or at least 40% or more, such as when assayed by a method as described herein.

The siRNA molecules included in the compositions featured herein comprise a dsRNA having an antisense strand (the antisense strand) having a region that is 30 nucleotides or less, generally 19 to 25, 19 to 24 or 19 to 21 nucleotides in length, that is substantially complementary to at least part of a mRNA transcript of the HTT gene.

According to the present invention, AAV vectors comprising the nucleic acids of the siRNA duplexes, one strand of the siRNA duplex or the dsRNA targeting HTT gene are produced, where the AAV vector serotypes may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A (PHP.A), and/or AAV-PHP.B (PHP.B) and variants thereof.

According to the present invention, siRNA duplexes or the encoded dsRNA targeting the HTT gene in HD is selected from the siRNA duplexes listed in Table 7 or Table 8. In some embodiments, the siRNA duplexes or dsRNA targeting the HTT in HD is D-3500 to D-3570.

The present invention also provides pharmaceutical compositions comprising at least one siRNA duplex targeting the HTT gene and a pharmaceutically acceptable carrier. In some aspects, the siRNA duplex is encoded by an AAV vector.

In some embodiments, the present invention provides methods for inhibiting/silencing HTT gene expression in a cell. Accordingly, the siRNA duplexes or encoded dsRNA can be used to substantially inhibit HTT gene expression in a cell, in particular in a neuron. In some aspects, the inhibition of HTT gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the present invention provides methods for inhibiting/silencing HTT gene expression in a cell, in particular in a medium spiny neuron. In some aspects, the inhibition of HTT gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the present invention provides methods for inhibiting/silencing gene expression in a cell, in particular in a motor neuron. In some aspects, the inhibition of gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In some embodiments, the present invention provides methods for inhibiting/silencing HTT gene expression in a cell, in particular in an astrocyte. In some aspects, the inhibition of HTT gene expression refers to an inhibition by at least about 15%, such as by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 15%, preferably by at least about 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

In one embodiment, the siRNA duplexes or encoded dsRNA may be used to reduce the expression of HTT protein by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of HTT protein may be reduced by 50-90%. As a non-limiting example, the expression of HTT protein may be reduced by 30-70%. As a non-limiting example, the expression of protein may be reduced by 20-70%. As a non-limiting example, the expression of protein may be reduced by 15-30%.

In one embodiment, the siRNA duplexes or encoded dsRNA may be used to reduce the expression of HTT mRNA by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of HTT mRNA may be reduced by 50-90%. As a non-limiting example, the expression of HTT mRNA may be reduced by 30-70%. As a non-limiting example, the expression of HTT mRNA may be reduced by 20-70%. As a non-limiting example, the expression of HTT mRNA may be reduced by 15-30%.

In one embodiment, the siRNA duplexes or encoded dsRNA may be used to reduce the expression of HTT protein and/or mRNA in at least one region of the CNS such as, but not limited to, the midbrain. The expression of HTT protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of HTT protein and mRNA in the striatum and/or cortex is reduced by 50-90%. As a non-limiting example, the expression of HTT protein and mRNA in the striatum is reduced by 40-50%. As a non-limiting example, the expression of HTT protein and mRNA in the striatum is reduced by 20-50%. As a non-limiting example, the expression of HTT protein and mRNA in the striatum is reduced by 15-50%. As a non-limiting example, the expression of HTT protein and mRNA in the cortex is reduced by 40-50%. As a non-limiting example, the expression of HTT protein and mRNA in the cortex is reduced by 30-70%. As a non-limiting example, the expression of HTT protein and mRNA in the cortex is reduced by 20-70%. As a non-limiting example, the expression of protein and mRNA in the cortex is reduced by 15-70%. As a non-limiting example, the expression of protein and mRNA in the cortex is reduced by 20-70%. As a non-limiting example, the expression of protein and mRNA in the striatum and/or cortex is reduced by 15-70%. As a non-limiting example, the expression of HTT protein and mRNA in the striatum and/or cortex is reduced by 40-70%. As a non-limiting example, the expression of HTT protein and mRNA in the striatum and/or cortex is reduced by 40-50%. As a non-limiting example, the expression of HTT protein and mRNA in the striatum and/or cortex is reduced by 50-70%. As a non-limiting example, the expression of HTT protein and mRNA in the striatum and/or cortex is reduced by 50-60%. As a non-limiting example, the expression of HTT protein and mRNA in the striatum and/or cortex is reduced by 50%. As a non-limiting example, the expression of HTT protein and mRNA in the striatum and/or cortex is reduced by 51%. As a non-limiting example, the expression of HTT protein and mRNA in the striatum and/or cortex is reduced by 52%. As a non-limiting example, the expression of HTT protein and mRNA in the striatum and/or cortex is reduced by 53%. As a non-limiting example, the expression of HTT protein and mRNA in the striatum and/or cortex is reduced by 54%. As a non-limiting example, the expression of HTT protein and mRNA in the striatum and/or cortex is reduced by 55%. As a non-limiting example, the expression of HTT protein and mRNA in the striatum and/or cortex is reduced by 56%. As a non-limiting example, the expression of HTT protein and mRNA in the striatum and/or cortex is reduced by 57%. As a non-limiting example, the expression of HTT protein and mRNA in the striatum and/or cortex is reduced by 58%. As a non-limiting example, the expression of HTT protein and mRNA in the striatum and/or cortex is reduced by 59%. As a non-limiting example, the expression of HTT protein and mRNA in the striatum and/or cortex is reduced by 60%.

In one embodiment, the siRNA duplexes or encoded dsRNA may be used to reduce the expression of HTT protein and/or mRNA in at least one region of the CNS such as, but not limited to the forebrain. The expression of HTT protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of HTT protein and mRNA in the putamen is reduced by 50-90%. As a non-limiting example, the expression of HTT protein and mRNA in the striatum is reduced by 40-50%. As a non-limiting example, the expression of HTT protein and mRNA in the cortex is reduced by 40-50%. As a non-limiting example, the expression of HTT protein and mRNA in the cortex is reduced by 30-70%. As a non-limiting example, the expression of HTT protein and mRNA in the cortex is reduced by 20-70%. As a non-limiting example, the expression of protein and mRNA in the cortex is reduced by 15-70%. As a non-limiting example, the expression of protein and mRNA in the striatum and/or cortex is reduced by 15-70%. As a non-limiting example, the expression of protein and mRNA in the striatum and/or cortex is reduced by 20-70%. As a non-limiting example, the expression of HTT protein and mRNA in the striatum and/or cortex is reduced by 40-70%. As a non-limiting example, the expression of HTT protein and mRNA in the striatum and/or cortex is reduced by 40-50%. As a non-limiting example, the expression of HTT protein and mRNA in the striatum and/or cortex is reduced by 50-70%. As a non-limiting example, the expression of HTT protein and mRNA in the striatum and/or cortex is reduced by 50-60%. As a non-limiting example, the expression of HTT protein and mRNA in the striatum and/or cortex is reduced by 50%. As a non-limiting example, the expression of HTT protein and mRNA in the striatum and/or cortex is reduced by 51%. As a non-limiting example, the expression of HTT protein and mRNA in the striatum and/or cortex is reduced by 52%. As a non-limiting example, the expression of HTT protein and mRNA in the striatum and/or cortex is reduced by 53%. As a non-limiting example, the expression of HTT protein and mRNA in the striatum and/or cortex is reduced by 54%. As a non-limiting example, the expression of HTT protein and mRNA in the striatum and/or cortex is reduced by 55%. As a non-limiting example, the expression of HTT protein and mRNA in the striatum and/or cortex is reduced by 56%. As a non-limiting example, the expression of HTT protein and mRNA in the striatum and/or cortex is reduced by 57%. As a non-limiting example, the expression of HTT protein and mRNA in the striatum and/or cortex is reduced by 58%. As a non-limiting example, the expression of HTT protein and mRNA in the striatum and/or cortex is reduced by 59%. As a non-limiting example, the expression of HTT protein and mRNA in the striatum and/or cortex is reduced by 60%. As a non-limiting example, the expression of protein and mRNA in the striatum and/or cortex is reduced by 61%. As a non-limiting example, the expression of protein and mRNA in the striatum and/or cortex is reduced by 62%. As a non-limiting example, the expression of protein and mRNA in the striatum and/or cortex is reduced by 63%. As a non-limiting example, the expression of protein and mRNA in the striatum and/or cortex is reduced by 64%. As a non-limiting example, the expression of protein and mRNA in the striatum and/or cortex is reduced by 65%. As a non-limiting example, the expression of protein and mRNA in the striatum and/or cortex is reduced by 66%. As a non-limiting example, the expression of protein and mRNA in the striatum and/or cortex is reduced by 67%. As a non-limiting example, the expression of protein and mRNA in the striatum and/or cortex is reduced by 68%. As a non-limiting example, the expression of protein and mRNA in the striatum and/or cortex is reduced by 69%. As a non-limiting example, the expression of protein and mRNA in the striatum and/or cortex is reduced by 70%.

In one embodiment, the siRNA duplexes or encoded dsRNA may be used to reduce the expression of HTT protein and/or mRNA in the putamen. The expression of HTT protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 55-60%, 55-70%, 55-80%, 55-90%, 55-95%, 55-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of HTT protein and mRNA in the putamen is reduced by 40-70%. As a non-limiting example, the expression of HTT protein and mRNA in the putamen is reduced by 40-50%. As a non-limiting example, the expression of HTT protein and mRNA in the putamen is reduced by 50-70%. As a non-limiting example, the expression of HTT protein and mRNA in the putamen is reduced by 50-60%. As a non-limiting example, the expression of HTT protein and mRNA in the putamen is reduced by 50%. As a non-limiting example, the expression of HTT protein and mRNA in the putamen is reduced by 51%. As a non-limiting example, the expression of HTT protein and mRNA in the putamen is reduced by 52%. As a non-limiting example, the expression of HTT protein and mRNA in the putamen is reduced by 53%. As a non-limiting example, the expression of HTT protein and mRNA in the putamen is reduced by 54%. As a non-limiting example, the expression of HTT protein and mRNA in the putamen is reduced by 55%. As a non-limiting example, the expression of HTT protein and mRNA in the putamen is reduced by 56%. As a non-limiting example, the expression of HTT protein and mRNA in the putamen is reduced by 57%. As a non-limiting example, the expression of HTT protein and mRNA in the putamen is reduced by 58%. As a non-limiting example, the expression of HTT protein and mRNA in the putamen is reduced by 59%. As a non-limiting example, the expression of HTT protein and mRNA in the putamen is reduced by 60%. As a non-limiting example, the expression of protein and mRNA in the putamen is reduced by 61%. As a non-limiting example, the expression of protein and mRNA in the putamen is reduced by 62%. As a non-limiting example, the expression of protein and mRNA in the putamen is reduced by 63%. As a non-limiting example, the expression of protein and mRNA in the putamen is reduced by 64%. As a non-limiting example, the expression of protein and mRNA in the putamen is reduced by 65%. As a non-limiting example, the expression of protein and mRNA in the putamen is reduced by 66%. As a non-limiting example, the expression of protein and mRNA in the putamen is reduced by 67%. As a non-limiting example, the expression of protein and mRNA in the putamen is reduced by 68%. As a non-limiting example, the expression of protein and mRNA in the putamen is reduced by 69%. As a non-limiting example, the expression of protein and mRNA in the putamen is reduced by 70%.

In one embodiment, the siRNA duplexes or encoded dsRNA may be used to reduce the expression of HTT protein and/or mRNA in the cortex. The expression of HTT protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of HTT protein and mRNA in the cortex is reduced by 40-50%. As a non-limiting example, the expression of HTT protein and mRNA in the cortex is reduced by 30-70%. As a non-limiting example, the expression of HTT protein and mRNA in the cortex is reduced by 20-70%. As a non-limiting example, the expression of HTT protein and mRNA in the cortex is reduced by 15-70%. As a non-limiting example, the expression of HTT protein and mRNA in the cortex is reduced by at least 30%. As a non-limiting example, the expression of HTT protein and mRNA in the cortex is reduced by 40-70%. As a non-limiting example, the expression of HTT protein and mRNA in the cortex is reduced by 40-50%. As a non-limiting example, the expression of HTT protein and mRNA in the cortex is reduced by 50-70%. As a non-limiting example, the expression of HTT protein and mRNA in the cortex is reduced by 50-60%. As a non-limiting example, the expression of HTT protein and mRNA in the cortex is reduced by 50%. As a non-limiting example, the expression of HTT protein and mRNA in the cortex is reduced by 51%. As a non-limiting example, the expression of HTT protein and mRNA in the cortex is reduced by 52%. As a non-limiting example, the expression of HTT protein and mRNA in the cortex is reduced by 53%. As a non-limiting example, the expression of HTT protein and mRNA in the cortex is reduced by 54%. As a non-limiting example, the expression of HTT protein and mRNA in the cortex is reduced by 55%. As a non-limiting example, the expression of HTT protein and mRNA in the cortex is reduced by 56%. As a non-limiting example, the expression of HTT protein and mRNA in the cortex is reduced by 57%. As a non-limiting example, the expression of HTT protein and mRNA in the cortex is reduced by 58%. As a non-limiting example, the expression of HTT protein and mRNA in the cortex is reduced by 59%. As a non-limiting example, the expression of HTT protein and mRNA in the cortex is reduced by 60%. As a non-limiting example, the expression of protein and mRNA in the cortex is reduced by 61%. As a non-limiting example, the expression of protein and mRNA in the cortex is reduced by 62%. As a non-limiting example, the expression of protein and mRNA in the cortex is reduced by 63%. As a non-limiting example, the expression of protein and mRNA in the cortex is reduced by 64%. As a non-limiting example, the expression of protein and mRNA in the cortex is reduced by 65%. As a non-limiting example, the expression of protein and mRNA in the cortex is reduced by 66%. As a non-limiting example, the expression of protein and mRNA in the cortex is reduced by 67%. As a non-limiting example, the expression of protein and mRNA in the cortex is reduced by 68%. As a non-limiting example, the expression of protein and mRNA in the cortex is reduced by 69%. As a non-limiting example, the expression of protein and mRNA in the cortex is reduced by 70%.

In one embodiment, the siRNA duplexes or encoded dsRNA may be used to reduce the expression of HTT protein and/or mRNA in the motor cortex. The expression of HTT protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of HTT protein and mRNA in the motor cortex is reduced by 40-50%. As a non-limiting example, the expression of HTT protein and mRNA in the motor cortex is reduced by 30-70%. As a non-limiting example, the expression of HTT protein and mRNA in the motor cortex is reduced by 20-70%. As a non-limiting example, the expression of HTT protein and mRNA in the motor cortex is reduced by 15-70%. As a non-limiting example, the expression of HTT protein and mRNA in the motor cortex is reduced by at least 30%. As a non-limiting example, the expression of HTT protein and mRNA in the motor cortex is reduced by 40-70%. As a non-limiting example, the expression of HTT protein and mRNA in the motor cortex is reduced by 50-70%. As a non-limiting example, the expression of HTT protein and mRNA in the motor cortex is reduced by 50-60%. As a non-limiting example, the expression of HTT protein and mRNA in the motor cortex is reduced by 50%. As a non-limiting example, the expression of HTT protein and mRNA in the motor cortex is reduced by 51%. As a non-limiting example, the expression of HTT protein and mRNA in the motor cortex is reduced by 52%. As a non-limiting example, the expression of HTT protein and mRNA in the motor cortex is reduced by 53%. As a non-limiting example, the expression of HTT protein and mRNA in the motor cortex is reduced by 54%. As a non-limiting example, the expression of HTT protein and mRNA in the motor cortex is reduced by 55%. As a non-limiting example, the expression of HTT protein and mRNA in the motor cortex is reduced by 56%. As a non-limiting example, the expression of HTT protein and mRNA in the motor cortex is reduced by 57%. As a non-limiting example, the expression of HTT protein and mRNA in the motor cortex is reduced by 58%. As a non-limiting example, the expression of HTT protein and mRNA in the motor cortex is reduced by 59%. As a non-limiting example, the expression of HTT protein and mRNA in the motor cortex is reduced by 60%. As a non-limiting example, the expression of protein and mRNA in the motor cortex is reduced by 61%. As a non-limiting example, the expression of protein and mRNA in the motor cortex is reduced by 62%. As a non-limiting example, the expression of protein and mRNA in the motor cortex is reduced by 63%. As a non-limiting example, the expression of protein and mRNA in the motor cortex is reduced by 64%. As a non-limiting example, the expression of protein and mRNA in the motor cortex is reduced by 65%. As a non-limiting example, the expression of protein and mRNA in the motor cortex is reduced by 66%. As a non-limiting example, the expression of protein and mRNA in the motor cortex is reduced by 67%. As a non-limiting example, the expression of protein and mRNA in the motor cortex is reduced by 68%. As a non-limiting example, the expression of protein and mRNA in the motor cortex is reduced by 69%. As a non-limiting example, the expression of protein and mRNA in the motor cortex is reduced by 70%.

In one embodiment, the siRNA duplexes or encoded dsRNA may be used to reduce the expression of HTT protein and/or mRNA in the somatosensory cortex. The expression of HTT protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of HTT protein and mRNA in the somatosensory cortex is reduced by 40-50%. As a non-limiting example, the expression of HTT protein and mRNA in the somatosensory cortex is reduced by 30-70%. As a non-limiting example, the expression of HTT protein and mRNA in the somatosensory cortex is reduced by 20-70%. As a non-limiting example, the expression of HTT protein and mRNA in the somatosensory cortex is reduced by 15-70%. As a non-limiting example, the expression of HTT protein and mRNA in the somatosensory cortex is reduced by at least 30%. As a non-limiting example, the expression of HTT protein and mRNA in the somatosensory cortex is reduced by 40-70%. As a non-limiting example, the expression of HTT protein and mRNA in the somatosensory cortex is reduced by 40-50%. As a non-limiting example, the expression of HTT protein and mRNA in the somatosensory cortex is reduced by 50-70%. As a non-limiting example, the expression of HTT protein and mRNA in the somatosensory cortex is reduced by 50-60%. As a non-limiting example, the expression of HTT protein and mRNA in the somatosensory cortex is reduced by 50%. As a non-limiting example, the expression of HTT protein and mRNA in the somatosensory cortex is reduced by 51%. As a non-limiting example, the expression of HTT protein and mRNA in the somatosensory cortex is reduced by 52%. As a non-limiting example, the expression of HTT protein and mRNA in the somatosensory cortex is reduced by 53%. As a non-limiting example, the expression of HTT protein and mRNA in the somatosensory cortex is reduced by 54%. As a non-limiting example, the expression of HTT protein and mRNA in the somatosensory cortex is reduced by 55%. As a non-limiting example, the expression of HTT protein and mRNA in the somatosensory cortex is reduced by 56%. As a non-limiting example, the expression of HTT protein and mRNA in the somatosensory cortex is reduced by 57%. As a non-limiting example, the expression of HTT protein and mRNA in the somatosensory cortex is reduced by 58%. As a non-limiting example, the expression of HTT protein and mRNA in the somatosensory cortex is reduced by 59%. As a non-limiting example, the expression of HTT protein and mRNA in the somatosensory cortex is reduced by 60%. As a non-limiting example, the expression of protein and mRNA in the somatosensory cortex is reduced by 61%. As a non-limiting example, the expression of protein and mRNA in the somatosensory cortex is reduced by 62%. As a non-limiting example, the expression of protein and mRNA in the somatosensory cortex is reduced by 63%. As a non-limiting example, the expression of protein and mRNA in the somatosensory cortex is reduced by 64%. As a non-limiting example, the expression of protein and mRNA in the somatosensory cortex is reduced by 65%. As a non-limiting example, the expression of protein and mRNA in the somatosensory cortex is reduced by 66%. As a non-limiting example, the expression of protein and mRNA in the somatosensory cortex is reduced by 67%. As a non-limiting example, the expression of protein and mRNA in the somatosensory cortex is reduced by 68%. As a non-limiting example, the expression of protein and mRNA in the somatosensory cortex is reduced by 69%. As a non-limiting example, the expression of protein and mRNA in the somatosensory cortex is reduced by 70%.

In one embodiment, the siRNA duplexes or encoded dsRNA may be used to reduce the expression of HTT protein and/or mRNA in the temporal cortex. The expression of HTT protein and/or mRNA is reduced by at least about 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 85%, 90%, 95% and 100%, or at least 15-20%, 15-30%, 15-40%, 15-50%, 15-60%, 15-70%, 15-80%, 15-90%, 15-95%, 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of HTT protein and mRNA in the temporal cortex is reduced by 40-50%. As a non-limiting example, the expression of HTT protein and mRNA in the temporal cortex is reduced by 30-70%. As a non-limiting example, the expression of HTT protein and mRNA in the temporal cortex is reduced by 20-70%. As a non-limiting example, the expression of HTT protein and mRNA in the temporal cortex is reduced by 15-70%. As a non-limiting example, the expression of HTT protein and mRNA in the temporal cortex is reduced by at least 30%. As a non-limiting example, the expression of HTT protein and mRNA in the temporal cortex is reduced by 40-70%. As a non-limiting example, the expression of HTT protein and mRNA in the temporal cortex is reduced by 50-70%. As a non-limiting example, the expression of HTT protein and mRNA in the temporal cortex is reduced by 50-60%. As a non-limiting example, the expression of HTT protein and mRNA in the temporal cortex is reduced by 50%. As a non-limiting example, the expression of HTT protein and mRNA in the temporal cortex is reduced by 51%. As a non-limiting example, the expression of HTT protein and mRNA in the temporal cortex is reduced by 52%. As a non-limiting example, the expression of HTT protein and mRNA in the temporal cortex is reduced by 53%. As a non-limiting example, the expression of HTT protein and mRNA in the temporal cortex is reduced by 54%. As a non-limiting example, the expression of HTT protein and mRNA in the temporal cortex is reduced by 55%. As a non-limiting example, the expression of HTT protein and mRNA in the temporal cortex is reduced by 56%. As a non-limiting example, the expression of HTT protein and mRNA in the temporal cortex is reduced by 57%. As a non-limiting example, the expression of HTT protein and mRNA in the temporal cortex is reduced by 58%. As a non-limiting example, the expression of HTT protein and mRNA in the temporal cortex is reduced by 59%. As a non-limiting example, the expression of HTT protein and mRNA in the temporal cortex is reduced by 60%. As a non-limiting example, the expression of protein and mRNA in the temporal cortex is reduced by 61%. As a non-limiting example, the expression of protein and mRNA in the temporal cortex is reduced by 62%. As a non-limiting example, the expression of protein and mRNA in the temporal cortex is reduced by 63%. As a non-limiting example, the expression of protein and mRNA in the temporal cortex is reduced by 64%. As a non-limiting example, the expression of protein and mRNA in the temporal cortex is reduced by 65%. As a non-limiting example, the expression of protein and mRNA in the temporal cortex is reduced by 66%. As a non-limiting example, the expression of protein and mRNA in the temporal cortex is reduced by 67%. As a non-limiting example, the expression of protein and mRNA in the temporal cortex is reduced by 68%. As a non-limiting example, the expression of protein and mRNA in the temporal cortex is reduced by 69%. As a non-limiting example, the expression of protein and mRNA in the temporal cortex is reduced by 70%.

In some embodiments, the present invention provides methods for treating, or ameliorating Huntington's Disease associated with HTT gene and/or HTT protein in a subject in need of treatment, the method comprising administering to the subject a pharmaceutically effective amount of at least one siRNA duplex or a nucleic acid encoding a siRNA duplex targeting the HTT gene, delivering said siRNA duplex (or encoded duplex) into targeted cells, inhibiting HTT gene expression and protein production, and ameliorating symptoms of HD in the subject.

In some embodiments, an AAV vector comprising the nucleic acid sequence of at least one siRNA duplex targeting the HTT gene is administered to the subject in need for treating and/or ameliorating HD. The AAV vector serotype may be selected from the group consisting of AAV1, AAV2, AAV3, AAV4, AAV5, AAV6, AAV7, AAV5, AAV5, AAV9.47, AAV9(hu14), AAV10, AAV11, AAV12, AAVrh8, AAVrh10, AAV-DJ8 (AAVDJ8), AAV-DJ (AAVDJ), AAV-PHP.A (PHP.A), and/or AAV-PHP.B (PHP.B) and variants thereof. In one embodiment, the AAV vector serotype is AAV1. In one embodiment, the AAV vector serotype is AAV2. In another embodiment, the AAV vector serotype is AAV5 (e.g., as described by Miniarikova et al. Mol Ther (2016) 5, e297 and International Publication No. WO2016102664; the contents of each of which are herein incorporated by reference in their entireties). In another embodiment, the AAV vector is AAV-DJ. In yet another embodiment, the AAV vector serotype is AAV-DJ8.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ8 sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the siRNA molecules or the AAV vectors comprising such siRNA molecules may be introduced directly into the central nervous system of the subject, for example, by infusion into the putamen.

In some embodiments, the siRNA molecules or the AAV vectors comprising such siRNA molecules may be introduced directly into the central nervous system of the subject, for example, by infusion into the thalamus of a subject. While not wishing to be bound by theory, the thalamus is an area of the brain which is relatively spared in subjects with Huntington's Disease which means it may allow for more widespread cortical transduction via axonal transport of the AAV vectors.

In some embodiments, the siRNA molecules or the AAV vectors comprising such siRNA molecules may be introduced indirectly into the central nervous system of the subject, for example, by intravenous administration.

In some embodiments, the siRNA molecules or the AAV vectors comprising such siRNA molecules may be introduced directly into the central nervous system of the subject, for example, by infusion to the white matter of a subject. While not wishing to be bound by theory, distribution via direct white matter infusion may be independent of axonal transport mechanisms which may be impaired in subjects with Huntington's Disease which means white matter infusion may allow for more transport of the AAV vectors.

In some embodiments, the pharmaceutical composition of the present invention is used as a solo therapy. In other embodiments, the pharmaceutical composition of the present invention is used in combination therapy. The combination therapy may be in combination with one or more neuroprotective agents such as small molecule compounds, growth factors and hormones which have been tested for their neuroprotective effect on neuron degeneration.

In some embodiments, the present invention provides methods for treating, or ameliorating Huntington's Disease (HD) by administering to a subject in need thereof a therapeutically effective amount of a plasmid or AAV vector described herein.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

I. COMPOSITIONS OF THE INVENTION

Huntington's Disease (HD)

Huntington's Disease (HD) is a monogenic fatal neurodegenerative disease characterized by progressive chorea, neuropsychiatric and cognitive dysfunction. Huntington's disease is known to be caused by an autosomal dominant triplet (CAG) repeat expansion in the huntingtin (HTT) gene, which encodes HTT protein with poly-glutamine stretch at its N-terminus. This repeat expansion results in a toxic gain of function of HTT and ultimately leads to striatal neurodegeneration which progresses to widespread brain atrophy. Medium spiny neurons of the striatum appear to be especially vulnerable in HD with up to 95% loss, whereas interneurons are largely spared.

Huntington's Disease has a profound impact on quality of life. Symptoms typically appear between the ages of 35-44 and the average life expectancy subsequent to disease onset is 10-25 years. In a small percentage of the HD population (~6%), disease onset occurs prior to the age of 21 with appearance of an akinetic-rigid syndrome. These cases tend to progress faster than those of the later onset variety and have been classified as juvenile or Westphal variant HD. It is estimated that approximately 35,000-70,000 patients are currently suffering from HD in the US and Europe. Currently, only symptomatic relief and supportive therapies are available for treatment of HD, with a cure yet to be identified. Ultimately, individuals with HD succumb to pneumonia, heart failure or other complications such as physical injury from falls.

While not wishing to be bound by theory, the function of the wild type HTT protein may serve as a scaffold to coordinate complexes of other proteins. HTT is a very large protein (67 exons, 3144 amino acids, ~350 kDa) that undergoes extensive post-translational modification and has numerous sites for interaction with other proteins, particularly at its N-terminus (coincidently the region that carries the repeats in HD). HTT localizes primarily to the cytoplasm but has been shown to shuttle into the nucleus where it may regulate gene transcription. It has also been suggested that HTT has a role in vesicular transport and regulating RNA trafficking.

As a non-limiting example, the HTT protein sequence is SEQ ID NO: 1 (NCBI NP_002102.4) and the HTT nucleic acid sequence is SEQ ID NO: 2 (NCBI NM_002111.7).

The mechanisms by which polyglutamine-expanded HTT protein disrupts normal HTT function and results in neurotoxicity were initially thought to be a disease of haploinsufficiency, this theory was disproven when terminal deletion of the HTT gene in man did not lead to development of HD, suggesting that fully expressed HTT protein is not critical to survival. However, conditional knockout of HTT in mouse led to neurodegeneration, indicating that some amount of HTT is necessary for cell survival. Huntingtin protein is expressed in all cells, though its concentration is highest in the brain where large aggregates of abnormal HTT are found in neuronal nuclei. In the brains of HD patients, HTT aggregates into abnormal nuclear inclusions. It is now believed that it is this process of misfolding and aggregating along with the associated protein intermediates (i.e. the soluble species and toxic N-terminal fragments) that result in neurotoxicity. In fact, HD belongs to a family of nine additional human genetic disorders all of which are characterized by CAG-expanded genes and resultant polyglutamine (poly-Q) protein products with subsequent formation of intraneuronal aggregates. Interestingly, in all of these diseases the length of the expansion correlates with both age of onset and rate of disease progression, with longer expansions linked to greater severity of disease.

Hypotheses on the molecular mechanisms underlying the neurotoxicity of polyglutamine-expanded HTT protein and its resultant aggregates have been wide ranging, but include, caspase activation, dysregulation of transcriptional pathways, increased production of reactive oxygen species, mitochondrial dysfunction, disrupted axonal transport and/ or inhibition of protein degradation systems within the cell. Polyglutamine-expanded HTT may not only have a toxic gain of function, but also exert a dominant negative effect by interfering with the normal function of other cellular proteins and processes. HTT has also been implicated in non-cell autonomous neurotoxicity, whereby a cell hosting HTT spreads the HTT to other neurons nearby.

Studies in animal models of HD have suggested that phenotypic reversal is feasible, for example, subsequent to gene shut off in regulated-expression models. In a mouse model allowing shut off of expression of a 94-polyglutamine repeat HTT protein, not only was the clinical syndrome reversed but also the intracellular aggregates were resolved. Further, animal models in which silencing of HTT was tested, demonstrated promising results with the therapy being both well tolerated and showing potential therapeutic benefit.

The present invention provides modulatory polynucleotides, e.g., siRNA molecules targeting the HTT gene and methods for their design and manufacture. While not wishing to be bound by a single theory of operability, the invention provides modulatory polynucleotides, including siRNAs, that interfere with HTT expression, including HTT mutant and/or wild-type HTT gene expression. Particularly, the present invention employs viral vectors such as adeno-associated viral (AAV) vectors comprising the nucleic acid sequence encoding the siRNA molecules of the present invention. The AAV vectors comprising the nucleic acid sequence encoding the siRNA molecules of the present invention may increase the delivery of active agents into neurons of interest such as medium spiny neurons of the striatum and cortical neurons. The siRNA duplexes or encoding dsRNA targeting the HTT gene may be able to inhibit HTT gene expression (e.g., mRNA level) significantly inside cells; therefore, ameliorating HTT expression-induced stress inside the cells such as aggregation of protein and formation of inclusions, increased free radicals, mitochondrial dysfunction and RNA metabolism.

Symptoms of HD may include features attributed to CNS degeneration such as, but are not limited to, chorea, dystonia, bradykinesia, incoordination, irritability and depression, problem-solving difficulties, reduction in the ability of a person to function in their normal day to day life, diminished speech, and difficulty swallowing, as well as features not attributed to CNS degeneration such as, but not limited to, weight loss, muscle wasting, metabolic dysfunction and endocrine disturbances.

Such siRNA-mediated HTT expression inhibition may be used for treating HD. According to the present invention, methods for treating and/or ameliorating HD in a patient comprises administering to the patient an effective amount of AAV vector comprising a nucleic acid sequence encoding the siRNA molecules of the present invention into cells. The administration of the AAV vector comprising such a nucleic acid sequence will encode the siRNA molecules which cause the inhibition/silence of HTT gene expression.

In one embodiment, the vector, e.g., AAV vectors, reduces the amount of HTT in a subject in need thereof and thus provides a therapeutic benefit as described herein.

In one embodiment, a subject has fully penetrant HD where the HTT gene has 41 or more CAG repeats (e.g., 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 or more than 90 CAG repeats).

In one embodiment, a subject has incomplete penetrance where the HTT gene has between 36 and 40 CAG repeats (e.g., 36, 37, 38, 39 and 40 CAG repeats).

Model systems for studying Huntington's Disease which may be used with the siRNAs and vectors described herein include, but are not limited to, cell models (e.g., primary neurons and induced pluripotent stem cells), invertebrate models (e.g., *Drosophila* or *Caenorhabditis elegans*), mouse models (e.g., YAC128 mouse model; R6/2 mouse model; BAC, YAC and knock-in mouse model), rat models (e.g., BAC) and large mammal models (e.g., pigs, sheep or monkeys).

Modulatory Polynucleotides

In one embodiment, modulatory polynucleotides, e.g., RNA or DNA molecules, may be used to treat neurodegenerative disease, in particular, Huntington's Disease (HD). As used herein, a "modulatory polynucleotide" is any nucleic acid sequence(s) which functions to modulate (either increase or decrease) the level or amount of a target gene, e.g., mRNA or protein levels.

In one embodiment, the modulatory polynucleotides may comprise at least one nucleic acid sequence encoding at least one siRNA molecule. The nucleic acids may, independently if there is more than one, encode 1, 2, 3, 4, 5, 6, 7, 8, 9, or more than 9 siRNA molecules.

siRNA Molecules

The present invention relates to RNA interference (RNAi) induced inhibition of gene expression for treating neurodegenerative disorders. Provided herein are siRNA duplexes or encoded dsRNA that target the HTT gene (referred to herein collectively as "siRNA molecules"). Such siRNA duplexes or encoded dsRNA can reduce or silence HTT gene expression in cells, for example, medium spiny neurons, cortical neurons and/or astrocytes, thereby, ameliorating symptoms of Huntington's Disease (HD).

RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2 nucleotide 3' overhangs and that match the nucleic acid sequence of the target gene. These short RNA species may be naturally produced in vivo by Dicer-mediated cleavage of larger dsRNAs and they are functional in mammalian cells.

Naturally expressed small RNA molecules, named microRNAs (miRNAs), elicit gene silencing by regulating the expression of mRNAs. The miRNAs-containing RNA Induced Silencing Complex (RISC) targets mRNAs presenting a perfect sequence complementarity with nucleotides 2-7 in the 5' region of the miRNA which is called the seed region, and other base pairs with its 3' region. miRNA-mediated down-regulation of gene expression may be caused by cleavage of the target mRNAs, translational inhibition of the target mRNAs, or mRNA decay. miRNA targeting sequences are usually located in the 3'-UTR of the target mRNAs. A single miRNA may target more than 100 transcripts from various genes, and one mRNA may be targeted by different miRNAs.

siRNA duplexes or dsRNA targeting a specific mRNA may be designed and synthesized in vitro and introduced into cells for activating RNAi processes. Elbashir et al. demonstrated that 21-nucleotide siRNA duplexes (termed small interfering RNAs) were capable of effecting potent and specific gene knockdown without inducing immune response in mammalian cells (Elbashir S M et al., Nature, 2001, 411, 494-498). Since this initial report, post-transcriptional gene silencing by siRNAs quickly emerged as a powerful tool for genetic analysis in mammalian cells and has the potential to produce novel therapeutics.

RNAi molecules which were designed to target against a nucleic acid sequence that encodes poly-glutamine repeat proteins which cause poly-glutamine expansion diseases such as Huntington's Disease, are described in U.S. Pat. Nos. 9,169,483 and 9,181,544 and International Patent Publication No. WO2015179525, the content of each of which is herein incorporated by reference in their entirety. U.S. Pat. Nos. 9,169,483 and 9,181,544 and International Patent Publication No. WO2015179525 each provide isolated RNA duplexes comprising a first strand of RNA (e.g., 15 contiguous nucleotides) and second strand of RNA (e.g., complementary to at least 12 contiguous nucleotides of the first strand) where the RNA duplex is about 15 to 30 base pairs in length. The first strand of RNA and second strand of RNA may be operably linked by an RNA loop (~4 to 50 nucleotides) to form a hairpin structure which may be inserted into an expression cassette. Non-limiting examples of loop portions include SEQ ID NO: 9-14 of U.S. Pat. No. 9,169,483, the content of which is herein incorporated by reference in its entirety. Non-limiting examples of strands of RNA which may be used, either full sequence or part of the sequence, to form RNA duplexes include SEQ ID NO: 1-8 of U.S. Pat. No. 9,169,483 and SEQ ID NO: 1-11, 33-59, 208-210, 213-215 and 218-221 of U.S. Pat. No. 9,181,544, the contents of each of which is herein incorporated by reference in its entirety. Non-limiting examples of RNAi molecules include SEQ ID NOs: 1-8 of U.S. Pat. No. 9,169,483, SEQ ID NOs: 1-11, 33-59, 208-210, 213-215 and 218-221 of U.S. Pat. No. 9,181,544 and SEQ ID NOs: 1, 6, 7, and 35-38 of International Patent Publication No. WO2015179525, the contents of each of which is herein incorporated by reference in their entirety.

In vitro synthetized siRNA molecules may be introduced into cells in order to activate RNAi. An exogenous siRNA duplex, when it is introduced into cells, similar to the endogenous dsRNAs, can be assembled to form the RNA Induced Silencing Complex (RISC), a multiunit complex that interacts with RNA sequences that are complementary to one of the two strands of the siRNA duplex (i.e., the antisense strand). During the process, the sense strand (or passenger strand) of the siRNA is lost from the complex, while the antisense strand (or guide strand) of the siRNA is matched with its complementary RNA. In particular, the targets of siRNA containing RISC complexes are mRNAs presenting a perfect sequence complementarity. Then, siRNA mediated gene silencing occurs by cleaving, releasing and degrading the target.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases, it requires higher concentration of the ss-siRNA to achieve the effective gene silencing potency of the corresponding duplex.

Any of the foregoing molecules may be encoded by an AAV vector or vector genome.

Design and Sequences of siRNA Duplexes Targeting HTT Gene

Some guidelines for designing siRNAs have been proposed in the art. These guidelines generally recommend generating a 19-nucleotide duplexed region, symmetric 2-3 nucleotide 3' overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing mammalian target gene expression may be readily designed.

According to the present invention, siRNA molecules (e.g., siRNA duplexes or encoded dsRNA) that target the HTT gene are designed. Such siRNA molecules can specifically, suppress HTT gene expression and protein production. In some aspects, the siRNA molecules are designed and used to selectively "knock out" HTT gene variants in cells, i.e., mutated HTT transcripts that are identified in patients with HD disease. In some aspects, the siRNA molecules are designed and used to selectively "knock down" HTT gene variants in cells. In other aspects, the siRNA molecules are able to inhibit or suppress both the wild type and mutated HTT gene.

In one embodiment, an siRNA molecule of the present invention comprises a sense strand and a complementary antisense strand in which both strands are hybridized together to form a duplex structure. The antisense strand has sufficient complementarity to the HTT mRNA sequence to direct target-specific RNAi, i.e., the siRNA molecule has a sequence sufficient to trigger the destruction of the target mRNA by the RNAi machinery or process.

In one embodiment, an siRNA molecule of the present invention comprises a sense strand and a complementary antisense strand in which both strands are hybridized together to form a duplex structure and where the start site of the hybridization to the HTT mRNA is between nucleotide 100 and 7000 on the HTT mRNA sequence. As a non-limiting example, the start site may be between nucleotide 100-150, 150-200, 200-250, 250-300, 300-350, 350-400, 400-450, 450-500, 500-550, 550-600, 600-650, 650-700, 700-70, 750-800, 800-850, 850-900, 900-950, 950-1000, 1000-1050, 1050-1100, 1100-1150, 1150-1200, 1200-1250, 1250-1300, 1300-1350, 1350-1400, 1400-1450, 1450-1500, 1500-1550, 1550-1600, 1600-1650, 1650-1700, 1700-1750, 1750-1800, 1800-1850, 1850-1900, 1900-1950, 1950-2000, 2000-2050, 2050-2100, 2100-2150, 2150-2200, 2200-2250, 2250-2300, 2300-2350, 2350-2400, 2400-2450, 2450-2500, 2500-2550, 2550-2600, 2600-2650, 2650-2700, 2700-2750, 2750-2800, 2800-2850, 2850-2900, 2900-2950, 2950-3000, 3000-3050, 3050-3100, 3100-3150, 3150-3200, 3200-3250, 3250-3300, 3300-3350, 3350-3400, 3400-3450, 3450-3500, 3500-3550, 3550-3600, 3600-3650, 3650-3700, 3700-3750, 3750-3800, 3800-3850, 3850-3900, 3900-3950, 3950-4000, 4000-4050, 4050-4100, 4100-4150, 4150-4200, 4200-4250, 4250-4300, 4300-4350, 4350-4400, 4400-4450, 4450-4500, 4500-4550, 4550-4600, 4600-4650, 4650-4700, 4700-4750, 4750-4800, 4800-4850, 4850-4900, 4900-4950, 4950-5000, 5000-5050, 5050-5100, 5100-5150, 5150-5200, 5200-5250, 5250-5300, 5300-5350, 5350-5400, 5400-5450, 5450-5500, 5500-5550, 5550-5600, 5600-5650, 5650-5700, 5700-5750, 5750-5800, 5800-5850, 5850-5900, 5900-5950, 5950-6000, 6000-6050, 6050-6100, 6100-6150, 6150-6200, 6200-

6250, 6250-6300, 6300-6350, 6350-6400, 6400-6450, 6450-6500, 6500-6550, 6550-6600, 6600-6650, 6650-6700, 6700-6750, 6750-6800, 6800-6850, 6850-6900, 6900-6950, 6950-7000, 7000-7050, 7050-7100, 7100-7150, 7150-7200, 7200-7250, 7250-7300, 7300-7350, 7350-7400, 7400-7450, 7450-7500, 7500-7550, 7550-7600, 7600-7650, 7650-7700, 7700-7750, 7750-7800, 7800-7850, 7850-7900, 7900-7950, 7950-8000, 8000-8050, 8050-8100, 8100-8150, 8150-8200, 8200-8250, 8250-8300, 8300-8350, 8350-8400, 8400-8450, 8450-8500, 8500-8550, 8550-8600, 8600-8650, 8650-8700, 8700-8750, 8750-8800, 8800-8850, 8850-8900, 8900-8950, 8950-9000, 9000-9050, 9050-9100, 9100-9150, 9150-9200, 9200-9250, 9250-9300, 9300-9350, 9350-9400, 9400-9450, 9450-9500, 9500-9550, 9550-9600, 9600-9650, 9650-9700, 9700-9750, 9750-9800, 9800-9850, 9850-9900, 9900-9950, 9950-10000, 10000-10050, 10050-10100, 10100-10150, 10150-10200, 10200-10250, 10250-10300, 10300-10350, 10350-10400, 10400-10450, 10450-10500, 10500-10550, 10550-10600, 10600-10650, 10650-10700, 10700-10750, 10750-10800, 10800-10850, 10850-10900, 10900-10950, 10950-11000, 11050-11100, 11100-11150, 11150-11200, 11200-11250, 11250-11300, 11300-11350, 11350-11400, 11400-11450, 11450-11500, 11500-11550, 11550-11600, 11600-11650, 11650-11700, 11700-11750, 11750-11800, 11800-11850, 11850-11900, 11900-11950, 11950-12000, 12000-12050, 12050-12100, 12100-12150, 12150-12200, 12200-12250, 12250-12300, 12300-12350, 12350-12400, 12400-12450, 12450-12500, 12500-12550, 12550-12600, 12600-12650, 12650-12700, 12700-12750, 12750-12800, 12800-12850, 12850-12900, 12900-12950, 12950-13000, 13050-13100, 13100-13150, 13150-13200, 13200-13250, 13250-13300, 13300-13350, 13350-13400, 13400-13450, and 13450-13500 on the HTT mRNA sequence. As yet another non-limiting example, the start site may be nucleotide 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 715, 716, 717, 718, 719, 720, 721, 722, 723, 724, 725, 875, 876, 877, 878, 879, 880, 881, 882, 883, 884, 885, 886, 887, 888, 889, 890, 891, 892, 893, 894, 895, 896, 897, 898, 899, 900, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1660, 1661, 1662, 1663, 1664, 1665, 1666, 1667, 1668, 1669, 1670, 1671, 1672, 1673, 1674, 1675, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 4525, 4526, 4527, 4528, 4529, 4530, 4531, 4532, 4533, 4534, 4535, 4536, 4537, 4538, 4539, 4540, 4541, 4542, 4543, 4544, 4545, 4546, 4547, 4548, 4549, 4550, 4575, 4576, 4577, 4578, 4579, 4580, 4581, 4582, 4583, 4584, 4585, 4586, 4587, 4588, 4589, 4590, 4591, 4592, 4593, 4594, 4595, 4596, 4597, 4598, 4599, 4600, 4850, 4851, 4852, 4853, 4854, 4855, 4856, 4857, 4858, 4859, 4860, 4861, 4862, 4863, 4864, 4865, 4866, 4867, 4868, 4869, 4870, 4871, 4872, 4873, 4874, 4875, 4876, 4877, 4878, 4879, 4880, 4881, 4882, 4883, 4884, 4885, 4886, 4887, 4888, 4889, 4890, 4891, 4892, 4893, 4894, 4895, 4896, 4897, 4898, 4899, 4900, 5460, 5461, 5462, 5463, 5464, 5465, 5466, 5467, 5468, 5469, 5470, 5471, 5472, 5473, 5474, 5475, 5476, 5477, 5478, 5479, 5480, 6175, 6176, 6177, 6178, 6179, 6180, 6181, 6182, 6183, 6184, 6185, 6186, 6187, 6188, 6189, 6190, 6191, 6192, 6193, 6194, 6195, 6196, 6197, 6198, 6199, 6200, 6315, 6316, 6317, 6318, 6319, 6320, 6321, 6322, 6323, 6324, 6325, 6326, 6327, 6328, 6329, 6330, 6331, 6332, 6333, 6334, 6335, 6336, 6337, 6338, 6339, 6340, 6341, 6342, 6343, 6344, 6345, 6600, 6601, 6602, 6603, 6604, 6605, 6606, 6607, 6608, 6609, 6610, 6611, 6612, 6613, 6614, 6615, 6725, 6726, 6727, 6728, 6729, 6730, 6731, 6732, 6733, 6734, 6735, 6736, 6737, 6738, 6739, 6740, 6741, 6742, 6743, 6744, 6745, 6746, 6747, 6748, 6749, 6750, 6751, 6752, 6753, 6754, 6755, 6756, 6757, 6758, 6759, 6760, 6761, 6762, 6763, 6764, 6765, 6766, 6767, 6768, 6769, 6770, 6771, 6772, 6773, 6774, 6775, 7655, 7656, 7657, 7658, 7659, 7660, 7661, 7662, 7663, 7664, 7665, 7666, 7667, 7668, 7669, 7670, 7671, 7672, 8510, 8511, 8512, 8513, 8514, 8515, 8516, 8715, 8716, 8717, 8718, 8719, 8720, 8721, 8722, 8723, 8724, 8725, 8726, 8727, 8728, 8729, 8730, 8731, 8732, 8733, 8734, 8735, 8736, 8737, 8738, 8739, 8740, 8741, 8742, 8743, 8744, 8745, 9250, 9251, 9252, 9253, 9254, 9255, 9256, 9257, 9258, 9259, 9260, 9261, 9262, 9263, 9264, 9265, 9266, 9267, 9268, 9269, 9270, 9480, 9481, 9482, 9483, 9484, 9485, 9486, 9487, 9488, 9489, 9490, 9491, 9492, 9493, 9494, 9495, 9496, 9497, 9498, 9499, 9500, 9575, 9576, 9577, 9578, 9579, 9580, 9581, 9582, 9583, 9584, 9585, 9586, 9587, 9588, 9589, 9590, 10525, 10526, 10527, 10528, 10529, 10530, 10531, 10532, 10533, 10534, 10535, 10536, 10537, 10538, 10539, 10540, 11545, 11546, 11547, 11548, 11549, 11550, 11551, 11552, 11553, 11554, 11555, 11556, 11557, 11558, 11559, 11560, 11875, 11876, 11877, 11878, 11879, 11880, 11881, 11882, 11883, 11884, 11885, 11886, 11887, 11888, 11889, 11890, 11891, 11892, 11893, 11894, 11895, 11896, 11897, 11898, 11899, 11900, 11915, 11916, 11917, 11918, 11919, 11920, 11921, 11922, 11923, 11924, 11925, 11926, 11927, 11928, 11929, 11930, 11931, 11932, 11933, 11934, 11935, 11936, 11937, 11938, 11939, 11940, 13375, 13376, 13377, 13378, 13379, 13380, 13381, 13382, 13383, 13384, 13385, 13386, 13387, 13388, 13389 and 13390 on the HTT mRNA sequence.

In some embodiments, the antisense strand and target mRNA sequences have 100% complementary. The antisense strand may be complementary to any part of the target mRNA sequence.

In other embodiments, the antisense strand and target mRNA sequences comprise at least one mismatch. As a non-limiting example, the antisense strand and the target mRNA sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

According to the present invention, the siRNA molecule has a length from about 10-50 or more nucleotides, i.e., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementarity to a target region. In one embodiment, the siRNA molecule has a length from about 19 to 25, 19 to 24 or 19 to 21 nucleotides.

In some embodiments, the siRNA molecules of the present invention can be synthetic RNA duplexes comprising about 19 nucleotides to about 25 nucleotides, and two overhanging nucleotides at the 3'-end. In some aspects, the siRNA molecules may be unmodified RNA molecules. In other aspects, the siRNA molecules may contain at least one modified nucleotide, such as base, sugar or backbone modifications.

In one embodiment, the siRNA molecules of the present invention may comprise a nucleotide sequence such as, but not limited to, the antisense (guide) sequences in Table 1 or a fragment or variant thereof. As a non-limiting example, the antisense sequence used in the siRNA molecule of the present invention is at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% of a nucleotide sequence in Table 1. As another non-limiting example, the antisense sequence used in the siRNA molecule of the present invention comprises at least 3, 4, 5, 6, 7, 8, 9, 10, 11, 12, 13, 14, 15, 16, 17, 18, 19, 20, 21 or more than 21 consecutive nucleotides of a nucleotide sequence in Table 1. As yet another non-limiting example, the antisense sequence used in the siRNA molecule of the present invention comprises nucleotides 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 2 to 22, 2 to 21, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 3 to 22, 3 to 21, 3 to 20, 3 to 19, 3 to 18, 3 to 17, 3 to 16, 3 to 15, 3 to 14, 3 to 13, 3 to 12, 3 to 11, 3 to 10, 3 to 9, 3 to 8, 4 to 22, 4 to 21, 4 to 20, 4 to 19, 4 to 18, 4 to 17, 4 to 16, 4 to 15, 4 to 14, 4 to 13, 4 to 12, 4 to 11, 4 to 10, 4 to 9, 4 to 8, 5 to 22, 5 to 21, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 6 to 22, 6 to 21, 6 to 20, 6 to 19, 6 to 18, 6 to 17, 6 to 16, 6 to 15, 6 to 14, 6 to 13, 6 to 12, 6 to 11, 6 to 10, 7 to 22, 7 to 21, 7 to 20, 7 to 19, 7 to 18, 7 to 17, 7 to 16, 7 to 15, 7 to 14, 7 to 13, 7 to 12, 8 to 22, 8 to 21, 8 to 20, 8 to 19, 8 to 18, 8 to 17, 8 to 16, 8 to 15, 8 to 14, 8 to 13, 8 to 12, 9 to 22, 9 to 21, 9 to 20, 9 to 19, 9 to 18, 9 to 17, 9 to 16, 9 to 15, 9 to 14, 10 to 22, 10 to 21, 10 to 20, 10 to 19, 10 to 18, 10 to 17, 10 to 16, 10 to 15, 10 to 14, 11 to 22, 11 to 21, 11 to 20, 11 to 19, 11 to 18, 11 to 17, 11 to 16, 11 to 15, 11 to 14, 12 to 22, 12 to 21, 12 to 20, 12 to 19, 12 to 18, 12 to 17, 12 to 16, 13 to 22, 13 to 21, 13 to 20, 13 to 19, 13 to 18, 13 to 17, 13 to 16, 14 to 22, 14 to 21, 14 to 20, 14 to 19, 14 to 18, 14 to 17, 15 to 22, 15 to 21, 15 to 20, 15 to 19, 15 to 18, 16 to 22, 16 to 21, 16 to 20, 17 to 22, 17 to 21, or 18 to 22 of the sequences in Table 1.

TABLE 1

Antisense Sequences

| Antisense ID | Sequence | SEQ ID NO |
|---|---|---|
| A-2000 | UUAACGUCAGUUCAUAAACUU | 3 |
| A-2000dt | UUAACGUCAGUUCAUAAACdTdT | 4 |
| A-2001 | UGUCGGUACCGUCUAACACUU | 5 |
| A-2001dt | UGUCGGUACCGUCUAACACdTdT | 6 |
| A-2002 | UAAGCAUGGAGCUAGCAGGUU | 7 |
| A-2002dt | UAAGCAUGGAGCUAGCAGGdTdT | 8 |
| A-2003 | UACAACGAGACUGAAUUGCUU | 9 |
| A-2003dt | UACAACGAGACUGAAUUGCdTdT | 10 |
| A-2004 | UUCAGUUCAUAAACCUGGAUU | 11 |
| A-2004dt | UUCAGUUCAUAAACCUGGAdTdT | 12 |
| A-2005 | UAACGUCAGUUCAUAAACCUU | 13 |
| A-2005dt | UAACGUCAGUUCAUAAACCdTdT | 14 |
| A-2006 | UCCGGUCACAACAUUGUGGUU | 15 |
| A-2006dt | UCCGGUCACAACAUUGUGGdTdT | 16 |
| A-2007 | UUGCACGGUUCUUUGUGACUU | 17 |
| A-2007dt | UUGCACGGUUCUUUGUGACdTdT | 18 |
| A-2008 | UUUUAUAACAAGAGGUUCAUU | 19 |
| A-2008dt | UUUUAUAACAAGAGGUUCAdTdT | 20 |
| A-2009 | UCCAAAUACUGGUUGUCGGUU | 21 |
| A-2009dt | UCCAAAUACUGGUUGUCGGdTdT | 22 |
| A-2010 | UAUUUUAGGAAUUCCAAUGUU | 23 |
| A-2010dt | UAUUUUAGGAAUUCCAAUGdTdT | 24 |
| A-2011 | UUUAGGAAUUCCAAUGAUCUU | 25 |
| A-2011dt | UUUAGGAAUUCCAAUGAUCdTdT | 26 |
| A-2012dt | UUAAUCUCUUUACUGAUAUdTdT | 27 |
| A-2013dt | GAUUUUAGGAAUUCCAAUGdTdT | 28 |
| A-2014 | UAAGCAUGGAGCUAGCAGGCUU | 29 |
| A-2015 | UAAGCAUGGAGCUAGCAGGGU | 30 |
| A-2016 | AAGGACUUGAGGGACUCGAAGU | 31 |
| A-2017 | AAGGACUUGAGGGACUCGAAG | 32 |
| A-2018 | AAGGACUUGAGGGACUCGA | 33 |
| A-2019 | AGGACUUGAGGGACUCGAAGU | 34 |
| A-2020 | GAGGACUUGAGGGACUCGAAGU | 35 |
| A-2021 | AAGGACUUGAGGGACUCGAAGU | 36 |
| A-2022 | AAGGACUUGAGGGACUCGAAGUU | 37 |
| A-2023 | AAGGACUUGAGGGACUCGAAG | 38 |
| A-2024 | AAGGACUUGAGGGACUCGA | 39 |
| A-2025 | AAGGACUUGAGGGACUCGAAGG | 40 |

TABLE 1-continued

Antisense Sequences

| Antisense ID | Sequence | SEQ ID NO |
|---|---|---|
| A-2026 | AAGGACUUGAGGGACUCGAAU | 41 |
| A-2027 | AAGGACUUGAGGGACUCGAAGA | 42 |
| A-2028 | AAGGACUUGAGGGACUCGAAGG | 43 |
| A-2029 | AAGGACUUGAGGGACUCGAAGGU | 44 |
| A-2030 | AAGGACUUGAGGGACUCGAAGGA | 45 |
| A-2031 | AAGGACUUGAGGGACUCGAAG | 46 |
| A-2032 | AAGGACUUGAGGGACUCGAAGU | 47 |
| A-2033 | AAGGACUUGAGGGACUCGA | 48 |
| A-2034 | AAGGACUUGAGGGACUCGAAGGA | 49 |
| A-2035 | AAGGACUUGAGGGACUCGAAGG | 50 |
| A-2036 | AAGGACUUGAGGGACUCGAAGGAU | 51 |
| A-2037 | AAGGACUUGAGGGACUCGAAGGAUU | 52 |
| A-2038 | AAGGACUUGAGGGACUCGAAG | 53 |
| A-2039 | AAGGACUUGAGGGACUCGAAGGAA | 54 |
| A-2040 | GAUGAAGUGCACACAUUGGAUGA | 55 |
| A-2041 | GAUGAACUGCACACAUUGGAUG | 56 |
| A-2042 | GAUGAAUUGCACACAGUAGAUGA | 57 |
| A-2043 | AAGGACUUGAGGGACUCGAAGGUU | 58 |
| A-2044 | AAGGACUUGAGGGACUCGAAGGUUU | 59 |
| A-2045 | AAGGACUUGAGGGACUCGAAGGU | 60 |
| A-2046 | AAGGACUUGAGGGACUCGAAGGUUUU | 61 |
| A-2047 | AAGGACUUGAGGGACUCGAAGGUUUUU | 62 |
| A-2048 | AAGGACUUGAGGGACUCGAAGG | 63 |
| A-2049 | UAAGGACUUGAGGGACUCGAAG | 64 |
| A-2050 | AAGGACUUGAGGGACUCGAAG | 65 |
| A-2051 | AAGGACUUGAGGGACUCGAAGU | 66 |
| A-2052 | AAGGACUUGAGGGACUCGAAGACGAGUCCC | 67 |
| A-2053 | AAGGACUUGAGGGACUCGAAGACGAGUCCCA | 68 |
| A-2054 | AAGGACUUGAGGGACUCGAAGACGAGUCCCU | 69 |
| A-2055 | GAUGAAGUGCACACAUUGGAUAC | 70 |
| A-2056 | GAUGAAGUGCACACAUUGGAUACA | 71 |
| A-2057 | GAUGAAGUGCACACAUUGGAUACAAUGUGU | 72 |
| A-2058 | GAUGAAGUGCACACAUUGGAU | 73 |
| A-2059 | GAUGAAGUGCACACAUUGGAUA | 74 |
| A-2060 | GAUGAAUUGCACACAGUAGAUAU | 75 |
| A-2061 | GAUGAAUUGCACACAGUAGAUAUAC | 76 |
| A-2062 | GAUGAAUUGCACACAGUAGAUAUACUGUGU | 77 |
| A-2063 | GAUGAAUUGCACACAGUAGAUAUA | 78 |
| A-2064 | AUGAAUUGCACACAGUAGAUAUAC | 79 |
| A-2065 | GAUGAAUUGCACACAGUAGAUA | 80 |
| A-2066 | GAUGAAUUGCACACAGUAGAUAUACUGUGU | 81 |
| A-2067 | UACAACGAGACUGAAUUGCU | 82 |
| A-2068 | ACAACGAGACUGAAUUGCUU | 83 |
| A-2069 | UCCGGUCACAACAUUGUGGUUC | 84 |
| A-2070 | UCCGGUCACAACAUUGUGGU | 85 |
| A-2071 | UCCGGUCACAACAUUGUG | 86 |
| A-2072 | CCGGUCACAACAUUGUGGUU | 87 |
| A-2073 | UUUUAUAACAAGAGGUUCAU | 88 |
| A-2074 | UUUAUAACAAGAGGUUCAUU | 89 |
| A-2075 | UAAGCAUGGAGCUAGCAGGU | 90 |
| A-2076 | AAGCAUGGAGCUAGCAGGUU | 91 |
| A-2077 | CCAAAUACUGGUUGUCGGUU | 92 |
| A-2078 | UACAACGAGACUGAAUUGCUUU | 93 |
| A-2079 | UAACGUCAGUUCAUAAACCUUU | 94 |
| A-2080 | GUCCGGUCACAACAUUGUGGUU | 95 |
| A-2081 | UCCGGUCACAACAUUGUGGUUUG | 96 |
| A-2082 | UCCGGUCACAACAUUGUGGUUU | 97 |
| A-2083 | UCCGGUCACAACAUUGUGG | 98 |
| A-2084 | UAAGCAUGGAGCUAGCAGGUUU | 99 |
| A-2085 | AAGCAUGGAGCUAGCAGGUUU | 100 |
| A-2086 | UCCAAAUACUGGUUGUCGGUUU | 101 |
| A-2087 | CCAAAUACUGGUUGUCGGUUU | 102 |

In one embodiment, the siRNA molecules of the present invention may comprise a nucleotide sequence such as, but not limited to, the sense (passenger) sequences in Table 2 or a fragment or variant thereof. As a non-limiting example, the sense sequence used in the siRNA molecule of the present invention is at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% of a nucleotide sequence in Table 2. As another non-limiting example, the sense sequence used in the siRNA molecule of the present invention comprises at least 3, 4, 5, 6, 7, 8, 9, 10, 11, 12, 13, 14, 15, 16, 17, 18, 19, 20, 21 or more than 21 consecutive nucleotides of a nucleotide sequence in Table 2. As yet another non-limiting example, the sense sequence used in the siRNA molecule of the present invention comprises nucleotides 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 2 to 22, 2 to 21, 2 to 20, 2 to 19, 2 to 18, 2 to 17, 2 to 16, 2 to 15, 2 to 14, 2 to 13, 2 to 12, 2 to 11, 2 to 10, 2 to 9, 2 to 8, 3 to 22, 3 to 21, 3 to 20, 3 to 19, 3 to 18, 3 to 17, 3 to 16, 3 to 15, 3 to 14, 3 to 13, 3 to 12, 3 to 11, 3 to 10, 3 to 9, 3 to 8, 4 to 22, 4 to 21, 4 to 20, 4 to 19, 4 to 18, 4 to 17, 4 to 16, 4 to 15, 4 to 14, 4 to 13, 4 to 12, 4 to 11, 4 to 10, 4 to 9, 4 to 8, 5 to 22, 5 to 21, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 6 to 22, 6 to 21, 6 to 20, 6 to 19, 6 to 18, 6 to 17, 6 to 16, 6 to 15, 6 to 14, 6 to 13, 6 to 12, 6 to 11, 6 to 10, 7 to 22, 7 to 21, 7 to 20, 7 to 19, 7 to 18, 7 to 17, 7 to 16, 7 to 15, 7 to 14, 7 to 13, 7 to 12, 8 to 22, 8 to 21, 8 to 20, 8 to 19, 8 to 18, 8 to 17, 8 to 16, 8 to 15, 8 to 14, 8 to 13, 8 to 12, 9 to 22, 9 to 21, 9 to 20, 9 to 19, 9 to 18, 9 to 17, 9 to 16, 9 to 15, 9 to 14, 10 to 22, 10 to 21, 10 to 20, 10 to 19, 10 to 18, 10 to 17, 10 to 16, 10 to 15, 10 to 14, 11 to 22, 11 to 21, 11 to 20, 11 to 19, 11 to 18, 11 to 17, 11 to 16, 11 to 15, 11 to 14, 12 to 22, 12 to 21, 12 to 20, 12 to 19, 12 to 18, 12 to 17, 12 to 16, 13 to 22, 13 to 21, 13 to 20, 13 to 19, 13 to 18, 13 to 17, 13 to 16, 14 to 22, 14 to 21, 14 to 20, 14 to 19, 14 to 18, 14 to 17, 15 to 22, 15 to 21, 15 to 20, 15 to 19, 15 to 18, 16 to 22, 16 to 21, 16 to 20, 17 to 22, 17 to 21, or 18 to 22 of the sequences in Table 2.

TABLE 2

Sense Sequences

| Sense ID | Sequence | SEQ ID NO |
|---|---|---|
| S-1000 | GUUUAUGAACUGAUCUUACCC | 103 |
| S-1001 | GUGUUAGACGGUACUGAUCCC | 104 |
| S-1002 | CCUGCUAGCUCCAUGCUUCCC | 105 |
| S-1003 | GUUUAUGAACUGAUCUUAGCC | 106 |
| S-1004 | GUGUUAGACGGUACUGAUGCC | 107 |
| S-1005 | CCUGCUAGCUCCAUGCUUGCC | 108 |
| S-1006 | GUUUAUGAAGUGAUCUUAACC | 109 |
| S-1007 | GUGUUAGACCGUACUGAUACC | 110 |
| S-1008 | CCUGCUAGCACCAUGCUUACC | 111 |
| S-1009 | GUUUAUGAACUGAUCUUAACC | 112 |
| S-1010 | GUGUUAGACGGUACUGAUACC | 113 |
| S-1011 | CCUGCUAGCUCCAUGCUUACC | 114 |
| S-1011dt | CCUGCUAGCUCCAUGCUUAdTdT | 115 |
| S-1012 | GUUUAUGAACUGAUCUUGCCC | 116 |
| S-1013 | GUUUAUGAACUGAUCUUGGCC | 117 |
| S-1014 | GUUUAUGAACUGAUCUUGACC | 118 |
| S-1015 | GCAAUUCAGUCUCGUUGUCCC | 119 |
| S-1016 | UCCAGGUUUAUGAACUGACCC | 120 |

TABLE 2-continued

Sense Sequences

| Sense ID | Sequence | SEQ ID NO |
|---|---|---|
| S-1017 | GGUUUAUGAACUGACGUUCCC | 121 |
| S-1018 | CCACAAUGUUGUGACUGGCCC | 122 |
| S-1019 | GUCACAAAGAACCGUGUACCC | 123 |
| S-1020 | UGAACCUCUUGUUAUAAACCC | 124 |
| S-1021 | CCGACAACCAGUAUUUGGCCC | 125 |
| S-1022 | GCAAUUCAGUCUCGUUGUGCC | 126 |
| S-1023 | UCCAGGUUUAUGAACUGAGCC | 127 |
| S-1024 | GGUUUAUGAACUGACGUUGCC | 128 |
| S-1025 | CCACAAUGUUGUGACUGGGCC | 129 |
| S-1026 | GUCACAAAGAACCGUGUAGCC | 130 |
| S-1027 | UGAACCUCUUGUUAUAAAGCC | 131 |
| S-1028 | CCGACAACCAGUAUUUGGGCC | 132 |
| S-1029 | GCAAUUCAGUCUCGUUGUACC | 133 |
| S-1029dt | GCAAUUCAGUCUCGUUGUAdTdT | 134 |
| S-1030 | UCCAGGUUUAUGAACUGAACC | 135 |
| S-1030dt | UCCAGGUUUAUGAACUGAAdTdT | 136 |
| S-1031 | GGUUUAUGAACUGACGUUACC | 137 |
| S-1032 | CCACAAUGUUGUGACUGGACC | 138 |
| S-1033 | GUCACAAAGAACCGUGUAACC | 139 |
| S-1034 | UGAACCUCUUGUUAUAAAACC | 140 |
| S-1034dt | UGAACCUCUUGUUAUAAAAdTdT | 141 |
| S-1035 | CCGACAACCAGUAUUUGGACC | 142 |
| S-1035dt | CCGACAACCAGUAUUUGGAdTdT | 143 |
| S-1036 | GCAAUUCAGACUCGUUGUACC | 144 |
| S-1037 | UCCAGGUUUUGAACUGAACC | 145 |
| S-1038 | GGUUUAUGAUCUGACGUUACC | 146 |
| S-1039 | CCACAAUGUAGUGACUGGACC | 147 |
| S-1040 | GUCACAAAGUACCGUGUAACC | 148 |
| S-1041 | UGAACCUCUAGUUAUAAACCC | 149 |
| S-1042 | CCGACAACCUGUAUUUGGACC | 150 |
| S-1043 | CAUUGGAAUUCCUAAAAUUCC | 151 |
| S-1044 | GAUCAUUGGAAUUCCUAAUCC | 152 |
| S-1045 | CAUUGGAAUUCCUAAAAUGCC | 153 |
| S-1046 | GAUCAUUGGAAUUCCUAAGCC | 154 |
| S-1047 | CAUUGGAAUUCCUAAAAUACC | 155 |
| S-1047dt | CAUUGGAAUUCCUAAAAUAdTdT | 156 |
| S-1048 | GAUCAUUGGAAUUCCUAAACC | 157 |

TABLE 2-continued

Sense Sequences

| Sense ID | Sequence | SEQ ID NO |
|---|---|---|
| S-1048dt | GAUCAUUGGAAUUCCUAAAdTdT | 158 |
| S-1049 | CAUUGGAAUACCUAAAAUACC | 159 |
| S-1050 | GAUCAUUGGUAUUCCUAAACC | 160 |
| S-1051dt | GUUUAUGAACUGACGUUAAdTdT | 161 |
| S-1052dt | GUGUUAGACGGUACCGACAdTdT | 162 |
| S-1053dt | AUAUCAGUAAAGAGAUUAAdTdT | 163 |
| S-1054dt | GGUUUAUGAACUGACGUUAdTdT | 164 |
| S-1055dt | CCACAAUGUUGUGACCGGAdTdT | 165 |
| S-1056dt | GUCACAAAGAACCGUGCAAdTdT | 166 |
| S-1057dt | CAUUGGAAUUCCUAAAAUCdTdT | 167 |
| S-1058 | CCUGCUAGCUCCAUGCUUGCU | 168 |
| S-1059 | CCUGCUAGCUCCAUGCUUGAU | 169 |
| S-1060 | CCUGCUAGCUCCAUGCUUAUU | 170 |
| S-1061 | CCUGCUAGCUCCAUGCUUGUU | 171 |
| S-1062 | UUCGAGUCCCUCAAGUAGCU | 172 |
| S-1063 | UUCGAGUCCCUCAAGUAGCUU | 173 |
| S-1064 | UCGAGUCCUCAAGUCCAUUCU | 174 |
| S-1065 | UUCCAGUCCAUCAAGUCAAUU | 175 |
| S-1066 | UUCCGAGUCUAAAAGUCCUUGG | 176 |
| S-1067 | UUCCGAGUCUAAAAGUCCUUGGC | 177 |
| S-1068 | CUUCCGAGUCUAAAAGUCCUUGG | 178 |
| S-1069 | UUCCGAGUCUAAAAGUCCUUGGU | 179 |
| S-1070 | UUCCGAGUCUAAAAGUCCUUGGCU | 180 |
| S-1071 | UCCAAUGUGAAACUUCAUCGGCU | 181 |
| S-1072 | UCCAAUGUGAAACUUCAUCGGC | 182 |
| S-1073 | AUCCAAUGUGAAACUUCAUCGU | 183 |
| S-1074 | AUCCAAUGUGAAACUUCAUCGGU | 184 |
| S-1075 | UCCAAUGUGAAACUUCAUCGGU | 185 |
| S-1076 | UCCAAUGUGAAACUUCAUCGGCUU | 186 |
| S-1077 | AUCUACUGUGAAAAUUCAUCGG | 187 |
| S-1078 | UCUACUGUGAAAAUUCAUCGG | 188 |
| S-1079 | UCUACUGUGAAAAUUCAUCGGC | 189 |
| S-1080 | AUCUACUGUGAAAAUUCAUCGGU | 190 |
| S-1081 | UCUACUGUGAAAAUUCAUCGGU | 191 |
| S-1082 | UCUACUGUGAAAAUUCAUCGGCU | 192 |
| S-1083 | CCUUCGGUCCUCAAGUCCUUCA | 193 |
| S-1084 | UUCGAGUCCAUCAAAUCCUAUAGU | 194 |
| S-1085 | UACAAUGUGUGCACUUCAUAU | 195 |
| S-1086 | UAUACUGUGUGCAAUUCAUUUCU | 196 |
| S-1087 | GCAAUUCAGUCUCGUUGUCC | 197 |
| S-1088 | GCAAUUCAGUCUCGUUGUC | 198 |
| S-1089 | CAAUUCAGUCUCGUUGUCCC | 199 |
| S-1090 | CAAUUCAGUCUCGUUGUCC | 200 |
| S-1091 | GCAAUUCAGUCUCGUUGUGC | 201 |
| S-1092 | CAAUUCAGUCUCGUUGUGCC | 202 |
| S-1093 | CCACAAUGUUGUGACUGGGCCU | 203 |
| S-1094 | CCACAAUGUUGUGACUGGGC | 204 |
| S-1095 | CACAAUGUUGUGACUGGGCC | 205 |
| S-1096 | UGAACCUCUUGUUAUAAAGCCU | 206 |
| S-1097 | UGAACCUCUUGUUAUAAAGC | 207 |
| S-1098 | GAACCUCUUGUUAUAAAGCC | 208 |
| S-1099 | CCUGCUAGCUCCAUGCUUGCU | 209 |
| S-1100 | CCUGCUAGCUCCAUGCUUGC | 210 |
| S-1101 | CCUGCUAGCUCCAUGCUUG | 211 |
| S-1102 | CUGCUAGCUCCAUGCUUGCC | 212 |
| S-1103 | CCGACAACCAGUAUUUGGGCCU | 213 |
| S-1104 | CCGACAACCAGUAUUUGGGC | 214 |
| S-1105 | CCGACAACCAGUAUUUGGG | 215 |
| S-1106 | CGACAACCAGUAUUUGGGCC | 216 |
| S-1107 | CGACAACCAGUAUUUGGGC | 217 |
| S-1108 | GCAAUUCAGUCUCGUUGUACCU | 218 |
| S-1109 | GCAAUUCAGUCUCGUUGUAC | 219 |
| S-1110 | GCAAUUCAGUCUCGUUGUA | 220 |
| S-1111 | CAAUUCAGUCUCGUUGUACC | 221 |
| S-1112 | GCAAUUCAGACUCGUUGUACCU | 222 |
| S-1113 | GCAAUUCAGACUCGUUGUAC | 223 |
| S-1114 | GCAAUUCAGACUCGUUGUA | 224 |
| S-1115 | CAAUUCAGACUCGUUGUACC | 225 |
| S-1116 | AGCAAUUCAGUCUCGUUGUACC | 226 |
| S-1117 | AGCAAUUCAGUCUCGUUGUAC | 227 |
| S-1118 | AGGUUUAUGAACUGACGUUAC | 228 |
| S-1119 | AGGUUUAUGAACUGACGUUACC | 229 |
| S-1120 | ACCACAAUGUUGUGACUGGAC | 230 |
| S-1121 | ACCACAAUGUUGUGACUGGACC | 231 |

TABLE 2-continued

Sense Sequences

| Sense ID | Sequence | SEQ ID NO |
|---|---|---|
| S-1122 | CCACAAUGUUGUGACUGGACCGU | 232 |
| S-1123 | CCACAAUGUUGUGACUGGACCG | 233 |
| S-1124 | CCACAAUGUUGUGACUGGAC | 234 |
| S-1125 | CACAAUGUUGUGACUGGACC | 235 |
| S-1126 | ACCUGCUAGCUCCAUGCUUCCC | 236 |
| S-1127 | ACCUGCUAGCUCCAUGCUUCC | 237 |
| S-1128 | ACCUGCUAGCUCCAUGCUUC | 238 |
| S-1129 | CCUGCUAGCUCCAUGCUUCC | 239 |
| S-1130 | CCUGCUAGCUCCAUGCUUC | 240 |
| S-1131 | CUGCUAGCUCCAUGCUUCCC | 241 |
| S-1132 | CUGCUAGCUCCAUGCUUCC | 242 |
| S-1133 | ACCGACAACCAGUAUUUGGACC | 243 |
| S-1134 | ACCGACAACCAGUAUUUGGAC | 244 |
| S-1135 | CCGACAACCAGUAUUUGGACCGU | 245 |
| S-1136 | CCGACAACCAGUAUUUGGACCGU | 246 |
| S-1137 | CCGACAACCAGUAUUUGGAC | 247 |
| S-1138 | CGACAACCAGUAUUUGGACC | 248 |
| S-1139 | CCUGCUAGCACCGUGCUUACC | 249 |

In one embodiment, the siRNA molecules of the present invention may comprise an antisense sequence from Table 1 and a sense sequence from Table 2, or a fragment or variant thereof. As a non-limiting example, the antisense sequence and the sense sequence have at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementarity.

In one embodiment, the siRNA molecules of the present invention may comprise the sense and antisense siRNA duplex as described in Tables 3-5. As a non-limiting example, these siRNA duplexes may be tested for in vitro inhibitory activity on endogenous HTT gene expression.

TABLE 3

Sense and antisense strand sequences of HTT dsRNA

| siRNA Duplex ID | SS ID | Start SS | Sense Strand Sequence (5'-3') | SS SEQ ID | AS ID | Start AS | Antisense Strand Sequence (5'-3') | AS SEQ ID |
|---|---|---|---|---|---|---|---|---|
| D-3566 | S-1058 | 6751 | CCUGCUAGCUCCAUGCUUGCU | 168 | A-2002 | 6751 | UAAGCAUGGAGCUAGCAGGUU | 7 |
| D-3567 | S-1058 | 6751 | CCUGCUAGCUCCAUGCUUGCU | 168 | A-2014 | 6748 | UAAGCAUGGAGCUAGCAGGCUU | 29 |
| D-3568 | S-1059 | 6751 | CCUGCUAGCUCCAUGCUUGAU | 169 | A-2002 | 6751 | UAAGCAUGGAGCUAGCAGGUU | 7 |
| D-3569 | S-1060 | 6751 | CCUGCUAGCUCCAUGCUUAUU | 170 | A-2015 | 6751 | UAAGCAUGGAGCUAGCAGGGU | 30 |
| D-3570 | S-1061 | 6751 | CCUGCUAGCUCCAUGCUUGUU | 171 | A-2002 | 6751 | UAAGCAUGGAGCUAGCAGGUU | 7 |
| D-3500 | S-1016 | 1386 | UCCAGGUUUAUGAACUGACCC | 120 | A-2004 | 1386 | UUCAGUUCAUAAACCUGGAUU | 11 |
| D-3501 | S-1023 | 1386 | UCCAGGUUUAUGAACUGAGCC | 127 | A-2004 | 1386 | UUCAGUUCAUAAACCUGGAUU | 11 |
| D-3502 | S-1030 | 1386 | UCCAGGUUUAUGAACUGAACC | 135 | A-2004 | 1386 | UUCAGUUCAUAAACCUGGAUU | 11 |
| D-3503 | S-1037 | 1386 | UCCAGGUUUUUGAACUGAACC | 145 | A-2004 | 1386 | UUCAGUUCAUAAACCUGGAUU | 11 |
| D-3504 | S-1030 | 1386 | UCCAGGUUUAUGAACUGAACC | 135 | A-2001 | 2066 | UGUCGGUACCGUCUAACACUU | 5 |
| D-3505 | S-1017 | 1390 | GGUUUAUGAACUGACGUUCCC | 121 | A-2005 | 1389 | UAACGUCAGUUCAUAAACCUU | 13 |

TABLE 3-continued

Sense and antisense strand sequences of HTT dsRNA

| siRNA Duplex ID | SS ID | Start SS | Sense Strand Sequence (5'-3') | SS SEQ ID | AS ID | Start AS | Antisense Strand Sequence (5'-3') | AS SEQ ID |
|---|---|---|---|---|---|---|---|---|
| D-3506 | S-1024 | 1390 | GGUUUAUGAACUGACGUUGCC | 128 | A-2005 | 1389 | UAACGUCAGUUCAUAAACCUU | 13 |
| D-3507 | S-1031 | 1390 | GGUUUAUGAACUGACGUUACC | 137 | A-2005 | 1389 | UAACGUCAGUUCAUAAACCUU | 13 |
| D-3508 | S-1038 | 1390 | GGUUUAUGAUCUGACGUUACC | 146 | A-2005 | 1389 | UAACGUCAGUUCAUAAACCUU | 13 |
| D-3509 | S-1000 | 1391 | GUUUAUGAACUGAUCUUACCC | 103 | A-2000 | 1391 | UUAACGUCAGUUCAUAAACUU | 3 |
| D-3510 | S-1003 | 1391 | GUUUAUGAACUGAUCUUAGCC | 106 | A-2000 | 1391 | UUAACGUCAGUUCAUAAACUU | 3 |
| D-3511 | S-1006 | 1391 | GUUUAUGAAGUGAUCUUAACC | 109 | A-2000 | 1391 | UUAACGUCAGUUCAUAAACUU | 3 |
| D-3512 | S-1009 | 1391 | GUUUAUGAACUGAUCUUAACC | 112 | A-2000 | 1391 | UUAACGUCAGUUCAUAAACUU | 3 |
| D-3513 | S-1012 | 1391 | GUUUAUGAACUGAUCUUGCCC | 116 | A-2000 | 1391 | UUAACGUCAGUUCAUAAACUU | 3 |
| D-3514 | S-1013 | 1391 | GUUUAUGAACUGAUCUUGGCC | 117 | A-2000 | 1391 | UUAACGUCAGUUCAUAAACUU | 3 |
| D-3515 | S-1014 | 1391 | GUUUAUGAACUGAUCUUGACC | 118 | A-2000 | 1391 | UUAACGUCAGUUCAUAAACUU | 3 |
| D-3516 | S-1018 | 1429 | CCACAAUGUUGUGACUGGCCC | 122 | A-2006 | 1428 | UCCGGUCACAACAUUGUGGUU | 15 |
| D-3517 | S-1025 | 1429 | CCACAAUGUUGUGACUGGGCC | 129 | A-2006 | 1428 | UCCGGUCACAACAUUGUGGUU | 15 |
| D-3518 | S-1032 | 1429 | CCACAAUGUUGUGACUGGACC | 138 | A-2006 | 1428 | UCCGGUCACAACAUUGUGGUU | 15 |
| D-3519 | S-1039 | 1429 | CCACAAUGUAGUGACUGGACC | 147 | A-2006 | 1428 | UCCGGUCACAACAUUGUGGUU | 15 |
| D-3520 | S-1001 | 2066 | GUGUUAGACGGUACUGAUCCC | 104 | A-2001 | 2066 | UGUCGGUACCGUCUAACACUU | 5 |
| D-3521 | S-1004 | 2066 | GUGUUAGACGGUACUGAUGCC | 107 | A-2001 | 2066 | UGUCGGUACCGUCUAACACUU | 5 |
| D-3522 | S-1007 | 2066 | GUGUUAGACCGUACUGAUACC | 110 | A-2001 | 2066 | UGUCGGUACCGUCUAACACUU | 5 |
| D-3523 | S-1010 | 2066 | GUGUUAGACGGUACUGAUACC | 113 | A-2001 | 2066 | UGUCGGUACCGUCUAACACUU | 5 |
| D-3524 | S-1021 | 2079 | CCGACAACCAGUAUUUGGCCC | 125 | A-2009 | 2078 | UCCAAAUACUGGUUGUCGGUU | 21 |
| D-3525 | S-1028 | 2079 | CCGACAACCAGUAUUUGGGCC | 132 | A-2009 | 2078 | UCCAAAUACUGGUUGUCGGUU | 21 |
| D-3526 | S-1035 | 2079 | CCGACAACCAGUAUUUGGACC | 142 | A-2009 | 2078 | UCCAAAUACUGGUUGUCGGUU | 21 |
| D-3527 | S-1042 | 2079 | CCGACAACCUGUAUUUGGACC | 150 | A-2009 | 2078 | UCCAAAUACUGGUUGUCGGUU | 21 |
| D-3528 | S-1019 | 4544 | GUCACAAAGAACCGUGUACCC | 123 | A-2007 | 4544 | UUGCACGGUUCUUUGUGACUU | 17 |
| D-3529 | S-1026 | 4544 | GUCACAAAGAACCGUGUAGCC | 130 | A-2007 | 4544 | UUGCACGGUUCUUUGUGACUU | 17 |
| D-3530 | S-1033 | 4544 | GUCACAAAGAACCGUGUACC | 139 | A-2007 | 4544 | UUGCACGGUUCUUUGUGACUU | 17 |

TABLE 3-continued

Sense and antisense strand sequences of HTT dsRNA

| siRNA Duplex ID | SS ID | Start SS | Sense Strand Sequence (5'-3') | SS SEQ ID | AS ID | Start AS | Antisense Strand Sequence (5'-3') | AS SEQ ID |
|---|---|---|---|---|---|---|---|---|
| D-3531 | S-1040 | 4544 | GUCACAAAGUACCGUGUAACC | 148 | A-2007 | 4544 | UUGCACGGUUCUUUGUGACUU | 17 |
| D-3532 | S-1020 | 4597 | UGAACCUCUUGUUAUAAACCC | 124 | A-2008 | 4597 | UUUUAUAACAAGAGGUUCAUU | 19 |
| D-3533 | S-1027 | 4597 | UGAACCUCUUGUUAUAAAGCC | 131 | A-2008 | 4597 | UUUUAUAACAAGAGGUUCAUU | 19 |
| D-3534 | S-1034 | 4597 | UGAACCUCUUGUUAUAAAACC | 140 | A-2008 | 4597 | UUUUAUAACAAGAGGUUCAUU | 19 |
| D-3535 | S-1041 | 4597 | UGAACCUCUAGUUAUAAACC | 149 | A-2008 | 4597 | UUUUAUAACAAGAGGUUCAUU | 19 |
| D-3536 | S-1044 | 4861 | GAUCAUUGGAAUUCCUAAUCC | 152 | A-2011 | 4860 | UUUAGGAAUUCCAAUGAUCUU | 25 |
| D-3537 | S-1046 | 4861 | GAUCAUUGGAAUUCCUAAGCC | 154 | A-2011 | 4860 | UUUAGGAAUUCCAAUGAUCUU | 25 |
| D-3538 | S-1048 | 4861 | GAUCAUUGGAAUUCCUAAACC | 157 | A-2011 | 4860 | UUUAGGAAUUCCAAUGAUCUU | 25 |
| D-3539 | S-1050 | 4861 | GAUCAUUGGUAUUCCUAAACC | 160 | A-2011 | 4860 | UUUAGGAAUUCCAAUGAUCUU | 25 |
| D-3540 | S-1043 | 4864 | CAUUGGAAUUCCUAAAAUUCC | 151 | A-2010 | 4864 | UAUUUUAGGAAUUCCAAUGUU | 23 |
| D-3541 | S-1045 | 4864 | CAUUGGAAUUCCUAAAAUGCC | 153 | A-2010 | 4864 | UAUUUUAGGAAUUCCAAUGUU | 23 |
| D-3542 | S-1047 | 4864 | CAUUGGAAUUCCUAAAAUACC | 155 | A-2010 | 4864 | UAUUUUAGGAAUUCCAAUGUU | 23 |
| D-3543 | S-1049 | 4864 | CAUUGGAAUACCUAAAAUACC | 159 | A-2010 | 4864 | UAUUUUAGGAAUUCCAAUGUU | 23 |
| D-3544 | S-1015 | 6188 | GCAAUUCAGUCUCGUUGUCCC | 119 | A-2003 | 6188 | UACAACGAGACUGAAUUGCUU | 9 |
| D-3545 | S-1022 | 6188 | GCAAUUCAGUCUCGUUGUGCC | 126 | A-2003 | 6188 | UACAACGAGACUGAAUUGCUU | 9 |
| D-3546 | S-1029 | 6188 | GCAAUUCAGUCUCGUUGUACC | 133 | A-2003 | 6188 | UACAACGAGACUGAAUUGCUU | 9 |
| D-3547 | S-1036 | 6188 | GCAAUUCAGACUCGUUGUACC | 144 | A-2003 | 6188 | UACAACGAGACUGAAUUGCUU | 9 |
| D-3548 | S-1002 | 6751 | CCUGCUAGCUCCAUGCUUCCC | 105 | A-2002 | 6751 | UAAGCAUGGAGCUAGCAGGUU | 7 |
| D-3549 | S-1005 | 6751 | CCUGCUAGCUCCAUGCUUGCC | 108 | A-2002 | 6751 | UAAGCAUGGAGCUAGCAGGUU | 7 |
| D-3550 | S-1008 | 6751 | CCUGCUAGCACCAUGCUUACC | 111 | A-2002 | 6751 | UAAGCAUGGAGCUAGCAGGUU | 7 |
| D-3551 | S-1011 | 6751 | CCUGCUAGCUCCAUGCUUACC | 114 | A-2002 | 6751 | UAAGCAUGGAGCUAGCAGGUU | 7 |

TABLE 4

Sense and antisense strand sequences of HTT dsRNA

| siRNA Duplex ID | SS ID | Start SS | Sense Strand Sequence (5'-3') | SS SEQ ID | AS ID | Start AS | Antisense Strand Sequence (5'-3') | AS SEQ ID |
|---|---|---|---|---|---|---|---|---|
| D-3552 | S-1051dt | 1391 | GUUUAUGAACUG ACGUUAAdTdT | 161 | A-2000dt | 1391 | UUAACGUCAGU UCAUAAACdTdT | 4 |
| D-3553 | S-1052dt | 2066 | GUGUUAGACGGU ACCGACAdTdT | 162 | A-2001dt | 2066 | UGUCGGUACCG UCUAACACdTdT | 6 |
| D-3554 | S-1011dt | 6751 | CCUGCUAGCUCC AUGCUUAdTdT | 115 | A-2002dt | 6751 | UAAGCAUGGAG CUAGCAGGdTdT | 8 |
| D-3555 | S-1053dt | 10322 | AUAUCAGUAAAG AGAUUAAdTdT | 163 | A-2012dt | 10322 | UUAAUCUCUUU ACUGAUAUdTdT | 27 |
| D-3556 | S-1030dt | 1386 | UCCAGGUUUAUG AACUGAAdTdT | 136 | A-2004dt | 1386 | UUCAGUUCAUA AACCUGGAdTdT | 12 |
| D-3557 | S-1054dt | 1390 | GGUUUAUGAACU GACGUUAdTdT | 164 | A-2005dt | 1390 | UAACGUCAGUU CAUAAACCdTdT | 14 |
| D-3558 | S-1055dt | 1429 | CCACAAUGUUGU GACCGGAdTdT | 165 | A-2006dt | 1429 | UCCGGUCACAA CAUUGUGGdTdT | 16 |
| D-3559 | S-1035dt | 2079 | CCGACAACCAGU AUUUGGAdTdT | 143 | A-2009dt | 2079 | UCCAAAUACUG GUUGUCGGdTdT | 22 |
| D-3560 | S-1056dt | 4544 | GUCACAAAGAAC CGUGCAAdTdT | 166 | A-2007dt | 4544 | UUGCACGGUUC UUUGUGACdTdT | 18 |
| D-3561 | S-1034dt | 4597 | UGAACCUCUUGU UAUAAAAdTdT | 141 | A-2008dt | 4597 | UUUUAUAACAA GAGGUUCAdTdT | 20 |
| D-3562 | S-1029dt | 6188 | GCAAUUCAGUCU CGUUGUAdTdT | 134 | A-2003dt | 6188 | UACAACGAGAC UGAAUUGCdTdT | 10 |
| D-3563 | S-1047dt | 4864 | CAUUGGAAUUCC UAAAAUAdTdT | 156 | A-2010dt | 4864 | UAUUUUAGGAA UUCCAAUGdTdT | 24 |
| D-3564 | S-1048dt | 4861 | GAUCAUUGGAAU UCCUAAAdTdT | 158 | A-2011dt | 4861 | UUUAGGAAUUC CAAUGAUCdTdT | 26 |
| D-3565 | S-1057dt | 4864 | CAUUGGAAUUCC UAAAAUCdTdT | 167 | A-2013dt | 4864 | GAUUUUAGGAA UUCCAAUGdTdT | 28 |

TABLE 5

Antisense and Sense strand sequences of HTT dsRNA

| siRNA Duplex ID | AS ID | Start AS | Antisense Strand Sequence (5'-3') | AS SEQ ID | SS ID | Start SS | Sense Strand Sequence (5'-3') | SS SEQ ID |
|---|---|---|---|---|---|---|---|---|
| D-3569 | S-1060 | 6751 | CCUGCUAGCUC CAUGCUUAUU | 170 | A-2015 | 6751 | UAAGCAUGGAG CUAGCAGGGU | 30 |
| D-3570 | S-1061 | 6751 | CCUGCUAGCUC CAUGCUUGUU | 171 | A-2002 | 6751 | UAAGCAUGGAG CUAGCAGGUU | 7 |

In other embodiments, the siRNA molecules of the present invention can be encoded in plasmid vectors, viral vectors (e.g., AAV vectors), genome or other nucleic acid expression vectors for delivery to a cell.

DNA expression plasmids can be used to stably express the siRNA duplexes or dsRNA of the present invention in cells and achieve long-term inhibition of the target gene expression. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

In one embodiment, the sense and antisense strands of a siRNA duplex may be linked by a short spacer sequence, which may optionally be linked to additional flanking sequence, leading to the expression of a flanking arm-stem-loop structure termed primary microRNA (pri-miRNA). The pri-miRNA may be recognized and cleaved by Drosha and Dicer, and thus generate mature siRNA molecules.

According to the present invention, AAV vectors comprising the nucleic acids encoding the siRNA molecules targeting HTT mRNA are produced, the AAV vector serotypes may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A (PHP.A), and/or AAV-PHP.B (PHP.B) and variants thereof.

In some embodiments, the siRNA duplexes or encoded dsRNA of the present invention suppress (or degrade) target mRNA (e.g., HTT). Accordingly, the siRNA duplexes or encoded dsRNA can be used to substantially inhibit HTT gene expression in a cell, for example a neuron. In some aspects, the inhibition of HTT gene expression refers to an inhibition by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%.

According to the present invention, the siRNA molecules are designed and tested for their ability to reduce HTT mRNA levels in cultured cells. Such siRNA molecules may form a duplex such as, but not limited to, include those listed in Table 3, Table 4 or Table 5. As a non-limiting example, the siRNA duplexes may be siRNA duplex IDs: D-3500 to D-3570.

In one embodiment, the siRNA molecules comprise a miRNA seed match for the target (e.g., HTT) located in the guide strand. In another embodiment, the siRNA molecules comprise a miRNA seed match for the target (e.g., HTT) located in the passenger strand. In yet another embodiment, the siRNA duplexes or encoded dsRNA targeting HTT gene do not comprise a seed match for the target (e.g., HTT) located in the guide or passenger strand.

In one embodiment, the siRNA duplexes or encoded dsRNA targeting HTT gene may have almost no significant full-length off targets for the guide strand. In another embodiment, the siRNA duplexes or encoded dsRNA targeting HTT gene may have almost no significant full-length off target effects for the passenger strand. The siRNA duplexes or encoded dsRNA targeting HTT gene may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the passenger strand. In yet another embodiment, the siRNA duplexes or encoded dsRNA targeting HTT gene may have almost no significant full-length off targets for the guide strand or the passenger strand. The siRNA duplexes or encoded dsRNA targeting HTT gene may have less than 1%, 2%, 3%, 4%, 5%, 6%, 7%, 8%, 9%, 10%, 11%, 12%, 13%, 14%, 15%, 20%, 25%, 30%, 35%, 40%, 45%, 50%, 1-5%, 2-6%, 3-7%, 4-8%, 5-9%, 5-10%, 6-10%, 5-15%, 5-20%, 5-25% 5-30%, 10-20%, 10-30%, 10-40%, 10-50%, 15-30%, 15-40%, 15-45%, 20-40%, 20-50%, 25-50%, 30-40%, 30-50%, 35-50%, 40-50%, 45-50% full-length off target effects for the guide or passenger strand.

In one embodiment, the siRNA duplexes or encoded dsRNA targeting HTT gene may have high activity in vitro. In another embodiment, the siRNA molecules may have low activity in vitro. In yet another embodiment, the siRNA duplexes or dsRNA targeting the HTT gene may have high guide strand activity and low passenger strand activity in vitro.

In one embodiment, the siRNA molecules have a high guide strand activity and low passenger strand activity in vitro. The target knock-down (KD) by the guide strand may be at least 40%, 50%, 60%, 65%, 70%, 75%, 80%, 85%, 90%, 95%, 99%, 99.5% or 100%. The target knock-down by the guide strand may be 40-50%, 45-50%, 50-55%, 50-60%, 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%. As a non-limiting example, the target knock-down (KD) by the guide strand is greater than 60%.

In one embodiment, the siRNA duplex is designed so there is no miRNA seed match for the sense or antisense sequence to non-Htt sequences.

In one embodiment, the $IC_{50}$ of the guide strand for the nearest off target is greater than 100 multiplied by the $IC_{50}$ of the guide strand for the target. As a non-limiting example, if the $IC_{50}$ of the guide strand for the nearest off target is greater than 100 multiplied by the $IC_{50}$ of the guide strand for the target then the siRNA molecule is said to have high guide strand selectivity for inhibiting Htt in vitro.

In one embodiment, the 5' processing of the guide strand has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo. As a non-limiting example, the 5' processing of the guide strand is precise and has a correct start (n) at the 5' end at least 90% of the time in vitro. As a non-limiting example, the 5' processing of the guide strand is precise and has a correct start (n) at the 5' end at least 90% of the time in vivo. As a non-limiting example, the 5' processing of the guide strand is precise and has a correct start (n) at the 5' end at least 85% of the time in vitro. As a non-limiting example, the 5' processing of the guide strand is precise and has a correct start (n) at the 5' end at least 85% of the time in vivo.

In one embodiment, the guide to passenger (G:P) (also referred to as the antisense to sense) strand ratio expressed is 1:10, 1:9, 1:8, 1:7, 1:6, 1:5, 1:4, 1:3, 1:2, 1;1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The guide to passenger ratio refers to the ratio of the guide strands to the passenger strands after the intracellular processing of the pri-microRNA. For example, a 80:20 guide-to-passenger ratio would have 8 guide strands to every 2 passenger strands processed from the precursor. As a non-limiting example, the guide-to-passenger strand ratio is 8:2 in vitro. As a non-limiting example, the guide-to-passenger strand ratio is 8:2 in vivo. As a non-limiting example, the guide-to-passenger strand ratio is 9:1 in vitro. As a non-limiting example, the guide-to-passenger strand ratio is 9:1 in vivo.

In one embodiment, the guide to passenger (G:P) (also referred to as the antisense to sense) strand ratio expressed is greater than 1.

In one embodiment, the guide to passenger (G:P) (also referred to as the antisense to sense) strand ratio expressed is greater than 2.

In one embodiment, the guide to passenger (G:P) (also referred to as the antisense to sense) strand ratio expressed is greater than 5.

In one embodiment, the guide to passenger (G:P) (also referred to as the antisense to sense) strand ratio expressed is greater than 10.

In one embodiment, the guide to passenger (G:P) (also referred to as the antisense to sense) strand ratio expressed is greater than 20.

In one embodiment, the guide to passenger (G:P) (also referred to as the antisense to sense) strand ratio expressed is greater than 50.

In one embodiment, the guide to passenger (G:P) (also referred to as the antisense to sense) strand ratio expressed is at least 3:1.

In one embodiment, the guide to passenger (G:P) (also referred to as the antisense to sense) strand ratio expressed is at least 5:1.

In one embodiment, the guide to passenger (G:P) (also referred to as the antisense to sense) strand ratio expressed is at least 10:1.

In one embodiment, the guide to passenger (G:P) (also referred to as the antisense to sense) strand ratio expressed is at least 20:1.

In one embodiment, the guide to passenger (G:P) (also referred to as the antisense to sense) strand ratio expressed is at least 50:1.

In one embodiment, the passenger to guide (P:G) (also referred to as the sense to antisense) strand ratio expressed is 1:10, 1:9, 1:8, 1:7, 1:6, 1:5, 1:4, 1:3, 1:2, 1;1, 2:10, 2:9, 2:8, 2:7, 2:6, 2:5, 2:4, 2:3, 2:2, 2:1, 3:10, 3:9, 3:8, 3:7, 3:6, 3:5, 3:4, 3:3, 3:2, 3:1, 4:10, 4:9, 4:8, 4:7, 4:6, 4:5, 4:4, 4:3, 4:2, 4:1, 5:10, 5:9, 5:8, 5:7, 5:6, 5:5, 5:4, 5:3, 5:2, 5:1, 6:10, 6:9, 6:8, 6:7, 6:6, 6:5, 6:4, 6:3, 6:2, 6:1, 7:10, 7:9, 7:8, 7:7, 7:6, 7:5, 7:4, 7:3, 7:2, 7:1, 8:10, 8:9, 8:8, 8:7, 8:6, 8:5, 8:4, 8:3, 8:2, 8:1, 9:10, 9:9, 9:8, 9:7, 9:6, 9:5, 9:4, 9:3, 9:2, 9:1, 10:10, 10:9, 10:8, 10:7, 10:6, 10:5, 10:4, 10:3, 10:2, 10:1, 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. The passenger to guide ratio refers to the ratio of the passenger strands to the guide strands after the excision of the guide strand. For example, a 80:20 passenger to guide ratio would have 8 passenger strands to every 2 guide strands processed from the precursor. As a non-limiting example, the passenger-to-guide strand ratio is 80:20 in vitro. As a non-limiting example, the passenger-to-guide strand ratio is 80:20 in vivo. As a non-limiting example, the passenger-to-guide strand ratio is 8:2 in vitro. As a non-limiting example, the passenger-to-guide strand ratio is 8:2 in vivo. As a non-limiting example, the passenger-to-guide strand ratio is 9:1 in vitro. As a non-limiting example, the passenger-to-guide strand ratio is 9:1 in vivo.

In one embodiment, the passenger to guide (P:G) (also referred to as the sense to antisense) strand ratio expressed is greater than 1.

In one embodiment, the passenger to guide (P:G) (also referred to as the sense to antisense) strand ratio expressed is greater than 2.

In one embodiment, the passenger to guide (P:G) (also referred to as the sense to antisense) strand ratio expressed is greater than 5.

In one embodiment, the passenger to guide (P:G) (also referred to as the sense to antisense) strand ratio expressed is greater than 10.

In one embodiment, the passenger to guide (P:G) (also referred to as the sense to antisense) strand ratio expressed is greater than 20.

In one embodiment, the passenger to guide (P:G) (also referred to as the sense to antisense) strand ratio expressed is greater than 50.

In one embodiment, the passenger to guide (P:G) (also referred to as the sense to antisense) strand ratio expressed is at least 3:1.

In one embodiment, the passenger to guide (P:G) (also referred to as the sense to antisense) strand ratio expressed is at least 5:1.

In one embodiment, the passenger to guide (P:G) (also referred to as the sense to antisense) strand ratio expressed is at least 10:1.

In one embodiment, the passenger to guide (P:G) (also referred to as the sense to antisense) strand ratio expressed is at least 20:1.

In one embodiment, the passenger to guide (P:G) (also referred to as the sense to antisense) strand ratio expressed is at least 50:1.

In one embodiment, a passenger-guide strand duplex is considered effective when the pri- or pre-microRNAs demonstrate, but methods known in the art and described herein, greater than 2-fold guide to passenger strand ratio when processing is measured. As a non-limiting examples, the pri- or pre-microRNAs demonstrate great than 2-fold, 3-fold, 4-fold, 5-fold, 6-fold, 7-fold, 8-fold, 9-fold, 10-fold, 11-fold, 12-fold, 13-fold, 14-fold, 15-fold, or 2 to 5-fold, 2 to 10-fold, 2 to 15-fold, 3 to 5-fold, 3 to 10-fold, 3 to 15-fold, 4 to 5-fold, 4 to 10-fold, 4 to 15-fold, 5 to 10-fold, 5 to 15-fold, 6 to 10-fold, 6 to 15-fold, 7 to 10-fold, 7 to 15-fold, 8 to 10-fold, 8 to 15-fold, 9 to 10-fold, 9 to 15-fold, 10 to 15-fold, 11 to 15-fold, 12 to 15-fold, 13 to 15-fold, or 14 to 15-fold guide to passenger strand ratio when processing is measured.

In one embodiment, the vector genome encoding the dsRNA comprises a sequence which is at least 60%, 65%, 70%, 75%, 80%, 85%, 90%, 95%, 99% or more than 99% of the full length of the construct. As a non-limiting example, the vector genome comprises a sequence which is at least 80% of the full length sequence of the construct.

In one embodiment, the siRNA molecules may be used to silence wild type or mutant HTT by targeting at least one exon on the htt sequence. The exon may be exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, and/or exon 67. As a non-limiting example, the siRNA molecules may be used to silence wild type or mutant HTT by targeting exon 1. As another non-limiting example, the siRNA molecules may be used to silence wild type or mutant HTT by targeting an exon other than exon 1. As another non-limiting example, the siRNA molecules may be used to silence wild type or mutant HTT by targeting exon 50. As another non-limiting example, the siRNA molecules may be used to silence wild type or mutant HTT by targeting exon 67.

In one embodiment, the siRNA molecules may be used to silence wild type and/or mutant HTT by targeting at least one exon on the htt sequence. The exon may be exon 1, exon 2, exon 3, exon 4, exon 5, exon 6, exon 7, exon 8, exon 9, exon 10, exon 11, exon 12, exon 13, exon 14, exon 15, exon 16, exon 17, exon 18, exon 19, exon 20, exon 21, exon 22, exon 23, exon 24, exon 25, exon 26, exon 27, exon 28, exon 29, exon 30, exon 31, exon 32, exon 33, exon 34, exon 35, exon 36, exon 37, exon 38, exon 39, exon 40, exon 41, exon 42, exon 43, exon 44, exon 45, exon 46, exon 47, exon 48, exon 49, exon 50, exon 51, exon 52, exon 53, exon 54, exon 55, exon 56, exon 57, exon 58, exon 59, exon 60, exon 61, exon 62, exon 63, exon 64, exon 65, exon 66, and/or exon 67. As a non-limiting example, the siRNA molecules may be used to silence wild type and/or mutant HTT by targeting exon 1. As another non-limiting example, the siRNA molecules may be used to silence wild type and/or mutant HTT by targeting an exon other than exon 1. As another non-limiting example, the siRNA molecules may be used to silence wild type and/or mutant HTT by targeting exon 50. As another non-limiting example, the siRNA molecules may be used to silence wild type and/or mutant HTT by targeting exon 67.

siRNA Modification

In some embodiments, the siRNA molecules of the present invention, when not delivered as a precursor or DNA, may be chemically modified to modulate some features of RNA molecules, such as, but not limited to, increasing the stability of siRNAs in vivo. The chemically modified siRNA molecules can be used in human therapeutic applications, and are improved without compromising the RNAi activity of the siRNA molecules. As a non-limiting example, the siRNA molecules modified at both the 3' and the 5' end of both the sense strand and the antisense strand.

In some aspects, the siRNA duplexes of the present invention may contain one or more modified nucleotides such as, but not limited to, sugar modified nucleotides, nucleobase modifications and/or backbone modifications. In some aspects, the siRNA molecule may contain combined modifications, for example, combined nucleobase and backbone modifications.

In one embodiment, the modified nucleotide may be a sugar-modified nucleotide. Sugar modified nucleotides include, but are not limited to 2'-fluoro, 2'-amino and 2'-thio modified ribonucleotides, e.g. 2'-fluoro modified ribonucleotides. Modified nucleotides may be modified on the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

In one embodiment, the modified nucleotide may be a nucleobase-modified nucleotide.

In one embodiment, the modified nucleotide may be a backbone-modified nucleotide. In some embodiments, the siRNA duplexes of the present invention may further comprise other modifications on the backbone. A normal "backbone", as used herein, refers to the repeating alternating sugar-phosphate sequences in a DNA or RNA molecule. The deoxyribose/ribose sugars are joined at both the 3'-hydroxyl and 5'-hydroxyl groups to phosphate groups in ester links, also known as "phosphodiester" bonds/linker (PO linkage). The PO backbones may be modified as "phosphorothioate backbone (PS linkage). In some cases, the natural phosphodiester bonds may be replaced by amide bonds but the four atoms between two sugar units are kept. Such amide modifications can facilitate the solid phase synthesis of oligonucleotides and increase the thermodynamic stability of a duplex formed with siRNA complement. See e.g. Mesmaeker et al., *Pure & Appl. Chem.*, 1997, 3, 437-440; the content of which is incorporated herein by reference in its entirety.

Modified bases refer to nucleotide bases such as, for example, adenine, guanine, cytosine, thymine, uracil, xanthine, inosine, and queuosine that have been modified by the replacement or addition of one or more atoms or groups. Some examples of modifications on the nucleobase moieties include, but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

In one embodiment, the modified nucleotides may be on just the sense strand.

In another embodiment, the modified nucleotides may be on just the antisense strand.

In some embodiments, the modified nucleotides may be in both the sense and antisense strands.

In some embodiments, the chemically modified nucleotide does not affect the ability of the antisense strand to pair with the target mRNA sequence, such as the HTT mRNA sequence.

Molecular Scaffold

In one embodiment, the siRNA molecules may be encoded in a modulatory polynucleotide which also comprises a molecular scaffold. As used herein a "molecular scaffold" is a framework or starting molecule that forms the sequence or structural basis against which to design or make a subsequent molecule.

In one embodiment, the molecular scaffold comprises at least one 5' flanking region. As a non-limiting example, the 5' flanking region may comprise a 5' flanking sequence which may be of any length and may be derived in whole or in part from wild type microRNA sequence or be a completely artificial sequence.

In one embodiment, the molecular scaffold comprises at least one 3' flanking region. As a non-limiting example, the 3' flanking region may comprise a 3' flanking sequence which may be of any length and may be derived in whole or in part from wild type microRNA sequence or be a completely artificial sequence.

In one embodiment, the molecular scaffold comprises at least one loop motif region. As a non-limiting example, the loop motif region may comprise a sequence which may be of any length.

In one embodiment, the molecular scaffold comprises a 5' flanking region, a loop motif region and/or a 3' flanking region.

In one embodiment, at least one payload (e.g., siRNA, miRNA or other RNAi agent described herein) may be encoded by a modulatory polynucleotide which may also comprise at least one molecular scaffold. The molecular scaffold may comprise a 5' flanking sequence which may be of any length and may be derived in whole or in part from wild type microRNA sequence or be completely artificial. The 3' flanking sequence may mirror the 5' flanking sequence and/or a 3' flanking sequence in size and origin. Either flanking sequence may be absent. The 3' flanking sequence may optionally contain one or more CNNC motifs, where "N" represents any nucleotide.

Forming the stem of a stem loop structure is a minimum of the modulatory polynucleotide encoding at least one payload sequence. In some embodiments the payload sequence comprises at least one nucleic acid sequence which is in part complementary or will hybridize to a target sequence. In some embodiments the payload is a siRNA molecule or fragment of a siRNA molecule.

In some embodiments, the 5' arm of the stem loop structure of the modulatory polynucleotide comprises a nucleic acid sequence encoding a sense sequence. Non-limiting examples of sense sequences, or fragments or variants thereof, which may be encoded by the modulatory polynucleotide are described in Table 2.

In some embodiments, the 3' arm of the stem loop of the modulatory polynucleotide comprises a nucleic acid sequence encoding an antisense sequence. The antisense sequence, in some instances, comprises a "G" nucleotide at the 5' most end. Non-limiting examples of antisense sequences, or fragments or variants thereof, which may be encoded by the modulatory polynucleotide are described in Table 3.

In other embodiments, the sense sequence may reside on the 3' arm while the antisense sequence resides on the 5' arm of the stem of the stem loop structure of the modulatory polynucleotide. Non-limiting examples of sense and antisense sequences which may be encoded by the modulatory polynucleotide are described in Tables 2 and 3.

In one embodiment, the sense and antisense sequences may be completely complementary across a substantial portion of their length. In other embodiments the sense sequence and antisense sequence may be at least 70, 80, 90, 95 or 99% complementarity across independently at least 50, 60, 70, 80, 85, 90, 95, or 99% of the length of the strands.

Neither the identity of the sense sequence nor the homology of the antisense sequence need to be 100% complementarity to the target sequence.

In one embodiment, separating the sense and antisense sequence of the stem loop structure of the modulatory polynucleotide is a loop sequence (also known as a loop motif, linker or linker motif). The loop sequence may be of any length, between 4-30 nucleotides, between 4-20 nucleotides, between 4-15 nucleotides, between 5-15 nucleotides, between 6-12 nucleotides, 6 nucleotides, 7 nucleotides, 8 nucleotides, 9 nucleotides, 10 nucleotides, 11 nucleotides, 12 nucleotides, 13 nucleotides, 14 nucleotides, and/or 15 nucleotides.

In some embodiments, the loop sequence comprises a nucleic acid sequence encoding at least one UGUG motif. In some embodiments, the nucleic acid sequence encoding the UGUG motif is located at the 5' terminus of the loop sequence.

In one embodiment, spacer regions may be present in the modulatory polynucleotide to separate one or more modules (e.g., 5' flanking region, loop motif region, 3' flanking region, sense sequence, antisense sequence) from one another. There may be one or more such spacer regions present.

In one embodiment, a spacer region of between 8-20, i.e., 8, 9, 10, 11, 12, 13, 14, 15, 16, 17, 18, 19, or 20 nucleotides may be present between the sense sequence and a flanking region sequence.

In one embodiment, the length of the spacer region is 13 nucleotides and is located between the 5' terminus of the sense sequence and the 3' terminus of the flanking sequence. In one embodiment, a spacer is of sufficient length to form approximately one helical turn of the sequence.

In one embodiment, a spacer region of between 8-20, i.e., 8, 9, 10, 11, 12, 13, 14, 15, 16, 17, 18, 19, or 20 nucleotides may be present between the antisense sequence and a flanking sequence.

In one embodiment, the spacer sequence is between 10-13, i.e., 10, 11, 12 or 13 nucleotides and is located between the 3' terminus of the antisense sequence and the 5' terminus of a flanking sequence. In one embodiment, a spacer is of sufficient length to form approximately one helical turn of the sequence.

In one embodiment, the modulatory polynucleotide comprises in the 5' to 3' direction, a 5' flanking sequence, a 5' arm, a loop motif, a 3' arm and a 3' flanking sequence. As a non-limiting example, the 5' arm may comprise a sense sequence and the 3' arm comprises the antisense sequence. In another non-limiting example, the 5' arm comprises the antisense sequence and the 3' arm comprises the sense sequence.

In one embodiment, the 5' arm, payload (e.g., sense and/or antisense sequence), loop motif and/or 3' arm sequence may be altered (e.g., substituting 1 or more nucleotides, adding nucleotides and/or deleting nucleotides). The alteration may cause a beneficial change in the function of the construct (e.g., increase knock-down of the target sequence, reduce degradation of the construct, reduce off target effect, increase efficiency of the payload, and reduce degradation of the payload).

In one embodiment, the molecular scaffold of the modulatory polynucleotides is aligned in order to have the rate of excision of the guide strand be greater than the rate of excision of the passenger strand. The rate of excision of the guide or passenger strand may be, independently, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99%. As a non-limiting example, the rate of excision of the guide strand is at least 80%. As another non-limiting example, the rate of excision of the guide strand is at least 90%.

In one embodiment, the rate of excision of the guide strand is greater than the rate of excision of the passenger strand. In one aspect, the rate of excision of the guide strand may be at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more than 99% greater than the passenger strand.

In one embodiment, the efficiency of excision of the guide strand is at least 60%, 65%, 70%, 75%, 80%, 85%, 90%, 95%, 99% or more than 99%. As a non-limiting example, the efficiency of the excision of the guide strand is greater than 80%.

In one embodiment, the efficiency of the excision of the guide strand is greater than the excision of the passenger strand from the molecular scaffold. The excision of the guide strand may be 2, 3, 4, 5, 6, 7, 8, 9, 10 or more than 10 times more efficient than the excision of the passenger strand from the molecular scaffold.

In one embodiment, the molecular scaffold comprises a dual-function targeting modulatory polynucleotide. As used herein, a "dual-function targeting" modulatory polynucleotide is a polynucleotide where both the guide and passenger strands knock down the same target or the guide and passenger strands knock down different targets.

In one embodiment, the molecular scaffold of the modulatory polynucleotides described herein may comprise a 5' flanking region, a loop motif region and a 3' flanking region. Non-limiting examples of the sequences for the 5' flanking region, loop motif region (may also be referred to as a linker region) and the 3' flanking region which may be encoded by the modulatory polynucleotides described herein are shown in Tables 6-8.

TABLE 6

5' Flanking Regions for Molecular Scaffold

| 5' Flanking Region Name | 5' Flanking Region Sequence | 5' Flanking Region SEQ ID |
|---|---|---|
| 5F3 | GUGCUGGGCGGGGGCGGCGGGCCCUCCCGCAGAACACCAUGCGCUCCACGGAA | 252 |
| 5F1 | GUGCUGGGCGGGGGCGGCGGGCCCUCCCGCAGAACACCAUGCGCUCUUCGGAA | 250 |
| 5F2 | GAAGCAAAGAAGGGCAGAGGGAGCCCGUGAGCUGAGUGGGCCAGGGACUGGGAGAAGGAGUGAGGAGGCAGGGCCGGCAUGCCUCUGCUGCUGGCCAGA | 251 |
| 5F4 | GGGCCCUCCCGCAGAACACCAUGCGCUCCACGGAA | 253 |
| 5F5 | CUCCCGCAGAACACCAUGCGCUCCACGGAA | 254 |
| 5F6 | GUGCUGGGCGGGGGCGGCGGGCCCUCCCGCAGAACACCAUGCGCUCCACGGAAG | 255 |
| 5F7 | GUGCUGGGCGGGGGCGGCGGGCCCUCCCGCAGAACACCAUGCGCUCCUCGGAA | 256 |

TABLE 7

Loop Motif Regions for Molecular Scaffold

| Loop Motif Region Name | Loop Motif Region Sequence | Loop Motif Region SEQ ID |
|---|---|---|
| L5 | GUGGCCACUGAGAAG | 261 |
| L1 | UGUGACCUGG | 257 |
| L2 | UGUGAUUUGG | 258 |
| L3 | GUCUGCACCUGUCACUAG | 259 |
| L4 | GUGACCCAAG | 260 |
| L6 | GUGACCCAAU | 262 |
| L7 | GUGACCCAAC | 263 |
| L8 | GUGGCCACUGAGAAA | 264 |

TABLE 8

3' Flanking Regions for Molecular Scaffold

| 3' Flanking Region Name | 3' Flanking Region Sequence | 3' Flanking Region SEQ ID |
|---|---|---|
| 3F1 | CUGAGGAGCGCCUUGACAGCAGCCAUGGGAGGGCCGCCCCCUACCUCAGUGA | 265 |
| 3F2 | CUGUGGAGCGCCUUGACAGCAGCCAUGGGAGGGCCGCCCCCUACCUCAGUGA | 266 |
| 3F3 | UGGCCGUGUAGUGCUACCCAGCGCUGGCUGCCUCCUCAGCAUUGCAAUUCCUCUCCCAUCUGGGCACCAGUCAGCUACCCUGGUGGGAAUCUGGGUAGCC | 267 |
| 3F4 | CUGAGGAGCGCCUUGACAGCAGCCAUGGGAGGGCC | 268 |
| 3F5 | CUGCGGAGCGCCUUGACAGCAGCCAUGGGAGGGCCGCCCCCUACCUCAGUGA | 269 |

Any of the regions, or fragments thereof described in Tables 6-8, where U is T, may be used as modules in the molecular scaffolds described herein.

In one embodiment, the molecular scaffold may comprise at least one nucleic acid sequence encoding at least one 5' flanking region listed in Table 6. As a non-limiting example, the 5' flanking region may be 5F1, 5F2, 5F3, 5F4, 5F5, 5F6, or 5F7.

In one embodiment, the molecular scaffold may comprise at least one nucleic acid sequence encoding at least one 5F1 flanking region.

In one embodiment, the molecular scaffold may comprise at least one nucleic acid sequence encoding at least one 5F2 flanking region.

In one embodiment, the molecular scaffold may comprise at least one nucleic acid sequence encoding at least one 5F3 flanking region.

In one embodiment, the molecular scaffold may comprise at least one nucleic acid sequence encoding at least one 5F4 flanking region.

In one embodiment, the molecular scaffold may comprise at least one nucleic acid sequence encoding at least one 5F5 flanking region.

In one embodiment, the molecular scaffold may comprise at least one nucleic acid sequence encoding at least one 5F6 flanking region.

In one embodiment, the molecular scaffold may comprise at least one nucleic acid sequence encoding at least one 5F7 flanking region.

In one embodiment, the molecular scaffold may comprise at least one nucleic acid sequence encoding at least one loop motif region listed in Table 7. As a non-limiting example, the loop motif region may be L1, L2, L3, L4, L5, L6, L7, or L8.

In one embodiment, the molecular scaffold may comprise at least one nucleic acid sequence encoding at least one L1 loop motif region.

In one embodiment, the molecular scaffold may comprise at least one nucleic acid sequence encoding at least one L2 loop motif region.

In one embodiment, the molecular scaffold may comprise at least one nucleic acid sequence encoding at least one L3 loop motif region.

In one embodiment, the molecular scaffold may comprise at least one nucleic acid sequence encoding at least one L4 loop motif region.

In one embodiment, the molecular scaffold may comprise at least one nucleic acid sequence encoding at least one L5 loop motif region.

In one embodiment, the molecular scaffold may comprise at least one nucleic acid sequence encoding at least one L6 loop motif region.

In one embodiment, the molecular scaffold may comprise at least one nucleic acid sequence encoding at least one L7 loop motif region.

In one embodiment, the molecular scaffold may comprise at least one nucleic acid sequence encoding at least one L8 loop motif region.

In one embodiment, the molecular scaffold may comprise at least one nucleic acid sequence encoding at least one 3' flanking region listed in Table 8. As a non-limiting example, the 3' flanking region may be 3F1, 3F2, 3F3, 3F4, or 3F5.

In one embodiment, the molecular scaffold may comprise at least one nucleic acid sequence encoding at least one 3F1 flanking region.

In one embodiment, the molecular scaffold may comprise at least one nucleic acid sequence encoding at least one 3F2 flanking region.

In one embodiment, the molecular scaffold may comprise at least one nucleic acid sequence encoding at least one 3F3 flanking region.

In one embodiment, the molecular scaffold may comprise at least one nucleic acid sequence encoding at least one 3F4 flanking region.

In one embodiment, the molecular scaffold may comprise at least one nucleic acid sequence encoding at least one 3F5 flanking region.

In one embodiment, the molecular scaffold may comprise at least one nucleic acid sequence encoding at least one 5' flanking region and at least one loop motif region as described in Tables 6 and 7. As a non-limiting example, the 5' flanking region and the loop motif region may be 5F1 and L1, 5F1 and L2, 5F1 and L3, 5F1 and L4, 5F1 and L5, 5F1 and L6, 5F1 and L7, 5F1 and L8, 5F2 and L1, 5F2 and L2, 5F2 and L3, 5F2 and L4, 5F2 and L5, 5F2 and L6, 5F2 and L7, 5F2 and L8, 5F3 and L1, 5F3 and L2, 5F3 and L3, 5F3 and L4, 5F3 and L5, 5F3 and L6, 5F3 and L7, 5F3 and L8, 5F4 and L1, 5F4 and L2, 5F4 and L3, 5F4 and L4, 5F4 and L5, 5F4 and L6, 5F4 and L7, 5F4 and L8, 5F5 and L1, 5F5 and L2, 5F5 and L3, 5F5 and L4, 5F5 and L5, 5F5 and L6, 5F5 and L7, 5F5 and L8, 5F6 and L1, 5F6 and L2, 5F6 and L3, 5F6 and L4, 5F6 and L5, 5F6 and L6, 5F6 and L7, 5F6 and L8, 5F7 and L1, 5F7 and L2, 5F7 and L3, 5F7 and L4, 5F7 and L5, 5F7 and L6, 5F7 and L7, and 5F7 and L8.

In one embodiment, the molecular scaffold may comprise at least one nucleic acid sequence encoding at least one 5F2 flanking region and at least one nucleic acid sequence encoding at least one L1 loop motif region.

In one embodiment, the molecular scaffold may comprise at least one nucleic acid sequence encoding at least one 5F1 flanking region and at least one nucleic acid sequence encoding at least one L4 loop motif region.

In one embodiment, the molecular scaffold may comprise at least one nucleic acid sequence encoding at least one 5F7 flanking region and at least one nucleic acid sequence encoding at least one L8 loop motif region.

In one embodiment, the molecular scaffold may comprise at least one nucleic acid sequence encoding at least one 5F3 flanking region and at least one nucleic acid sequence encoding at least one L4 loop motif region.

In one embodiment, the molecular scaffold may comprise at least one nucleic acid sequence encoding at least one 5F3 flanking region and at least one nucleic acid sequence encoding at least one L5 loop motif region.

In one embodiment, the molecular scaffold may comprise at least one nucleic acid sequence encoding at least one 5F4 flanking region and at least one nucleic acid sequence encoding at least one L4 loop motif region.

In one embodiment, the molecular scaffold may comprise at least one nucleic acid sequence encoding at least one 5F3 flanking region and at least one nucleic acid sequence encoding at least one L7 loop motif region.

In one embodiment, the molecular scaffold may comprise at least one nucleic acid sequence encoding at least one 5F5 flanking region and at least one nucleic acid sequence encoding at least one L4 loop motif region.

In one embodiment, the molecular scaffold may comprise at least one nucleic acid sequence encoding at least one 5F6 flanking region and at least one nucleic acid sequence encoding at least one L4 loop motif region.

In one embodiment, the molecular scaffold may comprise at least one nucleic acid sequence encoding at least one 5F3 flanking region and at least one nucleic acid sequence encoding at least one L6 loop motif region.

In one embodiment, the molecular scaffold may comprise at least one nucleic acid sequence encoding at least one 5F7 flanking region and at least one nucleic acid sequence encoding at least one L4 loop motif region.

In one embodiment, the molecular scaffold may comprise at least one nucleic acid sequence encoding at least one 5F2 flanking region and at least one nucleic acid sequence encoding at least one L2 loop motif region.

In one embodiment, the molecular scaffold may comprise at least one nucleic acid sequence encoding at least one 5F1 flanking region and at least one nucleic acid sequence encoding at least one L1 loop motif region.

In one embodiment, the molecular scaffold may comprise at least one nucleic acid sequence encoding at least one 5F1 flanking region and at least one nucleic acid sequence encoding at least one L2 loop motif region.

In one embodiment, the molecular scaffold may comprise at least one nucleic acid sequence encoding at least one 3' flanking region and at least one nucleic acid sequence encoding at least one loop motif region as described in Tables 7 and 8. As a non-limiting example, the 3' flanking region and the loop motif region may be 3F1 and L1, 3F1 and L2, 3F1 and L3, 3F1 and L4, 3F1 and L5, 3F1 and L6, 3F1 and L7, 3F1 and L8, 3F2 and L1, 3F2 and L2, 3F2 and L3, 3F2 and L4, 3F2 and L5, 3F2 and L6, 3F2 and L7, 3F2 and L8, 3F3 and L1, 3F3 and L2, 3F3 and L3, 3F3 and L4, 3F3 and L5, 3F3 and L6, 3F3 and L7, 3F3 and L8, 3F4 and L1, 3F4 and L2, 3F4 and L3, 3F4 and L4, 3F4 and L5, 3F4 and L6, 3F4 and L7, 3F4 and L8, 3F5 and L1, 3F5 and L2, 3F5 and L3, 3F5 and L4, 3F5 and L5, 3F5 and L6, 3F5 and L7, and 3F5 and L8.

In one embodiment, the molecular scaffold may comprise at least one nucleic acid sequence encoding at least one L1 loop motif region and at least one nucleic acid sequence encoding at least one 3F2 flanking region.

In one embodiment, the molecular scaffold may comprise at least one nucleic acid sequence encoding at least one L4 loop motif region and at least one nucleic acid sequence encoding at least one 3F1 flanking region.

In one embodiment, the molecular scaffold may comprise at least one nucleic acid sequence encoding at least one L8 loop motif region and at least one nucleic acid sequence encoding at least one 3F5 flanking region.

In one embodiment, the molecular scaffold may comprise at least one nucleic acid sequence encoding at least one L5 loop motif region and at least one nucleic acid sequence encoding at least one 3F1 flanking region.

In one embodiment, the molecular scaffold may comprise at least one nucleic acid sequence encoding at least one L4 loop motif region and at least one nucleic acid sequence encoding at least one 3F4 flanking region.

In one embodiment, the molecular scaffold may comprise at least one nucleic acid sequence encoding at least one L7 loop motif region and at least one nucleic acid sequence encoding at least one 3F1 flanking region.

In one embodiment, the molecular scaffold may comprise at least one nucleic acid sequence encoding at least one L6 loop motif region and at least one nucleic acid sequence encoding at least one 3F1 flanking region.

In one embodiment, the molecular scaffold may comprise at least one nucleic acid sequence encoding at least one L4 loop motif region and at least one nucleic acid sequence encoding at least one 3F5 flanking region.

In one embodiment, the molecular scaffold may comprise at least one nucleic acid sequence encoding at least one L2 loop motif region and at least one nucleic acid sequence encoding at least one 3F2 flanking region.

In one embodiment, the molecular scaffold may comprise at least one nucleic acid sequence encoding at least one L1 loop motif region and at least one nucleic acid sequence encoding at least one 3F3 flanking region.

In one embodiment, the molecular scaffold may comprise at least one nucleic acid sequence encoding at least one L5 loop motif region and at least one nucleic acid sequence encoding at least one 3F4 flanking region.

In one embodiment, the molecular scaffold may comprise at least one nucleic acid sequence encoding at least one L1 loop motif region and at least one nucleic acid sequence encoding at least one 3F1 flanking region.

In one embodiment, the molecular scaffold may comprise at least one nucleic acid sequence encoding at least one L2 loop motif region and at least one nucleic acid sequence encoding at least one 3F1 flanking region.

In one embodiment, the molecular scaffold may comprise at least one nucleic acid sequence encoding at least one 5' flanking region and at least one nucleic acid sequence encoding at least 3' flanking region as described in Tables 6 and 8. As a non-limiting example, the flanking regions may be 5F1 and 3F1, 5F1 and 3F2, 5F1 and 3F3, 5F1 and 3F4, 5F1 and 3F5, 5F2 and 3F1, 5F2 and 3F2, 5F2 and 3F3, 5F2 and 3F4, 5F2 and 3F5, 5F3 and 3F1, 5F3 and 3F2, 5F3, 5F3 and 3F4, 5F3 and 3F5, 5F4 and 3F1, 5F4 and 3F2, 5F4 and 3F3, 5F4 and 3F4, 5F4 and 3F5, 5F5 and 3F1, 5F5 and 3F2, 5F5 and 3F3, 5F5 and 3F4, 5F5 and 3F5, 5F6 and 3F1, 5F6 and 3F2, 5F6 and 3F3, 5F6 and 3F4, 5F6 and 3F5, 5F7 and 3F1, 5F7 and 3F2, 5F7 and 3F3, 5F7 and 3F4, and 5F7 and 3F5.

In one embodiment, the molecular scaffold may comprise at least one nucleic acid sequence encoding at least one 5F2 5' flanking region and at least one nucleic acid sequence encoding at least one 3F2 3' flanking region.

In one embodiment, the molecular scaffold may comprise at least one nucleic acid sequence encoding at least one 5F1 5' flanking region and at least one nucleic acid sequence encoding at least one 3F1 3' flanking region.

In one embodiment, the molecular scaffold may comprise at least one nucleic acid sequence encoding at least one 5F7 5' flanking region and at least one nucleic acid sequence encoding at least one 3F5 3' flanking region.

In one embodiment, the molecular scaffold may comprise at least one nucleic acid sequence encoding at least one 5F3 5' flanking region and at least one nucleic acid sequence encoding at least one 3F1 3' flanking region.

In one embodiment, the molecular scaffold may comprise at least one nucleic acid sequence encoding at least one 5F4 5' flanking region and at least one nucleic acid sequence encoding at least one 3F4 3' flanking region.

In one embodiment, the molecular scaffold may comprise at least one nucleic acid sequence encoding at least one 5F5 5' flanking region and at least one nucleic acid sequence encoding at least one 3F4 3' flanking region.

In one embodiment, the molecular scaffold may comprise at least one nucleic acid sequence encoding at least one 5F6 5' flanking region and at least one nucleic acid sequence encoding at least one 3F1 3' flanking region.

In one embodiment, the molecular scaffold may comprise at least one nucleic acid sequence encoding at least one 5F2 5' flanking region and at least one nucleic acid sequence encoding at least one 3F3 3' flanking region.

In one embodiment, the molecular scaffold may comprise at least one nucleic acid sequence encoding at least one 5F3 5' flanking region and at least one nucleic acid sequence encoding at least one 3F4 3' flanking region.

In one embodiment, the molecular scaffold may comprise at least one nucleic acid sequence encoding at least one 5F1 5' flanking region and at least one nucleic acid sequence encoding at least one 3F2 3' flanking region.

In one embodiment, the molecular scaffold may comprise at least one nucleic acid sequence encoding at least one 5' flanking region, at least one nucleic acid sequence encoding at least one loop motif region and at least one nucleic acid sequence encoding at least one 3' flanking region as described in Tables 6-8. As a non-limiting example, the flanking and loop motif regions may be 5F1, L1 and 3F1; 5F1, L1 and 3F2; 5F1, L1 and 3F3; 5F1, L1 and 3F4; 5F1, L1 and 3F5; 5F2, L1 and 3F1; 5F2, L1 and 3F2; 5F2, L1 and 3F3; 5F2, L1 and 3F4; 5F2, L1 and 3F5; 5F3, L1 and 3F3; 5F3, L1 and 3F2; 5F3, L1 and 3F3; 5F3, L1 and 3F4; 5F3, L1 and 3F5; 5F4, L1 and 3F4; 5F4, L1 and 3F2; 5F4, L1 and 3F3; 5F4, L1 and 3F4; 5F4, L1 and 3F5; 5F5, L1 and 3F1; 5F5, L1 and 3F2; 5F5, L1 and 3F3; 5F5, L1 and 3F4; 5F5, L1 and 3F5; 5F6, L1 and 3F1; 5F6, L1 and 3F2; 5F6, L1 and 3F3; 5F6, L1 and 3F4; 5F6, L1 and 3F5; 5F7, L1 and 3F1; 5F7, L1 and 3F2; 5F7, L1 and 3F3; 5F7, L1 and 3F4; 5F7, L1 and 3F5; 5F1, L2 and 3F1; 5F1, L2 and 3F2; 5F1, L2 and 3F3; 5F1, L2 and 3F4; 5F1, L2 and 3F5; 5F2, L2 and 3F1; 5F2, L2 and 3F2; 5F2, L2 and 3F3; 5F2, L2 and 3F4; 5F2, L2 and 3F5; 5F3, L2 and 3F1; 5F3, L2 and 3F2; 5F3, L2 and 3F3; 5F3, L2 and 3F4; 5F3, L2 and 3F5; 5F4, L2 and 3F1; 5F4, L2 and 3F2; 5F4, L2 and 3F3; 5F4, L2 and 3F4; 5F4, L2 and 3F5; 5F5, L2 and 3F1; 5F5, L2 and 3F2; 5F5, L2 and 3F3; 5F5, L2 and 3F4; 5F5, L2 and 3F5; 5F6, L2 and 3F1; 5F6, L2 and 3F2; 5F6, L2 and 3F3; 5F6, L2 and 3F4; 5F6, L2 and 3F5; 5F7, L2 and 3F1; 5F7, L2 and 3F2; 5F7, L2 and 3F3; 5F7, L2 and 3F4; 5F7, L2 and 3F5; 5F1, L3 and 3F1; 5F1, L3 and 3F2; 5F1, L3 and 3F3; 5F1, L3 and 3F4; 5F1, L3 and 3F5; 5F2, L3 and 3F1; 5F2, L3 and 3F2; 5F2, L3 and 3F3; 5F2, L3 and 3F4; 5F2, L3 and 3F5; 5F3, L3 and 3F1; 5F3, L3 and 3F2; 5F3, L3 and 3F3; 5F3, L3 and 3F4; 5F3, L3 and 3F5; 5F4, L3 and 3F1; 5F4, L3 and 3F2; 5F4, L3 and 3F3; 5F4, L3 and 3F4; 5F4, L3 and 3F5; 5F5, L3 and 3F1; 5F5, L3 and 3F2; 5F5, L3 and 3F3; 5F5, L3 and 3F4; 5F5, L3 and 3F5; 5F6, L3 and 3F1; 5F6, L3 and 3F2; 5F6, L3 and 3F3; 5F6, L3 and 3F4; 5F6, L3 and 3F5; 5F7, L3 and 3F1; 5F7, L3 and 3F2; 5F7, L3 and 3F3; 5F7, L3 and 3F4; 5F7, L3 and 3F5; 5F1, L4 and 3F1; 5F1, L4 and 3F2; 5F1, L4 and 3F3; 5F1, L4 and 3F4; 5F1, L4 and 3F5; 5F2, L4 and 3F1; 5F2, L4 and 3F2; 5F2, L4 and 3F3; 5F2, L4 and 3F4; 5F2, L4 and 3F5; 5F3, L4 and 3F1; 5F3, L4 and 3F2; 5F3, L4 and 3F3; 5F3, L4 and 3F4; 5F3, L4 and 3F5; 5F4, L4 and 3F1; 5F4, L4 and 3F2; 5F4, L4 and 3F3; 5F4, L4 and 3F4; 5F4, L4 and 3F5; 5F5, L4 and 3F1; 5F5, L4 and 3F2; 5F5, L4 and 3F3; 5F5, L4 and 3F4; 5F5, L4 and 3F5; 5F6, L4 and 3F1; 5F6, L4 and 3F2; 5F6, L4 and 3F3; 5F6, L4 and 3F4; 5F6, L4 and 3F5; 5F7, L4 and 3F1; 5F7, L4 and 3F2; 5F7, L4 and 3F3; 5F7, L4 and 3F4; 5F7, L4 and 3F5; 5F1, L5 and 3F1; 5F1, L5 and 3F2; 5F1, L5 and 3F3; 5F1, L5 and 3F4; 5F1, L5 and 3F5; 5F2, L5 and 3F1; 5F2, L5 and 3F2; 5F2, L5 and 3F3; 5F2, L5 and 3F4; 5F2, L5 and 3F5; 5F3, L5 and 3F1; 5F3, L5 and 3F2; 5F3, L5 and 3F3; 5F3, L5 and 3F4; 5F3, L5 and 3F5; 5F4, L5 and 3F1; 5F4, L5 and 3F2; 5F4, L5 and 3F3; 5F4, L5 and 3F4; 5F4, L5 and 3F5; 5F5, L5 and 3F1; 5F5, L5 and 3F2; 5F5, L5 and 3F3; 5F5, L5 and 3F4; 5F5, L5 and 3F5; 5F6, L5 and 3F1; 5F6, L5 and 3F2; 5F6, L5 and 3F3; 5F6, L5 and 3F4; 5F6, L5 and 3F5; 5F7, L5 and 3F1; 5F7, L5 and 3F2; 5F7, L5 and 3F3; 5F7, L5 and 3F4; 5F7, L5 and 3F5; 5F1, L6 and 3F1; 5F1, L6 and 3F2; 5F1, L6 and 3F3; 5F1, L6 and 3F4; 5F1, L6 and 3F5; 5F2, L6 and 3F1; 5F2, L6 and 3F2; 5F2, L6 and 3F3; 5F2, L6 and 3F4; 5F2, L6 and 3F5; 5F3, L6 and 3F1; 5F3, L6 and 3F2; 5F3, L6 and 3F3; 5F3, L6 and 3F4; 5F3, L6 and 3F5; 5F4, L6 and 3F1; 5F4, L6 and 3F2; 5F4, L6 and 3F3; 5F4, L6 and 3F4; 5F4, L6 and 3F5; 5F5, L6 and 3F1; 5F5, L6 and 3F2; 5F5, L6 and 3F3; 5F5, L6 and 3F4; 5F5, L6 and 3F5; 5F6, L6 and 3F1; 5F6, L6 and 3F2; 5F6, L6 and 3F3; 5F6, L6 and 3F4; 5F6, L6 and 3F5; 5F7, L6 and 3F1; 5F7, L6 and 3F2; 5F7, L6 and 3F3; 5F7, L6 and 3F4; 5F7, L6 and 3F5; 5F1, L7 and 3F1; 5F1, L7 and 3F2; 5F1, L7 and 3F3; 5F1, L7 and 3F4; 5F1, L7 and 3F5; 5F2, L7 and 3F1; 5F2, L7 and 3F2; 5F2, L7 and 3F3; 5F2, L7 and 3F4; 5F2, L7 and 3F5; 5F3, L7 and 3F1; 5F3, L7 and 3F2; 5F3, L7 and 3F3; 5F3, L7 and 3F4; 5F3, L7 and 3F5; 5F4, L7 and 3F1; 5F4, L7 and 3F2; 5F4, L7 and 3F3; 5F4, L7 and 3F4; 5F4, L7 and 3F5; 5F5, L7 and 3F1; 5F5, L7 and 3F2; 5F5, L7 and 3F3; 5F5, L7 and 3F4; 5F5, L7 and 3F5; 5F6, L7 and 3F1; 5F6, L7 and 3F2; 5F6, L7 and 3F3; 5F6, L7 and 3F4; 5F6, L7 and 3F5; 5F7, L7 and 3F1; 5F7, L7 and 3F2; 5F7, L7 and 3F3; 5F7, L7 and 3F4; 5F7, L7 and 3F5; 5F1, L8 and 3F1; 5F1, L8 and 3F2; 5F1, L8 and 3F3; 5F1, L8 and 3F4; 5F1, L8 and 3F5; 5F2, L8 and 3F1; 5F2, L8 and 3F2; 5F2, L8 and 3F3; 5F2, L8 and 3F4; 5F2, L8 and 3F5; 5F3, L8 and 3F1; 5F3, L8 and 3F2; 5F3, L8 and 3F3; 5F3, L8 and 3F4; 5F3, L8 and 3F5; 5F4, L8 and 3F1; 5F4, L8 and 3F2; 5F4, L8 and 3F3; 5F4, L8 and 3F4; 5F4, L8 and 3F5; 5F5, L8 and 3F1; 5F5, L8 and 3F2; 5F5, L8 and 3F3; 5F5, L8 and 3F4; 5F5, L8 and 3F5; 5F6, L8 and 3F1; 5F6, L8 and 3F2; 5F6, L8 and 3F3; 5F6, L8 and 3F4; 5F6, L8 and 3F5; 5F7, L8 and 3F1; 5F7, L8 and 3F2; 5F7, L8 and 3F3; 5F7, L8 and 3F4; and 5F7, L8 and 3F5.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F1 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F7 5' flanking region, at least one nucleic acid sequence encoding at least one L8 loop motif region, and at least one nucleic acid sequence encoding at least one 3F5 3' flanking region.

In one embodiment, the molecular scaffold may comprise at least one nucleic acid sequence encoding at least one 5F3 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F3 5' flanking region, at least one nucleic acid sequence encoding at least one L5 loop motif region, and at least one nucleic acid sequence encoding at least one 3F1 3' flanking region.

In one embodiment, the molecular scaffold may comprise at least one nucleic acid sequence encoding at least one 5F4 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F3 5' flanking region, at least one nucleic acid sequence encoding at least one L7 loop motif region, and at least one nucleic acid sequence encoding at least one 3F1 3' flanking region.

In one embodiment, the molecular scaffold may comprise at least one nucleic acid sequence encoding at least one 5F5 5' flanking region, at least one nucleic acid sequence encoding at least one L4 loop motif region, and at least one nucleic acid sequence encoding at least one 3F4 3' flanking region.

In one embodiment, the molecular scaffold may comprise at least one nucleic acid sequence encoding at least one 5F6 5' flanking region, at least one nucleic acid sequence encoding at least one L4 loop motif region, and at least one nucleic acid sequence encoding at least one 3F1 3' flanking region.

In one embodiment, the molecular scaffold may comprise at least one nucleic acid sequence encoding at least one 5F3 5' flanking region, at least one nucleic acid sequence encoding at least one L6 loop motif region, and at least one nucleic acid sequence encoding at least one 3F1 3' flanking region.

In one embodiment, the molecular scaffold may comprise at least one nucleic acid sequence encoding at least one 5F7 5' flanking region, at least one nucleic acid sequence encoding at least one L4 loop motif region, and at least one nucleic acid sequence encoding at least one 3F5 3' flanking region.

In one embodiment, the molecular scaffold may comprise at least one nucleic acid sequence encoding at least one 5F2 5' flanking region, at least one nucleic acid sequence encoding at least one L2 loop motif region, and at least one nucleic acid sequence encoding at least one 3F2 3' flanking region.

In one embodiment, the molecular scaffold may comprise at least one nucleic acid sequence encoding at least one 5F2 5' flanking region, at least one nucleic acid sequence encoding at least one L1 loop motif region, and at least one nucleic acid sequence encoding at least one 3F3 3' flanking region.

In one embodiment, the molecular scaffold may comprise at least one nucleic acid sequence encoding at least one 5F3

5' flanking region, at least one nucleic acid sequence encoding at least one L5 loop motif region, and at least one nucleic acid sequence encoding at least one 3F4 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F1 3' flanking region.

In one embodiment, the molecular scaffold may comprise at least one nucleic acid sequence encoding at least one 5F1 5' flanking region, at least one nucleic acid sequence encoding at least one L2 loop motif region, and at least one nucleic acid sequence encoding at least one 3F1 3' flanking region.

In one embodiment, the molecular scaffold may comprise at least one nucleic acid sequence encoding at least one 5F1 5' flanking region, at least one nucleic acid sequence encoding at least one L1 loop motif region, and at least one nucleic acid sequence encoding at least one 3F2 3' flanking region.

In one embodiment, the molecular scaffold may comprise at least one nucleic acid sequence encoding at least one 5F2 5' flanking region, at least one nucleic acid sequence encoding at least one L3 loop motif region, and at least one nucleic acid sequence encoding at least one 3F3 3' flanking region.

In one embodiment, the modulatory polynucleotide may comprise nucleic acid sequences encoding 5' and 3' flanking regions, loop motif region, sense sequence and antisense sequence as described in Tables 9 and 10. In Tables 9 and 10, the passenger and guide strands are described as well as the 5' and 3' Flanking Regions and the Loop region (also referred to as the linker region). In Tables 9 and 10, the "miR" component of the name of the sequence does not necessarily correspond to the sequence numbering of miRNA genes (e.g., VOYHTmiR-102 is the name of the sequence and does not necessarily mean that miR-102 is part of the sequence).

TABLE 9

Pri-miRNA Cassettes Containing Passenger and Guide Sequences (5'-3')

| Name | 5' Flanking to 3' Flanking SEQ ID NO | 5' Flanking SEQ ID NO | Passenger SEQ ID NO | Loop (Linker) SEQ ID NO | Guide SEQ ID NO | 3' Flanking SEQ ID NO |
|---|---|---|---|---|---|---|
| VOYHTmiR-102.214 | 270 | 250 | 120 | 257 | 11 | 265 |
| VOYHTmiR-104.214 | 271 | 250 | 127 | 257 | 11 | 265 |
| VOYHTmiR-109.214 | 272 | 250 | 135 | 258 | 11 | 265 |
| VOYHTmiR-114.214 | 273 | 250 | 145 | 257 | 11 | 266 |
| VOYHTmiR-116.214 | 274 | 250 | 135 | 257 | 11 | 266 |
| VOYHTmiR-127.214 | 275 | 251 | 135 | 259 | 5 | 267 |
| VOYHTmiR-102.218 | 276 | 250 | 121 | 257 | 13 | 265 |
| VOYHTmiR-104.218 | 277 | 250 | 128 | 257 | 13 | 265 |
| VOYHTmiR-109.218 | 278 | 250 | 137 | 258 | 13 | 265 |
| VOYHTmiR-114.218 | 279 | 250 | 146 | 257 | 13 | 266 |
| VOYHTmiR-116.218 | 280 | 250 | 137 | 257 | 13 | 266 |
| VOYHTmiR-127.218 | 281 | 251 | 137 | 259 | 13 | 267 |
| VOYHTmiR-102.219.o | 282 | 250 | 103 | 257 | 3 | 265 |
| VOYHTmiR-104.219.o | 283 | 250 | 106 | 257 | 3 | 265 |
| VOYHTmiR-109.219.o | 284 | 250 | 103 | 258 | 3 | 265 |
| VOYHTmiR-114.219 | 285 | 250 | 109 | 257 | 3 | 266 |
| VOYHTmiR-116.219.o | 286 | 250 | 112 | 257 | 3 | 266 |
| VOYHTmiR-127.219.o | 287 | 251 | 103 | 259 | 3 | 267 |
| VOYHTmiR-102.219.n | 288 | 250 | 116 | 257 | 3 | 265 |
| VOYHTmiR-104.219.n | 289 | 250 | 117 | 257 | 3 | 265 |
| VOYHTmiR-109.219.n | 290 | 250 | 116 | 258 | 3 | 265 |
| VOYHTmiR-116.219.n | 291 | 250 | 118 | 257 | 3 | 266 |
| VOYHTmiR-127.219.n | 292 | 251 | 116 | 259 | 3 | 267 |
| VOYHTmiR-102.257 | 293 | 250 | 122 | 257 | 15 | 265 |
| VOYHTmiR-104.257 | 294 | 250 | 129 | 257 | 15 | 265 |
| VOYHTmiR-109.257 | 295 | 250 | 138 | 258 | 15 | 265 |
| VOYHTmiR-114.257 | 296 | 250 | 147 | 257 | 15 | 266 |
| VOYHTmiR-116.257 | 297 | 250 | 138 | 257 | 15 | 266 |
| VOYHTmiR-127.257 | 298 | 251 | 138 | 259 | 15 | 267 |
| VOYHTmiR-102.894 | 299 | 250 | 104 | 257 | 5 | 265 |
| VOYHTmiR-104.894 | 300 | 250 | 107 | 257 | 5 | 265 |
| VOYHTmiR-109.894 | 301 | 250 | 104 | 258 | 5 | 265 |
| VOYHTmiR-114.894 | 302 | 250 | 110 | 257 | 5 | 266 |
| VOYHTmiR-116.894 | 303 | 250 | 113 | 257 | 5 | 266 |
| VOYHTmiR-127.894 | 304 | 251 | 104 | 259 | 5 | 267 |
| VOYHTmiR-102.907 | 305 | 250 | 125 | 257 | 21 | 265 |
| VOYHTmiR-104.907 | 306 | 250 | 132 | 257 | 21 | 265 |
| VOYHTmiR-109.907 | 307 | 250 | 142 | 258 | 21 | 265 |
| VOYHTmiR-114.907 | 308 | 250 | 150 | 257 | 21 | 266 |
| VOYHTmiR-116.907 | 309 | 250 | 142 | 257 | 21 | 266 |
| VOYHTmiR-127.907 | 310 | 251 | 142 | 259 | 21 | 267 |
| VOYHTmiR-102.372 | 311 | 250 | 123 | 257 | 17 | 265 |
| VOYHTmiR-104.372 | 312 | 250 | 130 | 257 | 17 | 265 |
| VOYHTmiR-109.372 | 313 | 250 | 139 | 258 | 17 | 265 |
| VOYHTmiR-114.372 | 314 | 250 | 148 | 257 | 17 | 266 |
| VOYHTmiR-116.372 | 315 | 250 | 139 | 257 | 17 | 266 |
| VOYHTmiR-127.372 | 316 | 251 | 139 | 259 | 17 | 267 |
| VOYHTmiR-102.425 | 317 | 250 | 124 | 257 | 19 | 265 |
| VOYHTmiR-104.425 | 318 | 250 | 131 | 257 | 19 | 265 |
| VOYHTmiR-109.425 | 319 | 250 | 140 | 258 | 19 | 265 |
| VOYHTmiR-114.425 | 320 | 250 | 149 | 257 | 19 | 266 |

TABLE 9-continued

Pri-miRNA Cassettes Containing Passenger and Guide Sequences (5'-3')

| Name | 5' Flanking to 3' Flanking SEQ ID NO | 5' Flanking SEQ ID NO | Passenger SEQ ID NO | Loop (Linker) SEQ ID NO | Guide SEQ ID NO | 3' Flanking SEQ ID NO |
|---|---|---|---|---|---|---|
| VOYHTmiR-116.425 | 321 | 250 | 140 | 257 | 19 | 266 |
| VOYHTmiR-127.425 | 322 | 251 | 140 | 259 | 19 | 267 |
| VOYHTmiR-102.032 | 323 | 250 | 152 | 257 | 25 | 265 |
| VOYHTmiR-104.032 | 324 | 250 | 154 | 257 | 25 | 265 |
| VOYHTmiR-109.032 | 325 | 250 | 157 | 258 | 25 | 265 |
| VOYHTmiR-114.032 | 326 | 250 | 160 | 257 | 25 | 266 |
| VOYHTmiR-116.032 | 327 | 250 | 157 | 257 | 25 | 266 |
| VOYHTmiR-127.032 | 328 | 251 | 157 | 259 | 25 | 267 |
| VOYHTmiR-102.020 | 329 | 250 | 151 | 257 | 23 | 265 |
| VOYHTmiR-104.020 | 330 | 250 | 153 | 257 | 23 | 265 |
| VOYHTmiR-109.020 | 331 | 250 | 155 | 258 | 23 | 265 |
| VOYHTmiR-114.020 | 332 | 250 | 159 | 257 | 23 | 266 |
| VOYHTmiR-116.020 | 333 | 250 | 155 | 257 | 23 | 266 |
| VOYHTmiR-127.020 | 334 | 251 | 155 | 259 | 23 | 267 |
| VOYHTmiR-102.016 | 335 | 250 | 119 | 257 | 9 | 265 |
| VOYHTmiR-104.016 | 336 | 250 | 126 | 257 | 9 | 265 |
| VOYHTmiR-109.016 | 337 | 250 | 133 | 258 | 9 | 265 |
| VOYHTmiR-114.016 | 338 | 250 | 144 | 257 | 9 | 266 |
| VOYHTmiR-116.016 | 339 | 250 | 133 | 257 | 9 | 266 |
| VOYHTmiR-127.016 | 340 | 251 | 133 | 259 | 9 | 267 |
| VOYHTmiR-102.579 | 341 | 250 | 105 | 257 | 7 | 265 |
| VOYHTmiR-104.579 | 342 | 250 | 108 | 257 | 7 | 265 |
| VOYHTmiR-109.579 | 343 | 250 | 105 | 258 | 7 | 265 |
| VOYHTmiR-114.579 | 344 | 250 | 111 | 257 | 7 | 266 |
| VOYHTmiR-116.579 | 345 | 250 | 114 | 257 | 7 | 266 |
| VOYHTmiR-127.579 | 346 | 251 | 105 | 259 | 7 | 267 |
| VOYHTmiR-104.579.1 | 347 | 250 | 168 | 260 | 7 | 265 |
| VOYHTmiR-104.579.2 | 348 | 252 | 168 | 260 | 7 | 265 |
| VOYHTmiR-104.579.3 | 349 | 252 | 168 | 261 | 7 | 265 |
| VOYHTmiR-104.579.4 | 350 | 253 | 168 | 260 | 7 | 268 |
| VOYHTmiR-104.579.6 | 351 | 254 | 168 | 260 | 7 | 268 |
| VOYHTmiR-104.579.7 | 352 | 255 | 168 | 260 | 29 | 265 |
| VOYHTmiR-104.579.8 | 353 | 252 | 169 | 262 | 7 | 265 |
| VOYHTmiR-104.579.9 | 354 | 256 | 168 | 260 | 7 | 269 |
| VOYHTmiR-102.020 | 355 | 250 | 151 | 257 | 23 | 265 |
| VOYHTmiR-102.032 | 356 | 250 | 152 | 257 | 25 | 265 |
| VOYHTmiR-104.020 | 357 | 250 | 153 | 257 | 23 | 265 |
| VOYHTmiR-104.032 | 358 | 250 | 154 | 257 | 25 | 265 |
| VOYHTmiR-109.020 | 359 | 250 | 155 | 258 | 23 | 265 |
| VOYHTmiR-109.032 | 360 | 250 | 157 | 258 | 25 | 265 |
| VOYHTmiR-114.020 | 361 | 250 | 159 | 257 | 23 | 266 |
| VOYHTmiR-114.032 | 362 | 250 | 160 | 257 | 25 | 266 |
| VOYHTmiR-116.020 | 363 | 250 | 155 | 257 | 23 | 266 |
| VOYHTmiR-116.032 | 364 | 250 | 157 | 257 | 25 | 266 |
| VOYHTmiR-127.020 | 365 | 251 | 155 | 259 | 23 | 267 |
| VOYHTmiR-127.032 | 366 | 251 | 157 | 259 | 25 | 267 |

TABLE 10

Pri-miRNA Cassettes Containing Guide and Passenger Sequences (5'-3')

| Name | 5' Flanking to 3' Flanking SEQ ID NO | 5' Flanking SEQ ID NO | Guide SEQ ID NO | Loop SEQ ID NO | Passenger SEQ ID NO | 3' Flanking SEQ ID NO |
|---|---|---|---|---|---|---|
| VOYHTmiR-104.579.5 | 367 | 252 | 170 | 263 | 30 | 265 |
| VOYHTmiR-104.579.10 | 368 | 256 | 171 | 264 | 7 | 279 |

In one embodiment, the molecular scaffold may comprise one or more linkers known in the art. The linkers may separate regions or one molecular scaffold from another. As a non-limiting example, the molecular scaffold may be polycistronic.

In one embodiment, the modulatory polynucleotide is designed using at least one of the following properties: loop variant, seed mismatch/bulge/wobble variant, stem mismatch, loop variant and vassal stem mismatch variant, seed mismatch and basal stem mismatch variant, stem mismatch and basal stem mismatch variant, seed wobble and basal stem wobble variant, or a stem sequence variant.

In one embodiment, the molecular scaffold may be a natural pri-miRNA scaffold. As a non-limiting example, the molecular scaffold may be a scaffold derived from the human miR155 scaffold.

In one embodiment, the molecular scaffold may be located downstream of a CMV promoter, fragment or variant thereof.

In one embodiment, the molecular scaffold may be located downstream of a CBA promoter, fragment or variant thereof.

In one embodiment, the molecular scaffold may be a natural pri-miRNA scaffold located downstream of a CMV promoter. As a non-limiting example, the natural pri-miRNA scaffold is derived from the human miR155 scaffold.

In one embodiment, the molecular scaffold may be a natural pri-miRNA scaffold located downstream of a CBA promoter.

In one embodiment, the selection of a molecular scaffold and modulatory polynucleotide is determined by a method of comparing modulatory polynucleotides in pri-miRNA (see e.g., the method described by Miniarikova et al. *Design, Characterization, and Lead Selection of Therapeutic miR-NAs Targeting Huntingtin for Development of Gene Therapy for Huntington's Disease*. Molecular Therapy-Nucleic Acids (2016) 5, e297 and International Publication No. WO2016102664; the contents of each of which are herein incorporated by reference in their entireties). The modulatory polynucleotide may, but it not limited to, targeting exon 1, CAG repeats, SNP rs362331 in exon 50 and/or SNP rs362307 in exon 67. To evaluate the activities of the modulatory polynucleotides, the molecular scaffold used which may be used is a human pri-miRNA scaffold (e.g., miR155 scaffold) and the promoter may be CMV. The activity may be determined in vitro using HEK293T cells and a reporter (e.g., Luciferase). For exon 1 targeting, the modulatory polynucleotide is determined to be efficient at HTT knockdown if the knockdown is 80% or greater. For CAG targeting, the modulatory polynucleotide is determined to be efficient at HTT knockdown if the knockdown is at least 60%. For SNP targeting, the modulatory polynucleotide is determined to be efficient at HTT knockdown if the knockdown is at least 60%. For allele selectivity for CAG repeats or SNP targeting the modulatory polynucleotides may comprise at least 1 substitution in order to improve allele selectivity. As a non-limiting example, substitution may be a G or C replaced with a T or corresponding U and A or T/U replaced by a C.

In order to evaluate the optimal molecular scaffold for the modulatory polynucleotide, the modulatory polynucleotide is used in pri-miRNA scaffolds with a CAG promoter. The constructs are co-transfected with a reporter (e.g., luciferase reporter) at 50 ng. Constructs with greater than 80% knockdown at 50 ng co-transfection are considered efficient. In one aspect, the constructs with strong guide-strand activity are preferred. In one aspect, the constructs with strong passenger-strand activity are preferred. The molecular scaffolds can be processed in HEK293T cells by NGS to determine guide-passenger ratios, and processing variability.

To evaluate the molecular scaffolds and modulatory polynucleotides in vivo the molecular scaffolds comprising the modulatory polynucleotides are packaged in AAV (e.g., the serotype may be AAV5 (see e.g., the method and constructs described in WO2015060722, the contents of which are herein incorporated by reference in their entirety)) and administered to an in vivo model (e.g., Hu128/21 HD mouse) and the guide-passenger ratios, 5' and 3' end processing, reversal of guide and passenger strands, and knockdown can be determined in different areas of the model.

In one embodiment, the selection of a molecular scaffold and modulatory polynucleotide is determined by a method of comparing modulatory polynucleotides in natural pri-miRNA and synthetic pri-miRNA. The modulatory polynucleotide may, but it not limited to, targeting an exon other than exon 1. To evaluate the activities of the modulatory polynucleotides, the molecular scaffold is used with a CBA promoter. In one aspect, the activity may be determined in vitro using HEK293T cells, HeLa cell and a reporter (e.g., Luciferase) and knockdown efficient modulatory polynucleotides showed HTT knockdown of at least 80% in the cell tested. Additionally, the modulatory polynucleotides which are considered most efficient showed low to no significant passenger strand (p-strand) activity. In another aspect, the endogenous HTT knockdown efficacy is evaluated by transfection in vitro using HEK293T cells, HeLa cell and a reporter. Efficient modulatory polynucleotides show greater than 50% endogenous HTT knockdown. In yet another aspect, the endogenous HTT knockdown efficacy is evaluated in different cell types (e.g., HEK293, HeLa, primary astrocytes, U251 astrocytes, SH—SY5Y neuron cells and fibroblasts from HD patients) by infection (e.g., AAV2). Efficient modulatory polynucleotides show greater than 60% endogenous HTT knockdown.

To evaluate the molecular scaffolds and modulatory polynucleotides in vivo the molecular scaffolds comprising the modulatory polynucleotides are packaged in AAV and administered to an in vivo model (e.g., YAC128 HD mouse) and the guide-passenger ratios, 5' and 3' end processing, ratio of guide to passenger strands, and knockdown can be determined in different areas of the model (e.g., tissue regions). The molecular scaffolds can be processed from in vivo samples by NGS to determine guide-passenger ratios, and processing variability.

Vectors

In some embodiments, the siRNA molecules described herein can be encoded by vectors such as plasmids or viral vectors. In one embodiment, the siRNA molecules are encoded by viral vectors. Viral vectors may be, but are not limited to, Herpesvirus (HSV) vectors, retroviral vectors, adenoviral vectors, adeno-associated viral vectors, lentiviral vectors, and the like. In some specific embodiments, the viral vectors are AAV vectors.

Retroviral Vectors

In some embodiments, the siRNA duplex targeting HTT gene may be encoded by a retroviral vector (See, e.g., U.S. Pat. Nos. 5,399,346; 5,124,263; 4,650,764 and 4,980,289; the content of each of which are incorporated herein by reference in their entirety).

Adenoviral Vectors

Adenoviruses are eukaryotic DNA viruses that can be modified to efficiently deliver a nucleic acid to a variety of cell types in vivo, and have been used extensively in gene therapy protocols, including for targeting genes to neural cells. Various replication defective adenovirus and minimum adenovirus vectors have been described for nucleic acid therapeutics (See, e.g., PCT Patent Publication Nos. WO199426914, WO 199502697, WO199428152, WO199412649, WO199502697 and WO199622378; the content of each of which is incorporated by reference in their entirety). Such adenoviral vectors may also be used to deliver siRNA molecules of the present invention to cells.

Adeno-Associated Viral (AAV) Vectors

An adeno-associated virus (AAV) is a dependent parvovirus (like other parvoviruses) which is a single stranded non-enveloped DNA virus having a genome of about 5000 nucleotides in length and which contains two open reading frames encoding the proteins responsible for replication (Rep) and the structural protein of the capsid (Cap). The open reading frames are flanked by two Inverted Terminal Repeat (ITR) sequences, which serve as the origin of replication of the viral genome. Furthermore, the AAV genome contains a packaging sequence, allowing packaging of the viral genome into an AAV capsid. The AAV vector requires a co-helper (e.g., adenovirus) to undergo productive infection in infected cells. In the absence of such helper functions, the AAV virions essentially enter host cells but do not integrate into the cells' genome.

AAV vectors have been investigated for siRNA delivery because of several unique features. Non-limiting examples of the features include (i) the ability to infect both dividing and non-dividing cells; (ii) a broad host range for infectivity, including human cells; (iii) wild-type AAV has not been associated with any disease and has not been shown to replicate in infected cells; (iv) the lack of cell-mediated immune response against the vector and (v) the non-integrative nature in a host chromosome thereby reducing potential for long-term genetic alterations. Moreover, infection with AAV vectors has minimal influence on changing the pattern of cellular gene expression (Stilwell and Samulski et al., *Biotechniques,* 2003, 34, 148).

Typically, AAV vectors for siRNA delivery may be recombinant viral vectors which are replication defective as they lack sequences encoding functional Rep and Cap proteins within the viral genome. In some cases, the defective AAV vectors may lack most or all coding sequences and essentially only contains one or two AAV ITR sequences and a packaging sequence.

In one embodiment, the AAV vectors comprising a nucleic acid sequence encoding the siRNA molecules of the present invention may be introduced into mammalian cells.

AAV vectors may be modified to enhance the efficiency of delivery. Such modified AAV vectors comprising the nucleic acid sequence encoding the siRNA molecules of the present invention can be packaged efficiently and can be used to successfully infect the target cells at high frequency and with minimal toxicity.

In some embodiments, the AAV vector comprising a nucleic acid sequence encoding the siRNA molecules of the present invention may be a human serotype AAV vector. Such human AAV vector may be derived from any known serotype, e.g., from any one of serotypes AAV1-AAV11. As non-limiting examples, AAV vectors may be vectors comprising an AAV1-derived genome in an AAV1-derived capsid; vectors comprising an AAV2-derived genome in an AAV2-derived capsid; vectors comprising an AAV4-derived genome in an AAV4 derived capsid; vectors comprising an AAV6-derived genome in an AAV6 derived capsid or vectors comprising an AAV9-derived genome in an AAV9 derived capsid.

In other embodiments, the AAV vector comprising a nucleic acid sequence for encoding siRNA molecules of the present invention may be a pseudotyped hybrid or chimeric AAV vector which contains sequences and/or components originating from at least two different AAV serotypes. Pseudotyped AAV vectors may be vectors comprising an AAV genome derived from one AAV serotype and a capsid protein derived at least in part from a different AAV serotype. As non-limiting examples, such pseudotyped AAV vectors may be vectors comprising an AAV2-derived genome in an AAV1-derived capsid; or vectors comprising an AAV2-derived genome in an AAV6-derived capsid; or vectors comprising an AAV2-derived genome in an AAV4-derived capsid; or an AAV2-derived genome in an AAV9-derived capsid. In like fashion, the present invention contemplates any hybrid or chimeric AAV vector.

In other embodiments, AAV vectors comprising a nucleic acid sequence encoding the siRNA molecules of the present invention may be used to deliver siRNA molecules to the central nervous system (e.g., U.S. Pat. No. 6,180,613; the contents of which is herein incorporated by reference in its entirety).

In some aspects, the AAV vectors comprising a nucleic acid sequence encoding the siRNA molecules of the present invention may further comprise a modified capsid including peptides from non-viral origin. In other aspects, the AAV vector may contain a CNS specific chimeric capsid to facilitate the delivery of encoded siRNA duplexes into the brain and the spinal cord. For example, an alignment of cap nucleotide sequences from AAV variants exhibiting CNS tropism may be constructed to identify variable region (VR) sequence and structure.

In one embodiment, the AAV vector comprising a nucleic acid sequence encoding the siRNA molecules of the present invention may encode siRNA molecules which are polycistronic molecules. The siRNA molecules may additionally comprise one or more linkers between regions of the siRNA molecules.

Self-Complementary and Single Strand Vectors

In one embodiment, the AAV vector used in the present invention is a single strand vector (ssAAV).

In another embodiment, the AAV vectors may be self-complementary AAV vectors (scAAVs). scAAV vectors contain both DNA strands which anneal together to form double stranded DNA. By skipping second strand synthesis, scAAVs allow for rapid expression in the cell.

In one embodiment, the AAV vector used in the present invention is a scAAV.

Methods for producing and/or modifying AAV vectors are disclosed in the art such as pseudotyped AAV vectors (International Patent Publication Nos. WO200028004; WO200123001; WO2004112727; WO 2005005610 and WO 2005072364, the content of each of which are incorporated herein by reference in their entirety).

AAV Serotypes

AAV particles of the present invention may comprise or be derived from any natural or recombinant AAV serotype. According to the present invention, the AAV particles may utilize or be based on a serotype selected from any of the following AAV1, AAV2, AAV2G9, AAV3, AAV3a, AAV3b, AAV3-3, AAV4, AAV4-4, AAV5, AAV6, AAV6.1, AAV6.2, AAV6.1.2, AAV7, AAV7.2, AAV8, AAV9, AAV9.11, AAV9.13, AAV9.16, AAV9.24, AAV9.45, AAV9.47, AAV9.61, AAV9.68, AAV9.84, AAV9.9, AAV10, AAV11, AAV12, AAV16.3, AAV24.1, AAV27.3, AAV42.12, AAV42-1b, AAV42-2, AAV42-3a, AAV42-3b, AAV42-4, AAV42-5a, AAV42-5b, AAV42-6b, AAV42-8, AAV42-10, AAV42-11, AAV42-12, AAV42-13, AAV42-15, AAV42-aa, AAV43-1, AAV43-12, AAV43-20, AAV43-21, AAV43-23, AAV43-25, AAV43-5, AAV44.1, AAV44.2, AAV44.5, AAV223.1, AAV223.2, AAV223.4, AAV223.5, AAV223.6, AAV223.7, AAV1-7/rh.48, AAV1-8/rh.49, AAV2-15/rh.62, AAV2-3/rh.61, AAV2-4/rh.50, AAV2-5/rh.51, AAV3.1/hu.6, AAV3.1/hu.9, AAV3-9/rh.52, AAV3-11/rh.53, AAV4-8/r11.64, AAV4-9/rh.54, AAV4-19/rh.55, AAV5-3/rh.57, AAV5-22/rh.58, AAV7.3/hu.7, AAV16.8/hu.10, AAV16.12/hu.11, AAV29.3/bb.1, AAV29.5/bb.2, AAV106.1/hu.37, AAV114.3/hu.40, AAV127.2/hu.41, AAV127.5/hu.42, AAV128.3/hu.44, AAV130.4/hu.48, AAV145.1/hu.53, AAV145.5/hu.54, AAV145.6/hu.55, AAV161.10/hu.60, AAV161.6/hu.61, AAV33.12/hu.17, AAV33.4/hu.15, AAV33.8/hu.16, AAV52/hu.19, AAV52.1/hu.20, AAV58.2/hu.25, AAVA3.3, AAVA3.4, AAVA3.5, AAVA3.7, AAVC1, AAVC2, AAVC5, AAV-DJ, AAV-DJ8, AAVF3, AAVF5, AAVH2, AAVrh.72, AAVhu.8, AAVrh.68, AAVrh.70, AAVpi.1, AAVpi.3, AAVpi.2, AAVrh.60, AAVrh.44, AAVrh.65, AAVrh.55, AAVrh.47, AAVrh.69, AAVrh.45, AAVrh.59, AAVhu.12, AAVH6, AAVLK03, AAVH-1/hu.1, AAVH-5/hu.3, AAVLG-10/rh.40, AAVLG-4/rh.38, AAVLG-9/hu.39, AAVN721-8/rh.43, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAVhu.1, AAVhu.2, AAVhu.3, AAVhu.4, AAVhu.5, AAVhu.6, AAVhu.7, AAVhu.9, AAVhu.10, AAVhu.11, AAVhu.13, AAVhu.15, AAVhu.16, AAVhu.17, AAVhu.18, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.31, AAVhu.32, AAVhu.34, AAVhu.35, AAVhu.37, AAVhu.39, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.51, AAVhu.52, AAVhu.54, AAVhu.55, AAVhu.56, AAVhu.57, AAVhu.58, AAVhu.60, AAVhu.61, AAVhu.63, AAVhu.64, AAVhu.66, AAVhu.67, AAVhu.14/9, AAVhu.t 19, AAVrh.2, AAVrh.2R, AAVrh.8, AAVrh.8R, AAVrh.10, AAVrh.12, AAVrh.13, AAVrh.13R, AAVrh.14, AAVrh.17, AAVrh.18, AAVrh.19, AAVrh.20, AAVrh.21, AAVrh.22, AAVrh.23, AAVrh.24, AAVrh.25, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.46, AAVrh.48, AAVrh.48.1, AAVrh.48.1.2, AAVrh.48.2, AAVrh.49, AAVrh.51, AAVrh.52, AAVrh.53, AAVrh.54, AAVrh.56, AAVrh.57, AAVrh.58, AAVrh.61, AAVrh.64, AAVrh.64R1, AAVrh.64R2, AAVrh.67, AAVrh.73, AAVrh.74, AAVrh8R, AAVrh8R A586R mutant, AAVrh8R R533A mutant, AAAV, BAAV, caprine AAV, bovine AAV, AAVhE1.1, AAVhEr1.5, AAVhER1.14, AAVhEr1.8, AAVhEr1.16, AAVhEr1.18, AAVhEr1.35, AAVhEr1.7, AAVhEr1.36, AAVhEr2.29, AAVhEr2.4, AAVhEr2.16, AAVhEr2.30, AAVhEr2.31, AAVhEr2.36, AAVhER1.23, AAVhEr3.1, AAV2.5T, AAV-PAEC, AAV-LK01, AAV-LK02, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK16, AAV-LK17, AAV-LK18, AAV-LK19, AAV-PAEC2, AAV-PAEC4, AAV-PAEC6, AAV-PAEC7, AAV-PAEC8, AAV-PAEC11, AAV-PAEC12, AAV-2-pre-miRNA-101, AAV-8h, AAV-8b, AAV-h, AAV-b, AAV SM 10-2, AAV Shuffle 100-1, AAV Shuffle 100-3, AAV Shuffle 100-7, AAV Shuffle 10-2, AAV Shuffle 10-6, AAV Shuffle 10-8, AAV Shuffle 100-2, AAV SM 10-1, AAV SM 10-8, AAV SM 100-3, AAV SM 100-10, BNP61 AAV, BNP62 AAV, BNP63 AAV, AAVrh.50, AAVrh.43, AAVrh.62, AAVrh.48, AAVhu.19, AAVhu.11, AAVhu.53, AAV4-8/rh.64, AAVLG-9/hu.39, AAV54.5/hu.23, AAV54.2/hu.22, AAV54.7/hu.24, AAV54.1/hu.21, AAV54.4R/hu.27, AAV46.2/hu.28, AAV46.6/hu.29, AAV128.1/hu.43, true type AAV (ttAAV), UPENN AAV 10, Japanese AAV 10 serotypes, AAV CBr-7.1, AAV CBr-7.10, AAV CBr-7.2, AAV CBr-7.3, AAV CBr-7.4, AAV CBr-7.5, AAV CBr-7.7, AAV CBr-7.8, AAV CBr-B7.3, AAV CBr-B7.4, AAV CBr-E1, AAV CBr-E2, AAV CBr-E3, AAV CBr-E4, AAV CBr-E5, AAV CBr-e5, AAV CBr-E6, AAV CBr-E7, AAV CBr-E8, AAV CHt-1, AAV CHt-2, AAV CHt-3, AAV CHt-6.1, AAV CHt-6.10, AAV CHt-6.5, AAV CHt-6.6, AAV CHt-6.7, AAV CHt-6.8, AAV CHt-P1, AAV CHt-P2, AAV CHt-P5, AAV CHt-P6, AAV CHt-P8, AAV CHt-P9, AAV CKd-1, AAV CKd-10, AAV CKd-2, AAV CKd-3, AAV CKd-4, AAV CKd-6, AAV CKd-7, AAV CKd-8, AAV CKd-B1, AAV CKd-B2, AAV CKd-B3, AAV CKd-B4, AAV CKd-B5, AAV CKd-B6, AAV CKd-B7, AAV CKd-B8, AAV CKd-H1, AAV CKd-H2, AAV CKd-H3, AAV CKd-H4, AAV CKd-H5, AAV CKd-H6, AAV CKd-N3, AAV CKd-N4, AAV CKd-N9, AAV CLg-F1, AAV CLg-F2, AAV CLg-F3, AAV CLg-F4, AAV CLg-F5, AAV CLg-F6, AAV CLg-F7, AAV CLg-F8, AAV CLv-1, AAV CLv1-1, AAV Clv1-10, AAV CLv1-2, AAV CLv-12, AAV CLv1-3, AAV CLv-13, AAV CLv1-4, AAV Clv1-7, AAV Clv1-8, AAV Clv1-9, AAV CLv-2, AAV CLv-3, AAV CLv-4, AAV CLv-6, AAV CLv-8, AAV CLv-D1, AAV CLv-D2, AAV CLv-D3, AAV CLv-D4, AAV CLv-D5, AAV CLv-D6, AAV CLv-D7, AAV CLv-D8, AAV CLv-E1, AAV CLv-K1, AAV CLv-K3, AAV CLv-K6, AAV CLv-L4, AAV CLv-L5, AAV CLv-L6, AAV CLv-M1, AAV CLv-M11, AAV CLv-M2, AAV CLv-M5, AAV CLv-M6, AAV CLv-M7, AAV CLv-M8, AAV CLv-M9, AAV CLv-R1, AAV CLv-R2, AAV CLv-R3, AAV CLv-R4, AAV CLv-R5, AAV CLv-R6, AAV CLv-R7, AAV CLv-R8, AAV CLv-R9, AAV CSp-1, AAV CSp-10, AAV CSp-11, AAV CSp-2, AAV CSp-3, AAV CSp-4, AAV CSp-6, AAV CSp-7, AAV CSp-8, AAV CSp-8.10, AAV CSp-8.2, AAV CSp-8.4, AAV CSp-8.5, AAV CSp-8.6, AAV CSp-8.7, AAV CSp-8.8, AAV CSp-8.9, AAV CSp-9, AAV.hu.48R3, AAV.VR-355, AAV3B, AAV4, AAV5, AAVF1/HSC1, AAVF11/HSC11, AAVF12/HSC12, AAVF13/HSC13, AAVF14/HSC14, AAVF15/HSC15, AAVF16/HSC16, AAVF17/HSC17, AAVF2/HSC2, AAVF3/HSC3, AAVF4/HSC4, AAVF5/HSC5, AAVF6/HSC6, AAVF7/HSC7, AAVF8/HSC8, AAVF9/HSC9, AAV-PHP.B (PHP.B), AAV-PHP.A (PHP.A), G2B-26, G2B-13, TH1.1-32 and/or TH1.1-35, and variants thereof. As a non-limiting example, the capsid of the recombinant AAV virus is AAV1. As a non-limiting example, the capsid of the recombinant AAV virus is AAV2. As a non-limiting example, the capsid of the recombinant AAV virus is AAVrh10. As a non-limiting example, the capsid of the recombinant AAV virus is AAV9(hu14). As a non-limiting example, the capsid of the recombinant AAV virus is AAV-DJ. As a non-limiting example, the capsid of the recombinant AAV virus is AAV9.47. As a non-limiting example, the capsid of the recombinant AAV virus is AAV-DJ8. As a non-limiting example, the capsid of the recombinant AAV virus is AAV-PHP.B. As a non-limiting example, the capsid of the recombinant AAV virus is AAV-PHP.A.

In some embodiments, the AAV serotype may be, or have, a sequence as described in United States Publication No. US20030138772, the contents of which are herein incorporated by reference in their entirety, such as, but not limited to, AAV1 (SEQ ID NO: 6 and 64 of US20030138772), AAV2 (SEQ ID NO: 7 and 70 of US20030138772), AAV3 (SEQ ID NO: 8 and 71 of US20030138772), AAV4 (SEQ ID NO: 63 of US20030138772), AAV5 (SEQ ID NO: 114 of US20030138772), AAV6 (SEQ ID NO: 65 of US20030138772), AAV7 (SEQ ID NO: 1-3 of US20030138772), AAV8 (SEQ ID NO: 4 and 95 of US20030138772), AAV5 (SEQ ID NO: 5 and 100 of US20030138772), AAV10 (SEQ ID NO: 117 of US20030138772), AAV11 (SEQ ID NO: 118 of US20030138772), AAV12 (SEQ ID NO: 119 of US20030138772), AAVrh10 (amino acids 1 to 738 of SEQ ID NO: 81 of US20030138772), AAV16.3 (US20030138772 SEQ ID NO: 10), AAV29.3/bb.1 (US20030138772 SEQ ID NO: 11), AAV29.4 (US20030138772 SEQ ID NO: 12), AAV29.5/bb.2 (US20030138772 SEQ ID NO: 13), AAV1.3 (US20030138772 SEQ ID NO: 14), AAV13.3 (US20030138772 SEQ ID NO: 15), AAV24.1 (US20030138772 SEQ ID NO: 16), AAV27.3 (US20030138772 SEQ ID NO: 17), AAV7.2 (US20030138772 SEQ ID NO: 18), AAVC1

(US20030138772 SEQ ID NO: 19), AAVC3 (US20030138772 SEQ ID NO: 20), AAVC5 (US20030138772 SEQ ID NO: 21), AAVF1 (US20030138772 SEQ ID NO: 22), AAVF3 (US20030138772 SEQ ID NO: 23), AAVF5 (US20030138772 SEQ ID NO: 24), AAVH6 (US20030138772 SEQ ID NO: 25), AAVH2 (US20030138772 SEQ ID NO: 26), AAV42-8 (US20030138772 SEQ ID NO: 27), AAV42-15 (US20030138772 SEQ ID NO: 28), AAV42-5b (US20030138772 SEQ ID NO: 29), AAV42-1b (US20030138772 SEQ ID NO: 30), AAV42-13 (US20030138772 SEQ ID NO: 31), AAV42-3a (US20030138772 SEQ ID NO: 32), AAV42-4 (US20030138772 SEQ ID NO: 33), AAV42-5a (US20030138772 SEQ ID NO: 34), AAV42-10 (US20030138772 SEQ ID NO: 35), AAV42-3b (US20030138772 SEQ ID NO: 36), AAV42-11 (US20030138772 SEQ ID NO: 37), AAV42-6b (US20030138772 SEQ ID NO: 38), AAV43-1 (US20030138772 SEQ ID NO: 39), AAV43-5 (US20030138772 SEQ ID NO: 40), AAV43-12 (US20030138772 SEQ ID NO: 41), AAV43-20 (US20030138772 SEQ ID NO: 42), AAV43-21 (US20030138772 SEQ ID NO: 43), AAV43-23 (US20030138772 SEQ ID NO: 44), AAV43-25 (US20030138772 SEQ ID NO: 45), AAV44.1 (US20030138772 SEQ ID NO: 46), AAV44.5 (US20030138772 SEQ ID NO: 47), AAV223.1 (US20030138772 SEQ ID NO: 48), AAV223.2 (US20030138772 SEQ ID NO: 49), AAV223.4 (US20030138772 SEQ ID NO: 50), AAV223.5 (US20030138772 SEQ ID NO: 51), AAV223.6 (US20030138772 SEQ ID NO: 52), AAV223.7 (US20030138772 SEQ ID NO: 53), AAVA3.4 (US20030138772 SEQ ID NO: 54), AAVA3.5 (US20030138772 SEQ ID NO: 55), AAVA3.7 (US20030138772 SEQ ID NO: 56), AAVA3.3 (US20030138772 SEQ ID NO: 57), AAV42.12 (US20030138772 SEQ ID NO: 58), AAV44.2 (US20030138772 SEQ ID NO: 59), AAV42-2 (US20030138772 SEQ ID NO: 9), or variants thereof.

In some embodiments, the AAV serotype may be, or have, a sequence as described in United States Publication No. US20150159173, the contents of which are herein incorporated by reference in their entirety, such as, but not limited to, AAV2 (SEQ ID NO: 7 and 23 of US20150159173), rh20 (SEQ ID NO: 1 of US20150159173), rh32/33 (SEQ ID NO: 2 of US20150159173), rh39 (SEQ ID NO: 3, 20 and 36 of US20150159173), rh46 (SEQ ID NO: 4 and 22 of US20150159173), rh73 (SEQ ID NO: 5 of US20150159173), rh74 (SEQ ID NO: 6 of US20150159173), AAV6.1 (SEQ ID NO: 29 of US20150159173), rh.8 (SEQ ID NO: 41 of US20150159173), rh.48.1 (SEQ ID NO: 44 of US20150159173), hu.44 (SEQ ID NO: 45 of US20150159173), hu.29 (SEQ ID NO: 42 of US20150159173), hu.48 (SEQ ID NO: 38 of US20150159173), rh54 (SEQ ID NO: 49 of US20150159173), AAV2 (SEQ ID NO: 7 of US20150159173), cy.5 (SEQ ID NO: 8 and 24 of US20150159173), rh.10 (SEQ ID NO: 9 and 25 of US20150159173), rh.13 (SEQ ID NO: 10 and 26 of US20150159173), AAV1 (SEQ ID NO: 11 and 27 of US20150159173), AAV3 (SEQ ID NO: 12 and 28 of US20150159173), AAV6 (SEQ ID NO: 13 and 29 of US20150159173), AAV7 (SEQ ID NO: 14 and 30 of US20150159173), AAV8 (SEQ ID NO: 15 and 31 of US20150159173), hu.13 (SEQ ID NO: 16 and 32 of US20150159173), hu.26 (SEQ ID NO: 17 and 33 of US20150159173), hu.37 (SEQ ID NO: 18 and 34 of US20150159173), hu.53 (SEQ ID NO: 19 and 35 of US20150159173), rh.43 (SEQ ID NO: 21 and 37 of US20150159173), rh2 (SEQ ID NO: 39 of US20150159173), rh.37 (SEQ ID NO: 40 of US20150159173), rh.64 (SEQ ID NO: 43 of US20150159173), rh.48 (SEQ ID NO: 44 of US20150159173), ch. 5 (SEQ ID NO 46 of US20150159173), rh.67 (SEQ ID NO: 47 of US20150159173), rh.58 (SEQ ID NO: 48 of US20150159173), or variants thereof including, but not limited to Cy5R1, Cy5R2, Cy5R3, Cy5R4, rh.13R, rh.37R2, rh.2R, rh.8R, rh.48.1, rh.48.2, rh.48.1.2, hu.44R1, hu.44R2, hu.44R3, hu.29R, ch.5R1, rh64R1, rh64R2, AAV6.2, AAV6.1, AAV6.12, hu.48R1, hu.48R2, and hu.48R3.

In some embodiments, the AAV serotype may be, or have, a sequence as described in U.S. Pat. No. 7,198,951, the contents of which are herein incorporated by reference in their entirety, such as, but not limited to, AAV9 (SEQ ID NO: 1-3 of U.S. Pat. No. 7,198,951), AAV2 (SEQ ID NO: 4 of U.S. Pat. No. 7,198,951), AAV1 (SEQ ID NO: 5 of U.S. Pat. No. 7,198,951), AAV3 (SEQ ID NO: 6 of U.S. Pat. No. 7,198,951), and AAV8 (SEQ ID NO: 7 of U.S. Pat. No. 7,198,951).

In some embodiments, the AAV serotype may be, or have, a mutation in the AAV9 sequence as described by N Pulicherla et al. (Molecular Therapy 19(6):1070-1078 (2011), herein incorporated by reference in its entirety), such as but not limited to, AAV9.9, AAV9.11, AAV9.13, AAV9.16, AAV9.24, AAV9.45, AAV9.47, AAV9.61, AAV9.68, AAV9.84.

In some embodiments, the AAV serotype may be, or have, a sequence as described in U.S. Pat. No. 6,156,303, the contents of which are herein incorporated by reference in their entirety, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some embodiments, the AAV serotype may be, or have, a sequence as described in United States Publication No. US20140359799, the contents of which are herein incorporated by reference in their entirety, such as, but not limited to, AAV8 (SEQ ID NO: 1 of US20140359799), AAVDJ (SEQ ID NO: 2 and 3 of US20140359799), or variants thereof.

In some embodiments, the serotype may be AAVDJ (or AAV-DJ) or a variant thereof, such as AAVDJ8 (or AAV-DJ8), as described by Grimm et al. (Journal of Virology 82(12): 5887-5911 (2008), herein incorporated by reference in its entirety). The amino acid sequence of AAVDJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some embodiments, the AAV serotype may be, or have, a sequence of AAV4 as described in International Publication No. WO1998011244, the contents of which are herein incorporated by reference in their entirety, such as, but not limited to AAV4 (SEQ ID NO: 1-20 of WO1998011244).

In some embodiments, the AAV serotype may be, or have, a mutation in the AAV2 sequence to generate AAV2G9 as described in International Publication No. WO2014144229 and herein incorporated by reference in its entirety.

In some embodiments, the AAV serotype may be, or have, a sequence as described in International Publication No. WO2005033321, the contents of which are herein incorporated by reference in their entirety, such as, but not limited to AAV3-3 (SEQ ID NO: 217 of WO2005033321), AAV1 (SEQ ID NO: 219 and 202 of WO2005033321), AAV106.1/hu.37 (SEQ ID No: 10 of WO2005033321), AAV114.3/hu.40 (SEQ ID No: 11 of WO2005033321), AAV127.2/hu.41 (SEQ ID NO:6 and 8 of WO2005033321), AAV128.3/hu.44 (SEQ ID No: 81 of WO2005033321), AAV130.4/hu.48 (SEQ ID NO: 78 of WO2005033321), AAV145.1/hu.53 (SEQ ID No: 176 and 177 of WO2005033321), AAV145.6/hu.56 (SEQ ID NO: 168 and 192 of WO2005033321), AAV16.12/hu.11 (SEQ ID NO: 153 and 57 of WO2005033321), AAV16.8/hu.10 (SEQ ID NO: 156 and 56 of WO2005033321), AAV161.10/hu.60 (SEQ ID No: 170 of WO2005033321), AAV161.6/hu.61 (SEQ ID No: 174 of WO2005033321), AAV1-7/rh.48 (SEQ ID NO: 32 of WO2005033321), AAV1-8/rh.49 (SEQ ID NOs: 103 and 25 of WO2005033321), AAV2 (SEQ ID NO: 211 and 221 of WO2005033321), AAV2-15/rh.62 (SEQ ID No: 33 and 114 of WO2005033321), AAV2-3/rh.61 (SEQ ID NO: 21 of WO2005033321), AAV2-4/rh.50 (SEQ ID No: 23 and 108 of WO2005033321), AAV2-5/rh.51 (SEQ ID NO: 104 and 22 of WO2005033321), AAV3.1/hu.6 (SEQ ID NO: 5 and 84 of WO2005033321), AAV3.1/hu.9 (SEQ ID NO: 155 and 58 of WO2005033321), AAV3-11/rh.53 (SEQ ID NO: 186 and 176 of WO2005033321), AAV3-3 (SEQ ID NO: 200 of WO2005033321), AAV33.12/hu.17 (SEQ ID NO:4 of WO2005033321), AAV33.4/hu.15 (SEQ ID No: 50 of WO2005033321), AAV33.8/hu.16 (SEQ ID No: 51 of WO2005033321), AAV3-9/rh.52 (SEQ ID NO: 96 and 18 of WO2005033321), AAV4-19/rh.55 (SEQ ID NO: 117 of WO2005033321), AAV4-4 (SEQ ID NO: 201 and 218 of WO2005033321), AAV4-9/rh.54 (SEQ ID NO: 116 of WO2005033321), AAV5 (SEQ ID NO: 199 and 216 of WO2005033321), AAV52.1/hu.20 (SEQ ID NO: 63 of WO2005033321), AAV52/hu.19 (SEQ ID NO: 133 of WO2005033321), AAV5-22/rh.58 (SEQ ID No: 27 of WO2005033321), AAV5-3/rh.57 (SEQ ID NO: 105 of WO2005033321), AAV5-3/rh.57 (SEQ ID No: 26 of WO2005033321), AAV58.2/hu.25 (SEQ ID No: 49 of WO2005033321), AAV6 (SEQ ID NO: 203 and 220 of WO2005033321), AAV7 (SEQ ID NO: 222 and 213 of WO2005033321), AAV7.3/hu.7 (SEQ ID No: 55 of WO2005033321), AAV8 (SEQ ID NO: 223 and 214 of WO2005033321), AAVH-1/hu.1 (SEQ ID No: 46 of WO2005033321), AAVH-5/hu.3 (SEQ ID No: 44 of WO2005033321), AAVhu.1 (SEQ ID NO: 144 of WO2005033321), AAVhu.10 (SEQ ID NO: 156 of WO2005033321), AAVhu.11 (SEQ ID NO: 153 of WO2005033321), AAVhu.12 (WO2005033321 SEQ ID NO: 59), AAVhu.13 (SEQ ID NO: 129 of WO2005033321), AAVhu.14/AAV9 (SEQ ID NO: 123 and 3 of WO2005033321), AAVhu.15 (SEQ ID NO: 147 of WO2005033321), AAVhu.16 (SEQ ID NO: 148 of WO2005033321), AAVhu.17 (SEQ ID NO: 83 of WO2005033321), AAVhu.18 (SEQ ID NO: 149 of WO2005033321), AAVhu.19 (SEQ ID NO: 133 of WO2005033321), AAVhu.2 (SEQ ID NO: 143 of WO2005033321), AAVhu.20 (SEQ ID NO: 134 of WO2005033321), AAVhu.21 (SEQ ID NO: 135 of WO2005033321), AAVhu.22 (SEQ ID NO: 138 of WO2005033321), AAVhu.23.2 (SEQ ID NO: 137 of WO2005033321), AAVhu.24 (SEQ ID NO: 136 of WO2005033321), AAVhu.25 (SEQ ID NO: 146 of WO2005033321), AAVhu.27 (SEQ ID NO: 140 of WO2005033321), AAVhu.29 (SEQ ID NO: 132 of WO2005033321), AAVhu.3 (SEQ ID NO: 145 of WO2005033321), AAVhu.31 (SEQ ID NO: 121 of WO2005033321), AAVhu.32 (SEQ ID NO: 122 of WO2005033321), AAVhu.34 (SEQ ID NO: 125 of WO2005033321), AAVhu.35 (SEQ ID NO: 164 of WO2005033321), AAVhu.37 (SEQ ID NO: 88 of WO2005033321), AAVhu.39 (SEQ ID NO: 102 of WO2005033321), AAVhu.4 (SEQ ID NO: 141 of WO2005033321), AAVhu.40 (SEQ ID NO: 87 of WO2005033321), AAVhu.41 (SEQ ID NO: 91 of WO2005033321), AAVhu.42 (SEQ ID NO: 85 of WO2005033321), AAVhu.43 (SEQ ID NO: 160 of WO2005033321), AAVhu.44 (SEQ ID NO: 144 of WO2005033321), AAVhu.45 (SEQ ID NO: 127 of WO2005033321), AAVhu.46 (SEQ ID NO: 159 of WO2005033321), AAVhu.47 (SEQ ID NO: 128 of WO2005033321), AAVhu.48 (SEQ ID NO: 157 of WO2005033321), AAVhu.49 (SEQ ID NO: 189 of WO2005033321), AAVhu.51 (SEQ ID NO: 190 of WO2005033321), AAVhu.52 (SEQ ID NO: 191 of WO2005033321), AAVhu.53 (SEQ ID NO: 186 of WO2005033321), AAVhu.54 (SEQ ID NO: 188 of WO2005033321), AAVhu.55 (SEQ ID NO: 187 of WO2005033321), AAVhu.56 (SEQ ID NO: 192 of WO2005033321), AAVhu.57 (SEQ ID NO: 193 of WO2005033321), AAVhu.58 (SEQ ID NO: 194 of WO2005033321), AAVhu.6 (SEQ ID NO: 84 of WO2005033321), AAVhu.60 (SEQ ID NO: 184 of WO2005033321), AAVhu.61 (SEQ ID NO: 185 of WO2005033321), AAVhu.63 (SEQ ID NO: 195 of WO2005033321), AAVhu.64 (SEQ ID NO: 196 of WO2005033321), AAVhu.66 (SEQ ID NO: 197 of WO2005033321), AAVhu.67 (SEQ ID NO: 198 of WO2005033321), AAVhu.7 (SEQ ID NO: 150 of WO2005033321), AAVhu.8 (WO2005033321 SEQ ID NO: 12), AAVhu.9 (SEQ ID NO: 155 of WO2005033321), AAVLG-10/rh.40 (SEQ ID No: 14 of WO2005033321), AAVLG-4/rh.38 (SEQ ID NO: 86 of WO2005033321), AAVLG-4/rh.38 (SEQ ID No: 7 of WO2005033321), AAVN721-8/rh.43 (SEQ ID NO: 163 of WO2005033321), AAVN721-8/rh.43 (SEQ ID No: 43 of WO2005033321), AAVpi.1 (WO2005033321 SEQ ID NO: 28), AAVpi.2 (WO2005033321 SEQ ID NO: 30), AAVpi.3 (WO2005033321 SEQ ID NO: 29), AAVrh.38 (SEQ ID NO: 86 of WO2005033321), AAVrh.40 (SEQ ID NO: 92 of WO2005033321), AAVrh.43 (SEQ ID NO: 163 of WO2005033321), AAVrh.44 (WO2005033321 SEQ ID NO: 34), AAVrh.45 (WO2005033321 SEQ ID NO: 41), AAVrh.47 (WO2005033321 SEQ ID NO: 38), AAVrh.48 (SEQ ID NO: 115 of WO2005033321), AAVrh.49 (SEQ ID NO: 103 of WO2005033321), AAVrh.50 (SEQ ID NO: 108 of WO2005033321), AAVrh.51 (SEQ ID NO: 104 of WO2005033321), AAVrh.52 (SEQ ID NO: 96 of WO2005033321), AAVrh.53 (SEQ ID NO: 97 of WO2005033321), AAVrh.55 (WO2005033321 SEQ ID NO:

37), AAVrh.56 (SEQ ID NO: 152 of WO2005033321), AAVrh.57 (SEQ ID NO: 105 of WO2005033321), AAVrh.58 (SEQ ID NO: 106 of WO2005033321), AAVrh.59 (WO2005033321 SEQ ID NO: 42), AAVrh.60 (WO2005033321 SEQ ID NO: 31), AAVrh.61 (SEQ ID NO: 107 of WO2005033321), AAVrh.62 (SEQ ID NO: 114 of WO2005033321), AAVrh.64 (SEQ ID NO: 99 of WO2005033321), AAVrh.65 (WO2005033321 SEQ ID NO: 35), AAVrh.68 (WO2005033321 SEQ ID NO: 16), AAVrh.69 (WO2005033321 SEQ ID NO: 39), AAVrh.70 (WO2005033321 SEQ ID NO: 20), AAVrh.72 (WO2005033321 SEQ ID NO: 9), or variants thereof including, but not limited to, AAVcy.2, AAVcy.3, AAVcy.4, AAVcy.5, AAVcy.6, AAVrh.12, AAVrh.17, AAVrh.18, AAVrh.19, AAVrh.21, AAVrh.22, AAVrh.23, AAVrh.24, AAVrh.25, AAVrh.25/42 15, AAVrh.31, AAVrh.32, AAVrh.33, AAVrh.34, AAVrh.35, AAVrh.36, AAVrh.37, AAVrh14. Non-limiting examples of variants include SEQ ID NO: 13, 15, 17, 19, 24, 36, 40, 45, 47, 48, 51-54, 60-62, 64-77, 79, 80, 82, 89, 90, 93-95, 98, 100, 101, 109-113, 118-120, 124, 126, 131, 139, 142, 151, 154, 158, 161, 162, 165-183, 202, 204-212, 215, 219, 224-236, of WO2005033321, the contents of which are herein incorporated by reference in their entirety.

In some embodiments, the AAV serotype may be, or have, a sequence as described in International Publication No. WO2015168666, the contents of which are herein incorporated by reference in their entirety, such as, but not limited to, AAVrh8R (SEQ ID NO: 9 of WO2015168666), AAVrh8R A586R mutant (SEQ ID NO: 10 of WO2015168666), AAVrh8R R533A mutant (SEQ ID NO: 11 of WO2015168666), or variants thereof.

In some embodiments, the AAV serotype may be, or have, a sequence as described in U.S. Pat. No. 9,233,131, the contents of which are herein incorporated by reference in their entirety, such as, but not limited to, AAVhE1.1 (SEQ ID NO:44 of U.S. Pat. No. 9,233,131), AAVhEr1.5 (SEQ ID NO:45 of U.S. Pat. No. 9,233,131), AAVhER1.14 (SEQ ID NO:46 of U.S. Pat. No. 9,233,131), AAVhEr1.8 (SEQ ID NO:47 of U.S. Pat. No. 9,233,131), AAVhEr1.16 (SEQ ID NO:48 of U.S. Pat. No. 9,233,131), AAVhEr1.18 (SEQ ID NO:49 of U.S. Pat. No. 9,233,131), AAVhEr1.35 (SEQ ID NO:50 of U.S. Pat. No. 9,233,131), AAVhEr1.7 (SEQ ID NO:51 of U.S. Pat. No. 9,233,131), AAVhEr1.36 (SEQ ID NO:52 of U.S. Pat. No. 9,233,131), AAVhEr2.29 (SEQ ID NO:53 of U.S. Pat. No. 9,233,131), AAVhEr2.4 (SEQ ID NO:54 of U.S. Pat. No. 9,233,131), AAVhEr2.16 (SEQ ID NO:55 of U.S. Pat. No. 9,233,131), AAVhEr2.30 (SEQ ID NO:56 of U.S. Pat. No. 9,233,131), AAVhEr2.31 (SEQ ID NO:58 of U.S. Pat. No. 9,233,131), AAVhEr2.36 (SEQ ID NO:57 of U.S. Pat. No. 9,233,131), AAVhER1.23 (SEQ ID NO:53 of U.S. Pat. No. 9,233,131), AAVhEr3.1 (SEQ ID NO:59 of U.S. Pat. No. 9,233,131), AAV2.5T (SEQ ID NO:42 of U.S. Pat. No. 9,233,131), or variants thereof.

In some embodiments, the AAV serotype may be, or have, a sequence as described in United States Patent Publication No. US20150376607, the contents of which are herein incorporated by reference in their entirety, such as, but not limited to, AAV-PAEC (SEQ ID NO:1 of US20150376607), AAV-LK01 (SEQ ID NO:2 of US20150376607), AAV-LK02 (SEQ ID NO:3 of US20150376607), AAV-LK03 (SEQ ID NO:4 of US20150376607), AAV-LK04 (SEQ ID NO:5 of US20150376607), AAV-LK05 (SEQ ID NO:6 of US20150376607), AAV-LK06 (SEQ ID NO:7 of US20150376607), AAV-LK07 (SEQ ID NO:8 of US20150376607), AAV-LK08 (SEQ ID NO:9 of US20150376607), AAV-LK09 (SEQ ID NO:10 of US20150376607), AAV-LK10 (SEQ ID NO:11 of US20150376607), AAV-LK11 (SEQ ID NO:12 of US20150376607), AAV-LK12 (SEQ ID NO:13 of US20150376607), AAV-LK13 (SEQ ID NO:14 of US20150376607), AAV-LK14 (SEQ ID NO:15 of US20150376607), AAV-LK15 (SEQ ID NO:16 of US20150376607), AAV-LK16 (SEQ ID NO:17 of US20150376607), AAV-LK17 (SEQ ID NO:18 of US20150376607), AAV-LK18 (SEQ ID NO:19 of US20150376607), AAV-LK19 (SEQ ID NO:20 of US20150376607), AAV-PAEC2 (SEQ ID NO:21 of US20150376607), AAV-PAEC4 (SEQ ID NO:22 of US20150376607), AAV-PAEC6 (SEQ ID NO:23 of US20150376607), AAV-PAEC7 (SEQ ID NO:24 of US20150376607), AAV-PAEC8 (SEQ ID NO:25 of US20150376607), AAV-PAEC11 (SEQ ID NO:26 of US20150376607), AAV-PAEC12 (SEQ ID NO:27, of US20150376607), or variants thereof.

In some embodiments, the AAV serotype may be, or have, a sequence as described in U.S. Pat. No. 9,163,261, the contents of which are herein incorporated by reference in their entirety, such as, but not limited to, AAV-2-pre-miRNA-101 (SEQ ID NO: 1 U.S. Pat. No. 9,163,261), or variants thereof.

In some embodiments, the AAV serotype may be, or have, a sequence as described in United States Patent Publication No. US20150376240, the contents of which are herein incorporated by reference in their entirety, such as, but not limited to, AAV-8h (SEQ ID NO: 6 of US20150376240), AAV-8b (SEQ ID NO: 5 of US20150376240), AAV-h (SEQ ID NO: 2 of US20150376240), AAV-b (SEQ ID NO: 1 of US20150376240), or variants thereof.

In some embodiments, the AAV serotype may be, or have, a sequence as described in United States Patent Publication No. US20160017295, the contents of which are herein incorporated by reference in their entirety, such as, but not limited to, AAV SM 10-2 (SEQ ID NO: 22 of US20160017295), AAV Shuffle 100-1 (SEQ ID NO: 23 of US20160017295), AAV Shuffle 100-3 (SEQ ID NO: 24 of US20160017295), AAV Shuffle 100-7 (SEQ ID NO: 25 of US20160017295), AAV Shuffle 10-2 (SEQ ID NO: 34 of US20160017295), AAV Shuffle 10-6 (SEQ ID NO: 35 of US20160017295), AAV Shuffle 10-8 (SEQ ID NO: 36 of US20160017295), AAV Shuffle 100-2 (SEQ ID NO: 37 of US20160017295), AAV SM 10-1 (SEQ ID NO: 38 of US20160017295), AAV SM 10-8 (SEQ ID NO: 39 of US20160017295), AAV SM 100-3 (SEQ ID NO: 40 of US20160017295), AAV SM 100-10 (SEQ ID NO: 41 of US20160017295), or variants thereof.

In some embodiments, the AAV serotype may be, or have, a sequence as described in United States Patent Publication No. US20150238550, the contents of which are herein incorporated by reference in their entirety, such as, but not limited to, BNP61 AAV (SEQ ID NO: 1 of US20150238550), BNP62 AAV (SEQ ID NO: 3 of US20150238550), BNP63 AAV (SEQ ID NO: 4 of US20150238550), or variants thereof.

In some embodiments, the AAV serotype may be or may have a sequence as described in United States Patent Publication No. US20150315612, the contents of which are herein incorporated by reference in their entirety, such as, but not limited to, AAVrh.50 (SEQ ID NO: 108 of US20150315612), AAVrh.43 (SEQ ID NO: 163 of US20150315612), AAVrh.62 (SEQ ID NO: 114 of US20150315612), AAVrh.48 (SEQ ID NO: 115 of US20150315612), AAVhu.19 (SEQ ID NO: 133 of US20150315612), AAVhu.11 (SEQ ID NO: 153 of US20150315612), AAVhu.53 (SEQ ID NO: 186 of US20150315612), AAV4-8/rh.64 (SEQ ID No: 15 of US20150315612), AAVLG-9/hu.39 (SEQ ID No: 24 of US20150315612), AAV54.5/hu.23 (SEQ ID No: 60 of US20150315612), AAV54.2/hu.22 (SEQ ID No: 67 of US20150315612), AAV54.7/hu.24 (SEQ ID No: 66 of US20150315612), AAV54.1/hu.21 (SEQ ID No: 65 of US20150315612), AAV54.4R/hu.27 (SEQ ID No: 64 of US20150315612), AAV46.2/hu.28 (SEQ ID No: 68 of US20150315612), AAV46.6/hu.29 (SEQ ID No: 69 of US20150315612), AAV128.1/hu.43 (SEQ ID No: 80 of US20150315612), or variants thereof.

In some embodiments, the AAV serotype may be, or have, a sequence as described in International Publication No. WO2015121501, the contents of which are herein incorporated by reference in their entirety, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present invention, AAV capsid serotype selection or use may be from a variety of species. In one embodiment, the AAV may be an avian AAV (AAAV). The AAAV serotype may be, or have, a sequence as described in U.S. Pat. No. 9,238,800, the contents of which are herein incorporated by reference in their entirety, such as, but not limited to, AAAV (SEQ ID NO: 1, 2, 4, 6, 8, 10, 12, and 14 of U.S. Pat. No. 9,238,800), or variants thereof.

In one embodiment, the AAV may be a bovine AAV (BAAV). The BAAV serotype may be, or have, a sequence as described in U.S. Pat. No. 9,193,769, the contents of which are herein incorporated by reference in their entirety, such as, but not limited to, BAAV (SEQ ID NO: 1 and 6 of U.S. Pat. No. 9,193,769), or variants thereof. The BAAV serotype may be or have a sequence as described in U.S. Pat. No. 7,427,396, the contents of which are herein incorporated by reference in their entirety, such as, but not limited to, BAAV (SEQ ID NO: 5 and 6 of U.S. Pat. No. 7,427,396), or variants thereof.

In one embodiment, the AAV may be a caprine AAV. The caprine AAV serotype may be, or have, a sequence as described in U.S. Pat. No. 7,427,396, the contents of which are herein incorporated by reference in their entirety, such as, but not limited to, caprine AAV (SEQ ID NO: 3 of U.S. Pat. No. 7,427,396), or variants thereof.

In other embodiments, the AAV may be engineered as a hybrid AAV from two or more parental serotypes. In one embodiment, the AAV may be AAV2G9 which comprises sequences from AAV2 and AAV9. The AAV2G9 AAV serotype may be, or have, a sequence as described in United States Patent Publication No. US20160017005, the contents of which are herein incorporated by reference in its entirety.

In one embodiment, the AAV may be a serotype generated by the AAV9 capsid library with mutations in amino acids 390-627 (VP1 numbering) as described by Pulicherla et al. (Molecular Therapy 19(6):1070-1078 (2011), the contents of which are herein incorporated by reference in their entirety. The serotype and corresponding nucleotide and amino acid substitutions may be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T4921, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T; G1732A, A1744T, A1832T; S425G, Q474R, Q546H, P571L, G578R, T582S, D611V), AAV9.94 (A1675T; M559L) and AAV9.95 (T1605A; F535L).

In some embodiments, the AAV serotype may be, or have, a sequence as described in International Publication No. WO2016049230, the contents of which are herein incorporated by reference in their entirety, such as, but not limited to AAVF1/HSC1 (SEQ ID NO: 2 and 20 of WO2016049230), AAVF2/HSC2 (SEQ ID NO: 3 and 21 of WO2016049230), AAVF3/HSC3 (SEQ ID NO: 5 and 22 of WO2016049230), AAVF4/HSC4 (SEQ ID NO: 6 and 23 of WO2016049230), AAVF5/HSC5 (SEQ ID NO: 11 and 25 of WO2016049230), AAVF6/HSC6 (SEQ ID NO: 7 and 24 of WO2016049230), AAVF7/HSC7 (SEQ ID NO: 8 and 27 of WO2016049230), AAVF8/HSC8 (SEQ ID NO: 9 and 28 of WO2016049230), AAVF9/HSC9 (SEQ ID NO: 10 and 29 of WO2016049230), AAVF11/HSC11 (SEQ ID NO: 4 and 26 of WO2016049230), AAVF12/HSC12 (SEQ ID NO: 12 and 30 of WO2016049230), AAVF13/HSC13 (SEQ ID NO: 14 and 31 of WO2016049230), AAVF14/HSC14 (SEQ ID NO: 15 and 32 of WO2016049230), AAVF15/HSC15 (SEQ ID NO: 16 and 33 of WO2016049230), AAVF16/HSC16 (SEQ ID NO: 17 and 34 of WO2016049230), AAVF17/HSC17 (SEQ ID NO: 13 and 35 of WO2016049230), or variants or derivatives thereof.

In some embodiments, the AAV serotype may be, or have, a sequence as described in U.S. Pat. No. 8,734,809, the contents of which are herein incorporated by reference in their entirety, such as, but not limited to, AAV CBr-E1 (SEQ ID NO: 13 and 87 of U.S. Pat. No. 8,734,809), AAV CBr-E2 (SEQ ID NO: 14 and 88 of U.S. Pat. No. 8,734,809), AAV CBr-E3 (SEQ ID NO: 15 and 89 of U.S. Pat. No. 8,734,809), AAV CBr-E4 (SEQ ID NO: 16 and 90 of U.S. Pat. No. 8,734,809), AAV CBr-E5 (SEQ ID NO: 17 and 91 of U.S. Pat. No. 8,734,809), AAV CBr-e5 (SEQ ID NO: 18 and 92 of U.S. Pat. No. 8,734,809), AAV CBr-E6 (SEQ ID NO: 19 and 93 of U.S. Pat. No. 8,734,809), AAV CBr-E7 (SEQ ID NO: 20 and 94 of U.S. Pat. No. 8,734,809), AAV CBr-E8 (SEQ ID NO: 21 and 95 of U.S. Pat. No. 8,734,809), AAV CLv-D1 (SEQ ID NO: 22 and 96 of U.S. Pat. No. 8,734, 809), AAV CLv-D2 (SEQ ID NO: 23 and 97 of U.S. Pat. No. 8,734,809), AAV CLv-D3 (SEQ ID NO: 24 and 98 of U.S. Pat. No. 8,734,809), AAV CLv-D4 (SEQ ID NO: 25 and 99 of U.S. Pat. No. 8,734,809), AAV CLv-D5 (SEQ ID NO: 26 and 100 of U.S. Pat. No. 8,734,809), AAV CLv-D6 (SEQ ID NO: 27 and 101 of U.S. Pat. No. 8,734,809), AAV CLv-D7 (SEQ ID NO: 28 and 102 of U.S. Pat. No. 8,734,809), AAV CLv-D8 (SEQ ID NO: 29 and 103 of U.S. Pat. No. 8,734,809), AAV CLv-E1 (SEQ ID NO: 13 and 87 of U.S. Pat. No. 8,734,809), AAV CLv-R1 (SEQ ID NO: 30 and 104 of U.S. Pat. No. 8,734,809), AAV CLv-R2 (SEQ ID NO: 31 and 105 of U.S. Pat. No. 8,734,809), AAV CLv-R3 (SEQ ID NO: 32 and 106 of U.S. Pat. No. 8,734,809), AAV CLv-R4 (SEQ ID NO: 33 and 107 of U.S. Pat. No. 8,734,809), AAV CLv-R5 (SEQ ID NO: 34 and 108 of U.S. Pat. No. 8,734,809), AAV CLv-R6 (SEQ ID NO: 35 and 109 of U.S. Pat. No. 8,734,809), AAV CLv-R7 (SEQ ID NO: 36 and 110 of U.S. Pat. No. 8,734,809), AAV CLv-R8 (SEQ ID NO: 37 and 111 of U.S. Pat. No. 8,734,809), AAV CLv-R9 (SEQ ID NO: 38 and 112 of U.S. Pat. No. 8,734,809), AAV CLg-F1 (SEQ ID NO: 39 and 113 of U.S. Pat. No. 8,734,809), AAV CLg-F2 (SEQ ID NO: 40 and 114 of U.S. Pat. No. 8,734,809), AAV CLg-F3 (SEQ ID NO: 41 and 115 of U.S. Pat. No. 8,734,809), AAV CLg-F4 (SEQ ID NO: 42 and 116 of U.S. Pat. No. 8,734,809), AAV CLg-F5 (SEQ ID NO: 43 and 117 of U.S. Pat. No. 8,734,809), AAV CLg-F6 (SEQ ID NO: 43 and 117 of U.S. Pat. No. 8,734,809), AAV CLg-F7 (SEQ ID NO: 44 and 118 of U.S. Pat. No. 8,734,809), AAV CLg-F8 (SEQ ID NO: 43 and 117 of U.S. Pat. No. 8,734,809), AAV CSp-1 (SEQ ID NO: 45 and 119 of U.S. Pat. No. 8,734,809), AAV CSp-10 (SEQ ID NO: 46 and 120 of U.S. Pat. No. 8,734,809), AAV CSp-11 (SEQ ID NO: 47 and 121 of U.S. Pat. No. 8,734,809), AAV CSp-2 (SEQ ID NO: 48 and 122 of U.S. Pat. No. 8,734,809), AAV CSp-3 (SEQ ID NO: 49 and 123 of U.S. Pat. No. 8,734,809), AAV CSp-4 (SEQ ID NO: 50 and 124 of U.S. Pat. No. 8,734,809), AAV CSp-6 (SEQ ID NO: 51 and 125 of U.S. Pat. No. 8,734,809), AAV CSp-7 (SEQ ID NO: 52 and 126 of U.S. Pat. No. 8,734,809), AAV CSp-8 (SEQ ID NO: 53 and 127 of U.S. Pat. No. 8,734,809), AAV CSp-9 (SEQ ID NO: 54 and 128 of U.S. Pat. No. 8,734,809), AAV CHt-2 (SEQ ID NO: 55 and 129 of U.S. Pat. No. 8,734,809), AAV CHt-3 (SEQ ID NO: 56 and 130 of U.S. Pat. No. 8,734,809), AAV CKd-1 (SEQ ID NO: 57 and 131 of U.S. Pat. No. 8,734,809), AAV CKd-10 (SEQ ID NO: 58 and 132 of U.S. Pat. No. 8,734,809), AAV CKd-2 (SEQ ID NO: 59 and 133 of U.S. Pat. No. 8,734,809), AAV CKd-3 (SEQ ID NO: 60 and 134 of U.S. Pat. No. 8,734,809), AAV CKd-4 (SEQ ID NO: 61 and 135 of U.S. Pat. No. 8,734,809), AAV CKd-6 (SEQ ID NO: 62 and 136 of U.S. Pat. No. 8,734,809), AAV CKd-7 (SEQ ID NO: 63 and 137 of U.S. Pat. No. 8,734,809), AAV CKd-8 (SEQ ID NO: 64 and 138 of U.S. Pat. No. 8,734,809), AAV CLv-1 (SEQ ID NO: 35 and 139 of U.S. Pat. No. 8,734,809), AAV CLv-12 (SEQ ID NO: 66 and 140 of U.S. Pat. No. 8,734,809), AAV CLv-13 (SEQ ID NO: 67 and 141 of U.S. Pat. No. 8,734,809), AAV CLv-2 (SEQ ID NO: 68 and 142 of U.S. Pat. No. 8,734,809), AAV CLv-3 (SEQ ID NO: 69 and 143 of U.S. Pat. No. 8,734,809), AAV CLv-4 (SEQ ID NO: 70 and 144 of U.S. Pat. No. 8,734,809), AAV CLv-6 (SEQ ID NO: 71 and 145 of U.S. Pat. No. 8,734,809), AAV CLv-8 (SEQ ID NO: 72 and 146 of U.S. Pat. No. 8,734,809), AAV CKd-B1 (SEQ ID NO: 73 and 147 of U.S. Pat. No. 8,734,809), AAV CKd-B2 (SEQ ID NO: 74 and 148 of U.S. Pat. No. 8,734,809), AAV CKd-B3 (SEQ ID NO: 75 and 149 of U.S. Pat. No. 8,734,809), AAV CKd-B4 (SEQ ID NO: 76 and 150 of U.S. Pat. No. 8,734,809), AAV CKd-B5 (SEQ ID NO: 77 and 151 of U.S. Pat. No. 8,734,809), AAV CKd-B6 (SEQ ID NO: 78 and 152 of U.S. Pat. No. 8,734,809), AAV CKd-B7 (SEQ ID NO: 79 and 153 of U.S. Pat. No. 8,734,809), AAV CKd-B8 (SEQ ID NO: 80 and 154 of U.S. Pat. No. 8,734,809), AAV CKd-H1 (SEQ ID NO: 81 and 155 of U.S. Pat. No. 8,734,809), AAV CKd-H2 (SEQ ID NO: 82 and 156 of U.S. Pat. No. 8,734,809), AAV CKd-H3 (SEQ ID NO: 83 and 157 of U.S. Pat. No. 8,734,809), AAV CKd-H4 (SEQ ID NO: 84 and 158 of U.S. Pat. No. 8,734,809), AAV CKd-H5 (SEQ ID NO: 85 and 159 of U.S. Pat. No. 8,734,809), AAV CKd-H6 (SEQ ID NO: 77 and 151 of U.S. Pat. No. 8,734,809), AAV CHt-1 (SEQ ID NO: 86 and 160 of U.S. Pat. No. 8,734,809), AAV CLv1-1 (SEQ ID NO: 171 of U.S. Pat. No. 8,734,809), AAV CLv1-2 (SEQ ID NO: 172 of U.S. Pat. No. 8,734,809), AAV CLv1-3 (SEQ ID NO: 173 of U.S. Pat. No. 8,734,809), AAV CLv1-4 (SEQ ID NO: 174 of U.S. Pat. No. 8,734,809), AAV Clv1-7 (SEQ ID NO: 175 of U.S. Pat. No. 8,734,809), AAV Clv1-8 (SEQ ID NO: 176 of U.S. Pat. No. 8,734,809), AAV Clv1-9 (SEQ ID NO: 177 of U.S. Pat. No. 8,734,809), AAV Clv1-10 (SEQ ID NO: 178 of U.S. Pat. No. 8,734,809), AAV.VR-355 (SEQ ID NO: 181 of U.S. Pat. No. 8,734,809), AAV.hu.48R3 (SEQ ID NO: 183 of U.S. Pat. No. 8,734,809), or variants or derivatives thereof.

In some embodiments, the AAV serotype may be, or have, a sequence as described in International Publication No. WO2016065001, the contents of which are herein incorporated by reference in their entirety, such as, but not limited to AAV CHt-P2 (SEQ ID NO: 1 and 51 of WO2016065001), AAV CHt-P5 (SEQ ID NO: 2 and 52 of WO2016065001), AAV CHt-P9 (SEQ ID NO: 3 and 53 of WO2016065001), AAV CBr-7.1 (SEQ ID NO: 4 and 54 of WO2016065001), AAV CBr-7.2 (SEQ ID NO: 5 and 55 of WO2016065001), AAV CBr-7.3 (SEQ ID NO: 6 and 56 of WO2016065001), AAV CBr-7.4 (SEQ ID NO: 7 and 57 of WO2016065001), AAV CBr-7.5 (SEQ ID NO: 8 and 58 of WO2016065001), AAV CBr-7.7 (SEQ ID NO: 9 and 59 of WO2016065001), AAV CBr-7.8 (SEQ ID NO: 10 and 60 of WO2016065001), AAV CBr-7.10 (SEQ ID NO: 11 and 61 of WO2016065001), AAV CKd-N3 (SEQ ID NO: 12 and 62 of WO2016065001), AAV CKd-N4 (SEQ ID NO: 13 and 63 of WO2016065001), AAV CKd-N9 (SEQ ID NO: 14 and 64 of WO2016065001), AAV CLv-L4 (SEQ ID NO: 15 and 65 of WO2016065001), AAV CLv-L5 (SEQ ID NO: 16 and 66 of WO2016065001), AAV CLv-L6 (SEQ ID NO: 17 and 67 of WO2016065001), AAV CLv-K1 (SEQ ID NO: 18 and 68 of WO2016065001), AAV CLv-K3 (SEQ ID NO: 19 and 69 of WO2016065001), AAV CLv-K6 (SEQ ID NO: 20 and 70 of WO2016065001), AAV CLv-M1 (SEQ ID NO: 21 and 71 of WO2016065001), AAV CLv-M11 (SEQ ID NO: 22 and 72 of WO2016065001), AAV CLv-M2 (SEQ ID NO: 23 and 73 of WO2016065001), AAV CLv-M5 (SEQ ID NO: 24 and 74 of WO2016065001), AAV CLv-M6 (SEQ ID NO: 25 and 75 of WO2016065001), AAV CLv-M7 (SEQ ID NO: 26 and 76 of WO2016065001), AAV CLv-M8 (SEQ ID NO: 27 and 77 of WO2016065001), AAV CLv-M9 (SEQ ID NO: 28 and 78 of WO2016065001), AAV CHt-P1 (SEQ ID NO: 29 and 79 of WO2016065001), AAV CHt-P6 (SEQ ID NO: 30 and 80 of WO2016065001), AAV CHt-P8 (SEQ ID NO: 31 and 81 of WO2016065001), AAV CHt-6.1 (SEQ ID NO: 32 and 82 of WO2016065001), AAV CHt-6.10 (SEQ ID NO: 33 and 83 of WO2016065001), AAV CHt-6.5 (SEQ ID NO: 34 and 84 of WO2016065001), AAV CHt-6.6 (SEQ ID NO: 35 and 85 of WO2016065001), AAV CHt-6.7 (SEQ ID NO: 36 and 86 of WO2016065001), AAV CHt-6.8 (SEQ ID NO: 37 and 87 of WO2016065001), AAV CSp-8.10 (SEQ ID NO: 38 and 88 of WO2016065001), AAV CSp-8.2 (SEQ ID NO: 39 and 89 of WO2016065001), AAV CSp-8.4 (SEQ ID NO: 40 and 90 of WO2016065001), AAV CSp-8.5 (SEQ ID NO: 41 and 91 of WO2016065001), AAV CSp-8.6 (SEQ ID NO: 42 and 92 of WO2016065001), AAV CSp-8.7 (SEQ ID NO: 43 and 93 of WO2016065001), AAV CSp-8.8 (SEQ ID NO: 44 and 94 of WO2016065001), AAV CSp-8.9 (SEQ ID NO: 45 and 95 of WO2016065001), AAV CBr-B7.3 (SEQ ID NO: 46 and 96 of WO2016065001), AAV CBr-B7.4 (SEQ ID NO: 47 and 97 of WO2016065001), AAV3B (SEQ ID NO: 48 and 98 of WO2016065001), AAV4 (SEQ ID NO: 49 and 99 of WO2016065001), AAV5 (SEQ ID NO: 50 and 100 of WO2016065001), or variants or derivatives thereof.

In one embodiment, the AAV may be a serotype comprising at least one AAV capsid CD8+ T-cell epitope. As a non-limiting example, the serotype may be AAV1, AAV2 or AAV8.

In one embodiment, the AAV may be a serotype selected from any of those found in Table 11.

In one embodiment, the AAV may comprise a sequence, fragment or variant thereof, of the sequences in Table 11.

In one embodiment, the AAV may be encoded by a sequence, fragment or variant as described in Table 11.

TABLE 11

AAV Serotypes

| Serotype | SEQ ID NO | Reference Information |
|---|---|---|
| AAV1 | 369 | US20150159173 SEQ ID NO: 11, US20150315612 SEQ ID NO: 202 |
| AAV1 | 370 | US20160017295 SEQ ID NO: 1US20030138772 SEQ ID NO: 64, US20150159173 SEQ ID NO: 27, US20150315612 SEQ ID NO: 219, U.S. Pat. No. 7,198,951 SEQ ID NO: 5 |
| AAV1 | 371 | US20030138772 SEQ ID NO: 6 |
| AAV1.3 | 372 | US20030138772 SEQ ID NO: 14 |
| AAV10 | 373 | US20030138772 SEQ ID NO: 117 |
| AAV10 | 374 | WO2015121501 SEQ ID NO: 9 |
| AAV10 | 375 | WO2015121501 SEQ ID NO: 8 |
| AAV11 | 376 | US20030138772 SEQ ID NO: 118 |
| AAV12 | 377 | US20030138772 SEQ ID NO: 119 |
| AAV2 | 378 | US20150159173 SEQ ID NO: 7, US20150315612 SEQ ID NO: 211 |
| AAV2 | 379 | US20030138772 SEQ ID NO: 70, US20150159173 SEQ ID NO: 23, US20150315612 SEQ ID NO: 221, US20160017295 SEQ ID NO: 2, U.S. Pat. No. 6,156,303 SEQ ID NO: 4, U.S. Pat. No. 7,198,951 SEQ ID NO: 4, WO2015121501 SEQ ID NO: 1 |
| AAV2 | 380 | U.S. Pat. No. 6,156,303 SEQ ID NO: 8 |
| AAV2 | 381 | US20030138772 SEQ ID NO: 7 |
| AAV2 | 382 | U.S. Pat. No. 6,156,303 SEQ ID NO: 3 |
| AAV2.5T | 383 | U.S. Pat. No. 9,233,131 SEQ ID NO: 42 |
| AAV223.10 | 384 | US20030138772 SEQ ID NO: 75 |
| AAV223.2 | 385 | US20030138772 SEQ ID NO: 49 |
| AAV223.2 | 386 | US20030138772 SEQ ID NO: 76 |
| AAV223.4 | 387 | US20030138772 SEQ ID NO: 50 |
| AAV223.4 | 388 | US20030138772 SEQ ID NO: 73 |
| AAV223.5 | 389 | US20030138772 SEQ ID NO: 51 |
| AAV223.5 | 390 | US20030138772 SEQ ID NO: 74 |
| AAV223.6 | 391 | US20030138772 SEQ ID NO: 52 |
| AAV223.6 | 392 | US20030138772 SEQ ID NO: 78 |
| AAV223.7 | 393 | US20030138772 SEQ ID NO: 53 |
| AAV223.7 | 394 | US20030138772 SEQ ID NO: 77 |
| AAV29.3 | 395 | US20030138772 SEQ ID NO: 82 |
| AAV29.4 | 396 | US20030138772 SEQ ID NO: 12 |
| AAV29.5 | 397 | US20030138772 SEQ ID NO: 83 |
| AAV29.5 (AAVbb.2) | 398 | US20030138772 SEQ ID NO: 13 |
| AAV3 | 399 | US20150159173 SEQ ID NO: 12 |
| AAV3 | 400 | US20030138772 SEQ ID NO: 71, US20150159173 SEQ ID NO: 28, US20160017295 SEQ ID NO: 3, U.S. Pat. No. 7,198,951 SEQ ID NO: 6 |
| AAV3 | 401 | US20030138772 SEQ ID NO: 8 |
| AAV3.3b | 402 | US20030138772 SEQ ID NO: 72 |
| AAV3-3 | 403 | US20150315612 SEQ ID NO: 200 |
| AAV3-3 | 404 | US20150315612 SEQ ID NO: 217 |
| AAV3a | 405 | U.S. Pat. No. 6,156,303 SEQ ID NO: 5 |
| AAV3a | 406 | U.S. Pat. No. 6,156,303 SEQ ID NO: 9 |
| AAV3b | 407 | U.S. Pat. No. 6,156,303 SEQ ID NO: 6 |
| AAV3b | 408 | U.S. Pat. No. 6,156,303 SEQ ID NO: 10 |
| AAV3b | 409 | U.S. Pat. No. 6,156,303 SEQ ID NO: 1 |
| AAV4 | 410 | US20140348794 SEQ ID NO: 17 |
| AAV4 | 411 | US20140348794 SEQ ID NO: 5 |
| AAV4 | 412 | US20140348794 SEQ ID NO: 3 |
| AAV4 | 413 | US20140348794 SEQ ID NO: 14 |
| AAV4 | 414 | US20140348794 SEQ ID NO: 15 |
| AAV4 | 415 | US20140348794 SEQ ID NO: 19 |
| AAV4 | 416 | US20140348794 SEQ ID NO: 12 |
| AAV4 | 417 | US20140348794 SEQ ID NO: 13 |
| AAV4 | 418 | US20140348794 SEQ ID NO: 7 |
| AAV4 | 419 | US20140348794 SEQ ID NO: 8 |
| AAV4 | 420 | US20140348794 SEQ ID NO: 9 |
| AAV4 | 421 | US20140348794 SEQ ID NO: 2 |
| AAV4 | 422 | US20140348794 SEQ ID NO: 10 |
| AAV4 | 423 | US20140348794 SEQ ID NO: 11 |

TABLE 11-continued

AAV Serotypes

| Serotype | SEQ ID NO | Reference Information |
|---|---|---|
| AAV4 | 424 | US20140348794 SEQ ID NO: 18 |
| AAV4 | 425 | US20030138772 SEQ ID NO: 63, US20160017295 SEQ ID NO: 4, US20140348794 SEQ ID NO: 4 |
| AAV4 | 426 | US20140348794 SEQ ID NO: 16 |
| AAV4 | 427 | US20140348794 SEQ ID NO: 20 |
| AAV4 | 428 | US20140348794 SEQ ID NO: 6 |
| AAV4 | 429 | US20140348794 SEQ ID NO: 1 |
| AAV42.2 | 430 | US20030138772 SEQ ID NO: 9 |
| AAV42.2 | 431 | US20030138772 SEQ ID NO: 102 |
| AAV42.3b | 432 | US20030138772 SEQ ID NO: 36 |
| AAV42.3B | 433 | US20030138772 SEQ ID NO: 107 |
| AAV42.4 | 434 | US20030138772 SEQ ID NO: 33 |
| AAV42.4 | 435 | US20030138772 SEQ ID NO: 88 |
| AAV42.8 | 436 | US20030138772 SEQ ID NO: 27 |
| AAV42.8 | 437 | US20030138772 SEQ ID NO: 85 |
| AAV43.1 | 438 | US20030138772 SEQ ID NO: 39 |
| AAV43.1 | 439 | US20030138772 SEQ ID NO: 92 |
| AAV43.12 | 440 | US20030138772 SEQ ID NO: 41 |
| AAV43.12 | 441 | US20030138772 SEQ ID NO: 93 |
| AAV43.20 | 442 | US20030138772 SEQ ID NO: 42 |
| AAV43.20 | 443 | US20030138772 SEQ ID NO: 99 |
| AAV43.21 | 444 | US20030138772 SEQ ID NO: 43 |
| AAV43.21 | 445 | US20030138772 SEQ ID NO: 96 |
| AAV43.23 | 446 | US20030138772 SEQ ID NO: 44 |
| AAV43.23 | 447 | US20030138772 SEQ ID NO: 98 |
| AAV43.25 | 448 | US20030138772 SEQ ID NO: 45 |
| AAV43.25 | 449 | US20030138772 SEQ ID NO: 97 |
| AAV43.5 | 450 | US20030138772 SEQ ID NO: 40 |
| AAV43.5 | 451 | US20030138772 SEQ ID NO: 94 |
| AAV4-4 | 452 | US20150315612 SEQ ID NO: 201 |
| AAV4-4 | 453 | US20150315612 SEQ ID NO: 218 |
| AAV44.1 | 454 | US20030138772 SEQ ID NO: 46 |
| AAV44.1 | 455 | US20030138772 SEQ ID NO: 79 |
| AAV44.5 | 456 | US20030138772 SEQ ID NO: 47 |
| AAV44.5 | 457 | US20030138772 SEQ ID NO: 80 |
| AAV4407 | 458 | US20150315612 SEQ ID NO: 90 |
| AAV5 | 459 | U.S. Pat. No. 7,427,396 SEQ ID NO: 1 |
| AAV5 | 460 | US20030138772 SEQ ID NO: 114 |
| AAV5 | 461 | US20160017295 SEQ ID NO: 5, U.S. Pat. No. 7,427,396 SEQ ID NO: 2, US20150315612 SEQ ID NO: 216 |
| AAV5 | 462 | US20150315612 SEQ ID NO: 199 |
| AAV6 | 463 | US20150159173 SEQ ID NO: 13 |
| AAV6 | 464 | US20030138772 SEQ ID NO: 65, US20150159173 SEQ ID NO: 29, US20160017295 SEQ ID NO: 6, U.S. Pat. No. 6,156,303 SEQ ID NO: 7 |
| AAV6 | 465 | U.S. Pat. No. 6,156,303 SEQ ID NO: 11 |
| AAV6 | 466 | U.S. Pat. No. 6,156,303 SEQ ID NO: 2 |
| AAV6 | 467 | US20150315612 SEQ ID NO: 203 |
| AAV6 | 468 | US20150315612 SEQ ID NO: 220 |
| AAV6.1 | 469 | US20150159173 |
| AAV6.12 | 470 | US20150159173 |
| AAV6.2 | 471 | US20150159173 |
| AAV7 | 472 | US20150159173 SEQ ID NO: 14 |
| AAV7 | 473 | US20150315612 SEQ ID NO: 183 |
| AAV7 | 474 | US20030138772 SEQ ID NO: 2, US20150159173 SEQ ID NO: 30, US20150315612 SEQ ID NO: 181, US20160017295 SEQ ID NO: 7 |
| AAV7 | 475 | US20030138772 SEQ ID NO: 3 |
| AAV7 | 476 | US20030138772 SEQ ID NO: 1, US20150315612 SEQ ID NO: 180 |
| AAV7 | 477 | US20150315612 SEQ ID NO: 213 |
| AAV7 | 478 | US20150315612 SEQ ID NO: 222 |
| AAV8 | 479 | US20150159173 SEQ ID NO: 15 |
| AAV8 | 480 | US20150376240 SEQ ID NO: 7 |
| AAV8 | 481 | US20030138772 SEQ ID NO: 4, US20150315612 SEQ ID NO: 182 |
| AAV8 | 482 | US20030138772 SEQ ID NO: 95, US20140359799 SEQ ID NO: 1, US20150159173 SEQ ID NO: 31, US20160017295 SEQ ID NO: 8, U.S. Pat. No. 7,198,951 SEQ ID NO: 7, US20150315612 SEQ ID NO: 223 |
| AAV8 | 483 | US20150376240 SEQ ID NO: 8 |
| AAV8 | 484 | US20150315612 SEQ ID NO: 214 |
| AAV-8b | 485 | US20150376240 SEQ ID NO: 5 |
| AAV-8b | 486 | US20150376240 SEQ ID NO: 3 |
| AAV-8h | 487 | US20150376240 SEQ ID NO: 6 |
| AAV-8h | 488 | US20150376240 SEQ ID NO: 4 |
| AAV9 | 489 | US20030138772 SEQ ID NO: 5 |
| AAV9 | 490 | U.S. Pat. No. 7,198,951 SEQ ID NO: 1 |
| AAV9 | 491 | US20160017295 SEQ ID NO: 9 |
| AAV9 | 492 | US20030138772 SEQ ID NO: 100, U.S. Pat. No. 7,198,951 SEQ ID NO: 2 |

TABLE 11-continued

AAV Serotypes

| Serotype | SEQ ID NO | Reference Information |
|---|---|---|
| AAV9 | 493 | U.S. Pat. No. 7,198,951 SEQ ID NO: 3 |
| AAV9 (AAVhu.14) | 494 | U.S. Pat. No. 7,906,111 SEQ ID NO: 3; WO2015038958 SEQ ID NO: 11 |
| AAV9 (AAVhu.14) | 495 | U.S. Pat. No. 7,906,111 SEQ ID NO: 123; WO2015038958 SEQ ID NO: 2 |
| AAVA3.1 | 496 | US20030138772 SEQ ID NO: 120 |
| AAVA3.3 | 497 | US20030138772 SEQ ID NO: 57 |
| AAVA3.3 | 498 | US20030138772 SEQ ID NO: 66 |
| AAVA3.4 | 499 | US20030138772 SEQ ID NO: 54 |
| AAVA3.4 | 500 | US20030138772 SEQ ID NO: 68 |
| AAVA3.5 | 501 | US20030138772 SEQ ID NO: 55 |
| AAVA3.5 | 502 | US20030138772 SEQ ID NO: 69 |
| AAVA3.7 | 503 | US20030138772 SEQ ID NO: 56 |
| AAVA3.7 | 504 | US20030138772 SEQ ID NO: 67 |
| AAV29.3 (AAVbb.1) | 505 | US20030138772 SEQ ID NO: 11 |
| AAVC2 | 506 | US20030138772 SEQ ID NO: 61 |
| AAVCh.5 | 507 | US20150159173 SEQ ID NO: 46, US20150315612 SEQ ID NO: 234 |
| AAVcy.2 (AAV13.3) | 508 | US20030138772 SEQ ID NO: 15 |
| AAV24.1 | 509 | US20030138772 SEQ ID NO: 101 |
| AAVcy.3 (AAV24.1) | 510 | US20030138772 SEQ ID NO: 16 |
| AAV27.3 | 511 | US20030138772 SEQ ID NO: 104 |
| AAVcy.4 (AAV27.3) | 512 | US20030138772 SEQ ID NO: 17 |
| AAVcy.5 | 513 | US20150315612 SEQ ID NO: 227 |
| AAV7.2 | 514 | US20030138772 SEQ ID NO: 103 |
| AAVcy.5 (AAV7.2) | 515 | US20030138772 SEQ ID NO: 18 |
| AAV16.3 | 516 | US20030138772 SEQ ID NO: 105 |
| AAVcy.6 (AAV16.3) | 517 | US20030138772 SEQ ID NO: 10 |
| AAVcy.5 | 518 | US20150159173 SEQ ID NO: 8 |
| AAVcy.5 | 519 | US20150159173 SEQ ID NO: 24 |
| AAVCy.5R1 | 520 | US20150159173 |
| AAVCy.5R2 | 521 | US20150159173 |
| AAVCy.5R3 | 522 | US20150159173 |
| AAVCy.5R4 | 523 | US20150159173 |
| AAVDJ | 524 | US20140359799 SEQ ID NO: 3, U.S. Pat. No. 7,588,772 SEQ ID NO: 2 |
| AAVDJ | 525 | US20140359799 SEQ ID NO: 2, U.S. Pat. No. 7,588,772 SEQ ID NO: 1 |
| AAVDJ-8 | 526 | U.S. Pat. No. 7,588,772; Grimm et al 2008 |
| AAVDJ-8 | 527 | U.S. Pat. No. 7,588,772; Grimm et al 2008 |
| AAVF5 | 528 | US20030138772 SEQ ID NO: 110 |
| AAVH2 | 529 | US20030138772 SEQ ID NO: 26 |
| AAVH6 | 530 | US20030138772 SEQ ID NO: 25 |
| AAVhE1.1 | 531 | U.S. Pat. No. 9,233,131 SEQ ID NO: 44 |
| AAVhEr1.14 | 532 | U.S. Pat. No. 9,233,131 SEQ ID NO: 46 |
| AAVhEr1.16 | 533 | U.S. Pat. No. 9,233,131 SEQ ID NO: 48 |
| AAVhEr1.18 | 534 | U.S. Pat. No. 9,233,131 SEQ ID NO: 49 |
| AAVhEr1.23 (AAVhEr2.29) | 535 | U.S. Pat. No. 9,233,131 SEQ ID NO: 53 |
| AAVhEr1.35 | 536 | U.S. Pat. No. 9,233,131 SEQ ID NO: 50 |
| AAVhEr1.36 | 537 | U.S. Pat. No. 9,233,131 SEQ ID NO: 52 |
| AAVhEr1.5 | 538 | U.S. Pat. No. 9,233,131 SEQ ID NO: 45 |
| AAVhEr1.7 | 539 | U.S. Pat. No. 9,233,131 SEQ ID NO: 51 |
| AAVhEr1.8 | 540 | U.S. Pat. No. 9,233,131 SEQ ID NO: 47 |
| AAVhEr2.16 | 541 | U.S. Pat. No. 9,233,131 SEQ ID NO: 55 |
| AAVhEr2.30 | 542 | U.S. Pat. No. 9,233,131 SEQ ID NO: 56 |
| AAVhEr2.31 | 543 | U.S. Pat. No. 9,233,131 SEQ ID NO: 58 |
| AAVhEr2.36 | 544 | U.S. Pat. No. 9,233,131 SEQ ID NO: 57 |
| AAVhEr2.4 | 545 | U.S. Pat. No. 9,233,131 SEQ ID NO: 54 |
| AAVhEr3.1 | 546 | U.S. Pat. No. 9,233,131 SEQ ID NO: 59 |
| AAVhu.1 | 547 | US20150315612 SEQ ID NO: 46 |
| AAVhu.1 | 548 | US20150315612 SEQ ID NO: 144 |
| AAVhu.10 (AAV16.8) | 549 | US20150315612 SEQ ID NO: 56 |
| AAVhu.10 (AAV16.8) | 550 | US20150315612 SEQ ID NO: 156 |
| AAVhu.11 (AAV16.12) | 551 | US20150315612 SEQ ID NO: 57 |
| AAVhu.11 (AAV16.12) | 552 | US20150315612 SEQ ID NO: 153 |
| AAVhu.12 | 553 | US20150315612 SEQ ID NO: 59 |
| AAVhu.12 | 554 | US20150315612 SEQ ID NO: 154 |
| AAVhu.13 | 555 | US20150159173 SEQ ID NO: 16, US20150315612 SEQ ID NO: 71 |
| AAVhu.13 | 556 | US20150159173 SEQ ID NO: 32, US20150315612 SEQ ID NO: 129 |
| AAVhu.136.1 | 557 | US20150315612 SEQ ID NO: 165 |
| AAVhu.140.1 | 558 | US20150315612 SEQ ID NO: 166 |
| AAVhu.140.2 | 559 | US20150315612 SEQ ID NO: 167 |
| AAVhu.145.6 | 560 | US20150315612 SEQ ID No: 178 |
| AAVhu.15 | 561 | US20150315612 SEQ ID NO: 147 |

TABLE 11-continued

AAV Serotypes

| Serotype | SEQ ID NO | Reference Information |
| --- | --- | --- |
| AAVhu.15 (AAV33.4) | 562 | US20150315612 SEQ ID NO: 50 |
| AAVhu.156.1 | 563 | US20150315612 SEQ ID No: 179 |
| AAVhu.16 | 564 | US20150315612 SEQ ID NO: 148 |
| AAVhu.16 (AAV33.8) | 565 | US20150315612 SEQ ID NO: 51 |
| AAVhu.17 | 566 | US20150315612 SEQ ID NO: 83 |
| AAVhu.17 (AAV33.12) | 567 | US20150315612 SEQ ID NO: 4 |
| AAVhu.172.1 | 568 | US20150315612 SEQ ID NO: 171 |
| AAVhu.172.2 | 569 | US20150315612 SEQ ID NO: 172 |
| AAVhu.173.4 | 570 | US20150315612 SEQ ID NO: 175 |
| AAVhu.173.8 | 571 | US20150315612 SEQ ID NO: 175 |
| AAVhu.18 | 572 | US20150315612 SEQ ID NO: 52 |
| AAVhu.18 | 573 | US20150315612 SEQ ID NO: 149 |
| AAVhu.19 | 574 | US20150315612 SEQ ID NO: 62 |
| AAVhu.19 | 575 | US20150315612 SEQ ID NO: 133 |
| AAVhu.2 | 576 | US20150315612 SEQ ID NO: 48 |
| AAVhu.2 | 577 | US20150315612 SEQ ID NO: 143 |
| AAVhu.20 | 578 | US20150315612 SEQ ID NO: 63 |
| AAVhu.20 | 579 | US20150315612 SEQ ID NO: 134 |
| AAVhu.21 | 580 | US20150315612 SEQ ID NO: 65 |
| AAVhu.21 | 581 | US20150315612 SEQ ID NO: 135 |
| AAVhu.22 | 582 | US20150315612 SEQ ID NO: 67 |
| AAVhu.22 | 583 | US20150315612 SEQ ID NO: 138 |
| AAVhu.23 | 584 | US20150315612 SEQ ID NO: 60 |
| AAVhu.23.2 | 585 | US20150315612 SEQ ID NO: 137 |
| AAVhu.24 | 586 | US20150315612 SEQ ID NO: 66 |
| AAVhu.24 | 587 | US20150315612 SEQ ID NO: 136 |
| AAVhu.25 | 588 | US20150315612 SEQ ID NO: 49 |
| AAVhu.25 | 589 | US20150315612 SEQ ID NO: 146 |
| AAVhu.26 | 590 | US20150159173 SEQ ID NO: 17, US20150315612 SEQ ID NO: 61 |
| AAVhu.26 | 591 | US20150159173 SEQ ID NO: 33, US20150315612 SEQ ID NO: 139 |
| AAVhu.27 | 592 | US20150315612 SEQ ID NO: 64 |
| AAVhu.27 | 593 | US20150315612 SEQ ID NO: 140 |
| AAVhu.28 | 594 | US20150315612 SEQ ID NO: 68 |
| AAVhu.28 | 595 | US20150315612 SEQ ID NO: 130 |
| AAVhu.29 | 596 | US20150315612 SEQ ID NO: 69 |
| AAVhu.29 | 597 | US20150159173 SEQ ID NO: 42, US20150315612 SEQ ID NO: 132 |
| AAVhu.29 | 598 | US20150315612 SEQ ID NO: 225 |
| AAVhu.29R | 599 | US20150159173 |
| AAVhu.3 | 600 | US20150315612 SEQ ID NO: 44 |
| AAVhu.3 | 601 | US20150315612 SEQ ID NO: 145 |
| AAVhu.30 | 602 | US20150315612 SEQ ID NO: 70 |
| AAVhu.30 | 603 | US20150315612 SEQ ID NO: 131 |
| AAVhu.31 | 604 | US20150315612 SEQ ID NO: 1 |
| AAVhu.31 | 605 | US20150315612 SEQ ID NO: 121 |
| AAVhu.32 | 606 | US20150315612 SEQ ID NO: 2 |
| AAVhu.32 | 607 | US20150315612 SEQ ID NO: 122 |
| AAVhu.33 | 608 | US20150315612 SEQ ID NO: 75 |
| AAVhu.33 | 609 | US20150315612 SEQ ID NO: 124 |
| AAVhu.34 | 610 | US20150315612 SEQ ID NO: 72 |
| AAVhu.34 | 611 | US20150315612 SEQ ID NO: 125 |
| AAVhu.35 | 612 | US20150315612 SEQ ID NO: 73 |
| AAVhu.35 | 613 | US20150315612 SEQ ID NO: 164 |
| AAVhu.36 | 614 | US20150315612 SEQ ID NO: 74 |
| AAVhu.36 | 615 | US20150315612 SEQ ID NO: 126 |
| AAVhu.37 | 616 | US20150159173 SEQ ID NO: 34, US20150315612 SEQ ID NO: 88 |
| AAVhu.37 (AAV106.1) | 617 | US20150315612 SEQ ID NO: 10, US20150159173 SEQ ID NO: 18 |
| AAVhu.38 | 618 | US20150315612 SEQ ID NO: 161 |
| AAVhu.39 | 619 | US20150315612 SEQ ID NO: 102 |
| AAVhu.39 (AAVLG-9) | 620 | US20150315612 SEQ ID NO: 24 |
| AAVhu.4 | 621 | US20150315612 SEQ ID NO: 47 |
| AAVhu.4 | 622 | US20150315612 SEQ ID NO: 141 |
| AAVhu.40 | 623 | US20150315612 SEQ ID NO: 87 |
| AAVhu.40 (AAV114.3) | 624 | US20150315612 SEQ ID No: 11 |
| AAVhu.41 | 625 | US20150315612 SEQ ID NO: 91 |
| AAVhu.41 (AAV127.2) | 626 | US20150315612 SEQ ID NO: 6 |
| AAVhu.42 | 627 | US20150315612 SEQ ID NO: 85 |
| AAVhu.42 (AAV127.5) | 628 | US20150315612 SEQ ID NO: 8 |

TABLE 11-continued

AAV Serotypes

| Serotype | SEQ ID NO | Reference Information |
|---|---|---|
| AAVhu.43 | 629 | US20150315612 SEQ ID NO: 160 |
| AAVhu.43 | 630 | US20150315612 SEQ ID NO: 236 |
| AAVhu.43 (AAV128.1) | 631 | US20150315612 SEQ ID NO: 80 |
| AAVhu.44 | 632 | US20150159173 SEQ ID NO: 45, US20150315612 SEQ ID NO: 158 |
| AAVhu.44 (AAV128.3) | 633 | US20150315612 SEQ ID NO: 81 |
| AAVhu.44R1 | 634 | US20150159173 |
| AAVhu.44R2 | 635 | US20150159173 |
| AAVhu.44R3 | 636 | US20150159173 |
| AAVhu.45 | 637 | US20150315612 SEQ ID NO: 76 |
| AAVhu.45 | 638 | US20150315612 SEQ ID NO: 127 |
| AAVhu.46 | 639 | US20150315612 SEQ ID NO: 82 |
| AAVhu.46 | 640 | US20150315612 SEQ ID NO: 159 |
| AAVhu.46 | 641 | US20150315612 SEQ ID NO: 224 |
| AAVhu.47 | 642 | US20150315612 SEQ ID NO: 77 |
| AAVhu.47 | 643 | US20150315612 SEQ ID NO: 128 |
| AAVhu.48 | 644 | US20150159173 SEQ ID NO: 38 |
| AAVhu.48 | 645 | US20150315612 SEQ ID NO: 157 |
| AAVhu.48 (AAV130.4) | 646 | US20150315612 SEQ ID NO: 78 |
| AAVhu.48R1 | 647 | US20150159173 |
| AAVhu.48R2 | 648 | US20150159173 |
| AAVhu.48R3 | 649 | US20150159173 |
| AAVhu.49 | 650 | US20150315612 SEQ ID NO: 209 |
| AAVhu.49 | 651 | US20150315612 SEQ ID NO: 189 |
| AAVhu.5 | 652 | US20150315612 SEQ ID NO: 45 |
| AAVhu.5 | 653 | US20150315612 SEQ ID NO: 142 |
| AAVhu.51 | 654 | US20150315612 SEQ ID NO: 208 |
| AAVhu.51 | 655 | US20150315612 SEQ ID NO: 190 |
| AAVhu.52 | 656 | US20150315612 SEQ ID NO: 210 |
| AAVhu.52 | 657 | US20150315612 SEQ ID NO: 191 |
| AAVhu.53 | 658 | US20150159173 SEQ ID NO: 19 |
| AAVhu.53 | 659 | US20150159173 SEQ ID NO: 35 |
| AAVhu.53 (AAV145.1) | 660 | US20150315612 SEQ ID NO: 176 |
| AAVhu.54 | 661 | US20150315612 SEQ ID NO: 188 |
| AAVhu.54 (AAV145.5) | 662 | US20150315612 SEQ ID No: 177 |
| AAVhu.55 | 663 | US20150315612 SEQ ID NO: 187 |
| AAVhu.56 | 664 | US20150315612 SEQ ID NO: 205 |
| AAVhu.56 (AAV145.6) | 665 | US20150315612 SEQ ID NO: 168 |
| AAVhu.56 (AAV145.6) | 666 | US20150315612 SEQ ID NO: 192 |
| AAVhu.57 | 667 | US20150315612 SEQ ID NO: 206 |
| AAVhu.57 | 668 | US20150315612 SEQ ID NO: 169 |
| AAVhu.57 | 669 | US20150315612 SEQ ID NO: 193 |
| AAVhu.58 | 670 | US20150315612 SEQ ID NO: 207 |
| AAVhu.58 | 671 | US20150315612 SEQ ID NO: 194 |
| AAVhu.6 (AAV3.1) | 672 | US20150315612 SEQ ID NO: 5 |
| AAVhu.6 (AAV3.1) | 673 | US20150315612 SEQ ID NO: 84 |
| AAVhu.60 | 674 | US20150315612 SEQ ID NO: 184 |
| AAVhu.60 (AAV161.10) | 675 | US20150315612 SEQ ID NO: 170 |
| AAVhu.61 | 676 | US20150315612 SEQ ID NO: 185 |
| AAVhu.61 (AAV161.6) | 677 | US20150315612 SEQ ID NO: 174 |
| AAVhu.63 | 678 | US20150315612 SEQ ID NO: 204 |
| AAVhu.63 | 679 | US20150315612 SEQ ID NO: 195 |
| AAVhu.64 | 680 | US20150315612 SEQ ID NO: 212 |
| AAVhu.64 | 681 | US20150315612 SEQ ID NO: 196 |
| AAVhu.66 | 682 | US20150315612 SEQ ID NO: 197 |
| AAVhu.67 | 683 | US20150315612 SEQ ID NO: 215 |
| AAVhu.67 | 684 | US20150315612 SEQ ID NO: 198 |
| AAVhu.7 | 685 | US20150315612 SEQ ID NO: 226 |
| AAVhu.7 | 686 | US20150315612 SEQ ID NO: 150 |
| AAVhu.7 (AAV7.3) | 687 | US20150315612 SEQ ID NO: 55 |
| AAVhu.71 | 688 | US20150315612 SEQ ID NO: 79 |
| AAVhu.8 | 689 | US20150315612 SEQ ID NO: 53 |
| AAVhu.8 | 690 | US20150315612 SEQ ID NO: 12 |
| AAVhu.8 | 691 | US20150315612 SEQ ID NO: 151 |
| AAVhu.9 (AAV3.1) | 692 | US20150315612 SEQ ID NO: 58 |
| AAVhu.9 (AAV3.1) | 693 | US20150315612 SEQ ID NO: 155 |
| AAV-LK01 | 694 | US20150376607 SEQ ID NO: 2 |

TABLE 11-continued

AAV Serotypes

| Serotype | SEQ ID NO | Reference Information |
| --- | --- | --- |
| AAV-LK01 | 695 | US20150376607 SEQ ID NO: 29 |
| AAV-LK02 | 696 | US20150376607 SEQ ID NO: 3 |
| AAV-LK02 | 697 | US20150376607 SEQ ID NO: 30 |
| AAV-LK03 | 698 | US20150376607 SEQ ID NO: 4 |
| AAV-LK03 | 699 | WO2015121501 SEQ ID NO: 12, US20150376607 SEQ ID NO: 31 |
| AAV-LK04 | 700 | US20150376607 SEQ ID NO: 5 |
| AAV-LK04 | 701 | US20150376607 SEQ ID NO: 32 |
| AAV-LK05 | 702 | US20150376607 SEQ ID NO: 6 |
| AAV-LK05 | 703 | US20150376607 SEQ ID NO: 33 |
| AAV-LK06 | 704 | US20150376607 SEQ ID NO: 7 |
| AAV-LK06 | 705 | US20150376607 SEQ ID NO: 34 |
| AAV-LK07 | 706 | US20150376607 SEQ ID NO: 8 |
| AAV-LK07 | 707 | US20150376607 SEQ ID NO: 35 |
| AAV-LK08 | 708 | US20150376607 SEQ ID NO: 9 |
| AAV-LK08 | 709 | US20150376607 SEQ ID NO: 36 |
| AAV-LK09 | 710 | US20150376607 SEQ ID NO: 10 |
| AAV-LK09 | 711 | US20150376607 SEQ ID NO: 37 |
| AAV-LK10 | 712 | US20150376607 SEQ ID NO: 11 |
| AAV-LK10 | 713 | US20150376607 SEQ ID NO: 38 |
| AAV-LK11 | 714 | US20150376607 SEQ ID NO: 12 |
| AAV-LK11 | 715 | US20150376607 SEQ ID NO: 39 |
| AAV-LK12 | 716 | US20150376607 SEQ ID NO: 13 |
| AAV-LK12 | 717 | US20150376607 SEQ ID NO: 40 |
| AAV-LK13 | 718 | US20150376607 SEQ ID NO: 14 |
| AAV-LK13 | 719 | US20150376607 SEQ ID NO: 41 |
| AAV-LK14 | 720 | US20150376607 SEQ ID NO: 15 |
| AAV-LK14 | 721 | US20150376607 SEQ ID NO: 42 |
| AAV-LK15 | 722 | US20150376607 SEQ ID NO: 16 |
| AAV-LK15 | 723 | US20150376607 SEQ ID NO: 43 |
| AAV-LK16 | 724 | US20150376607 SEQ ID NO: 17 |
| AAV-LK16 | 725 | US20150376607 SEQ ID NO: 44 |
| AAV-LK17 | 726 | US20150376607 SEQ ID NO: 18 |
| AAV-LK17 | 727 | US20150376607 SEQ ID NO: 45 |
| AAV-LK18 | 728 | US20150376607 SEQ ID NO: 19 |
| AAV-LK18 | 729 | US20150376607 SEQ ID NO: 46 |
| AAV-LK19 | 730 | US20150376607 SEQ ID NO: 20 |
| AAV-LK19 | 731 | US20150376607 SEQ ID NO: 47 |
| AAV-PAEC | 732 | US20150376607 SEQ ID NO: 1 |
| AAV-PAEC | 733 | US20150376607 SEQ ID NO: 48 |
| AAV-PAEC11 | 734 | US20150376607 SEQ ID NO: 26 |
| AAV-PAEC11 | 735 | US20150376607 SEQ ID NO: 54 |
| AAV-PAEC12 | 736 | US20150376607 SEQ ID NO: 27 |
| AAV-PAEC12 | 737 | US20150376607 SEQ ID NO: 51 |
| AAV-PAEC13 | 738 | US20150376607 SEQ ID NO: 28 |
| AAV-PAEC13 | 739 | US20150376607 SEQ ID NO: 49 |
| AAV-PAEC2 | 740 | US20150376607 SEQ ID NO: 21 |
| AAV-PAEC2 | 741 | US20150376607 SEQ ID NO: 56 |
| AAV-PAEC4 | 742 | US20150376607 SEQ ID NO: 22 |
| AAV-PAEC4 | 743 | US20150376607 SEQ ID NO: 55 |
| AAV-PAEC6 | 744 | US20150376607 SEQ ID NO: 23 |
| AAV-PAEC6 | 745 | US20150376607 SEQ ID NO: 52 |
| AAV-PAEC7 | 746 | US20150376607 SEQ ID NO: 24 |
| AAV-PAEC7 | 747 | US20150376607 SEQ ID NO: 53 |
| AAV-PAEC8 | 748 | US20150376607 SEQ ID NO: 25 |
| AAV-PAEC8 | 749 | US20150376607 SEQ ID NO: 50 |
| AAVpi.1 | 750 | US20150315612 SEQ ID NO: 28 |
| AAVpi.1 | 751 | US20150315612 SEQ ID NO: 93 |
| AAVpi.2 | 752 | US20150315612 SEQ ID NO: 30 |
| AAVpi.2 | 753 | US20150315612 SEQ ID NO: 95 |
| AAVpi.3 | 754 | US20150315612 SEQ ID NO: 29 |
| AAVpi.3 | 755 | US20150315612 SEQ ID NO: 94 |
| AAVrh.10 | 756 | US20150159173 SEQ ID NO: 9 |
| AAVrh.10 | 757 | US20150159173 SEQ ID NO: 25 |
| AAV44.2 | 758 | US20030138772 SEQ ID NO: 59 |
| AAVrh.10 (AAV44.2) | 759 | US20030138772 SEQ ID NO: 81 |
| AAV42.1B | 760 | US20030138772 SEQ ID NO: 90 |
| AAVrh.12 (AAV42.1b) | 761 | US20030138772 SEQ ID NO: 30 |
| AAVrh.13 | 762 | US20150159173 SEQ ID NO: 10 |
| AAVrh.13 | 763 | US20150159173 SEQ ID NO: 26 |
| AAVrh.13 | 764 | US20150315612 SEQ ID NO: 228 |
| AAVrh.13R | 765 | US20150159173 |
| AAV42.3A | 766 | US20030138772 SEQ ID NO: 87 |
| AAVrh.14 (AAV42.3a) | 767 | US20030138772 SEQ ID NO: 32 |

TABLE 11-continued

AAV Serotypes

| Serotype | SEQ ID NO | Reference Information |
|---|---|---|
| AAV42.5A | 768 | US20030138772 SEQ ID NO: 89 |
| AAVrh.17 (AAV42.5a) | 769 | US20030138772 SEQ ID NO: 34 |
| AAV42.5B | 770 | US20030138772 SEQ ID NO: 91 |
| AAVrh.18 (AAV42.5b) | 771 | US20030138772 SEQ ID NO: 29 |
| AAV42.6B | 772 | US20030138772 SEQ ID NO: 112 |
| AAVrh.19 (AAV42.6b) | 773 | US20030138772 SEQ ID NO: 38 |
| AAVrh.2 | 774 | US20150159173 SEQ ID NO: 39 |
| AAVrh.2 | 775 | US20150315612 SEQ ID NO: 231 |
| AAVrh.20 | 776 | US20150159173 SEQ ID NO: 1 |
| AAV42.10 | 777 | US20030138772 SEQ ID NO: 106 |
| AAVrh.21 (AAV42.10) | 778 | US20030138772 SEQ ID NO: 35 |
| AAV42.11 | 779 | US20030138772 SEQ ID NO: 108 |
| AAVrh.22 (AAV42.11) | 780 | US20030138772 SEQ ID NO: 37 |
| AAV42.12 | 781 | US20030138772 SEQ ID NO: 113 |
| AAVrh.23 (AAV42.12) | 782 | US20030138772 SEQ ID NO: 58 |
| AAV42.13 | 783 | US20030138772 SEQ ID NO: 86 |
| AAVrh.24 (AAV42.13) | 784 | US20030138772 SEQ ID NO: 31 |
| AAV42.15 | 785 | US20030138772 SEQ ID NO: 84 |
| AAVrh.25 (AAV42.15) | 786 | US20030138772 SEQ ID NO: 28 |
| AAVrh.2R | 787 | US20150159173 |
| AAVrh.31 (AAV223.1) | 788 | US20030138772 SEQ ID NO: 48 |
| AAVC1 | 789 | US20030138772 SEQ ID NO: 60 |
| AAVrh.32 (AAVC1) | 790 | US20030138772 SEQ ID NO: 19 |
| AAVrh.32/33 | 791 | US20150159173 SEQ ID NO: 2 |
| AAVrh.33 (AAVC3) | 792 | US20030138772 SEQ ID NO: 20 |
| AAVC5 | 793 | US20030138772 SEQ ID NO: 62 |
| AAVrh.34 (AAVC5) | 794 | US20030138772 SEQ ID NO: 21 |
| AAVF1 | 795 | US20030138772 SEQ ID NO: 109 |
| AAVrh.35 (AAVF1) | 796 | US20030138772 SEQ ID NO: 22 |
| AAVF3 | 797 | US20030138772 SEQ ID NO: 111 |
| AAVrh.36 (AAVF3) | 798 | US20030138772 SEQ ID NO: 23 |
| AAVrh.37 | 799 | US20030138772 SEQ ID NO: 24 |
| AAVrh.37 | 800 | US20150159173 SEQ ID NO: 40 |
| AAVrh.37 | 801 | US20150315612 SEQ ID NO: 229 |
| AAVrh.37R2 | 802 | US20150159173 |
| AAVrh.38 (AAVLG-4) | 803 | US20150315612 SEQ ID NO: 7 |
| AAVrh.38 (AAVLG-4) | 804 | US20150315612 SEQ ID NO: 86 |
| AAVrh.39 | 805 | US20150159173 SEQ ID NO: 20, US20150315612 SEQ ID NO: 13 |
| AAVrh.39 | 806 | US20150159173 SEQ ID NO: 3, US20150159173 SEQ ID NO: 36, US20150315612 SEQ ID NO: 89 |
| AAVrh.40 | 807 | US20150315612 SEQ ID NO: 92 |
| AAVrh.40 (AAVLG-10) | 808 | US20150315612 SEQ ID No: 14 |
| AAVrh.43 (AAVN721-8) | 809 | US20150315612 SEQ ID NO: 43, US20150159173 SEQ ID NO: 21 |
| AAVrh.43 (AAVN721-8) | 810 | US20150315612 SEQ ID NO: 163, US20150159173 SEQ ID NO: 37 |
| AAVrh.44 | 811 | US20150315612 SEQ ID NO: 34 |
| AAVrh.44 | 812 | US20150315612 SEQ ID NO: 111 |
| AAVrh.45 | 813 | US20150315612 SEQ ID NO: 41 |
| AAVrh.45 | 814 | US20150315612 SEQ ID NO: 109 |
| AAVrh.46 | 815 | US20150159173 SEQ ID NO: 22, US20150315612 SEQ ID NO: 19 |
| AAVrh.46 | 816 | US20150159173 SEQ ID NO: 4, US20150315612 SEQ ID NO: 101 |
| AAVrh.47 | 817 | US20150315612 SEQ ID NO: 38 |
| AAVrh.47 | 818 | US20150315612 SEQ ID NO: 118 |
| AAVrh.48 | 819 | US20150159173 SEQ ID NO: 44, US20150315612 SEQ ID NO: 115 |
| AAVrh.48.1 | 820 | US20150159173 |
| AAVrh.48.1.2 | 821 | US20150159173 |
| AAVrh.48.2 | 822 | US20150159173 |
| AAVrh.48 (AAV1-7) | 823 | US20150315612 SEQ ID NO: 32 |
| AAVrh.49 (AAV1-8) | 824 | US20150315612 SEQ ID NO: 25 |
| AAVrh.49 (AAV1-8) | 825 | US20150315612 SEQ ID NO: 103 |
| AAVrh.50 (AAV2-4) | 826 | US20150315612 SEQ ID NO: 23 |
| AAVrh.50 (AAV2-4) | 827 | US20150315612 SEQ ID NO: 108 |

TABLE 11-continued

AAV Serotypes

| Serotype | SEQ ID NO | Reference Information |
|---|---|---|
| AAVrh.51 (AAV2-5) | 828 | US20150315612 SEQ ID No: 22 |
| AAVrh.51 (AAV2-5) | 829 | US20150315612 SEQ ID NO: 104 |
| AAVrh.52 (AAV3-9) | 830 | US20150315612 SEQ ID NO: 18 |
| AAVrh.52 (AAV3-9) | 831 | US20150315612 SEQ ID NO: 96 |
| AAVrh.53 | 832 | US20150315612 SEQ ID NO: 97 |
| AAVrh.53 (AAV3-11) | 833 | US20150315612 SEQ ID NO: 17 |
| AAVrh.53 (AAV3-11) | 834 | US20150315612 SEQ ID NO: 186 |
| AAVrh.54 | 835 | US20150315612 SEQ ID NO: 40 |
| AAVrh.54 | 836 | US20150159173 SEQ ID NO: 49, US20150315612 SEQ ID NO: 116 |
| AAVrh.55 | 837 | US20150315612 SEQ ID NO: 37 |
| AAVrh.55 (AAV4-19) | 838 | US20150315612 SEQ ID NO: 117 |
| AAVrh.56 | 839 | US20150315612 SEQ ID NO: 54 |
| AAVrh.56 | 840 | US20150315612 SEQ ID NO: 152 |
| AAVrh.57 | 841 | US20150315612 SEQ ID NO: 26 |
| AAVrh.57 | 842 | US20150315612 SEQ ID NO: 105 |
| AAVrh.58 | 843 | US20150315612 SEQ ID NO: 27 |
| AAVrh.58 | 844 | US20150159173 SEQ ID NO: 48, US20150315612 SEQ ID NO: 106 |
| AAVrh.58 | 845 | US20150315612 SEQ ID NO: 232 |
| AAVrh.59 | 846 | US20150315612 SEQ ID NO: 42 |
| AAVrh.59 | 847 | US20150315612 SEQ ID NO: 110 |
| AAVrh.60 | 848 | US20150315612 SEQ ID NO: 31 |
| AAVrh.60 | 849 | US20150315612 SEQ ID NO: 120 |
| AAVrh.61 | 850 | US20150315612 SEQ ID NO: 107 |
| AAVrh.61 (AAV2-3) | 851 | US20150315612 SEQ ID NO: 21 |
| AAVrh.62 (AAV2-15) | 852 | US20150315612 SEQ ID No: 33 |
| AAVrh.62 (AAV2-15) | 853 | US20150315612 SEQ ID NO: 114 |
| AAVrh.64 | 854 | US20150315612 SEQ ID No: 15 |
| AAVrh.64 | 855 | US20150159173 SEQ ID NO: 43, US20150315612 SEQ ID NO: 99 |
| AAVrh.64 | 856 | US20150315612 SEQ ID NO: 233 |
| AAVRh.64R1 | 857 | US20150159173 |
| AAVRh.64R2 | 858 | US20150159173 |
| AAVrh.65 | 859 | US20150315612 SEQ ID NO: 35 |
| AAVrh.65 | 860 | US20150315612 SEQ ID NO: 112 |
| AAVrh.67 | 861 | US20150315612 SEQ ID NO: 36 |
| AAVrh.67 | 862 | US20150315612 SEQ ID NO: 230 |
| AAVrh.67 | 863 | US20150159173 SEQ ID NO: 47, US20150315612 SEQ ID NO: 113 |
| AAVrh.68 | 864 | US20150315612 SEQ ID NO: 16 |
| AAVrh.68 | 865 | US20150315612 SEQ ID NO: 100 |
| AAVrh.69 | 866 | US20150315612 SEQ ID NO: 39 |
| AAVrh.69 | 867 | US20150315612 SEQ ID NO: 119 |
| AAVrh.70 | 868 | US20150315612 SEQ ID NO: 20 |
| AAVrh.70 | 869 | US20150315612 SEQ ID NO: 98 |
| AAVrh.71 | 870 | US20150315612 SEQ ID NO: 162 |
| AAVrh.72 | 871 | US20150315612 SEQ ID NO: 9 |
| AAVrh.73 | 872 | US20150159173 SEQ ID NO: 5 |
| AAVrh.74 | 873 | US20150159173 SEQ ID NO: 6 |
| AAVrh.8 | 874 | US20150159173 SEQ ID NO: 41 |
| AAVrh.8 | 875 | US20150315612 SEQ ID NO: 235 |
| AAVrh.8R | 876 | US20150159173, WO2015168666 SEQ ID NO: 9 |
| AAVrh.8R A586R mutant | 877 | WO2015168666 SEQ ID NO: 10 |
| AAVrh.8R R533A mutant | 878 | WO2015168666 SEQ ID NO: 11 |
| BAAV (bovine AAV) | 879 | U.S. Pat. No. 9,193,769 SEQ ID NO: 8 |
| BAAV (bovine AAV) | 880 | U.S. Pat. No. 9,193,769 SEQ ID NO: 10 |
| BAAV (bovine AAV) | 881 | U.S. Pat. No. 9,193,769 SEQ ID NO: 4 |
| BAAV (bovine AAV) | 882 | U.S. Pat. No. 9,193,769 SEQ ID NO: 2 |
| BAAV (bovine AAV) | 883 | U.S. Pat. No. 9,193,769 SEQ ID NO: 6 |
| BAAV (bovine AAV) | 884 | U.S. Pat. No. 9,193,769 SEQ ID NO: 1 |
| BAAV (bovine AAV) | 885 | U.S. Pat. No. 9,193,769 SEQ ID NO: 5 |
| BAAV (bovine AAV) | 886 | U.S. Pat. No. 9,193,769 SEQ ID NO: 3 |
| BAAV (bovine AAV) | 887 | U.S. Pat. No. 9,193,769 SEQ ID NO: 11 |
| BAAV (bovine AAV) | 888 | U.S. Pat. No. 7,427,396 SEQ ID NO: 5 |
| BAAV (bovine AAV) | 889 | U.S. Pat. No. 7,427,396 SEQ ID NO: 6 |
| BAAV (bovine AAV) | 890 | U.S. Pat. No. 9,193,769 SEQ ID NO: 7 |
| BAAV (bovine AAV) | 891 | U.S. Pat. No. 9,193,769 SEQ ID NO: 9 |
| BNP61 AAV | 892 | US20150238550 SEQ ID NO: 1 |
| BNP61 AAV | 893 | US20150238550 SEQ ID NO: 2 |
| BNP62 AAV | 894 | US20150238550 SEQ ID NO: 3 |
| BNP63 AAV | 895 | US20150238550 SEQ ID NO: 4 |
| caprine AAV | 896 | U.S. Pat. No. 7,427,396 SEQ ID NO: 3 |
| caprine AAV | 897 | U.S. Pat. No. 7,427,396 SEQ ID NO: 4 |
| true type AAV (ttAAV) | 898 | WO2015121501 SEQ ID NO: 2 |

TABLE 11-continued

AAV Serotypes

| Serotype | SEQ ID NO | Reference Information |
|---|---|---|
| AAAV (Avian AAV) | 899 | U.S. Pat. No. 9,238,800 SEQ ID NO: 12 |
| AAAV (Avian AAV) | 900 | U.S. Pat. No. 9,238,800 SEQ ID NO: 2 |
| AAAV (Avian AAV) | 901 | U.S. Pat. No. 9,238,800 SEQ ID NO: 6 |
| AAAV (Avian AAV) | 902 | U.S. Pat. No. 9,238,800 SEQ ID NO: 4 |
| AAAV (Avian AAV) | 903 | U.S. Pat. No. 9,238,800 SEQ ID NO: 8 |
| AAAV (Avian AAV) | 904 | U.S. Pat. No. 9,238,800 SEQ ID NO: 14 |
| AAAV (Avian AAV) | 905 | U.S. Pat. No. 9,238,800 SEQ ID NO: 10 |
| AAAV (Avian AAV) | 906 | U.S. Pat. No. 9,238,800 SEQ ID NO: 15 |
| AAAV (Avian AAV) | 907 | U.S. Pat. No. 9,238,800 SEQ ID NO: 5 |
| AAAV (Avian AAV) | 908 | U.S. Pat. No. 9,238,800 SEQ ID NO: 9 |
| AAAV (Avian AAV) | 909 | U.S. Pat. No. 9,238,800 SEQ ID NO: 3 |
| AAAV (Avian AAV) | 910 | U.S. Pat. No. 9,238,800 SEQ ID NO: 7 |
| AAAV (Avian AAV) | 911 | U.S. Pat. No. 9,238,800 SEQ ID NO: 11 |
| AAAV (Avian AAV) | 912 | U.S. Pat. No. 9,238,800 SEQ ID NO: 13 |
| AAAV (Avian AAV) | 913 | U.S. Pat. No. 9,238,800 SEQ ID NO: 1 |
| AAV Shuffle 100-1 | 914 | US20160017295 SEQ ID NO: 23 |
| AAV Shuffle 100-1 | 915 | US20160017295 SEQ ID NO: 11 |
| AAV Shuffle 100-2 | 916 | US20160017295 SEQ ID NO: 37 |
| AAV Shuffle 100-2 | 917 | US20160017295 SEQ ID NO: 29 |
| AAV Shuffle 100-3 | 918 | US20160017295 SEQ ID NO: 24 |
| AAV Shuffle 100-3 | 919 | US20160017295 SEQ ID NO: 12 |
| AAV Shuffle 100-7 | 920 | US20160017295 SEQ ID NO: 25 |
| AAV Shuffle 100-7 | 921 | US20160017295 SEQ ID NO: 13 |
| AAV Shuffle 10-2 | 922 | US20160017295 SEQ ID NO: 34 |
| AAV Shuffle 10-2 | 923 | US20160017295 SEQ ID NO: 26 |
| AAV Shuffle 10-6 | 924 | US20160017295 SEQ ID NO: 35 |
| AAV Shuffle 10-6 | 925 | US20160017295 SEQ ID NO: 27 |
| AAV Shuffle 10-8 | 926 | US20160017295 SEQ ID NO: 36 |
| AAV Shuffle 10-8 | 927 | US20160017295 SEQ ID NO: 28 |
| AAV SM 100-10 | 928 | US20160017295 SEQ ID NO: 41 |
| AAV SM 100-10 | 929 | US20160017295 SEQ ID NO: 33 |
| AAV SM 100-3 | 930 | US20160017295 SEQ ID NO: 40 |
| AAV SM 100-3 | 931 | US20160017295 SEQ ID NO: 32 |
| AAV SM 10-1 | 932 | US20160017295 SEQ ID NO: 38 |
| AAV SM 10-1 | 933 | US20160017295 SEQ ID NO: 30 |
| AAV SM 10-2 | 934 | US20160017295 SEQ ID NO: 10 |
| AAV SM 10-2 | 935 | US20160017295 SEQ ID NO: 22 |
| AAV SM 10-8 | 936 | US20160017295 SEQ ID NO: 39 |
| AAV SM 10-8 | 937 | US20160017295 SEQ ID NO: 31 |
| AAV SM 100-10 | 928 | US20160017295 SEQ ID NO: 41 |
| AAV SM 100-10 | 929 | US20160017295 SEQ ID NO: 33 |
| AAV SM 100-3 | 930 | US20160017295 SEQ ID NO: 40 |
| AAV SM 100-3 | 931 | US20160017295 SEQ ID NO: 32 |
| AAV SM 10-1 | 932 | US20160017295 SEQ ID NO: 38 |
| AAV SM 10-1 | 933 | US20160017295 SEQ ID NO: 30 |
| AAV SM 10-2 | 934 | US20160017295 SEQ ID NO: 10 |
| AAV SM 10-2 | 935 | US20160017295 SEQ ID NO: 22 |
| AAV SM 10-8 | 936 | US20160017295 SEQ ID NO: 39 |
| AAV SM 10-8 | 937 | US20160017295 SEQ ID NO: 31 |
| AAVF1/HSC1 | 938 | WO2016049230 SEQ ID NO: 20 |
| AAVF2/HSC2 | 939 | WO2016049230 SEQ ID NO: 21 |
| AAVF3/HSC3 | 940 | WO2016049230 SEQ ID NO: 22 |
| AAVF4/HSC4 | 941 | WO2016049230 SEQ ID NO: 23 |
| AAVF5/HSC5 | 942 | WO2016049230 SEQ ID NO: 25 |
| AAVF6/HSC6 | 943 | WO2016049230 SEQ ID NO: 24 |
| AAVF7/HSC7 | 944 | WO2016049230 SEQ ID NO: 27 |
| AAVF8/HSC8 | 945 | WO2016049230 SEQ ID NO: 28 |
| AAVF9/HSC9 | 946 | WO2016049230 SEQ ID NO: 29 |
| AAVF11/HSC11 | 947 | WO2016049230 SEQ ID NO: 26 |
| AAVF12/HSC12 | 948 | WO2016049230 SEQ ID NO: 30 |
| AAVF13/HSC13 | 949 | WO2016049230 SEQ ID NO: 31 |
| AAVF14/HSC14 | 950 | WO2016049230 SEQ ID NO: 32 |
| AAVF15/HSC15 | 951 | WO2016049230 SEQ ID NO: 33 |
| AAVF16/HSC16 | 952 | WO2016049230 SEQ ID NO: 34 |
| AAVF17/HSC17 | 953 | WO2016049230 SEQ ID NO: 35 |
| AAVF1/HSC1 | 954 | WO2016049230 SEQ ID NO: 2 |
| AAVF2/HSC2 | 955 | WO2016049230 SEQ ID NO: 3 |
| AAVF3/HSC3 | 956 | WO2016049230 SEQ ID NO: 5 |
| AAVF4/HSC4 | 957 | WO2016049230 SEQ ID NO: 6 |
| AAVF5/HSC5 | 958 | WO2016049230 SEQ ID NO: 11 |
| AAVF6/HSC6 | 959 | WO2016049230 SEQ ID NO: 7 |
| AAVF7/HSC7 | 960 | WO2016049230 SEQ ID NO: 8 |
| AAVF8/HSC8 | 961 | WO2016049230 SEQ ID NO: 9 |
| AAVF9/HSC9 | 962 | WO2016049230 SEQ ID NO: 10 |
| AAVF11/HSC11 | 963 | WO2016049230 SEQ ID NO: 4 |

TABLE 11-continued

AAV Serotypes

| Serotype | SEQ ID NO | Reference Information |
|---|---|---|
| AAVF12/HSC12 | 964 | WO2016049230 SEQ ID NO: 12 |
| AAVF13/HSC13 | 965 | WO2016049230 SEQ ID NO: 14 |
| AAVF14/HSC14 | 966 | WO2016049230 SEQ ID NO: 15 |
| AAVF15/HSC15 | 967 | WO2016049230 SEQ ID NO: 16 |
| AAVF16/HSC16 | 968 | WO2016049230 SEQ ID NO: 17 |
| AAVF17/HSC17 | 969 | WO2016049230 SEQ ID NO: 13 |
| AAV CBr-E1 | 970 | U.S. Pat. No. 8,734,809 SEQ ID NO: 13 |
| AAV CBr-E2 | 971 | U.S. Pat. No. 8,734,809 SEQ ID NO: 14 |
| AAV CBr-E3 | 972 | U.S. Pat. No. 8,734,809 SEQ ID NO: 15 |
| AAV CBr-E4 | 973 | U.S. Pat. No. 8,734,809 SEQ ID NO: 16 |
| AAV CBr-E5 | 974 | U.S. Pat. No. 8,734,809 SEQ ID NO: 17 |
| AAV CBr-e5 | 975 | U.S. Pat. No. 8,734,809 SEQ ID NO: 18 |
| AAV CBr-E6 | 976 | U.S. Pat. No. 8,734,809 SEQ ID NO: 19 |
| AAV CBr-E7 | 977 | U.S. Pat. No. 8,734,809 SEQ ID NO: 20 |
| AAV CBr-E8 | 978 | U.S. Pat. No. 8,734,809 SEQ ID NO: 21 |
| AAV CLv-D1 | 979 | U.S. Pat. No. 8,734,809 SEQ ID NO: 22 |
| AAV CLv-D2 | 980 | U.S. Pat. No. 8,734,809 SEQ ID NO: 23 |
| AAV CLv-D3 | 981 | U.S. Pat. No. 8,734,809 SEQ ID NO: 24 |
| AAV CLv-D4 | 982 | U.S. Pat. No. 8,734,809 SEQ ID NO: 25 |
| AAV CLv-D5 | 983 | U.S. Pat. No. 8,734,809 SEQ ID NO: 26 |
| AAV CLv-D6 | 984 | U.S. Pat. No. 8,734,809 SEQ ID NO: 27 |
| AAV CLv-D7 | 985 | U.S. Pat. No. 8,734,809 SEQ ID NO: 28 |
| AAV CLv-D8 | 986 | U.S. Pat. No. 8,734,809 SEQ ID NO: 29 |
| AAV CLv-E1 | 987 | U.S. Pat. No. 8,734,809 SEQ ID NO: 13 |
| AAV CLv-R1 | 988 | U.S. Pat. No. 8,734,809 SEQ ID NO: 30 |
| AAV CLv-R2 | 989 | U.S. Pat. No. 8,734,809 SEQ ID NO: 31 |
| AAV CLv-R3 | 990 | U.S. Pat. No. 8,734,809 SEQ ID NO: 32 |
| AAV CLv-R4 | 991 | U.S. Pat. No. 8,734,809 SEQ ID NO: 33 |
| AAV CLv-R5 | 992 | U.S. Pat. No. 8,734,809 SEQ ID NO: 34 |
| AAV CLv-R6 | 993 | U.S. Pat. No. 8,734,809 SEQ ID NO: 35 |
| AAV CLv-R7 | 994 | U.S. Pat. No. 8,734,809 SEQ ID NO: 36 |
| AAV CLv-R8 | 995 | U.S. Pat. No. 8,734,809 SEQ ID NO: 37 |
| AAV CLv-R9 | 996 | U.S. Pat. No. 8,734,809 SEQ ID NO: 38 |
| AAV CLg-F1 | 997 | U.S. Pat. No. 8,734,809 SEQ ID NO: 39 |
| AAV CLg-F2 | 998 | U.S. Pat. No. 8,734,809 SEQ ID NO: 40 |
| AAV CLg-F3 | 999 | U.S. Pat. No. 8,734,809 SEQ ID NO: 41 |
| AAV CLg-F4 | 1000 | U.S. Pat. No. 8,734,809 SEQ ID NO: 42 |
| AAV CLg-F5 | 1001 | U.S. Pat. No. 8,734,809 SEQ ID NO: 43 |
| AAV CLg-F6 | 1002 | U.S. Pat. No. 8,734,809 SEQ ID NO: 43 |
| AAV CLg-F7 | 1003 | U.S. Pat. No. 8,734,809 SEQ ID NO: 44 |
| AAV CLg-F8 | 1004 | U.S. Pat. No. 8,734,809 SEQ ID NO: 43 |
| AAV CSp-1 | 1005 | U.S. Pat. No. 8,734,809 SEQ ID NO: 45 |
| AAV CSp-10 | 1006 | U.S. Pat. No. 8,734,809 SEQ ID NO: 46 |
| AAV CSp-11 | 1007 | U.S. Pat. No. 8,734,809 SEQ ID NO: 47 |
| AAV CSp-2 | 1008 | U.S. Pat. No. 8,734,809 SEQ ID NO: 48 |
| AAV CSp-3 | 1009 | U.S. Pat. No. 8,734,809 SEQ ID NO: 49 |
| AAV CSp-4 | 1010 | U.S. Pat. No. 8,734,809 SEQ ID NO: 50 |
| AAV CSp-6 | 1011 | U.S. Pat. No. 8,734,809 SEQ ID NO: 51 |
| AAV CSp-7 | 1012 | U.S. Pat. No. 8,734,809 SEQ ID NO: 52 |
| AAV CSp-8 | 1013 | U.S. Pat. No. 8,734,809 SEQ ID NO: 53 |
| AAV CSp-9 | 1014 | U.S. Pat. No. 8,734,809 SEQ ID NO: 54 |
| AAV CHt-2 | 1015 | U.S. Pat. No. 8,734,809 SEQ ID NO: 55 |
| AAV CHt-3 | 1016 | U.S. Pat. No. 8,734,809 SEQ ID NO: 56 |
| AAV CKd-1 | 1017 | U.S. Pat. No. 8,734,809 SEQ ID NO: 57 |
| AAV CKd-10 | 1018 | U.S. Pat. No. 8,734,809 SEQ ID NO: 58 |
| AAV CKd-2 | 1019 | U.S. Pat. No. 8,734,809 SEQ ID NO: 59 |
| AAV CKd-3 | 1020 | U.S. Pat. No. 8,734,809 SEQ ID NO: 60 |
| AAV CKd-4 | 1021 | U.S. Pat. No. 8,734,809 SEQ ID NO: 61 |
| AAV CKd-6 | 1022 | U.S. Pat. No. 8,734,809 SEQ ID NO: 62 |
| AAV CKd-7 | 1023 | U.S. Pat. No. 8,734,809 SEQ ID NO: 63 |
| AAV CKd-8 | 1024 | U.S. Pat. No. 8,734,809 SEQ ID NO: 64 |
| AAV CLv-1 | 1025 | U.S. Pat. No. 8,734,809 SEQ ID NO: 65 |
| AAV CLv-12 | 1026 | U.S. Pat. No. 8,734,809 SEQ ID NO: 66 |
| AAV CLv-13 | 1027 | U.S. Pat. No. 8,734,809 SEQ ID NO: 67 |
| AAV CLv-2 | 1028 | U.S. Pat. No. 8,734,809 SEQ ID NO: 68 |
| AAV CLv-3 | 1029 | U.S. Pat. No. 8,734,809 SEQ ID NO: 69 |
| AAV CLv-4 | 1030 | U.S. Pat. No. 8,734,809 SEQ ID NO: 70 |
| AAV CLv-6 | 1031 | U.S. Pat. No. 8,734,809 SEQ ID NO: 71 |
| AAV CLv-8 | 1032 | U.S. Pat. No. 8,734,809 SEQ ID NO: 72 |
| AAV CKd-B1 | 1033 | U.S. Pat. No. 8,734,809 SEQ ID NO: 73 |
| AAV CKd-B2 | 1034 | U.S. Pat. No. 8,734,809 SEQ ID NO: 74 |
| AAV CKd-B3 | 1035 | U.S. Pat. No. 8,734,809 SEQ ID NO: 75 |
| AAV CKd-B4 | 1036 | U.S. Pat. No. 8,734,809 SEQ ID NO: 76 |
| AAV CKd-B5 | 1037 | U.S. Pat. No. 8,734,809 SEQ ID NO: 77 |
| AAV CKd-B6 | 1038 | U.S. Pat. No. 8,734,809 SEQ ID NO: 78 |

TABLE 11-continued

AAV Serotypes

| Serotype | SEQ ID NO | Reference Information |
|---|---|---|
| AAV CKd-B7 | 1039 | U.S. Pat. No. 8,734,809 SEQ ID NO: 79 |
| AAV CKd-B8 | 1040 | U.S. Pat. No. 8,734,809 SEQ ID NO: 80 |
| AAV CKd-H1 | 1041 | U.S. Pat. No. 8,734,809 SEQ ID NO: 81 |
| AAV CKd-H2 | 1042 | U.S. Pat. No. 8,734,809 SEQ ID NO: 82 |
| AAV CKd-H3 | 1043 | U.S. Pat. No. 8,734,809 SEQ ID NO: 83 |
| AAV CKd-H4 | 1044 | U.S. Pat. No. 8,734,809 SEQ ID NO: 84 |
| AAV CKd-H5 | 1045 | U.S. Pat. No. 8,734,809 SEQ ID NO: 85 |
| AAV CKd-H6 | 1046 | U.S. Pat. No. 8,734,809 SEQ ID NO: 77 |
| AAV CHt-1 | 1047 | U.S. Pat. No. 8,734,809 SEQ ID NO: 86 |
| AAV CLv1-1 | 1048 | U.S. Pat. No. 8,734,809 SEQ ID NO: 171 |
| AAV CLv1-2 | 1049 | U.S. Pat. No. 8,734,809 SEQ ID NO: 172 |
| AAV CLv1-3 | 1050 | U.S. Pat. No. 8,734,809 SEQ ID NO: 173 |
| AAV CLv1-4 | 1051 | U.S. Pat. No. 8,734,809 SEQ ID NO: 174 |
| AAV Clv1-7 | 1052 | U.S. Pat. No. 8,734,809 SEQ ID NO: 175 |
| AAV Clv1-8 | 1053 | U.S. Pat. No. 8,734,809 SEQ ID NO: 176 |
| AAV Clv1-9 | 1054 | U.S. Pat. No. 8,734,809 SEQ ID NO: 177 |
| AAV Clv1-10 | 1055 | U.S. Pat. No. 8,734,809 SEQ ID NO: 178 |
| AAV.VR-355 | 1056 | U.S. Pat. No. 8,734,809 SEQ ID NO: 181 |
| AAV.hu.48R3 | 1057 | U.S. Pat. No. 8,734,809 SEQ ID NO: 183 |
| AAV CBr-E1 | 1058 | U.S. Pat. No. 8,734,809 SEQ ID NO: 87 |
| AAV CBr-E2 | 1059 | U.S. Pat. No. 8,734,809 SEQ ID NO: 88 |
| AAV CBr-E3 | 1060 | U.S. Pat. No. 8,734,809 SEQ ID NO: 89 |
| AAV CBr-E4 | 1061 | U.S. Pat. No. 8,734,809 SEQ ID NO: 90 |
| AAV CBr-E5 | 1062 | U.S. Pat. No. 8,734,809 SEQ ID NO: 91 |
| AAV CBr-e5 | 1063 | U.S. Pat. No. 8,734,809 SEQ ID NO: 92 |
| AAV CBr-E6 | 1064 | U.S. Pat. No. 8,734,809 SEQ ID NO: 93 |
| AAV CBr-E7 | 1065 | U.S. Pat. No. 8,734,809 SEQ ID NO: 94 |
| AAV CBr-E8 | 1066 | U.S. Pat. No. 8,734,809 SEQ ID NO: 95 |
| AAV CLv-D1 | 1067 | U.S. Pat. No. 8,734,809 SEQ ID NO: 96 |
| AAV CLv-D2 | 1068 | U.S. Pat. No. 8,734,809 SEQ ID NO: 97 |
| AAV CLv-D3 | 1069 | U.S. Pat. No. 8,734,809 SEQ ID NO: 98 |
| AAV CLv-D4 | 1070 | U.S. Pat. No. 8,734,809 SEQ ID NO: 99 |
| AAV CLv-D5 | 1071 | U.S. Pat. No. 8,734,809 SEQ ID NO: 100 |
| AAV CLv-D6 | 1072 | U.S. Pat. No. 8,734,809 SEQ ID NO: 101 |
| AAV CLv-D7 | 1073 | U.S. Pat. No. 8,734,809 SEQ ID NO: 102 |
| AAV CLv-D8 | 1074 | U.S. Pat. No. 8,734,809 SEQ ID NO: 103 |
| AAV CLv-E1 | 1075 | U.S. Pat. No. 8,734,809 SEQ ID NO: 87 |
| AAV CLv-R1 | 1076 | U.S. Pat. No. 8,734,809 SEQ ID NO: 104 |
| AAV CLv-R2 | 1077 | U.S. Pat. No. 8,734,809 SEQ ID NO: 105 |
| AAV CLv-R3 | 1078 | U.S. Pat. No. 8,734,809 SEQ ID NO: 106 |
| AAV CLv-R4 | 1079 | U.S. Pat. No. 8,734,809 SEQ ID NO: 107 |
| AAV CLv-R5 | 1080 | U.S. Pat. No. 8,734,809 SEQ ID NO: 108 |
| AAV CLv-R6 | 1081 | U.S. Pat. No. 8,734,809 SEQ ID NO: 109 |
| AAV CLv-R7 | 1082 | U.S. Pat. No. 8,734,809 SEQ ID NO: 110 |
| AAV CLv-R8 | 1083 | U.S. Pat. No. 8,734,809 SEQ ID NO: 111 |
| AAV CLv-R9 | 1084 | U.S. Pat. No. 8,734,809 SEQ ID NO: 112 |
| AAV CLg-F1 | 1085 | U.S. Pat. No. 8,734,809 SEQ ID NO: 113 |
| AAV CLg-F2 | 1086 | U.S. Pat. No. 8,734,809 SEQ ID NO: 114 |
| AAV CLg-F3 | 1087 | U.S. Pat. No. 8,734,809 SEQ ID NO: 115 |
| AAV CLg-F4 | 1088 | U.S. Pat. No. 8,734,809 SEQ ID NO: 116 |
| AAV CLg-F5 | 1089 | U.S. Pat. No. 8,734,809 SEQ ID NO: 117 |
| AAV CLg-F6 | 1090 | U.S. Pat. No. 8,734,809 SEQ ID NO: 117 |
| AAV CLg-F7 | 1091 | U.S. Pat. No. 8,734,809 SEQ ID NO: 118 |
| AAV CLg-F8 | 1092 | U.S. Pat. No. 8,734,809 SEQ ID NO: 117 |
| AAV CSp-1 | 1093 | U.S. Pat. No. 8,734,809 SEQ ID NO: 119 |
| AAV CSp-10 | 1094 | U.S. Pat. No. 8,734,809 SEQ ID NO: 120 |
| AAV CSp-11 | 1095 | U.S. Pat. No. 8,734,809 SEQ ID NO: 121 |
| AAV CSp-2 | 1096 | U.S. Pat. No. 8,734,809 SEQ ID NO: 122 |
| AAV CSp-3 | 1097 | U.S. Pat. No. 8,734,809 SEQ ID NO: 123 |
| AAV CSp-4 | 1098 | U.S. Pat. No. 8,734,809 SEQ ID NO: 124 |
| AAV CSp-6 | 1099 | U.S. Pat. No. 8,734,809 SEQ ID NO: 125 |
| AAV CSp-7 | 1100 | U.S. Pat. No. 8,734,809 SEQ ID NO: 126 |
| AAV CSp-8 | 1101 | U.S. Pat. No. 8,734,809 SEQ ID NO: 127 |
| AAV CSp-9 | 1102 | U.S. Pat. No. 8,734,809 SEQ ID NO: 128 |
| AAV CHt-2 | 1103 | U.S. Pat. No. 8,734,809 SEQ ID NO: 129 |
| AAV CHt-3 | 1104 | U.S. Pat. No. 8,734,809 SEQ ID NO: 130 |
| AAV CKd-1 | 1105 | U.S. Pat. No. 8,734,809 SEQ ID NO: 131 |
| AAV CKd-10 | 1106 | U.S. Pat. No. 8,734,809 SEQ ID NO: 132 |
| AAV CKd-2 | 1107 | U.S. Pat. No. 8,734,809 SEQ ID NO: 133 |
| AAV CKd-3 | 1108 | U.S. Pat. No. 8,734,809 SEQ ID NO: 134 |
| AAV CKd-4 | 1109 | U.S. Pat. No. 8,734,809 SEQ ID NO: 135 |
| AAV CKd-6 | 1110 | U.S. Pat. No. 8,734,809 SEQ ID NO: 136 |
| AAV CKd-7 | 1111 | U.S. Pat. No. 8,734,809 SEQ ID NO: 137 |
| AAV CKd-8 | 1112 | U.S. Pat. No. 8,734,809 SEQ ID NO: 138 |
| AAV CLv-1 | 1113 | U.S. Pat. No. 8,734,809 SEQ ID NO: 139 |

TABLE 11-continued

AAV Serotypes

| Serotype | SEQ ID NO | Reference Information |
|---|---|---|
| AAV CLv-12 | 1114 | U.S. Pat. No. 8,734,809 SEQ ID NO: 140 |
| AAV CLv-13 | 1115 | U.S. Pat. No. 8,734,809 SEQ ID NO: 141 |
| AAV CLv-2 | 1116 | U.S. Pat. No. 8,734,809 SEQ ID NO: 142 |
| AAV CLv-3 | 1117 | U.S. Pat. No. 8,734,809 SEQ ID NO: 143 |
| AAV CLv-4 | 1118 | U.S. Pat. No. 8,734,809 SEQ ID NO: 144 |
| AAV CLv-6 | 1119 | U.S. Pat. No. 8,734,809 SEQ ID NO: 145 |
| AAV CLv-8 | 1120 | U.S. Pat. No. 8,734,809 SEQ ID NO: 146 |
| AAV CKd-B1 | 1121 | U.S. Pat. No. 8,734,809 SEQ ID NO: 147 |
| AAV CKd-B2 | 1122 | U.S. Pat. No. 8,734,809 SEQ ID NO: 148 |
| AAV CKd-B3 | 1123 | U.S. Pat. No. 8,734,809 SEQ ID NO: 149 |
| AAV CKd-B4 | 1124 | U.S. Pat. No. 8,734,809 SEQ ID NO: 150 |
| AAV CKd-B5 | 1125 | U.S. Pat. No. 8,734,809 SEQ ID NO: 151 |
| AAV CKd-B6 | 1126 | U.S. Pat. No. 8,734,809 SEQ ID NO: 152 |
| AAV CKd-B7 | 1127 | U.S. Pat. No. 8,734,809 SEQ ID NO: 153 |
| AAV CKd-B8 | 1128 | U.S. Pat. No. 8,734,809 SEQ ID NO: 154 |
| AAV CKd-H1 | 1129 | U.S. Pat. No. 8,734,809 SEQ ID NO: 155 |
| AAV CKd-H2 | 1130 | U.S. Pat. No. 8,734,809 SEQ ID NO: 156 |
| AAV CKd-H3 | 1131 | U.S. Pat. No. 8,734,809 SEQ ID NO: 157 |
| AAV CKd-H4 | 1132 | U.S. Pat. No. 8,734,809 SEQ ID NO: 158 |
| AAV CKd-H5 | 1133 | U.S. Pat. No. 8,734,809 SEQ ID NO: 159 |
| AAV CKd-H6 | 1134 | U.S. Pat. No. 8,734,809 SEQ ID NO: 151 |
| AAV CHt-1 | 1135 | U.S. Pat. No. 8,734,809 SEQ ID NO: 160 |
| AAV CHt-P2 | 1136 | WO2016065001 SEQ ID NO: 1 |
| AAV CHt-P5 | 1137 | WO2016065001 SEQ ID NO: 2 |
| AAV CHt-P9 | 1138 | WO2016065001 SEQ ID NO: 3 |
| AAV CBr-7.1 | 1139 | WO2016065001 SEQ ID NO: 4 |
| AAV CBr-7.2 | 1140 | WO2016065001 SEQ ID NO: 5 |
| AAV CBr-7.3 | 1141 | WO2016065001 SEQ ID NO: 6 |
| AAV CBr-7.4 | 1142 | WO2016065001 SEQ ID NO: 7 |
| AAV CBr-7.5 | 1143 | WO2016065001 SEQ ID NO: 8 |
| AAV CBr-7.7 | 1144 | WO2016065001 SEQ ID NO: 9 |
| AAV CBr-7.8 | 1145 | WO2016065001 SEQ ID NO: 10 |
| AAV CBr-7.10 | 1146 | WO2016065001 SEQ ID NO: 11 |
| AAV CKd-N3 | 1147 | WO2016065001 SEQ ID NO: 12 |
| AAV CKd-N4 | 1148 | WO2016065001 SEQ ID NO: 13 |
| AAV CKd-N9 | 1149 | WO2016065001 SEQ ID NO: 14 |
| AAV CLv-L4 | 1150 | WO2016065001 SEQ ID NO: 15 |
| AAV CLv-L5 | 1151 | WO2016065001 SEQ ID NO: 16 |
| AAV CLv-L6 | 1152 | WO2016065001 SEQ ID NO: 17 |
| AAV CLv-K1 | 1153 | WO2016065001 SEQ ID NO: 18 |
| AAV CLv-K3 | 1154 | WO2016065001 SEQ ID NO: 19 |
| AAV CLv-K6 | 1155 | WO2016065001 SEQ ID NO: 20 |
| AAV CLv-M1 | 1156 | WO2016065001 SEQ ID NO: 21 |
| AAV CLv-M11 | 1157 | WO2016065001 SEQ ID NO: 22 |
| AAV CLv-M2 | 1158 | WO2016065001 SEQ ID NO: 23 |
| AAV CLv-M5 | 1159 | WO2016065001 SEQ ID NO: 24 |
| AAV CLv-M6 | 1160 | WO2016065001 SEQ ID NO: 25 |
| AAV CLv-M7 | 1161 | WO2016065001 SEQ ID NO: 26 |
| AAV CLv-M8 | 1162 | WO2016065001 SEQ ID NO: 27 |
| AAV CLv-M9 | 1163 | WO2016065001 SEQ ID NO: 28 |
| AAV CHt-P1 | 1164 | WO2016065001 SEQ ID NO: 29 |
| AAV CHt-P6 | 1165 | WO2016065001 SEQ ID NO: 30 |
| AAV CHt-P8 | 1166 | WO2016065001 SEQ ID NO: 31 |
| AAV CHt-6.1 | 1167 | WO2016065001 SEQ ID NO: 32 |
| AAV CHt-6.10 | 1168 | WO2016065001 SEQ ID NO: 33 |
| AAV CHt-6.5 | 1169 | WO2016065001 SEQ ID NO: 34 |
| AAV CHt-6.6 | 1170 | WO2016065001 SEQ ID NO: 35 |
| AAV CHt-6.7 | 1171 | WO2016065001 SEQ ID NO: 36 |
| AAV CHt-6.8 | 1172 | WO2016065001 SEQ ID NO: 37 |
| AAV CSp-8.10 | 1173 | WO2016065001 SEQ ID NO: 38 |
| AAV CSp-8.2 | 1174 | WO2016065001 SEQ ID NO: 39 |
| AAV CSp-8.4 | 1175 | WO2016065001 SEQ ID NO: 40 |
| AAV CSp-8.5 | 1176 | WO2016065001 SEQ ID NO: 41 |
| AAV CSp-8.6 | 1177 | WO2016065001 SEQ ID NO: 42 |
| AAV CSp-8.7 | 1178 | WO2016065001 SEQ ID NO: 43 |
| AAV CSp-8.8 | 1179 | WO2016065001 SEQ ID NO: 44 |
| AAV CSp-8.9 | 1180 | WO2016065001 SEQ ID NO: 45 |
| AAV CBr-B7.3 | 1181 | WO2016065001 SEQ ID NO: 46 |
| AAV CBr-B7.4 | 1182 | WO2016065001 SEQ ID NO: 47 |
| AAV3B | 1183 | WO2016065001 SEQ ID NO: 48 |
| AAV4 | 1184 | WO2016065001 SEQ ID NO: 49 |
| AAV5 | 1185 | WO2016065001 SEQ ID NO: 50 |
| AAV CHt-P2 | 1186 | WO2016065001 SEQ ID NO: 51 |
| AAV CHt-P5 | 1187 | WO2016065001 SEQ ID NO: 52 |
| AAV CHt-P9 | 1188 | WO2016065001 SEQ ID NO: 53 |

TABLE 11-continued

AAV Serotypes

| Serotype | SEQ ID NO | Reference Information |
|---|---|---|
| AAV CBr-7.1 | 1189 | WO2016065001 SEQ ID NO: 54 |
| AAV CBr-7.2 | 1190 | WO2016065001 SEQ ID NO: 55 |
| AAV CBr-7.3 | 1191 | WO2016065001 SEQ ID NO: 56 |
| AAV CBr-7.4 | 1192 | WO2016065001 SEQ ID NO: 57 |
| AAV CBr-7.5 | 1193 | WO2016065001 SEQ ID NO: 58 |
| AAV CBr-7.7 | 1194 | WO2016065001 SEQ ID NO: 59 |
| AAV CBr-7.8 | 1195 | WO2016065001 SEQ ID NO: 60 |
| AAV CBr-7.10 | 1196 | WO2016065001 SEQ ID NO: 61 |
| AAV CKd-N3 | 1197 | WO2016065001 SEQ ID NO: 62 |
| AAV CKd-N4 | 1198 | WO2016065001 SEQ ID NO: 63 |
| AAV CKd-N9 | 1199 | WO2016065001 SEQ ID NO: 64 |
| AAV CLv-L4 | 1200 | WO2016065001 SEQ ID NO: 65 |
| AAV CLv-L5 | 1201 | WO2016065001 SEQ ID NO: 66 |
| AAV CLv-L6 | 1202 | WO2016065001 SEQ ID NO: 67 |
| AAV CLv-K1 | 1203 | WO2016065001 SEQ ID NO: 68 |
| AAV CLv-K3 | 1204 | WO2016065001 SEQ ID NO: 69 |
| AAV CLv-K6 | 1205 | WO2016065001 SEQ ID NO: 70 |
| AAV CLv-M1 | 1206 | WO2016065001 SEQ ID NO: 71 |
| AAV CLv-M11 | 1207 | WO2016065001 SEQ ID NO: 72 |
| AAV CLv-M2 | 1208 | WO2016065001 SEQ ID NO: 73 |
| AAV CLv-M5 | 1209 | WO2016065001 SEQ ID NO: 74 |
| AAV CLv-M6 | 1210 | WO2016065001 SEQ ID NO: 75 |
| AAV CLv-M7 | 1211 | WO2016065001 SEQ ID NO: 76 |
| AAV CLv-M8 | 1212 | WO2016065001 SEQ ID NO: 77 |
| AAV CLv-M9 | 1213 | WO2016065001 SEQ ID NO: 78 |
| AAV CHt-P1 | 1214 | WO2016065001 SEQ ID NO: 79 |
| AAV CHt-P6 | 1215 | WO2016065001 SEQ ID NO: 80 |
| AAV CHt-P8 | 1216 | WO2016065001 SEQ ID NO: 81 |
| AAV CHt-6.1 | 1217 | WO2016065001 SEQ ID NO: 82 |
| AAV CHt-6.10 | 1218 | WO2016065001 SEQ ID NO: 83 |
| AAV CHt-6.5 | 1219 | WO2016065001 SEQ ID NO: 84 |
| AAV CHt-6.6 | 1220 | WO2016065001 SEQ ID NO: 85 |
| AAV CHt-6.7 | 1221 | WO2016065001 SEQ ID NO: 86 |
| AAV CHt-6.8 | 1222 | WO2016065001 SEQ ID NO: 87 |
| AAV CSp-8.10 | 1223 | WO2016065001 SEQ ID NO: 88 |
| AAV CSp-8.2 | 1224 | WO2016065001 SEQ ID NO: 89 |
| AAV CSp-8.4 | 1225 | WO2016065001 SEQ ID NO: 90 |
| AAV CSp-8.5 | 1226 | WO2016065001 SEQ ID NO: 91 |
| AAV CSp-8.6 | 1227 | WO2016065001 SEQ ID NO: 92 |
| AAV CSp-8.7 | 1228 | WO2016065001 SEQ ID NO: 93 |
| AAV CSp-8.8 | 1229 | WO2016065001 SEQ ID NO: 94 |
| AAV CSp-8.9 | 1230 | WO2016065001 SEQ ID NO: 95 |
| AAV CBr-B7.3 | 1231 | WO2016065001 SEQ ID NO: 96 |
| AAV CBr-B7.4 | 1232 | WO2016065001 SEQ ID NO: 97 |
| AAV3B | 1233 | WO2016065001 SEQ ID NO: 98 |
| AAV4 | 1234 | WO2016065001 SEQ ID NO: 99 |
| AAV5 | 1235 | WO2016065001 SEQ ID NO: 100 |
| AAVPHP.B or G2B-26 | 1236 | WO2015038958 SEQ ID NO: 8 and 13; GenBankALU85156.1 |
| AAVPHP.B | 1237 | WO2015038958 SEQ ID NO: 9 |
| AAVG2B-13 | 1238 | WO2015038958 SEQ ID NO: 12 |
| AAVTH1.1-32 | 1239 | WO2015038958 SEQ ID NO: 14 |
| AAVTH1.1-35 | 1240 | WO2015038958 SEQ ID NO: 15 |

Each of the patents, applications and/or publications listed in Table 11 are hereby incorporated by reference in their entirety.

In one embodiment, the AAV serotype may be, or may have a sequence as described in International Patent Publication WO2015038958, the contents of which are herein incorporated by reference in their entirety, such as, but not limited to, AAV9 (SEQ ID NO: 2 and 11 of WO2015038958 or SEQ ID NO: 494 and 495 respectively herein), AAV-PHP.B (PHP.B) (SEQ ID NO: 8 and 9 of WO2015038958, herein SEQ ID NO: 1236 and 1237), G2B-13 (SEQ ID NO: 12 of WO2015038958, herein SEQ ID NO: 1238), G2B-26 (SEQ ID NO: 13 of WO2015038958, herein SEQ ID NO: 1236 and 1237), TH1.1-32 (SEQ ID NO: 14 of WO2015038958, herein SEQ ID NO: 1239), TH1.1-35 (SEQ ID NO: 15 of WO2015038958, herein SEQ ID NO: 1240) or variants thereof. Further, any of the targeting peptides or amino acid inserts described in WO2015038958, may be inserted into any parent AAV serotype, such as, but not limited to, AAV9 (SEQ ID NO: 494 for the DNA sequence and SEQ ID NO: 495 for the amino acid sequence). In one embodiment, the amino acid insert is inserted between amino acids 586-592 of the parent AAV (e.g., AAV9). In another embodiment, the amino acid insert is inserted between amino acids 588-589 of the parent AAV sequence. The amino acid insert may be, but is not limited to, any of the following amino acid sequences, TLAVPFK (SEQ ID NO: 1 of WO2015038958; herein SEQ ID NO: 1241), KFPVALT (SEQ ID NO: 3 of WO2015038958; herein SEQ ID NO: 1242), LAVPFK (SEQ ID NO: 31 of WO2015038958; herein SEQ ID NO: 1243), AVPFK (SEQ ID NO: 32 of WO2015038958; herein SEQ ID NO: 1244), VPFK (SEQ ID NO: 33 of WO2015038958; herein SEQ ID NO: 1245), TLAVPF (SEQ ID NO: 34 of WO2015038958; herein SEQ ID NO: 1246), TLAVP (SEQ ID NO: 35 of WO2015038958; herein SEQ ID NO: 1247), TLAV (SEQ ID NO: 36 of WO2015038958; herein SEQ ID NO: 1248), SVSKPFL (SEQ ID NO: 28 of WO2015038958; herein SEQ ID NO: 1249), FTLTTPK (SEQ ID NO: 29 of WO2015038958; herein SEQ ID NO: 1250), MNATKNV (SEQ ID NO: 30 of WO2015038958; herein SEQ ID NO: 1251), QSSQTPR (SEQ ID NO: 54 of WO2015038958; herein SEQ ID NO: 1252), ILGTGTS (SEQ ID NO: 55 of WO2015038958; herein SEQ ID NO: 1253), TRTNPEA (SEQ ID NO: 56 of WO2015038958; herein SEQ ID NO: 1254), NGGTSSS (SEQ ID NO: 58 of WO2015038958; herein SEQ ID NO: 1255), or YTLSQGW (SEQ ID NO: 60 of WO2015038958; herein SEQ ID NO: 1256). Non-limiting examples of nucleotide sequences that may encode the amino acid inserts include the following, AAGTTTCCTGTGGCGTTGACT (for SEQ ID NO: 3 of WO2015038958; herein SEQ ID NO: 1257), ACTTTGGCGGTGCCTTTTAAG (SEQ ID NO: 24 and 49 of WO2015038958; herein SEQ ID NO: 1258), AGTGTGAGTAAGCCTTTTTG (SEQ ID NO: 25 of WO2015038958; herein SEQ ID NO: 1259), TTTACGTTGACGACGCCTAAG (SEQ ID NO: 26 of WO2015038958; herein SEQ ID NO: 1260), ATGAATGCTACGAAGAATGTG (SEQ ID NO: 27 of WO2015038958; herein SEQ ID NO: 1261), CAGTCGTCGCAGACGCCTAGG (SEQ ID NO: 48 of WO2015038958; herein SEQ ID NO: 1262), ATTCTGGGGACTGGTACTTCG (SEQ ID NO: 50 and 52 of WO2015038958; herein SEQ ID NO: 1263), ACGCGGACTAATCCTGAGGCT (SEQ ID NO: 51 of WO2015038958; herein SEQ ID NO: 1264), AATGGGGGGACTAGTAGTTCT (SEQ ID NO: 53 of WO2015038958; herein SEQ ID NO: 1265), or TATACTTTGTCGCAGGGTTGG (SEQ ID NO: 59 of WO2015038958; herein SEQ ID NO: 1266).

In one embodiment, the AAV serotype may be engineered to comprise at least one AAV capsid CD8+ T-cell epitope. Hui et al. (Molecular Therapy—Methods & Clinical Development (2015) 2, 15029 doi:10.1038/mtm.2015.29; the contents of which are herein incorporated by reference in its entirety) identified AAV capsid-specific CD8+ T-cell epitopes for AAV1 and AAV2 (see e.g., Table 2 in the publication). As a non-limiting example, the capsid-specific CD8+ T-cell epitope may be for an AAV2 serotype. As a non-limiting example, the capsid-specific CD8+ T-cell epitope may be for an AAV1 serotype.

In one embodiment, the AAV serotype may be engineered to comprise at least one AAV capsid CD8+ T-cell epitope for AAV2 such as, but not limited to, SADNNNSEY (SEQ ID NO: 1267), LIDQYLYYL (SEQ ID NO: 1268), VPQYGYLTL (SEQ ID NO: 1269), TTSTRTWAL (SEQ ID NO: 1270), YHLNGRDSL (SEQ ID NO: 1271), SQAVGRSSF (SEQ ID NO: 1272), VPANPSTTF (SEQ ID NO: 1273), FPQSGVLIF (SEQ ID NO: 1274), YFDFNRFHCHFSPRD (SEQ ID NO: 1275), VGNSSGNWHCDSTWM (SEQ ID NO: 1276), QFSQAGASDIRDQSR (SEQ ID NO: 1277), GASDIRQSRNWLP (SEQ ID NO: 1278) and GNRQAATADVNTQGV (SEQ ID NO: 1279).

In one embodiment, the AAV serotype may be engineered to comprise at least one AAV capsid CD8+ T-cell epitope for AAV1 such as, but not limited to, LDRLMNPLI (SEQ ID NO: 1280), TTSTRTWAL (SEQ ID NO: 1270), and QPAKKRLNF (SEQ ID NO: 1281)).

In one embodiment, peptides for inclusion in an AAV serotype may be identified using the methods described by Hui et al. (Molecular Therapy—Methods & Clinical Development (2015) 2, 15029 doi:10.1038/mtm.2015.29; the contents of which are herein incorporated by reference in its entirety). As a non-limiting example, the procedure includes isolating human splenocytes, restimulating the splenocytes in vitro using individual peptides spanning the amino acid sequence of the AAV capsid protein, IFN-gamma ELISpot with the individual peptides used for the in vitro restimulation, bioinformatics analysis to determine the HLA restriction of 15-mers identified by IFN-gamma ELISpot, identification of candidate reactive 9-mer epitopes for a given HLA allele, synthesis candidate 9-mers, second IFN-gamma ELISpot screening of splenocytes from subjects carrying the HLA alleles to which identified AAV epitopes are predicted to bind, determine the AAV capsid-reactive CD8+ T cell epitopes and determine the frequency of subjects reacting to a given AAV epitope.

In one embodiment, the AAV may be a serotype generated by Cre-recombination-based AAV targeted evolution (CREATE) as described by Deverman et al., (Nature Biotechnology 34(2):204-209 (2016)), the contents of which are herein incorporated by reference in their entirety. In one embodiment, AAV serotypes generated in this manner have improved CNS transduction and/or neuronal and astrocytic tropism, as compared to other AAV serotypes. As non-limiting examples, the AAV serotype may be PHP.B, PHP.B2, PHP.B3, PHP.A, G2A12, G2A15. In one embodiment, these AAV serotypes may be AAV9 (SEQ ID NO: 494 and 495) derivatives with a 7-amino acid insert between amino acids 588-589. Non-limiting examples of these 7-amino acid inserts include TLAVPFK (SEQ ID NO: 1241), SVSKPFL (SEQ ID NO: 1249), FTLTTPK (SEQ ID NO: 1250), YTLSQGW (SEQ ID NO: 1256), QAVRTSL (SEQ ID NO: 1282) and/or LAKERLS (SEQ ID NO: 1283).

In one embodiment, the AAV serotype may be as described in Jackson et al (Frontiers in Molecular Neuroscience 9:154 (2016)), the contents of which are herein incorporated by reference in their entirety. In some embodiments, the AAV serotype is PHP.B or AAV9. In some embodiments, the AAV serotype is paired with a synapsin promoter to enhance neuronal transduction, as compared to when more ubiquitous promoters are used (i.e., CBA or CMV).

In one embodiment, peptides for inclusion in an AAV serotype may be identified by isolating human splenocytes, restimulating the splenocytes in vitro using individual peptides spanning the amino acid sequence of the AAV capsid protein, IFN-gamma ELISpot with the individual peptides used for the in vitro restimulation, bioinformatics analysis to determine the given allele restriction of 15-mers identified by IFN-gamma ELISpot, identification of candidate reactive 9-mer epitopes for a given allele, synthesis candidate 9-mers, second IFN-gamma ELISpot screening of splenocytes from subjects carrying the specific alleles to which identified AAV epitopes are predicted to bind, determine the AAV capsid-reactive CD8+ T cell epitopes and determine the frequency of subjects reacting to a given AAV epitope.

AAV vectors comprising the nucleic acid sequence for the siRNA molecules may be prepared or derived from various serotypes of AAVs, including, but not limited to, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8, AAV-DJ, AAV-PHP.A (PHP.A), and/or AAV-PHP.B (PHP.B). In some cases, different serotypes of AAVs may be mixed together or with other types of viruses to produce chimeric AAV vectors. As a non-limiting example, the AAV vector is derived from the AAV9 serotype.

Viral Genome Component: Inverted Terminal Repeats (ITRs)

The AAV particles of the present invention comprise a viral genome with at least one ITR region and a payload region. In one embodiment, the viral genome has two ITRs. These two ITRs flank the payload region at the 5' and 3' ends. The ITRs function as origins of replication comprising recognition sites for replication. ITRs comprise sequence regions which can be complementary and symmetrically arranged. ITRs incorporated into viral genomes of the invention may be comprised of naturally occurring polynucleotide sequences or recombinantly derived polynucleotide sequences.

The ITRs may be derived from the same serotype as the capsid, selected from any of the serotypes listed in Table 6, or a derivative thereof. The ITR may be of a different serotype from the capsid. In one embodiment, the AAV particle has more than one ITR. In a non-limiting example, the AAV particle has a viral genome comprising two ITRs. In one embodiment, the ITRs are of the same serotype as one another. In another embodiment, the ITRs are of different serotypes. Non-limiting examples include zero, one or both of the ITRs having the same serotype as the capsid. In one embodiment, both ITRs of the viral genome of the AAV particle are AAV2 ITRs.

Independently, each ITR may be about 100 to about 150 nucleotides in length. An ITR may be about 100-105 nucleotides in length, 106-110 nucleotides in length, 111-115 nucleotides in length, 116-120 nucleotides in length, 121-125 nucleotides in length, 126-130 nucleotides in length, 131-135 nucleotides in length, 136-140 nucleotides in length, 141-145 nucleotides in length or 146-150 nucleotides in length. In one embodiment, the ITRs are 140-142 nucleotides in length. Non-limiting examples of ITR length are 102, 140, 141, 142, 145 nucleotides in length, and those having at least 95% identity thereto.

In one embodiment, the encoded siRNA molecule may be located near the 5' end of the flip ITR in an expression vector. In another embodiment, the encoded siRNA molecule may be located near the 3' end of the flip ITR in an expression vector. In yet another embodiment, the encoded siRNA molecule may be located near the 5' end of the flop ITR in an expression vector. In yet another embodiment, the encoded siRNA molecule may be located near the 3' end of the flop ITR in an expression vector. In one embodiment, the encoded siRNA molecule may be located between the 5' end of the flip ITR and the 3' end of the flop ITR in an expression vector. In one embodiment, the encoded siRNA molecule may be located between (e.g., half-way between the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the 5' or 3' end of an ITR (e.g., Flip or Flop ITR) in an expression vector.

Viral Genome Component: Promoters

A person skilled in the art may recognize that a target cell may require a specific promoter including but not limited to a promoter that is species specific, inducible, tissue-specific, or cell cycle-specific (Parr et al., *Nat. Med.* 3:1145-9 (1997); the contents of which are herein incorporated by reference in its entirety).

In one embodiment, the promoter is a promoter deemed to be efficient to drive the expression of the modulatory polynucleotide.

In one embodiment, the promoter is a promoter having a tropism for the cell being targeted.

In one embodiment, the promoter is a weak promoter which provides expression of a payload e.g., a modulatory polynucleotide, e.g., siRNA or dsRNA, for a period of time in targeted tissues such as, but not limited to, nervous system tissues. Expression may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a weak promoter for sustained expression of a payload in nervous tissues.

In one embodiment, the promoter may be a promoter which is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. As a non-limiting example, the promoter is a combination of a 382 nucleotide CMV-enhancer sequence and a 260 nucleotide CBA-promoter sequence.

In one embodiment, the vector genome comprises at least one element to enhance the target specificity and expression (See e.g., Powell et al. *Viral Expression Cassette Elements to Enhance Transgene Target Specificity and Expression in Gene Therapy*, 2015; the contents of which are herein incorporated by reference in its entirety). Non-limiting examples of elements to enhance the transgene target specificity and expression include promoters, endogenous miR-NAs, post-transcriptional regulatory elements (PREs), polyadenylation (PolyA) signal sequences and upstream enhancers (USEs), CMV enhancers and introns.

In one embodiment, the vector genome comprises at least one element to enhance the target specificity and expression (See e.g., Powell et al. *Viral Expression Cassette Elements to Enhance Transgene Target Specificity and Expression in Gene Therapy*, 2015; the contents of which are herein incorporated by reference in its entirety) such as promoters.

Promoters for which promote expression in most tissues include, but are not limited to, human elongation factor 1α-subunit (EF1α), immediate-early cytomegalovirus (CMV), chicken β-actin (CBA) and its derivative CAG, the β glucuronidase (GUSB), or ubiquitin C (UBC). Tissue-specific expression elements can be used to restrict expression to certain cell types such as, but not limited to, nervous system promoters which can be used to restrict expression to neurons, astrocytes, or oligodendrocytes. Non-limiting example of tissue-specific expression elements for neurons include neuron-specific enolase (NSE), platelet-derived growth factor (PDGF), platelet-derived growth factor B-chain (PDGF-β), the synapsin (Syn), the methyl-CpG binding protein 2 (MeCP2), CaMKII, mGluR2, NFL, NFH, nβ2, PPE, Enk and EAAT2 promoters. A non-limiting example of tissue-specific expression elements for astrocytes include the glial fibrillary acidic protein (GFAP) and EAAT2 promoters. A non-limiting example of a tissue-specific expression element for oligodendrocytes include the myelin basic protein (MBP) promoter.

In one embodiment, the vector genome comprises a ubiquitous promoter. Non-limiting examples of ubiquitous promoters include H1, U6, CMV, CBA (including derivatives CAG, CBh, etc.), EF-1α, PGK, UBC, GUSB (hGBp), and UCOE (promoter of HNRPA2B1-CBX3). Yu et al. (Molecular Pain 2011, 7:63; the contents of which are herein incorporated by reference in its entirety) evaluated the expression of eGFP under the CAG, EFIα, PGK and UBC promoters in rat DRG cells and primary DRG cells using lentiviral vectors and found that UBC showed weaker expression than the other 3 promoters and there was only 10-12% glia expression seen for all promoters. Soderblom et al. (E. Neuro 2015; the contents of which are herein incorporated by reference in its entirety) the expression of eGFP in AAV8 with CMV and UBC promoters and AAV2 with the CMV promoter after injection in the motor cortex. Intranasal administration of a plasmid containing a UBC or EFIα promoter showed a sustained airway expression greater than the expression with the CMV promoter (See e.g., Gill et al., Gene Therapy 2001, Vol. 8, 1539-1546; the contents of which are herein incorporated by reference in its entirety). Husain et al. (Gene Therapy 2009; the contents of which are herein incorporated by reference in its entirety) evaluated a HβH construct with a hGUSB promoter, a HSV-1LAT promoter and a NSE promoter and found that the HβH construct showed weaker expression than NSE in mice brain. Passini and Wolfe (J. Virol. 2001, 12382-12392, the contents of which are herein incorporated by reference in its entirety) evaluated the long-term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in its entirety) when NF-L and NF—H promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650 nucleotide promoter and NFH is a 920 nucleotide promoter which are both absent in the liver but NFH is abundant in the sensory proprioceptive neurons, brain and spinal cord and NFH is present in the heart. Scn8a is a 470 nucleotide promoter which expresses throughout the DRG, spinal cord and brain with particularly high expression seen in the hippocampal neurons and cerebellar Purkinje cells, cortex, thalamus and hypothalamus (See e.g., Drews et al. 2007 and Raymond et al. 2004; the contents of each of which are herein incorporated by reference in their entireties).

In one embodiment, the vector genome comprises an UBC promoter. The UBC promoter may have a size of 300-350 nucleotides. As a non-limiting example, the UBC promoter is 332 nucleotides.

In one embodiment, the vector genome comprises a GUSB promoter. The GUSB promoter may have a size of 350-400 nucleotides. As a non-limiting example, the GUSB promoter is 378 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a NFL promoter. The NFL promoter may have a size of 600-700 nucleotides. As a non-limiting example, the NFL promoter is 650 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a NFH promoter. The NFH promoter may have a size of 900-950 nucleotides. As a non-limiting example, the NFH promoter is 920 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a scn8a promoter. The scn8a promoter may have a size of 450-500 nucleotides. As a non-limiting example, the scn8a promoter is 470 nucleotides. As a non-limiting example, the construct may be AAV-promoter-CMV/globin intron-modulatory polynucleotide-RBG, where the AAV may be self-complementary and the AAV may be the DJ serotype.

In one embodiment, the vector genome comprises a Pol III promoter.

In one embodiment, the vector genome comprises a P1 promoter.

In one embodiment, the vector genome comprises a FXN promoter.

In one embodiment, the vector genome comprises a PGK promoter.

In one embodiment, the vector genome comprises a CBA promoter.

In one embodiment, the vector genome comprises a CMV promoter.

In one embodiment, the vector genome comprises a H1 promoter.

In one embodiment, the vector genome comprises a U6 promoter.

In one embodiment, the vector genome comprises a liver or a skeletal muscle promoter. Non-limiting examples of liver promoters include hAAT and TBG. Non-limiting examples of skeletal muscle promoters include Desmin, MCK and C5-12.

In one embodiment, the AAV vector comprises an enhancer element, a promoter and/or a 5'UTR intron. The enhancer may be, but is not limited to, a CMV enhancer, the promoter may be, but is not limited to, a CMV, CBA, UBC, GUSB, NSE, Synapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter; (9) GFAP promoter, (10) H1 promoter; and (11) U6 promoter.

In one embodiment, the AAV vector has an engineered promoter.

Viral Genome Component: Introns

In one embodiment, the vector genome comprises at least one element to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety) such as an intron. Non-limiting examples of introns include, MVM (67-97 bps), F.IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The promoter may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

In one embodiment, the AAV vector genome may comprise a promoter such as, but not limited to, CMV or U6. As a non-limiting example, the promoter for the AAV comprising the nucleic acid sequence for the siRNA molecules of the present invention is a CMV promoter. As another non-limiting example, the promoter for the AAV comprising the nucleic acid sequence for the siRNA molecules of the present invention is a U6 promoter.

In one embodiment, the AAV vector may comprise a CMV promoter.

In one embodiment, the AAV vector may comprise a U6 promoter.

In one embodiment, the AAV vector may comprise a CMV and a U6 promoter.

In one embodiment, the AAV vector may comprise a H1 promoter.

In one embodiment, the AAV vector may comprise a CBA promoter.

In one embodiment, the encoded siRNA molecule may be located downstream of a promoter in an expression vector such as, but not limited to, CMV, U6, H1, CBA or a CBA promoter with an intron such as SV40, betaGlobin or others known in the art. Further, the encoded siRNA molecule may also be located upstream of the polyadenylation sequence in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

Viral Genome Component: Polyadenylation Sequence

In one embodiment, the viral genome of the AAV particles of the present invention comprise at least one polyadenylation sequence. The viral genome of the AAV particle may comprise a polyadenylation sequence between the 3' end of the payload coding sequence and the 5' end of the 3'ITR.

In one embodiment, the polyadenylation sequence or "polyA sequence" may range from absent to about 500 nucleotides in length. The polyadenylation sequence may be, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, and 500 nucleotides in length.

In one embodiment, the polyadenylation sequence is 50-100 nucleotides in length.

In one embodiment, the polyadenylation sequence is 50-150 nucleotides in length.

In one embodiment, the polyadenylation sequence is 50-160 nucleotides in length.

In one embodiment, the polyadenylation sequence is 50-200 nucleotides in length.

In one embodiment, the polyadenylation sequence is 60-100 nucleotides in length.

In one embodiment, the polyadenylation sequence is 60-150 nucleotides in length.

In one embodiment, the polyadenylation sequence is 60-160 nucleotides in length.

In one embodiment, the polyadenylation sequence is 60-200 nucleotides in length.

In one embodiment, the polyadenylation sequence is 70-100 nucleotides in length.

In one embodiment, the polyadenylation sequence is 70-150 nucleotides in length.

In one embodiment, the polyadenylation sequence is 70-160 nucleotides in length.

In one embodiment, the polyadenylation sequence is 70-200 nucleotides in length.

In one embodiment, the polyadenylation sequence is 80-100 nucleotides in length.

In one embodiment, the polyadenylation sequence is 80-150 nucleotides in length.

In one embodiment, the polyadenylation sequence is 80-160 nucleotides in length.

In one embodiment, the polyadenylation sequence is 80-200 nucleotides in length.

In one embodiment, the polyadenylation sequence is 90-100 nucleotides in length.

In one embodiment, the polyadenylation sequence is 90-150 nucleotides in length.

In one embodiment, the polyadenylation sequence is 90-160 nucleotides in length.

In one embodiment, the polyadenylation sequence is 90-200 nucleotides in length.

In one embodiment, the encoded siRNA molecule may be located upstream of the polyadenylation sequence in an expression vector. Further, the encoded siRNA molecule may be located downstream of a promoter such as, but not limited to, CMV, U6, H1, CBA or a CBA promoter with a SV40 or betaGlobin intron in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

Expression Vector

In one embodiment, an expression vector (e.g., AAV vector) may comprise at least one of the modulatory polynucleotides encoding at least one of the siRNA sequences or duplexes described herein.

In one embodiment, an expression vector may comprise, from ITR to ITR recited 5' to 3', an ITR, a promoter, an intron, a modulatory polynucleotide, a polyA sequence and an ITR.

Genome Size

In one embodiment, the vector genome which comprises a nucleic acid sequence encoding the modulatory polynucleotides described herein may be single stranded or double stranded vector genome. The size of the vector genome may be small, medium, large or the maximum size. Additionally, the vector genome may comprise a promoter and a polyA tail.

In one embodiment, the vector genome which comprises a nucleic acid sequence encoding the modulatory polynucleotides described herein may be a small single stranded vector genome. A small single stranded vector genome may be 2.7 to 3.5 kb in size such as about 2.7, 2.8, 2.9, 3.0, 3.1, 3.2, 3.3, 3.4, and 3.5 kb in size. As a non-limiting example, the small single stranded vector genome may be 3.2 kb in size. Additionally, the vector genome may comprise a promoter and a polyA tail.

In one embodiment, the vector genome which comprises a nucleic acid sequence encoding the modulatory polynucleotides described herein may be a small double stranded vector genome. A small double stranded vector genome may be 1.3 to 1.7 kb in size such as about 1.3, 1.4, 1.5, 1.6, and 1.7 kb in size. As a non-limiting example, the small double stranded vector genome may be 1.6 kb in size. Additionally, the vector genome may comprise a promoter and a polyA tail.

In one embodiment, the vector genome which comprises a nucleic acid sequence encoding the modulatory polynucleotides described herein e.g., siRNA or dsRNA, may be a medium single stranded vector genome. A medium single stranded vector genome may be 3.6 to 4.3 kb in size such as about 3.6, 3.7, 3.8, 3.9, 4.0, 4.1, 4.2 and 4.3 kb in size. As a non-limiting example, the medium single stranded vector genome may be 4.0 kb in size. Additionally, the vector genome may comprise a promoter and a polyA tail.

In one embodiment, the vector genome which comprises a nucleic acid sequence encoding the modulatory polynucleotides described herein may be a medium double stranded vector genome. A medium double stranded vector genome may be 1.8 to 2.1 kb in size such as about 1.8, 1.9, 2.0, and 2.1 kb in size. As a non-limiting example, the medium double stranded vector genome may be 2.0 kb in size. Additionally, the vector genome may comprise a promoter and a polyA tail.

In one embodiment, the vector genome which comprises a nucleic acid sequence encoding the modulatory polynucleotides described herein may be a large single stranded vector genome. A large single stranded vector genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded vector genome may be 4.7 kb in size. As another non-limiting example, the large single stranded vector genome may be 4.8 kb in size. As yet another non-limiting example, the large single stranded vector genome may be 6.0 kb in size. Additionally, the vector genome may comprise a promoter and a polyA tail.

In one embodiment, the vector genome which comprises a nucleic acid sequence encoding the modulatory polynucleotides described herein may be a large double stranded vector genome. A large double stranded vector genome may be 2.2 to 3.0 kb in size such as about 2.2, 2.3, 2.4, 2.5, 2.6, 2.7, 2.8, 2.9 and 3.0 kb in size. As a non-limiting example, the large double stranded vector genome may be 2.4 kb in size. Additionally, the vector genome may comprise a promoter and a polyA tail.

Viral Production

The present disclosure provides a method for the generation of parvoviral particles, e.g. AAV particles, by viral genome replication in a viral replication cell comprising contacting the viral replication cell with an AAV polynucleotide or AAV genome.

The present disclosure provides a method for producing an AAV particle having enhanced (increased, improved) transduction efficiency comprising the steps of: 1) co-transfecting competent bacterial cells with a bacmid vector and either a viral construct vector and/or AAV payload construct vector, 2) isolating the resultant viral construct expression vector and AAV payload construct expression vector and separately transfecting viral replication cells, 3) isolating and purifying resultant payload and viral construct particles comprising viral construct expression vector or AAV payload construct expression vector, 4) co-infecting a viral replication cell with both the AAV payload and viral construct particles comprising viral construct expression vector or AAV payload construct expression vector, 5) harvesting and purifying the viral particle comprising a parvoviral genome.

In one embodiment, the present invention provides a method for producing an AAV particle comprising the steps of 1) simultaneously co-transfecting mammalian cells, such as, but not limited to HEK293 cells, with a payload region, a construct expressing rep and cap genes and a helper construct, 2) harvesting and purifying the AAV particle comprising a viral genome.

Cells

The present disclosure provides a cell comprising an AAV polynucleotide and/or AAV genome.

Viral production disclosed herein describes processes and methods for producing AAV particles that contact a target cell to deliver a payload construct, e.g. a recombinant viral construct, which comprises a polynucleotide sequence encoding a payload molecule.

In one embodiment, the AAV particles may be produced in a viral replication cell that comprises an insect cell.

Growing conditions for insect cells in culture, and production of heterologous products in insect cells in culture are well-known in the art, see U.S. Pat. No. 6,204,059, the contents of which are herein incorporated by reference in their entirety.

Any insect cell which allows for replication of parvovirus and which can be maintained in culture can be used in accordance with the present invention. Cell lines may be used from *Spodoptera frugiperda*, including, but not limited to the Sf9 or Sf21 cell lines, *Drosophila* cell lines, or mosquito cell lines, such as *Aedes albopictus* derived cell lines. Use of insect cells for expression of heterologous proteins is well documented, as are methods of introducing nucleic acids, such as vectors, e.g., insect-cell compatible vectors, into such cells and methods of maintaining such cells in culture. See, for example, Methods in Molecular Biology, ed. Richard, Humana Press, NJ (1995); O'Reilly et al., Baculovirus Expression Vectors, A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., J. *Vir.* 66:6922-30 (1992); Kimbauer et al., *Vir.* 219:37-44 (1996); Zhao et al., Vir. 272:382-93 (2000); and Samulski et al., U.S. Pat. No. 6,204,059, the contents of each of which is herein incorporated by reference in its entirety.

The viral replication cell may be selected from any biological organism, including prokaryotic (e.g., bacterial) cells, and eukaryotic cells, including, insect cells, yeast cells and mammalian cells. Viral replication cells may comprise mammalian cells such as A549, WEH1, 3T3, 10T1/2, BHK, MDCK, COS 1, COS 7, BSC 1, BSC 40, BMT 10, VERO. W138, HeLa, HEK293, Saos, C2C12, L cells, HT1080, HepG2 and primary fibroblast, hepatocyte and myoblast cells derived from mammals. Viral replication cells comprise cells derived from mammalian species including, but not limited to, human, monkey, mouse, rat, rabbit, and hamster or cell type, including but not limited to fibroblast, hepatocyte, tumor cell, cell line transformed cell, etc.

Small Scale Production of AAV Particles

Viral production disclosed herein describes processes and methods for producing AAV particles that contact a target cell to deliver a payload, e.g. a recombinant viral construct, which comprises a polynucleotide sequence encoding a payload.

In one embodiment, the AAV particles may be produced in a viral replication cell that comprises a mammalian cell.

Viral replication cells commonly used for production of recombinant AAV particles include, but are not limited to 293 cells, COS cells, HeLa cells, KB cells, and other mammalian cell lines as described in U.S. Pat. Nos. 6,156, 303, 5,387,484, 5,741,683, 5,691,176, and 5,688,676; U.S. patent application 2002/0081721, and International Patent Applications WO 00/47757, WO 00/24916, and WO 96/17947, the contents of each of which are herein incorporated by reference in their entireties.

In one embodiment, AAV particles are produced in mammalian-cells wherein all three VP proteins are expressed at a stoichiometry approaching 1:1:10 (VP1:VP2:VP3). The regulatory mechanisms that allow this controlled level of expression include the production of two mRNAs, one for VP1, and the other for VP2 and VP3, produced by differential splicing.

In another embodiment, AAV particles are produced in mammalian cells using a triple transfection method wherein a payload construct, parvoviral Rep and parvoviral Cap and a helper construct are comprised within three different constructs. The triple transfection method of the three components of AAV particle production may be utilized to produce small lots of virus for assays including transduction efficiency, target tissue (tropism) evaluation, and stability.

Baculovirus

Particle production disclosed herein describes processes and methods for producing AAV particles that contact a target cell to deliver a payload construct which comprises a polynucleotide sequence encoding a payload.

Briefly, the viral construct vector and the AAV payload construct vector are each incorporated by a transposon donor/acceptor system into a bacmid, also known as a baculovirus plasmid, by standard molecular biology techniques known and performed by a person skilled in the art. Transfection of separate viral replication cell populations produces two baculoviruses, one that comprises the viral construct expression vector, and another that comprises the AAV payload construct expression vector. The two baculoviruses may be used to infect a single viral replication cell population for production of AAV particles.

Baculovirus expression vectors for producing viral particles in insect cells, including but not limited to *Spodoptera frugiperda* (Sf9) cells, provide high titers of viral particle product. Recombinant baculovirus encoding the viral construct expression vector and AAV payload construct expression vector initiates a productive infection of viral replicating cells. Infectious baculovirus particles released from the primary infection secondarily infect additional cells in the culture, exponentially infecting the entire cell culture population in a number of infection cycles that is a function of the initial multiplicity of infection, see Urabe, M. et al., J Virol. 2006 February; 80 (4):1874-85, the contents of which are herein incorporated by reference in their entirety.

Production of AAV particles with baculovirus in an insect cell system may address known baculovirus genetic and physical instability. In one embodiment, the production system addresses baculovirus instability over multiple passages by utilizing a titerless infected-cells preservation and scale-up system. Small scale seed cultures of viral producing cells are transfected with viral expression constructs encoding the structural, non-structural, components of the viral particle. Baculovirus-infected viral producing cells are harvested into aliquots that may be cryopreserved in liquid nitrogen; the aliquots retain viability and infectivity for infection of large scale viral producing cell culture Wasilko D J et al., Protein Expr Purif. 2009 June; 65(2):122-32, the contents of which are herein incorporated by reference in their entirety.

A genetically stable baculovirus may be used to produce source of the one or more of the components for producing AAV particles in invertebrate cells. In one embodiment, defective baculovirus expression vectors may be maintained episomally in insect cells. In such an embodiment the bacmid vector is engineered with replication control elements, including but not limited to promoters, enhancers, and/or cell-cycle regulated replication elements.

In one embodiment, baculoviruses may be engineered with a (non-) selectable marker for recombination into the chitinase/cathepsin locus. The chia/v-cath locus is non-essential for propagating baculovirus in tissue culture, and the V-cath (EC 3.4.22.50) is a cysteine endoprotease that is most active on Arg-Arg dipeptide containing substrates. The Arg-Arg dipeptide is present in densovirus and parvovirus capsid structural proteins but infrequently occurs in dependovirus VP1.

In one embodiment, stable viral replication cells permissive for baculovirus infection are engineered with at least one stable integrated copy of any of the elements necessary for AAV replication and viral particle production including, but not limited to, the entire AAV genome, Rep and Cap genes, Rep genes, Cap genes, each Rep protein as a separate transcription cassette, each VP protein as a separate transcription cassette, the AAP (assembly activation protein), or at least one of the baculovirus helper genes with native or non-native promoters.

Large-Scale Production

In some embodiments, AAV particle production may be modified to increase the scale of production. Large scale viral production methods according to the present disclosure may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety. Methods of increasing viral particle production scale typically comprise increasing the number of viral replication cells. In some embodiments, viral replication cells comprise adherent cells. To increase the scale of viral particle production by adherent viral replication cells, larger cell culture surfaces are required. In some cases, large-scale production methods comprise the use of roller bottles to increase cell culture surfaces. Other cell culture substrates with increased surface areas are known in the art. Examples of additional adherent cell culture products with increased surface areas include, but are not limited to CELLSTACK®, CELLCUBE® (Corning Corp., Corning, NY) and NUNC™ CELL FACTORY™ (Thermo Scientific, Waltham, MA) In some cases, large-scale adherent cell surfaces may comprise from about 1,000 $cm^2$ to about 100,000 $cm^2$. In some cases, large-scale adherent cell cultures may comprise from about $10^7$ to about $10^9$ cells, from about $10^8$ to about $10^{10}$ cells, from about $10^9$ to about $10^{12}$ cells or at least $10^{12}$ cells. In some cases, large-scale adherent cultures may produce from about $10^9$ to about $10^{12}$, from about $10^{10}$ to about $10^{13}$, from about $10^{11}$ to about $10^{14}$, from about $10^{12}$ to about $10^{15}$ or at least $10^{15}$ viral particles.

In some embodiments, large-scale viral production methods of the present disclosure may comprise the use of suspension cell cultures. Suspension cell culture allows for significantly increased numbers of cells. Typically, the number of adherent cells that can be grown on about 10-50 $cm^2$ of surface area can be grown in about 1 $cm^3$ volume in suspension.

Transfection of replication cells in large-scale culture formats may be carried out according to any methods known in the art. For large-scale adherent cell cultures, transfection methods may include, but are not limited to the use of inorganic compounds (e.g. calcium phosphate), organic compounds [e.g. polyethyleneimine (PEI)] or the use of non-chemical methods (e.g. electroporation.) With cells grown in suspension, transfection methods may include, but are not limited to the use of calcium phosphate and the use of PEI. In some cases, transfection of large scale suspension cultures may be carried out according to the section entitled "Transfection Procedure" described in Feng, L. et al., 2008. Biotechnol Appl. Biochem. 50:121-32, the contents of which are herein incorporated by reference in their entirety. According to such embodiments, PEI-DNA complexes may be formed for introduction of plasmids to be transfected. In some cases, cells being transfected with PEI-DNA complexes may be 'shocked' prior to transfection. This comprises lowering cell culture temperatures to 4° C. for a period of about 1 hour. In some cases, cell cultures may be shocked for a period of from about 10 minutes to about 5 hours. In some cases, cell cultures may be shocked at a temperature of from about 0° C. to about 20° C.

In some cases, transfections may include one or more vectors for expression of an RNA effector molecule to reduce expression of nucleic acids from one or more AAV payload construct. Such methods may enhance the production of viral particles by reducing cellular resources wasted on expressing payload constructs. In some cases, such methods may be carried according to those taught in US Publication No. US2014/0099666, the contents of which are herein incorporated by reference in their entirety.

Bioreactors

In some embodiments, cell culture bioreactors may be used for large scale viral production. In some cases, bioreactors comprise stirred tank reactors. Such reactors generally comprise a vessel, typically cylindrical in shape, with a stirrer (e.g. impeller.) In some embodiments, such bioreactor vessels may be placed within a water jacket to control vessel temperature and/or to minimize effects from ambient temperature changes. Bioreactor vessel volume may range in size from about 500 ml to about 2 L, from about 1 L to about 5 L, from about 2.5 L to about 20 L, from about 10 L to about 50 L, from about 25 L to about 100 L, from about 75 L to about 500 L, from about 250 L to about 2,000 L, from about 1,000 L to about 10,000 L, from about 5,000 L to about 50,000 L or at least 50,000 L. Vessel bottoms may be rounded or flat. In some cases, animal cell cultures may be maintained in bioreactors with rounded vessel bottoms.

In some cases, bioreactor vessels may be warmed through the use of a thermocirculator. Thermocirculators pump heated water around water jackets. In some cases, heated water may be pumped through pipes (e.g. coiled pipes) that are present within bioreactor vessels. In some cases, warm air may be circulated around bioreactors, including, but not limited to air space directly above culture medium. Additionally, pH and $CO_2$ levels may be maintained to optimize cell viability.

In some cases, bioreactors may comprise hollow-fiber reactors. Hollow-fiber bioreactors may support the culture of both anchorage dependent and anchorage independent cells. Further bioreactors may include, but are not limited to packed-bed or fixed-bed bioreactors. Such bioreactors may comprise vessels with glass beads for adherent cell attachment. Further packed-bed reactors may comprise ceramic beads.

In some cases, viral particles are produced through the use of a disposable bioreactor. In some embodiments, such bioreactors may include WAVE™ disposable bioreactors.

In some embodiments, AAV particle production in animal cell bioreactor cultures may be carried out according to the methods taught in U.S. Pat. Nos. 5,064,764, 6,194,191, 6,566,118, 8,137,948 or US Patent Application No. US2011/0229971, the contents of each of which are herein incorporated by reference in their entirety.

Cell Lysis

Cells of the invention, including, but not limited to viral production cells, may be subjected to cell lysis according to any methods known in the art. Cell lysis may be carried out to obtain one or more agents (e.g. viral particles) present within any cells of the invention. In some embodiments, cell lysis may be carried out according to any of the methods listed in U.S. Pat. Nos. 7,326,555, 7,579,181, 7,048,920, 6,410,300, 6,436,394, 7,732,129, 7,510,875, 7,445,930, 6,726,907, 6,194,191, 7,125,706, 6,995,006, 6,676,935, 7,968,333, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety. Cell lysis methods may be chemical or mechanical. Chemical cell lysis typically comprises contacting one or more cells with one or more lysis agent. Mechanical lysis typically comprises subjecting one or more cells to one or more lysis condition and/or one or more lysis force.

In some embodiments, chemical lysis may be used to lyse cells. As used herein, the term "lysis agent" refers to any agent that may aid in the disruption of a cell. In some cases, lysis agents are introduced in solutions, termed lysis solutions or lysis buffers. As used herein, the term "lysis solution" refers to a solution (typically aqueous) comprising one or more lysis agent. In addition to lysis agents, lysis solutions may include one or more buffering agents, solubilizing agents, surfactants, preservatives, cryoprotectants, enzymes, enzyme inhibitors and/or chelators. Lysis buffers are lysis solutions comprising one or more buffering agent. Additional components of lysis solutions may include one or more solubilizing agent. As used herein, the term "solubilizing agent" refers to a compound that enhances the solubility of one or more components of a solution and/or the solubility of one or more entities to which solutions are applied. In some cases, solubilizing agents enhance protein solubility. In some cases, solubilizing agents are selected based on their ability to enhance protein solubility while maintaining protein conformation and/or activity.

Exemplary lysis agents may include any of those described in U.S. Pat. Nos. 8,685,734, 7,901,921, 7,732,129, 7,223,585, 7,125,706, 8,236,495, 8,110,351, 7,419,956, 7,300,797, 6,699,706 and 6,143,567, the contents of each of which are herein incorporated by reference in their entirety. In some cases, lysis agents may be selected from lysis salts, amphoteric agents, cationic agents, ionic detergents and non-ionic detergents. Lysis salts may include, but are not limited to sodium chloride (NaCl) and potassium chloride (KCl.) Further lysis salts may include any of those described in U.S. Pat. Nos. 8,614,101, 7,326,555, 7,579,181, 7,048, 920, 6,410,300, 6,436,394, 7,732,129, 7,510,875, 7,445,930, 6,726,907, 6,194,191, 7,125,706, 6,995,006, 6,676,935 and 7,968,333, the contents of each of which are herein incorporated by reference in their entirety. Concentrations of salts may be increased or decreased to obtain an effective concentration for rupture of cell membranes. Amphoteric agents, as referred to herein, are compounds capable of reacting as an acid or a base. Amphoteric agents may include, but are not limited to lysophosphatidylcholine, 3-((3-Cholamidopropyl) dimethylammonium)-1-propanesulfonate (CHAPS), ZWITTERGENT® and the like. Cationic agents may include, but are not limited to cetyltrimethylammonium bromide (C (16) TAB) and Benzalkonium chloride. Lysis agents comprising detergents may include ionic detergents or non-ionic detergents. Detergents may function to break apart or dissolve cell structures including, but not limited to cell membranes, cell walls, lipids, carbohydrates, lipoproteins and glycoproteins. Exemplary ionic detergents include any of those taught in U.S. Pat. Nos. 7,625,570 and 6,593,123 or US Publication No. US2014/0087361, the contents of each of which are herein incorporated by reference in their entirety. Some ionic detergents may include, but are not limited to sodium dodecyl sulfate (SDS), cholate and deoxycholate. In some cases, ionic detergents may be included in lysis solutions as a solubilizing agent. Non-ionic detergents may include, but are not limited to octylglucoside, digitonin, lubrol, C12E8, TWEEN®-20, TWEEN®-80, Triton X-100 and Noniodet P-40. Non-ionic detergents are typically weaker lysis agents, but may be included as solubilizing agents for solubilizing cellular and/or viral proteins. Further lysis agents may include enzymes and urea. In some cases, one or more lysis agents may be combined in a lysis solution in order to enhance one or more of cell lysis and protein solubility. In some cases, enzyme inhibitors may be included in lysis solutions in order to prevent proteolysis that may be triggered by cell membrane disruption.

In some embodiments, mechanical cell lysis is carried out. Mechanical cell lysis methods may include the use of one or more lysis condition and/or one or more lysis force. As used herein, the term "lysis condition" refers to a state or circumstance that promotes cellular disruption. Lysis conditions may comprise certain temperatures, pressures, osmotic purity, salinity and the like. In some cases, lysis conditions comprise increased or decreased temperatures. According to some embodiments, lysis conditions comprise changes in temperature to promote cellular disruption. Cell lysis carried out according to such embodiments may include freeze-thaw lysis. As used herein, the term "freeze-thaw lysis" refers to cellular lysis in which a cell solution is subjected to one or more freeze-thaw cycle. According to freeze-thaw lysis methods, cells in solution are frozen to induce a mechanical disruption of cellular membranes caused by the formation and expansion of ice crystals. Cell solutions used according freeze-thaw lysis methods, may further comprise one or more lysis agents, solubilizing agents, buffering agents, cryoprotectants, surfactants, preservatives, enzymes, enzyme inhibitors and/or chelators. Once cell solutions subjected to freezing are thawed, such components may enhance the recovery of desired cellular products. In some cases, one or more cryoprotectants are included in cell solutions undergoing freeze-thaw lysis. As used herein, the term "cryoprotectant" refers to an agent used to protect one or more substance from damage due to freezing. Cryoprotectants may include any of those taught in US Publication No. US2013/0323302 or U.S. Pat. Nos. 6,503,888, 6,180,613, 7,888,096, 7,091,030, the contents of each of which are herein incorporated by reference in their entirety. In some cases, cryoprotectants may include, but are not limited to dimethyl sulfoxide, 1,2-propanediol, 2,3-butanediol, formamide, glycerol, ethylene glycol, 1,3-propanediol and n-dimethyl formamide, polyvinylpyrrolidone, hydroxyethyl starch, agarose, dextrans, inositol, glucose, hydroxyethyl-starch, lactose, sorbitol, methyl glucose, sucrose and urea. In some embodiments, freeze-thaw lysis may be carried out according to any of the methods described in U.S. Pat. No. 7,704,721, the contents of which are herein incorporated by reference in their entirety.

As used herein, the term "lysis force" refers to a physical activity used to disrupt a cell. Lysis forces may include, but are not limited to mechanical forces, sonic forces, gravitational forces, optical forces, electrical forces and the like. Cell lysis carried out by mechanical force is referred to herein as "mechanical lysis." Mechanical forces that may be used according to mechanical lysis may include high shear fluid forces. According to such methods of mechanical lysis, a microfluidizer may be used. Microfluidizers typically comprise an inlet reservoir where cell solutions may be applied. Cell solutions may then be pumped into an interaction chamber via a pump (e.g. high-pressure pump) at high speed and/or pressure to produce shear fluid forces. Resulting lysates may then be collected in one or more output reservoir. Pump speed and/or pressure may be adjusted to modulate cell lysis and enhance recovery of products (e.g. viral particles.) Other mechanical lysis methods may include physical disruption of cells by scraping.

Cell lysis methods may be selected based on the cell culture format of cells to be lysed. For example, with adherent cell cultures, some chemical and mechanical lysis methods may be used. Such mechanical lysis methods may include freeze-thaw lysis or scraping. In another example, chemical lysis of adherent cell cultures may be carried out through incubation with lysis solutions comprising surfactant, such as Triton-X-100. In some cases, cell lysates generated from adherent cell cultures may be treated with one more nuclease to lower the viscosity of the lysates caused by liberated DNA.

In one embodiment, a method for harvesting AAV particles without lysis may be used for efficient and scalable AAV particle production. In a non-limiting example, AAV particles may be produced by culturing an AAV particle lacking a heparin binding site, thereby allowing the AAV particle to pass into the supernatant, in a cell culture, collecting supernatant from the culture; and isolating the AAV particle from the supernatant, as described in US Patent Application 20090275107, the contents of which are incorporated herein by reference in their entirety.

Clarification

Cell lysates comprising viral particles may be subjected to clarification. Clarification refers to initial steps taken in purification of viral particles from cell lysates. Clarification serves to prepare lysates for further purification by removing larger, insoluble debris. Clarification steps may include, but are not limited to centrifugation and filtration. During clarification, centrifugation may be carried out at low speeds to remove larger debris only. Similarly, filtration may be carried out using filters with larger pore sizes so that only larger debris is removed. In some cases, tangential flow filtration may be used during clarification. Objectives of viral clarification include high throughput processing of cell lysates and to optimize ultimate viral recovery. Advantages of including a clarification step include scalability for processing of larger volumes of lysate. In some embodiments, clarification may be carried out according to any of the methods presented in U.S. Pat. Nos. 8,524,446, 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498, 7,491,508, US Publication Nos. US2013/0045186, US2011/0263027, US2011/0151434, US2003/0138772, and International Publication Nos. WO2002012455, WO1996039530, WO1998010088, WO1999014354, WO1999015685, WO1999047691, WO2000055342, WO2000075353 and WO2001023597, the contents of each of which are herein incorporated by reference in their entirety.

Methods of cell lysate clarification by filtration are well understood in the art and may be carried out according to a variety of available methods including, but not limited to passive filtration and flow filtration. Filters used may comprise a variety of materials and pore sizes. For example, cell lysate filters may comprise pore sizes of from about 1 µM to about 5 µM, from about 0.5 µM to about 2 µM, from about 0.1 µM to about 1 µM, from about 0.05 µM to about 0.05 µM and from about 0.001 µM to about 0.1 µM. Exemplary pore sizes for cell lysate filters may include, but are not limited to, 2.0, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, 0.95, 0.9, 0.85, 0.8, 0.75, 0.7, 0.65, 0.6, 0.55, 0.5, 0.45, 0.4, 0.35, 0.3, 0.25, 0.2, 0.15, 0.1, 0.05, 0.22, 0.21, 0.20, 0.19, 0.18, 0.17, 0.16, 0.15, 0.14, 0.13, 0.12, 0.11, 0.1, 0.09, 0.08, 0.07, 0.06, 0.05, 0.04, 0.03, 0.02, 0.01, 0.02, 0.019, 0.018, 0.017, 0.016, 0.015, 0.014, 0.013, 0.012, 0.011, 0.01, 0.009, 0.008, 0.007, 0.006, 0.005, 0.004, 0.003, 0.002, 0.001 and 0.001 µM. In one embodiment, clarification may comprise filtration through a filter with 2.0 µM pore size to remove large debris, followed by passage through a filter with 0.45 µM pore size to remove intact cells.

Filter materials may be composed of a variety of materials. Such materials may include, but are not limited to polymeric materials and metal materials (e.g. sintered metal and pored aluminum.) Exemplary materials may include, but are not limited to nylon, cellulose materials (e.g. cellulose acetate), polyvinylidene fluoride (PVDF), polyethersulfone, polyamide, polysulfone, polypropylene, and polyethylene terephthalate. In some cases, filters useful for clarification of cell lysates may include, but are not limited to ULTIPLEAT PROFILE™ filters (Pall Corporation, Port Washington, NY), SUPOR™ membrane filters (Pall Corporation, Port Washington, NY)

In some cases, flow filtration may be carried out to increase filtration speed and/or effectiveness. In some cases, flow filtration may comprise vacuum filtration. According to such methods, a vacuum is created on the side of the filter opposite that of cell lysate to be filtered. In some cases, cell lysates may be passed through filters by centrifugal forces. In some cases, a pump is used to force cell lysate through clarification filters. Flow rate of cell lysate through one or more filters may be modulated by adjusting one of channel size and/or fluid pressure.

According to some embodiments, cell lysates may be clarified by centrifugation. Centrifugation may be used to pellet insoluble particles in the lysate. During clarification, centrifugation strength [expressed in terms of gravitational units (g), which represents multiples of standard gravitational force] may be lower than in subsequent purification steps. In some cases, centrifugation may be carried out on cell lysates at from about 200 g to about 800 g, from about 500 g to about 1500 g, from about 1000 g to about 5000 g, from about 1200 g to about 10000 g or from about 8000 g to about 15000 g. In some embodiments, cell lysate centrifugation is carried out at 8000 g for 15 minutes. In some cases, density gradient centrifugation may be carried out in order to partition particulates in the cell lysate by sedimentation rate. Gradients used according to methods of the present disclosure may include, but are not limited to cesium chloride gradients and iodixanol step gradients.

Purification: Chromatography

In some cases, AAV particles may be purified from clarified cell lysates by one or more methods of chromatography. Chromatography refers to any number of methods known in the art for separating out one or more elements from a mixture. Such methods may include, but are not limited to ion exchange chromatography (e.g. cation exchange chromatography and anion exchange chromatography), immunoaffinity chromatography and size-exclusion chromatography. In some embodiments, methods of viral chromatography may include any of those taught in U.S. Pat. Nos. 5,756,283, 6,258,595, 6,261,551, 6,270,996, 6,281,010, 6,365,394, 6,475,769, 6,482,634, 6,485,966, 6,943,019, 6,953,690, 7,022,519, 7,238,526, 7,291,498 and 7,491,508 or International Publication Nos. WO1996039530, WO1998010088, WO1999014354, WO1999015685, WO1999047691, WO2000055342, WO2000075353 and WO2001023597, the contents of each of which are herein incorporated by reference in their entirety.

In some embodiments, ion exchange chromatography may be used to isolate viral particles. Ion exchange chromatography is used to bind viral particles based on charge-charge interactions between capsid proteins and charged sites present on a stationary phase, typically a column through which viral preparations (e.g. clarified lysates) are passed. After application of viral preparations, bound viral particles may then be eluted by applying an elution solution to disrupt the charge-charge interactions. Elution solutions may be optimized by adjusting salt concentration and/or pH to enhance recovery of bound viral particles. Depending on the charge of viral capsids being isolated, cation or anion exchange chromatography methods may be selected. Methods of ion exchange chromatography may include, but are not limited to any of those taught in U.S. Pat. Nos. 7,419,817, 6,143,548, 7,094,604, 6,593,123, 7,015,026 and 8,137,948, the contents of each of which are herein incorporated by reference in their entirety.

In some embodiments, immunoaffinity chromatography may be used. Immunoaffinity chromatography is a form of chromatography that utilizes one or more immune compounds (e.g. antibodies or antibody-related structures) to retain viral particles. Immune compounds may bind specifically to one or more structures on viral particle surfaces, including, but not limited to one or more viral coat protein. In some cases, immune compounds may be specific for a particular viral variant. In some cases, immune compounds may bind to multiple viral variants. In some embodiments, immune compounds may include recombinant single-chain antibodies. Such recombinant single chain antibodies may include those described in Smith, R. H. et al., 2009. Mol. Ther. 17(11):1888-96, the contents of which are herein incorporated by reference in their entirety. Such immune compounds are capable of binding to several AAV capsid variants, including, but not limited to AAV1, AAV2, AAV6 and AAV8.

In some embodiments, size-exclusion chromatography (SEC) may be used. SEC may comprise the use of a gel to separate particles according to size. In viral particle purification, SEC filtration is sometimes referred to as "polishing." In some cases, SEC may be carried out to generate a final product that is near-homogenous. Such final products may in some cases be used in pre-clinical studies and/or clinical studies (Kotin, R. M. 2011. Human Molecular Genetics. 20(1):R2-R6, the contents of which are herein incorporated by reference in their entirety.) In some cases, SEC may be carried out according to any of the methods taught in U.S. Pat. Nos. 6,143,548, 7,015,026, 8,476,418, 6,410,300, 8,476,418, 7,419,817, 7,094,604, 6,593,123, and 8,137,948, the contents of each of which are herein incorporated by reference in their entirety.

In one embodiment, the compositions comprising at least one AAV particle may be isolated or purified using the methods described in U.S. Pat. No. 6,146,874, the contents of which are herein incorporated by reference in its entirety.

In one embodiment, the compositions comprising at least one AAV particle may be isolated or purified using the methods described in U.S. Pat. No. 6,660,514, the contents of which are herein incorporated by reference in its entirety.

In one embodiment, the compositions comprising at least one AAV particle may be isolated or purified using the methods described in U.S. Pat. No. 8,283,151, the contents of which are herein incorporated by reference in its entirety.

In one embodiment, the compositions comprising at least one AAV particle may be isolated or purified using the methods described in U.S. Pat. No. 8,524,446, the contents of which are herein incorporated by reference in its entirety.

II. FORMULATION AND DELIVERY

Pharmaceutical Compositions and Formulation

In addition to the pharmaceutical compositions (vectors, e.g., AAV vectors, comprising a nucleic acid sequence encoding the siRNA molecules), provided herein are pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients or subjects. For the purposes of the present disclosure, the phrase "active ingredient" generally refers either to the synthetic siRNA duplexes, the vector, e.g., AAV vector, encoding the siRNA duplexes, or to the siRNA molecule delivered by a vector as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

The vectors e.g., AAV vectors, comprising the nucleic acid sequence encoding the siRNA molecules of the present invention can be formulated using one or more excipients to: (1) increase stability; (2) increase cell transfection or transduction; (3) permit the sustained or delayed release; or (4) alter the biodistribution (e.g., target the viral vector to specific tissues or cell types such as brain and neurons).

Formulations of the present invention can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In some embodiments, the formulations may comprise at least one inactive ingredient. As used herein, the term "inactive ingredient" refers to one or more inactive agents included in formulations. In some embodiments, all, none or some of the inactive ingredients which may be used in the formulations of the present invention may be approved by the US Food and Drug Administration (FDA).

Formulations of vectors comprising the nucleic acid sequence for the siRNA molecules of the present invention may include cations or anions. In one embodiment, the formulations include metal cations such as, but not limited to, $Zn^{2+}$, $Ca^{2+}$, $Cu^{2+}$, $Mg+$ and combinations thereof.

As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977); the content of each of which is incorporated herein by reference in their entirety.

The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

According to the present invention, the vector, e.g., AAV vector, comprising the nucleic acid sequence for the siRNA molecules of the present invention may be formulated for CNS delivery. Agents that cross the brain blood barrier (BBB) may be used. For example, some cell-penetrating peptides that can target siRNA molecules to the BBB endothelium may be used to formulate the siRNA duplexes targeting the HTT gene.

Inactive Ingredients

In some embodiments, formulations may comprise at least one excipient which is an inactive ingredient. As used herein, the term "inactive ingredient" refers to one or more inactive agents included in formulations. In some embodiments, all, none or some of the inactive ingredients which may be used in the formulations of the present disclosure may be approved by the US Food and Drug Administration (FDA).

Formulations of AAV particles and viral vectors carrying compositions described herein may include cations or anions. In one embodiment, the formulations include metal cations such as, but not limited to, $Zn^{2+}$, $Ca^{2+}$, $Cu^{2+}$, $Mg+$ and combinations thereof. As a non-limiting example, formulations may include polymers and compositions described herein complexed with a metal cation (See e.g., U.S. Pat. Nos. 6,265,389 and 6,555,525, each of which is herein incorporated by reference in its entirety).

Delivery

In one embodiment, the viral vector comprising compositions described herein may be administered or delivered using the methods for the delivery of AAV virions described in European Patent Application No. EP1857552, the contents of which are herein incorporated by reference in its entirety.

In one embodiment, the viral vector comprising compositions described herein may be administered or delivered using the methods for delivering proteins using AAV vectors described in European Patent Application No. EP2678433, the contents of which are herein incorporated by reference in its entirety.

In one embodiment, the viral vector comprising compositions described herein may be administered or delivered using the methods for delivering DNA molecules using AAV vectors described in U.S. Pat. No. 5,858,351, the contents of which are herein incorporated by reference in its entirety.

In one embodiment, the viral vector comprising compositions described herein may be administered or delivered using the methods for delivering DNA to the bloodstream described in U.S. Pat. No. 6,211,163, the contents of which are herein incorporated by reference in its entirety.

In one embodiment, the viral vector comprising compositions described herein may be administered or delivered using the methods for delivering AAV virions described in U.S. Pat. No. 6,325,998, the contents of which are herein incorporated by reference in its entirety.

In one embodiment, the viral vector comprising compositions described herein may be administered or delivered using the methods for delivering a payload to the central nervous system described in U.S. Pat. No. 7,588,757, the contents of which are herein incorporated by reference in its entirety.

In one embodiment, the viral vector comprising compositions described herein may be administered or delivered using the methods for delivering a payload described in U.S. Pat. No. 8,283,151, the contents of which are herein incorporated by reference in its entirety.

In one embodiment, the viral vector comprising compositions described herein may be administered or delivered using the methods for delivering a payload using a glutamic acid decarboxylase (GAD) delivery vector described in International Patent Publication No. WO2001089583, the contents of which are herein incorporated by reference in its entirety.

In one embodiment, the viral vector comprising compositions described herein may be administered or delivered using the methods for delivering a payload to neural cells described in International Patent Publication No. WO2012057363, the contents of which are herein incorporated by reference in its entirety.

Delivery to Cells

The present disclosure provides a method of delivering to a cell or tissue any of the above-described AAV polynucleotides or AAV genomes, comprising contacting the cell or tissue with said AAV polynucleotide or AAV genomes or contacting the cell or tissue with a particle comprising said AAV polynucleotide or AAV genome, or contacting the cell or tissue with any of the described compositions, including pharmaceutical compositions. The method of delivering the AAV polynucleotide or AAV genome to a cell or tissue can be accomplished in vitro, ex vivo, or in vivo.

Introduction into Cells—Synthetic dsRNA

To ensure the chemical and biological stability of siRNA molecules (e.g., siRNA duplexes and dsRNA), it is important to deliver siRNA molecules inside the target cells. In some embodiments, the cells may include, but are not limited to, cells of mammalian origin, cells of human origins, embryonic stem cells, induced pluripotent stem cells, neural stem cells, and neural progenitor cells.

Nucleic acids, including siRNA, carry a net negative charge on the sugar-phosphate backbone under normal physiological conditions. In order to enter the cell, a siRNA molecule must come into contact with a lipid bilayer of the cell membrane, whose head groups are also negatively charged.

The siRNA duplexes can be complexed with a carrier that allows them to traverse cell membranes such as package particles to facilitate cellular uptake of the siRNA. The package particles may include, but are not limited to, liposomes, nanoparticles, cationic lipids, polyethylenimine derivatives, dendrimers, carbon nanotubes and the combination of carbon-made nanoparticles with dendrimers. Lipids may be cationic lipids and/or neutral lipids. In addition to well established lipophilic complexes between siRNA molecules and cationic carriers, siRNA molecules can be conjugated to a hydrophobic moiety, such as cholesterol (e.g., U.S. Patent Publication No. 20110110937; the content of which is herein incorporated by reference in its entirety). This delivery method holds a potential of improving in vitro cellular uptake and in vivo pharmacological properties of siRNA molecules. The siRNA molecules of the present invention may also be conjugated to certain cationic cell-penetrating peptides (CPPs), such as MPG, transportan or penetratin covalently or non-covalently (e.g., U.S. Patent Publication No. 20110086425; the content of which is herein incorporated by reference in its entirety).

Introduction into Cells—AAV Vectors

The siRNA molecules (e.g., siRNA duplexes) of the present invention may be introduced into cells using any of a variety of approaches such as, but not limited to, viral vectors (e.g., AAV vectors). These viral vectors are engineered and optimized to facilitate the entry of siRNA molecule into cells that are not readily amendable to transfection. Also, some synthetic viral vectors possess an ability to integrate the shRNA into the cell genome, thereby leading to stable siRNA expression and long-term knockdown of a target gene. In this manner, viral vectors are engineered as vehicles for specific delivery while lacking the deleterious replication and/or integration features found in wild-type virus.

In some embodiments, the siRNA molecules of the present invention are introduced into a cell by contacting the cell with a composition comprising a lipophilic carrier and a vector, e.g., an AAV vector, comprising a nucleic acid sequence encoding the siRNA molecules of the present invention. In other embodiments, the siRNA molecule is introduced into a cell by transfecting or infecting the cell with a vector, e.g., an AAV vector, comprising nucleic acid sequences capable of producing the siRNA molecule when transcribed in the cell. In some embodiments, the siRNA molecule is introduced into a cell by injecting into the cell a vector, e.g., an AAV vector, comprising a nucleic acid sequence capable of producing the siRNA molecule when transcribed in the cell.

In some embodiments, prior to transfection, a vector, e.g., an AAV vector, comprising a nucleic acid sequence encoding the siRNA molecules of the present invention may be transfected into cells.

In other embodiments, the vectors, e.g., AAV vectors, comprising the nucleic acid sequence encoding the siRNA molecules of the present invention may be delivered into cells by electroporation (e.g. U.S. Patent Publication No. 20050014264; the content of which is herein incorporated by reference in its entirety).

Other methods for introducing vectors, e.g., AAV vectors, comprising the nucleic acid sequence for the siRNA molecules described herein may include photochemical internalization as described in U. S. Patent publication No. 20120264807; the content of which is herein incorporated by reference in its entirety.

In some embodiments, the formulations described herein may contain at least one vector, e.g., AAV vectors, comprising the nucleic acid sequence encoding the siRNA molecules described herein. In one embodiment, the siRNA molecules may target the HTT gene at one target site. In another embodiment, the formulation comprises a plurality of vectors, e.g., AAV vectors, each vector comprising a nucleic acid sequence encoding a siRNA molecule targeting the HTT gene at a different target site. The HTT may be targeted at 2, 3, 4, 5 or more than 5 sites.

In one embodiment, the vectors, e.g., AAV vectors, from any relevant species, such as, but not limited to, human, dog, mouse, rat or monkey may be introduced into cells.

In one embodiment, the vectors, e.g., AAV vectors, may be introduced into cells which are relevant to the disease to be treated. As a non-limiting example, the disease is HD and the target cells are neurons and astrocytes. As another non-limiting example, the disease is HD and the target cells are medium spiny neurons, cortical neurons and astrocytes.

In one embodiment, the vectors, e.g., AAV vectors, may be introduced into cells which have a high level of endogenous expression of the target sequence.

In another embodiment, the vectors, e.g., AAV vectors, may be introduced into cells which have a low level of endogenous expression of the target sequence.

In one embodiment, the cells may be those which have a high efficiency of AAV transduction.

Delivery to Subjects

The present disclosure additionally provides a method of delivering to a subject, including a mammalian subject, any of the above-described AAV polynucleotides or AAV genomes comprising administering to the subject said AAV polynucleotide or AAV genome, or administering to the subject a particle comprising said AAV polynucleotide or AAV genome, or administering to the subject any of the described compositions, including pharmaceutical compositions.

The pharmaceutical compositions of viral vectors described herein may be characterized by one or more of bioavailability, therapeutic window and/or volume of distribution.

III. ADMINISTRATION AND DOSING

Administration

The vector, e.g., AAV vector, comprising a nucleic acid sequence encoding the siRNA molecules of the present invention may be administered by any route which results in a therapeutically effective outcome. These include, but are not limited to, within the parenchyma of an organ such as, but not limited to, a brain (e.g., intraparenchymal), corpus striatum (intrastriatal), enteral (into the intestine), gastroenteral, epidural, oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), subpial (between the pia and the underlying tissue), intraganglionic (into the ganglion), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In specific embodiments, compositions of vector, e.g., AAV vector, comprising a nucleic acid sequence encoding the siRNA molecules of the present invention may be administered in a way which facilitates the vectors or siRNA molecule to enter the central nervous system and penetrate into medium spiny and/or cortical neurons and/or astrocytes.

In some embodiments, the vector, e.g., AAV vector, comprising a nucleic acid sequence encoding the siRNA molecules of the present invention may be administered by intramuscular injection.

In one embodiment, the vector, e.g., AAV vector, comprising a nucleic acid sequence encoding the siRNA molecules of the present invention may be administered via intraparenchymal injection.

In one embodiment, the vector, e.g., AAV vector, comprising a nucleic acid sequence encoding the siRNA molecules of the present invention may be administered via intraparenchymal injection and intrathecal injection.

In one embodiment, the vector, e.g., AAV vector, comprising a nucleic acid sequence encoding the siRNA molecules of the present invention may be administered via intrastriatal injection.

In one embodiment, the vector, e.g., AAV vector, comprising a nucleic acid sequence encoding the siRNA molecules of the present invention may be administered via intrastriatal injection and another route of administration described herein.

In some embodiments, AAV vectors that express siRNA duplexes of the present invention may be administered to a subject by peripheral injections (e.g., intravenous) and/or intranasal delivery. It was disclosed in the art that the peripheral administration of AAV vectors for siRNA duplexes can be transported to the central nervous system, for example, to the neurons (e.g., U. S. Patent Publication Nos. 20100240739; and 20100130594; the content of each of which is incorporated herein by reference in their entirety).

In other embodiments, compositions comprising at least one vector, e.g., AAV vector, comprising a nucleic acid sequence encoding the siRNA molecules of the present invention may be administered to a subject by intracranial delivery (See, e.g., U.S. Pat. No. 8,119,611; the content of which is incorporated herein by reference in its entirety).

The vector, e.g., AAV vector, comprising a nucleic acid sequence encoding the siRNA molecules of the present invention may be administered in any suitable form, either as a liquid solution or suspension, as a solid form suitable for liquid solution or suspension in a liquid solution. The siRNA duplexes may be formulated with any appropriate and pharmaceutically acceptable excipient.

The vector, e.g., AAV vector, comprising a nucleic acid sequence encoding the siRNA molecules of the present invention may be administered in a "therapeutically effective" amount, i.e., an amount that is sufficient to alleviate and/or prevent at least one symptom associated with the disease, or provide improvement in the condition of the subject.

In one embodiment, the vector, e.g., AAV vector, may be administered to the CNS in a therapeutically effective amount to improve function and/or survival for a subject with Huntington's Disease (HD). As a non-limiting example, the vector may be administered by direct infusion into the striatum.

In one embodiment, the vector, e.g., AAV vector, may be administered to a subject (e.g., to the CNS of a subject via intrathecal administration) in a therapeutically effective amount for the siRNA duplexes or dsRNA to target the medium spiny neurons, cortical neurons and/or astrocytes. As a non-limiting example, the siRNA duplexes or dsRNA may reduce the expression of HTT protein or mRNA. As another non-limiting example, the siRNA duplexes or dsRNA can suppress HTT and reduce HTT mediated toxicity. The reduction of HTT protein and/or mRNA as well as HTT mediated toxicity may be accomplished with almost no enhanced inflammation.

In one embodiment, the vector, e.g., AAV vector, may be administered to a subject (e.g., to the CNS of a subject) in a therapeutically effective amount to slow the functional decline of a subject (e.g., determined using a known evaluation method such as the unified Huntington's disease rating scale (UHDRS)). As a non-limiting example, the vector may be administered via intraparenchymal injection.

In one embodiment, the vector, e.g., AAV vector, may be administered to the cisterna magna in a therapeutically effective amount to transduce medium spiny neurons, cortical neurons and/or astrocytes. As a non-limiting example, the vector may be administered intrathecally.

In one embodiment, the vector, e.g., AAV vector, may be administered using intrathecal infusion in a therapeutically effective amount to transduce medium spiny neurons, cortical neurons and/or astrocytes. As a non-limiting example, the vector may be administered intrathecally.

In one embodiment, the vector, e.g., AAV vector, may be administered to the cisterna magna in a therapeutically effective amount to transduce medium spiny neurons, cortical neurons and/or astrocytes. As a non-limiting example, the vector may be administered by intraparenchymal injection.

In one embodiment, the vector, e.g., AAV vector, comprising a modulatory polynucleotide may be formulated. As a non-limiting example the baricity and/or osmolality of the formulation may be optimized to ensure optimal drug distribution in the central nervous system or a region or component of the central nervous system.

In one embodiment, the vector, e.g., AAV vector, comprising a modulatory polynucleotide may be delivered to a subject via a single route administration.

In one embodiment, the vector, e.g., AAV vector, comprising a modulatory polynucleotide may be delivered to a subject via a multi-site route of administration. A subject may be administered the vector, e.g., AAV vector, comprising a modulatory polynucleotide at 2, 3, 4, 5 or more than 5 sites.

In one embodiment, a subject may be administered the vector, e.g., AAV vector, comprising a modulatory polynucleotide described herein using a bolus injection.

In one embodiment, a subject may be administered the vector, e.g., AAV vector, comprising a modulatory polynucleotide described herein using sustained delivery over a period of minutes, hours or days. The infusion rate may be changed depending on the subject, distribution, formulation or another delivery parameter.

In one embodiment, the vector, e.g., AAV vector, described herein is administered via putamen and caudate infusion. As a non-limiting example, the dual infusion provides a broad striatal distribution as well as a frontal and temporal cortical distribution.

In one embodiment, the vector, e.g., AAV vector, is AAV-DJ8 which is administered via unilateral putamen infusion. As a non-limiting example, the distribution of the administered AAV-DJ8 is similar to the distribution of AAV1 delivered via unilateral putamen infusion.

In one embodiment, the vector, e.g., AAV vector, described herein is administered via intrathecal (IT) infusion at C1. The infusion may be for 1, 2, 3, 4, 6, 7, 8, 9, 10, 11, 12, 13, 14, 15 or more than 15 hours.

In one embodiment, the selection of subjects for administration of the vector, e.g., AAV vector, described herein and/or the effectiveness of the dose, route of administration and/or volume of administration may be evaluated using imaging of the perivascular spaces (PVS) which are also known as Virchow-Robin spaces. PVS surround the arterioles and venules as they perforate brain parenchyma and are filled with cerebrospinal fluid (CSF)/interstitial fluid. PVS are common in the midbrain, basal ganglia, and centrum semiovale. While not wishing to be bound by theory, PVS may play a role in the normal clearance of metabolites and have been associated with worse cognition and several disease states including Parkinson's disease. PVS are usually are normal in size but they can increase in size in a number of disease states. Potter et al. (Cerebrovasc Dis. 2015 January; 39(4): 224-231; the contents of which are herein incorporated by reference in its entirety) developed a grading method where they studied a full range of PVS and rated basal ganglia, centrum semiovale and midbrain PVS. They used the frequency and range of PVS used by Mac and Lullich et al. (J Neurol Neurosurg Psychiatry. 2004 November; 75(11):1519-23; the contents of which are herein incorporated by reference in its entirety) and Potter et al. gave 5 ratings to basal ganglia and centrum semiovale PVS: 0 (none), 1 (1-10), 2 (11-20), 3 (21-40) and 4 (>40) and 2 ratings to midbrain PVS: 0 (non visible) or 1 (visible). The user guide for the rating system by Potter et al. can be found at: www.sbirc.ed.ac.uk/documents/epvs-rating-scale-user-guide.pdf.

Dosing

The pharmaceutical compositions of the present invention may be administered to a subject using any amount effective for reducing, preventing and/or treating a HTT-associated disorder (e.g., Huntington' Disease (HD)). The exact amount required will vary from subject to subject, depending on the species, age, and general condition of the subject, the severity of the disease, the particular composition, its mode of administration, its mode of activity, and the like.

The compositions of the present invention are typically formulated in unit dosage form for ease of administration and uniformity of dosage. It will be understood, however, that the total daily usage of the compositions of the present invention may be decided by the attending physician within the scope of sound medical judgment. The specific therapeutic effectiveness for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the siRNA duplexes employed; the duration of the treatment; drugs used in combination or coincidental with the specific compound employed; and like factors well known in the medical arts.

In one embodiment, the age and sex of a subject may be used to determine the dose of the compositions of the present invention. As a non-limiting example, a subject who is older may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a younger subject. As another non-limiting example, a subject who is younger may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to an older subject. As yet another non-limiting example, a subject who is female may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a male subject. As yet another non-limiting example, a subject who is male may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a female subject In some specific embodiments, the doses of AAV vectors for delivering siRNA duplexes of the present invention may be adapted depending on the disease condition, the subject and the treatment strategy.

In one embodiment, delivery of the compositions in accordance with the present invention to cells comprises a rate of delivery defined by [VG/hour=mL/hour*VG/mL] wherein VG is viral genomes, VG/mL is composition concentration, and mL/hour is rate of prolonged delivery.

In one embodiment, delivery of compositions in accordance with the present invention to cells may comprise a total concentration per subject between about $1\times10^6$ VG and about $1\times10^{16}$ VG. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$, $2.1\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{13}$, $1.7\times10^{13}$, $1.8\times10^{13}$, $1.9\times10^{13}$, $2\times10^{13}$, $3\times10^{13}$, $4\times10^{13}$, $5\times10^{13}$, $6\times10^{13}$, $6.7\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/subject.

In one embodiment, delivery of compositions in accordance with the present invention to cells may comprise a total concentration per subject between about $1\times10^6$ VG/kg and about $1\times10^{16}$ VG/kg. In some embodiments, delivery may comprise a composition concentration of about $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $1.1\times10^{11}$, $1.2\times10^{11}$, $1.3\times10^{11}$, $1.4\times10^{11}$, $1.5\times10^{11}$, $1.6\times10^{11}$, $1.7\times10^{11}$, $1.8\times10^{11}$, $1.9\times10^{11}$, $2\times10^{11}$, $2.1\times10^{11}$, $2.2\times10^{11}$, $2.3\times10^{11}$, $2.4\times10^{11}$, $2.5\times10^{11}$, $2.6\times10^{11}$, $2.7\times10^{11}$, $2.8\times10^{11}$, $2.9\times10^{11}$, $3\times10^{11}$, $4\times10^{11}$, $5\times10^{11}$, $6\times10^{11}$, $7\times10^{11}$, $7.1\times10^{11}$, $7.2\times10^{11}$, $7.3\times10^{11}$, $7.4\times10^{11}$, $7.5\times10^{11}$, $7.6\times10^{11}$, $7.7\times10^{11}$, $7.8\times10^{11}$, $7.9\times10^{11}$, $8\times10^{11}$, $9\times10^{11}$, $1\times10^{12}$, $1.1\times10^{12}$, $1.2\times10^{12}$, $1.3\times10^{12}$, $1.4\times10^{12}$, $1.5\times10^{12}$, $1.6\times10^{12}$, $1.7\times10^{12}$, $1.8\times10^{12}$, $1.9\times10^{12}$, $2\times10^{12}$, $2.1\times10^{12}$, $2.2\times10^{12}$, $2.3\times10^{12}$, $2.4\times10^{12}$, $2.5\times10^{12}$, $2.6\times10^{12}$, $2.7\times10^{12}$, $2.8\times10^{12}$, $2.9\times10^{12}$, $3\times10^{12}$, $3.1\times10^{12}$, $3.2\times10^{12}$, $3.3\times10^{12}$, $3.4\times10^{12}$, $3.5\times10^{12}$, $3.6\times10^{12}$, $3.7\times10^{12}$, $3.8\times10^{12}$, $3.9\times10^{12}$, $4\times10^{12}$, $4.1\times10^{12}$, $4.2\times10^{12}$, $4.3\times10^{12}$, $4.4\times10^{12}$, $4.5\times10^{12}$, $4.6\times10^{12}$, $4.7\times10^{12}$, $4.8\times10^{12}$, $4.9\times10^{12}$, $5\times10^{12}$, $6\times10^{12}$, $6.1\times10^{12}$, $6.2\times10^{12}$, $6.3\times10^{12}$, $6.4\times10^{12}$, $6.5\times10^{12}$, $6.6\times10^{12}$, $6.7\times10^{12}$, $6.8\times10^{12}$, $6.9\times10^{12}$, $7\times10^{12}$, $8\times10^{12}$, $8.1\times10^{12}$, $8.2\times10^{12}$, $8.3\times10^{12}$, $8.4\times10^{12}$, $8.5\times10^{12}$, $8.6\times10^{12}$, $8.7\times10^{12}$, $8.8\times10^{12}$, $8.9\times10^{12}$, $9\times10^{12}$, $1\times10^{13}$, $1.1\times10^{13}$, $1.2\times10^{13}$, $1.3\times10^{13}$, $1.4\times10^{13}$, $1.5\times10^{13}$, $1.6\times10^{13}$, $1.7\times10^{13}$, $1.8\times10^{13}$, $1.9\times10^{13}$, $2\times10^{13}$, $3\times10^{13}$, $4\times10^{13}$, $5\times10^{13}$, $6\times10^{13}$, $6.7\times10^{13}$, $7\times10^{13}$, $8\times10^{13}$, $9\times10^{13}$, $1\times10^{14}$, $2\times10^{14}$, $3\times10^{14}$, $4\times10^{14}$, $5\times10^{14}$, $6\times10^{14}$, $7\times10^{14}$, $8\times10^{14}$, $9\times10^{14}$, $1\times10^{15}$, $2\times10^{15}$, $3\times10^{15}$, $4\times10^{15}$, $5\times10^{15}$, $6\times10^{15}$, $7\times10^{15}$, $8\times10^{15}$, $9\times10^{15}$, or $1\times10^{16}$ VG/kg.

In one embodiment, about $10^5$ to $10^6$ viral genome (unit) may be administered per dose.

In one embodiment, delivery of the compositions in accordance with the present invention to cells may comprise a total concentration between about $1\times10^6$ VG/mL and about $1\times10^{16}$ VG/mL. In some embodiments, delivery may comprise a composition concentration of about $1\times10^6$, $2\times10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $1.1 \times 10^{11}$, $1.2 \times 10^{11}$, $1.3 \times 10^{11}$, $1.4 \times 10^{11}$, $1.5 \times 10^{11}$, $1.6 \times 10^{11}$, $1.7 \times 10^{11}$, $1.8 \times 10^{11}$, $1.9 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $2.1 \times 10^{12}$, $2.2 \times 10^{12}$, $2.3 \times 10^{12}$, $2.4 \times 10^{12}$, $2.5 \times 10^{12}$, $2.6 \times 10^{12}$, $2.7 \times 10^{12}$, $2.8 \times 10^{12}$, $2.9 \times 10^{12}$, $3 \times 10^{12}$, $3.1 \times 10^{12}$, $3.2 \times 10^{12}$, $3.3 \times 10^{12}$, $3.4 \times 10^{12}$, $3.5 \times 10^{12}$, $3.6 \times 10^{12}$, $3.7 \times 10^{12}$, $3.8 \times 10^{12}$, $3.9 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $6.1 \times 10^{12}$, $6.2 \times 10^{12}$, $6.3 \times 10^{12}$, $6.4 \times 10^{12}$, $6.5 \times 10^{12}$, $6.6 \times 10^{12}$, $6.7 \times 10^{12}$, $6.8 \times 10^{12}$, $6.9 \times 10^{12}$, $7 \times 10^{12}$, $8 \times 10^{12}$, $9 \times 10^{12}$, $1 \times 10^{13}$, $1.1 \times 10^{13}$, $1.2 \times 10^{13}$, $1.3 \times 10^{13}$, $1.4 \times 10^{13}$, $1.5 \times 10^{13}$, $1.6 \times 10^{13}$, $1.7 \times 10^{13}$, $1.8 \times 10^{13}$, $1.9 \times 10^{13}$, $2 \times 10^{13}$, $3 \times 10^{13}$, $4 \times 10^{13}$, $5 \times 10^{13}$, $6 \times 10^{13}$, $6.7 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/mL.

In certain embodiments, the desired siRNA duplex dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total daily dose into two or more doses, e.g., two or more administrations of the single unit dose. As used herein, a "single unit dose" is a dose of any modulatory polynucleotide therapeutic administered in one dose/at one time/single route/single point of contact, i.e., single administration event. As used herein, a "total daily dose" is an amount given or prescribed in a 24 hour period. It may be administered as a single unit dose. In one embodiment, the viral vectors comprising the modulatory polynucleotides of the present invention are administered to a subject in split doses. They may be formulated in buffer only or in a formulation described herein.

In one embodiment, the dose, concentration and/or volume of the composition described herein may be adjusted depending on the contribution of the caudate or putamen to cortical and subcortical distribution after administration. The administration may be intracerebroventricular, intraputamenal, intrathalamic, intraparenchymal, subpial, and/or intrathecal administration.

In one embodiment, the dose, concentration and/or volume of the composition described herein may be adjusted depending on the cortical and neuraxial distribution following administration by intracerebroventricular, intraputamenal, intrathalamic, intraparenchymal, subpial, and/or intrathecal delivery.

IV. METHODS AND USES OF THE COMPOSITIONS OF THE INVENTION

Methods of Treatment of Huntington's Disease

Provided in the present invention are methods for introducing the vectors, e.g., AAV vectors, comprising a nucleic acid sequence encoding the siRNA molecules of the present invention into cells, the method comprising introducing into said cells any of the vectors in an amount sufficient for degradation of target HTT mRNA to occur, thereby activating target-specific RNAi in the cells. In some aspects, the cells may be stem cells, neurons such as medium spiny or cortical neurons, muscle cells and glial cells such as astrocytes.

Disclosed in the present invention are methods for treating Huntington's Disease (HD) associated with HTT protein in a subject in need of treatment. The method optionally comprises administering to the subject a therapeutically effective amount of a composition comprising at least vectors, e.g., AAV vectors, comprising a nucleic acid sequence encoding the siRNA molecules of the present invention. As a non-limiting example, the siRNA molecules can silence HTT gene expression, inhibit HTT protein production, and reduce one or more symptoms of HD in the subject such that HD is therapeutically treated.

In some embodiments, the composition comprising the vectors, e.g., AAV vectors, comprising a nucleic acid sequence encoding the siRNA molecules of the present invention is administered to the central nervous system of the subject. In other embodiments, the composition comprising the vectors, e.g., AAV vectors, comprising a nucleic acid sequence encoding the siRNA molecules of the present invention is administered to a tissue of a subject (e.g., brain of the subject).

In one embodiment, the composition comprising the vectors, e.g., AAV vectors, comprising a nucleic acid sequence encoding the siRNA molecules of the present invention is administered to the central nervous system of the subject via intraparenchymal injection.

In one embodiment, the composition comprising the vectors, e.g., AAV vectors, comprising a nucleic acid sequence encoding the siRNA molecules of the present invention is administered to the central nervous system of the subject via intraparenchymal injection and intrathecal injection.

In one embodiment, the composition comprising the vectors, e.g., AAV vectors, comprising a nucleic acid sequence encoding the siRNA molecules of the present invention is administered to the central nervous system of the subject via intraparenchymal injection and intracerebroventricular injection.

In one embodiment, the vectors, e.g., AAV vectors, comprising a nucleic acid sequence encoding the siRNA molecules of the present invention may be delivered into specific types of targeted cells, including, but not limited to, neurons including medium spiny or cortical neurons; glial cells including oligodendrocytes, astrocytes and microglia; and/or other cells surrounding neurons such as T cells.

In one embodiment, the vectors, e.g., AAV vectors, comprising a nucleic acid sequence encoding the siRNA molecules of the present invention may be delivered to neurons in the striatum and/or neurons of the cortex.

In some embodiments, the vectors, e.g., AAV vectors, comprising a nucleic acid sequence encoding the siRNA molecules of the present invention may be used as a therapy for HD.

In some embodiments, the vectors, e.g., AAV vectors, comprising a nucleic acid sequence encoding the siRNA molecules of the present invention may be used to suppress HTT protein in neurons and/or astrocytes of the striatum and/or the cortex. As a non-limiting example, the suppression of HTT protein is in medium spiny neurons of the striatum and/or neurons of the cortex.

In some embodiments, the vectors, e.g., AAV vectors, comprising a nucleic acid sequence encoding the siRNA molecules of the present invention may be used to suppress HTT protein in neurons and/or astrocytes of the striatum and/or the cortex and reduce associated neuronal toxicity.

The suppression of HTT protein in the neurons and/or astrocytes of the striatum and/or the cortex may be, independently, suppressed by 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. The reduction of associated neuronal toxicity may be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%.

In one embodiment, the vectors, e.g., AAV vectors, comprising a nucleic acid sequence encoding the siRNA molecules of the present invention may be used to reduce the cognitive and/or motor decline of a subject with HD, where the amount of decline is determined by a standard evaluation system such as, but not limited to, Unified Huntington's Disease Ratings Scale (UHDRS) and subscores, and cognitive testing.

In one embodiment, the vectors, e.g., AAV vectors, comprising a nucleic acid sequence encoding the siRNA molecules of the present invention may be used to reduce the decline of functional capacity and activities of daily living as measured by a standard evaluation system such as, but not limited to, the total functional capacity (TFC) scale.

In some embodiments, the present composition is administered as a solo therapeutic or combination therapeutics for the treatment of HD.

The vectors, e.g., AAV vectors, encoding siRNA duplexes targeting the HTT gene may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the vectors, e.g., AAV vectors, encoding the nucleic acid sequence for the siRNA molecules of the present invention can be small molecule compounds which are antioxidants, anti-inflammatory agents, anti-apoptosis agents, calcium regulators, antiglutamatergic agents, structural protein inhibitors, compounds involved in muscle function, and compounds involved in metal ion regulation.

Compounds tested for treating HD which may be used in combination with the vectors described herein include, but are not limited to, dopamine-depleting agents (e.g., tetrabenazine for chorea), benzodiazepines (e.g., clonazepam for myoclonus, chorea, dystonia, rigidity, and/or spasticity), anticonvulsants (e.g., sodium valproate and levetiracetam for myoclonus), amino acid precursors of dopamine (e.g., levodopa for rigidity which is particularly associate with juvenile HD or young adult-onset parkinsonian phenotype), skeletal muscle relaxants (e.g., baclofen, tizanidine for rigidity and/or spasticity), inhibitors for acetylcholine release at the neuromuscular junction to cause muscle paralysis (e.g., botulinum toxin for bruxism and/or dystonia), atypical neuroleptics (e.g., olanzapine and quetiapine for psychosis and/or irritability, risperidone, sulpiride and haloperidol for psychosis, chorea and/or irritability, clozapine for treatment-resistant psychosis, aripiprazole for psychosis with prominent negative symptoms), agents to increase ATP/cellular energetics (e.g., creatine), selective serotonin reuptake inhibitors (SSRIs) (e.g., citalopram, fluoxetine, paroxetine, sertraline, mirtazapine, venlafaxine for depression, anxiety, obsessive compulsive behavior and/or irritability), hypnotics (e.g., xopiclone and/or zolpidem for altered sleep-wake cycle), anticonvulsants (e.g., sodium valproate and carbamazepine for mania or hypomania) and mood stabilizers (e.g., lithium for mania or hypomania).

Neurotrophic factors may be used in combination therapy with the vectors, e.g., AAV vectors, encoding the nucleic acid sequence for the siRNA molecules of the present invention for treating HD. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the vector, e.g., AAV vector, encoding the nucleic acid sequence for the at least one siRNA duplex targeting the HTT gene may be co-administered with AAV vectors expressing neurotrophic factors such as AAV-IGF-I (See e.g., Vincent et al., *Neuromolecular medicine*, 2004, 6, 79-85; the content of which is incorporated herein by reference in its entirety) and AAV-GDNF (See e.g., Wang et al., *J Neurosci.*, 2002, 22, 6920-6928; the content of which is incorporated herein by reference in its entirety).

In some embodiments, the composition of the present invention for treating HD is administered to the subject in need intravenously, intramuscularly, subcutaneously, intraperitoneally, intraparenchymally, subpially, intrathecally and/or intraventricularly, allowing the siRNA molecules or vectors comprising the siRNA molecules to pass through one or both the blood-brain barrier and the blood spinal cord barrier, or directly access the brain and/or spinal cord. In some aspects, the method includes administering (e.g., intraparenchymal administration, subpial administration, intraventricular administration and/or intrathecal administration) directly to the central nervous system (CNS) of a subject (using, e.g., an infusion pump and/or a delivery scaffold) a therapeutically effective amount of a composition comprising vectors, e.g., AAV vectors, encoding the nucleic acid sequence for the siRNA molecules of the present invention. The vectors may be used to silence or suppress HTT gene expression, and/or reducing one or more symptoms of HD in the subject such that HD is therapeutically treated.

In some embodiments, the composition of the present invention for treating HD is administered to the subject in need by intraparenchymal administration.

In certain aspects, the symptoms of HD include behavioral difficulties and symptoms such as, but not limited to, apathy or lack of initiative, dysphoria, irritability, agitation or anxiety, poor self-care, poor judgment, inflexibility, disinhibition, depression, suicidal ideation euphoria, aggression, delusions, compulsions, hypersexuality, hallucinations, speech deterioration, slurred speech, difficulty swallowing, weight loss, cognitive dysfunction which impairs executive functions (e.g., organizing, planning, checking or adapting alternatives, and delays in the acquisition of new motor skills), unsteady gait and involuntary movements (chorea). In other aspects, the composition of the present invention is applied to one or both of the brain and the spinal cord. In one embodiment, the survival of the subject is prolonged by treating any of the symptoms of HD described herein.

In one embodiment, administration of the vectors, e.g., AAV vectors encoding a siRNA of the invention, to a subject may lower HTT (e.g., mutant and/or wild-type HTT) in a subject. In one embodiment, administration of the vectors, e.g., AAV vectors, to a subject may lower wild-type HTT in a subject. In one embodiment, administration of the vectors, e.g., AAV vectors, to a subject may lower mutant HTT in a subject. In yet another embodiment, administration of the vectors, e.g., AAV vectors, to a subject may lower both mutant HTT and wild-type HTT in a subject. The mutant and/or wild-type HTT may be lowered by about 20%, 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in a subject such as, but not limited to, the CNS, a region of the CNS, or a specific cell of the CNS of a subject. As a non-limiting example, the vectors, e.g., AAV vectors may lower the expression of HTT by at least 50% in the medium spiny neurons. As a non-limiting example, the vectors, e.g., AAV vectors may lower the expression of HTT by at least 40% in the medium spiny neurons. As a non-limiting example, the vectors, e.g., AAV vectors may lower the expression of HTT by at least 40% in the medium spiny neurons of the putamen. As a non-limiting example, the vectors, e.g., AAV vectors may lower the expression of HTT by at least 30% in the medium spiny neurons of the putamen. As a non-limiting example, the vectors, e.g., AAV vectors, may lower the expression of HTT by at least 30% in the putamen. As yet another non-limiting example, the vectors, e.g., AAV vectors, may lower the expression of HTT in the putamen and cortex by at least 40%. As yet another non-limiting example, the vectors, e.g., AAV vectors, may lower the expression of HTT in the putamen and cortex by at least 30%. As yet another non-limiting example, the vectors, e.g., AAV vectors, may lower the expression of HTT in the putamen by at least 30% and in the cortex by at least 15%.

In one embodiment, administration of the vectors, e.g., AAV vectors, to a subject will reduce the expression of HTT in a subject and the reduction of expression of the HTT will reduce the effects of HD in a subject.

In one embodiment, the vectors, e.g., AAV vectors, may be administered to a subject who has undergone biomarker assessment. Potential biomarkers in blood for premanifest and early progression of HD include, but are not limited to, 8-OHdG oxidative stress marker, metabolic markers (e.g., creatine kinase, branched-chain amino acids), cholesterol metabolites (e.g., 24-OH cholesterol), immune and inflammatory proteins (e.g., clusterin, complement components, interleukins 6 and 8), gene expression changes (e.g., transcriptomic markers), endocrine markers (e.g., cortisol, ghrelin and leptin), BDNF, adenosine 2A receptors. Potential biomarkers for brain imaging for premanifest and early progression of HD include, but are not limited to, striatal volume, subcortical white-matter volume, cortical thickness, whole brain and ventricular volumes, functional imaging (e.g., functional MRI), PET (e.g., with fluorodeoxyglucose), and magnetic resonance spectroscopy (e.g., lactate). Potential biomarkers for quantitative clinical tools for premanifest and early progression of HD include, but are not limited to, quantitative motor assessments, motor physiological assessments (e.g., transcranial magnetic stimulation), and quantitative eye movement measurements. Non-limiting examples of quantitative clinical biomarker assessments include tongue force variability, metronome-guided tapping, grip force, oculomotor assessments and cognitive tests. Non-limiting examples of multicenter observational studies include PREDICT-HD and TRACK-HD. A subject may have symptoms of HD, diagnosed with HD or may be asymptomatic for HD.

In one embodiment, the vectors, e.g., AAV vectors, may be administered to a subject who has undergone biomarker assessment using neuroimaging. A subject may have symptoms of HD, diagnosed with HD or may be asymptomatic for HD.

In one embodiment, the vectors, e.g., AAV vectors, may be administered to a subject who is asymptomatic for HD. A subject may be asymptomatic but may have undergone predictive genetic testing or biomarker assessment to determine if they are at risk for HD and/or a subject may have a family member (e.g., mother, father, brother, sister, aunt, uncle, grandparent) who has been diagnosed with HD.

In one embodiment, the vectors, e.g., AAV vectors, may be administered to a subject who is in the early stages of HD. In the early stage a subject has subtle changes in coordination, some involuntary movements (chorea), changes in mood such as irritability and depression, problem solving difficulties, reduction in the ability of a person to function in their normal day to day life.

In one embodiment, the vectors, e.g., AAV vectors, may be administered to a subject who is in the middle stages of HD. In the middle stage a subject has an increase in the movement disorder, diminished speech, difficulty swallowing, and ordinary activities will become harder to do. At this stage a subject may have occupational and physical therapists to help maintain control of voluntary movements and a subject may have a speech language pathologist.

In one embodiment, the vectors, e.g., AAV vectors, may be administered to a subject who is in the late stages of HD. In the late stage, a subject with HD is almost completely or completely dependent on others for care as the subject can no longer walk and is unable to speak. A subject can generally still comprehend language and is aware of family and friends but choking is a major concern.

In one embodiment, the vectors, e.g., AAV vectors, may be used to treat a subject who has the juvenile form of HD which is the onset of HD before the age of 20 years and as early as 2 years.

In one embodiment, the vectors, e.g., AAV vectors, may be used to treat a subject with HD who has fully penetrant HD where the HTT gene has 41 or more CAG repeats (e.g., 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 or more than 90 CAG repeats).

In one embodiment, the vectors, e.g., AAV vectors, may be used to treat a subject with HD who has incomplete penetrance where the HTT gene has between 36 and 40 CAG repeats (e.g., 36, 37, 38, 39 and 40 CAG repeats).

In one embodiment, the vectors, e.g., AAV vectors, may be used to decrease HTT protein in a subject. The decrease may independently be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. As a non-limiting example, a subject may have a 50% decrease of HTT protein. As a non-limiting example, a subject may have a decrease of 70% of HTT protein and a decrease of 10% of wild type HTT protein. As a non-limiting example, the decrease of HTT in the medium spiny neurons of the putamen may be about 40%. As a non-limiting example, the decrease of HTT in the putamen and cortex may be about 40%. As a non-limiting example, the decrease of HTT in the putamen may be about 30% and in the cortex may be about 15%. As a non-limiting example, the decrease of HTT in the putamen and cortex may be about 40%. As a non-limiting example, the decrease of HTT in the medium spiny neurons of the putamen may be between 40%-70%. As a non-limiting example, the decrease of HTT in the putamen and cortex may be between 40%-70%.

In one embodiment, the vectors, e.g., AAV vectors, may be used to decrease wild type HTT protein in a subject. The decrease may independently be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. As a non-limiting example, a subject may have a 50% decrease of wild type HTT protein. As a non-limiting example, the decrease of wild type HTT in the medium spiny neurons of the putamen may be about 40%. As a non-limiting example, the decrease of wild type HTT in the medium spiny neurons of the putamen may be about 30%. As a non-limiting example, the decrease of wild type HTT in the medium spiny neurons of the putamen may be about 20%. As a non-limiting example, the decrease of wild type HTT in the medium spiny neurons of the putamen may be about 15%. As a non-limiting example, the decrease of wild type HTT in the putamen and cortex may be about 40%. As a non-limiting example, the decrease of wild type HTT in the putamen and cortex may be about 30%. As a non-limiting example, the decrease of wild type HTT in the putamen and cortex may be about 20%. As a non-limiting example, the decrease of wild type HTT in the putamen and cortex may be about 15%. As a non-limiting example, the decrease of wild type HTT in the medium spiny neurons of the putamen may be between 40%-70%. As a non-limiting example, the decrease of wild type HTT in the medium spiny neurons of the putamen may be between 30%-70%. As a non-limiting example, the decrease of wild type HTT in the medium spiny neurons of the putamen may be between 20%-70%. As a non-limiting example, the decrease of wild type HTT in the medium spiny neurons of the putamen may be between 15%-70%. As a non-limiting example, the decrease of wild type HTT in the putamen and cortex may be between 40%-70%. As a non-limiting example, the decrease of wild type HTT in the medium spiny neurons of the putamen may be between 30%-70%. As a non-limiting example, the decrease of wild type HTT in the medium spiny neurons of the putamen may be between 20%-70%. As a non-limiting example, the decrease of wild type HTT in the medium spiny neurons of the putamen may be between 15%-70%.

In one embodiment, the vectors, e.g., AAV vectors, may be used to decrease mutant HTT protein in a subject. The decrease may independently be 5%, 10%, 15%, 20%, 25%, 30%, 35%, 40%, 45%, 50%, 55%, 60%, 65%, 70%, 75%, 80%, 85%, 90%, 95%, or more than 95%, 5-15%, 5-20%, 5-25%, 5-30%, 5-35%, 5-40%, 5-45%, 5-50%, 5-55%, 5-60%, 5-65%, 5-70%, 5-75%, 5-80%, 5-85%, 5-90%, 5-95%, 10-20%, 10-25%, 10-30%, 10-35%, 10-40%, 10-45%, 10-50%, 10-55%, 10-60%, 10-65%, 10-70%, 10-75%, 10-80%, 10-85%, 10-90%, 10-95%, 15-25%, 15-30%, 15-35%, 15-40%, 15-45%, 15-50%, 15-55%, 15-60%, 15-65%, 15-70%, 15-75%, 15-80%, 15-85%, 15-90%, 15-95%, 20-30%, 20-35%, 20-40%, 20-45%, 20-50%, 20-55%, 20-60%, 20-65%, 20-70%, 20-75%, 20-80%, 20-85%, 20-90%, 20-95%, 25-35%, 25-40%, 25-45%, 25-50%, 25-55%, 25-60%, 25-65%, 25-70%, 25-75%, 25-80%, 25-85%, 25-90%, 25-95%, 30-40%, 30-45%, 30-50%, 30-55%, 30-60%, 30-65%, 30-70%, 30-75%, 30-80%, 30-85%, 30-90%, 30-95%, 35-45%, 35-50%, 35-55%, 35-60%, 35-65%, 35-70%, 35-75%, 35-80%, 35-85%, 35-90%, 35-95%, 40-50%, 40-55%, 40-60%, 40-65%, 40-70%, 40-75%, 40-80%, 40-85%, 40-90%, 40-95%, 45-55%, 45-60%, 45-65%, 45-70%, 45-75%, 45-80%, 45-85%, 45-90%, 45-95%, 50-60%, 50-65%, 50-70%, 50-75%, 50-80%, 50-85%, 50-90%, 50-95%, 55-65%, 55-70%, 55-75%, 55-80%, 55-85%, 55-90%, 55-95%, 60-70%, 60-75%, 60-80%, 60-85%, 60-90%, 60-95%, 65-75%, 65-80%, 65-85%, 65-90%, 65-95%, 70-80%, 70-85%, 70-90%, 70-95%, 75-85%, 75-90%, 75-95%, 80-90%, 80-95%, or 90-95%. As a non-limiting example, a subject may have a 50% decrease of mutant HTT protein. As a non-limiting example, the decrease of mutant HTT in the medium spiny neurons of the putamen may be about 40%. As a non-limiting example, the decrease of mutant HTT in the medium spiny neurons of the putamen may be about 30%. As a non-limiting example, the decrease of mutant HTT in the medium spiny neurons of the putamen may be about 20%. As a non-limiting example, the decrease of mutant HTT in the medium spiny neurons of the putamen may be about 15%. As a non-limiting example, the decrease of mutant HTT in the putamen and cortex may be about 40%. As a non-limiting example, the decrease of mutant HTT in the putamen and cortex may be about 30%. As a non-limiting example, the decrease of mutant HTT in the putamen and cortex may be about 20%. As a non-limiting example, the decrease of mutant HTT in the putamen and cortex may be about 15%. As a non-limiting example, the decrease of mutant HTT in the medium spiny neurons of the putamen may be between 40%-70%. As a non-limiting example, the decrease of mutant HTT in the medium spiny neurons of the putamen may be between 30%-70%. As a non-limiting example, the decrease of mutant HTT in the medium spiny neurons of the putamen may be between 20%-70%. As a non-limiting example, the decrease of mutant HTT in the medium spiny neurons of the putamen may be between 15%-70%. As a non-limiting example, the decrease of mutant HTT in the putamen and cortex may be between 40%-70%. As a non-limiting example, the decrease of mutant HTT in the medium spiny neurons of the putamen may be between 30%-70%. As a non-limiting example, the decrease of mutant HTT in the medium spiny neurons of the putamen may be between 20%-70%. As a non-limiting example, the decrease of mutant HTT in the medium spiny neurons of the putamen may be between 15%-70%.

The AAV vectors of the present invention may be used as a method of treating Huntington's disease in a subject in need of treatment. Any method known in the art for defining a subject in need of treatment may be used to identify said subject(s). A subject may have a clinical diagnosis of Huntington's disease, or may be pre-symptomatic. Any known method for diagnosing HD may be utilized, including, but not limited to, cognitive assessments and/or neurological or neuropsychiatric examinations, motor tests, sensory tests, psychiatric evaluations, brain imaging, family history and/or genetic testing.

In one embodiment, HD subject selection is determined with the use of the Prognostic Index for Huntington's Disease, or a derivative thereof (Long J D et al., Movement Disorders, 2017, 32(2), 256-263, the contents of which are herein incorporated by reference in their entirety). This prognostic index uses four components to predict probability of motor diagnosis, (1) total motor score (TMS) from the Unified Huntington's Disease Rating Scale (UHDRS), (2) Symbol Digit Modality Test (SDMT), (3) base-line age, and (4) cytosine-adenine-guanine (CAG) expansion.

In one embodiment, the prognostic index for Huntington's Disease is calculated with the following formula: $PI_{HD} = 51 \times TMS + (-34) \times SDMT + 7 \times Age \times (CAG-34)$, wherein larger values for $PI_{HD}$ indicate greater risk of diagnosis or onset of symptoms.

In another embodiment, the prognostic index for Huntington's Disease is calculated with the following normalized formula that gives standard deviation units to be interpreted in the context of 50% 10-year survival: $PIN_{HD} = (PI_{HD} - 883)/1044$, wherein $PIN_{HD} < 0$ indicates greater than 50% 10-year survival, and $PIN_{HD} > 0$ suggests less than 50% 10-year survival.

In one embodiment, the prognostic index may be used to identify subjects whom will develop symptoms of HD within several years, but that do not yet have clinically diagnosable symptoms. Further, these asymptomatic patients may be selected for and receive treatment using the AAV vectors and compositions of the present invention during the asymptomatic period.

V. DEFINITIONS

Unless stated otherwise, the following terms and phrases have the meanings described below. The definitions are not meant to be limiting in nature and serve to provide a clearer understanding of certain aspects of the present invention.

As used herein, the term "nucleic acid", "polynucleotide" and 'oligonucleotide" refer to any nucleic acid polymers composed of either polydeoxyribonucleotides (containing 2-deoxy-D-ribose), or polyribonucleotides (containing D-ribose), or any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex.

As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the other siRNA strand.

As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity.

As used herein, the term "substantially complementary" means that the siRNA has a sequence (e.g., in the antisense strand) which is sufficient to bind the desired target mRNA, and to trigger the RNA silencing of the target mRNA.

As used herein, "targeting" means the process of design and selection of nucleic acid sequence that will hybridize to a target nucleic acid and induce a desired effect.

The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides and peptides are well known in the art.

As used herein, the term "mutation" refers to any changing of the structure of a gene, resulting in a variant (also called "mutant") form that may be transmitted to subsequent generations. Mutations in a gene may be caused by the alternation of single base in DNA, or the deletion, insertion, or rearrangement of larger sections of genes or chromosomes.

As used herein, the term "vector" means any molecule or moiety which transports, transduces or otherwise acts as a carrier of a heterologous molecule such as the siRNA molecule of the invention. A "viral vector" is a vector which comprises one or more polynucleotide regions encoding or comprising a molecule of interest, e.g., a transgene, a polynucleotide encoding a polypeptide or multi-polypeptide or a modulatory nucleic acid such as small interfering RNA (siRNA). Viral vectors are commonly used to deliver genetic materials into cells. Viral vectors are often modified for specific applications. Types of viral vectors include retroviral vectors, lentiviral vectors, adenoviral vectors and adeno-associated viral vectors.

The term "adeno-associated virus" or "AAV" or "AAV vector" as used herein refers to any vector which comprises or derives from components of an adeno-associated vector and is suitable to infect mammalian cells, preferably human cells. The term AAV vector typically designates an AAV type viral particle or virion comprising a nucleic acid molecule encoding a siRNA duplex. The AAV vector may be derived from various serotypes, including combinations of serotypes (i.e., "pseudotyped" AAV) or from various genomes (e.g., single stranded or self-complementary). In addition, the AAV vector may be replication defective and/or targeted.

As used herein, the phrase "inhibit expression of a gene" means to cause a reduction in the amount of an expression product of the gene. The expression product can be a RNA molecule transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "modified" refers to a changed state or structure of a molecule of the invention. Molecules may be modified in many ways including chemically, structurally, and functionally.

As used herein, the term "synthetic" means produced, prepared, and/or manufactured by the hand of man. Synthesis of polynucleotides or polypeptides or other molecules of the present invention may be chemical or enzymatic.

As used herein, the term "transfection" refers to methods to introduce exogenous nucleic acids into a cell. Methods of transfection include, but are not limited to, chemical methods, physical treatments and cationic lipids or mixtures. The list of agents that can be transfected into a cell is large and includes, but is not limited to, siRNA, sense and/or antisense sequences, DNA encoding one or more genes and organized into an expression plasmid, proteins, protein fragments, and more.

As used herein, "off target" refers to any unintended effect on any one or more target, gene, or cellular transcript.

As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "effective amount" of an agent is that amount sufficient to effect beneficial or desired results, for example, clinical results, and, as such, an "effective amount" depends upon the context in which it is being applied. For example, in the context of administering an agent that treats HD, an effective amount of an agent is, for example, an amount sufficient to achieve treatment, as defined herein, of HD, as compared to the response obtained without administration of the agent.

As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates such as chimpanzees and other apes and monkey species, and humans) and/or plants.

As used herein, the term "preventing" or "prevention" refers to delaying or forestalling the onset, development or progression of a condition or disease for a period of time, including weeks, months, or years.

The term "treatment" or "treating," as used herein, refers to the application of one or more specific procedures used for the cure or amelioration of a disease. In certain embodiments, the specific procedure is the administration of one or more pharmaceutical agents. In the context of the present invention, the specific procedure is the administration of one or more siRNA molecules.

As used herein, the term "amelioration" or "ameliorating" refers to a lessening of severity of at least one indicator of a condition or disease. For example, in the context of neurodegeneration disorder, amelioration includes the reduction of neuron loss.

As used herein, the term "administering" refers to providing a pharmaceutical agent or composition to a subject.

As used herein, the term "neurodegeneration" refers to a pathologic state which results in neural cell death. A large number of neurological disorders share neurodegeneration as a common pathological state. For example, Alzheimer's disease, Parkinson's disease, Huntington's disease, and amyotrophic lateral sclerosis (ALS) all cause chronic neurodegeneration, which is characterized by a slow, progressive neural cell death over a period of several years, whereas acute neurodegeneration is characterized by a sudden onset of neural cell death as a result of ischemia, such as stroke, or trauma, such as traumatic brain injury, or as a result of axonal transection by demyelination or trauma caused, for example, by spinal cord injury or multiple sclerosis. In some neurological disorders, mainly one type of neuronal cell is degenerative, for example, medium spiny neuron degeneration in early HD.

VI. EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

VII. EXAMPLES

Example 1. Activity of Constructs in HEK293T and HeLa Cells

A. Transfection

The AAV-miRNA expression vectors were transfected into HEK293T and HeLa cells. mCherry-treated cells and untreated cells were also evaluated. After 48 hours, the relative HTT mRNA expression was determined. The relative HTT mRNA expression was obtained by normalizing the HTT mRNA level to the housekeeping gene mRNA level; this normalized HTT mRNA level was then expressed relative to the normalized HTT mRNA level in mCherry-treated and/or untreated cells, as determined by qRT-PCR. The results are shown in Tables 12-14.

TABLE 12

HTT mRNA Suppression in HEK293T and HeLa Cells after Transfection, Set I

| Name | Duplex ID | Expression Cassette | Relative HTT mRNA Level HEK293T Cells | HeLa Cells |
|---|---|---|---|---|
| VOYHTmiR-102.219.n | D-3513 | 288 | 0.65 | 0.8 |
| VOYHTmiR-102.894 | D-3520 | 299 | 0.55 | 0.76 |
| VOYHTmiR-102.579 | D-3548 | 341 | 0.47 | 0.5 |
| VOYHTmiR-104.219.n | D-3514 | 289 | 0.6 | 0.78 |
| VOYHTmiR-104.894 | D-3521 | 300 | 0.64 | 0.75 |
| VOYHTmiR-104.579 | D-3549 | 342 | 0.5 | 0.51 |
| VOYHTmiR-109.219.n | D-3513 | 290 | 0.63 | 0.75 |
| VOYHTmiR-109.894 | D-3520 | 301 | 0.7 | — |
| VOYHTmiR-109.579 | D-3548 | 343 | 0.55 | 0.52 |
| VOYHTmiR-116.219.n | D-3515 | 291 | 0.63 | 0.75 |
| VOYHTmiR-116.894 | D-3523 | 303 | 0.65 | 0.6 |
| VOYHTmiR-116.579 | D-3551 | 345 | 0.63 | 0.65 |
| VOYHTmiR-114.219 | D-3511 | 285 | 0.6 | 0.65 |
| VOYHTmiR-114.894 | D-3522 | 302 | 0.6 | 0.6 |
| VOYHTmiR-114.579 | D-3550 | 344 | 0.57 | 0.45 |
| VOYHTmiR-127.219.n | D-3513 | 292 | 0.85 | 0.9 |
| VOYHTmiR-127.894 | D-3520 | 304 | 0.58 | 0.5 |
| VOYHTmiR-127.579 | D-3548 | 346 | 0.5 | 0.45 |
| mcherry | N/A | — | 1.0 | 1.0 |
| Untreated | N/A | — | 0.8 | 1.2 |

TABLE 13

HTT mRNA Suppression in HEK293T and HeLa Cells after Transfection, Set II

| Name | Duplex ID | Expression Cassette | Relative HTT mRNA Level HEK293T Cells | HeLa Cells |
|---|---|---|---|---|
| VOYHTmiR-102.016 | D-3544 | 335 | 0.36 | 0.84 |
| VOYHTmiR-102.214 | D-3500 | 270 | 0.42 | 0.88 |
| VOYHTmiR-102.218 | D-3505 | 276 | 0.31 | 0.68 |
| VOYHTmiR-102.372 | D-3528 | 311 | 0.39 | 0.73 |
| VOYHTmiR-102.425 | D-3532 | 317 | 0.36 | 0.72 |
| VOYHTmiR-102.907 | D-3524 | 305 | 0.43 | 0.75 |
| VOYHTmiR-102.257 | D-3516 | 293 | 0.4 | 0.7 |
| VOYHTmiR-104.016 | D-3545 | 336 | 0.28 | 0.5 |
| VOYHTmiR-104.214 | D-3501 | 271 | 0.55 | 0.91 |
| VOYHTmiR-104.218 | D-3506 | 277 | 0.39 | 0.82 |
| VOYHTmiR-104.372 | D-3529 | 312 | 0.38 | 0.74 |
| VOYHTmiR-104.425 | D-3533 | 318 | 0.4 | 0.7 |
| VOYHTmiR-104.907 | D-3525 | 306 | 0.31 | 0.65 |
| VOYHTmiR-104.257 | D-3517 | 294 | 0.32 | 0.64 |
| VOYHTmiR-109.016 | D-3546 | 337 | 0.28 | 0.5 |
| VOYHTmiR-109.214 | D-3502 | 272 | 0.51 | 0.85 |
| VOYHTmiR-109.218 | D-3507 | 278 | 0.38 | 0.7 |
| VOYHTmiR-109.372 | D-3530 | 313 | 0.42 | 0.72 |
| VOYHTmiR-109.425 | D-3534 | 319 | 00.31 | 0.64 |
| VOYHTmiR-109.907 | D-3526 | 307 | 0.36 | 0.68 |
| VOYHTmiR-109.257 | D-3518 | 295 | 0.41 | 0.72 |
| VOYHTmiR-114.016 | D-3547 | 338 | 0.3 | 0.68 |
| VOYHTmiR-114.214 | D-3503 | 273 | 0.42 | 0.84 |
| VOYHTmiR-114.218 | D-3508 | 279 | 0.38 | 0.75 |
| VOYHTmiR-114.372 | D-3531 | 314 | 0.39 | 0.75 |
| VOYHTmiR-114.425 | D-3535 | 320 | 0.36 | 0.7 |
| VOYHTmiR-114.907 | D-3527 | 308 | 0.4 | 0.61 |
| VOYHTmiR-114.257 | D-3519 | 296 | 0.42 | 0.73 |

TABLE 13-continued

HTT mRNA Suppression in HEK293T and HeLa Cells after Transfection, Set II

| Name | Duplex ID | Expression Cassette | Relative HTT mRNA Level HEK293T Cells | HeLa Cells |
|---|---|---|---|---|
| VOYHTmiR-116.016 | D-3546 | 339 | 0.38 | 0.62 |
| VOYHTmiR-116.214 | D-3502 | 274 | 0.5 | 0.87 |
| VOYHTmiR-116.218 | D-3507 | 280 | 0.38 | 0.75 |
| VOYHTmiR-116.372 | D-3530 | 315 | 0.42 | 0.73 |
| VOYHTmiR-116.425 | D-3534 | 321 | 0.43 | 0.85 |
| VOYHTmiR-116.907 | D-3526 | 309 | 0.4 | 0.68 |
| VOYHTmiR-116.257 | D-3518 | 297 | 0.4 | 0.77 |
| VOYHTmiR-127.016 | D-3546 | 340 | 0.29 | 0.4 |
| VOYHTmiR-127.214 | D-3504 | 275 | 0.75 | 1.08 |
| VOYHTmiR-127.218 | D-3507 | 281 | 0.38 | 0.52 |
| VOYHTmiR-127.372 | D-3530 | 316 | 0.39 | 0.5 |
| VOYHTmiR-127.425 | D-3534 | 322 | 0.37 | 0.54 |
| VOYHTmiR-127.907 | D-3526 | 310 | 0.39 | 0.67 |
| VOYHTmiR-127.257 | D-3518 | 298 | 0.38 | 0.45 |
| mcherry | N/A | — | 0.8 | 1.0 |
| Untreated | N/A | — | 0.75 | 0.98 |

TABLE 14

HTT mRNA Suppression in HEK293T and HeLa Cells after Transfection, Set III

| Name | Duplex ID | Expression Cassette | Relative HTT mRNA Level HEK293T Cells | HeLa Cells |
|---|---|---|---|---|
| VOYHTmiR-104.579 | D-3549 | 342 | 0.18 | 0.62 |
| VOYHTmiR-104.579.1 | D-3566 | 347 | 0.15 | 0.58 |
| VOYHTmiR-104.579.2 | D-3566 | 348 | 0.18 | 0.5 |
| VOYHTmiR-104.579.3 | D-3566 | 349 | 0.15 | 0.52 |
| VOYHTmiR-104.579.4 | D-3566 | 350 | 0.15 | 0.48 |
| VOYHTmiR-104.579.5 | D-3569 | 367 | 0.16 | 0.8 |
| VOYHTmiR-104.579.6 | D-3566 | 351 | 0.11 | 0.5 |
| VOYHTmiR-104.579.7 | D-3567 | 352 | 0.19 | 0.65 |
| VOYHTmiR-104.579.8 | D-3568 | 353 | 0.2 | 0.6 |
| VOYHTmiR-104.579.9 | D-3566 | 354 | 0.19 | 0.73 |
| VOYHTmiR-104.579.10 | D-3570 | 368 | 0.34 | 0.7 |
| mcherry | N/A | — | 1.0 | 1.0 |

B. Infection

The AAV-miRNA expression vectors were packaged in AAV2 (referred to as AAV2-miRNA expression vectors) or mCherry vectors were packaged in AAV2, for infection of HEK293T and HeLa cells. Untreated cells were also evaluated. The AAV2 particles were used to infected HEK293T cells at a MOI of 1E4 or 1E5 vg/cell, and HeLa cells at a MOI of 1E5 vg/cell.

The relative expression of HTT was determined in HeLa cells at 24 hours after AAV-miRNA expression vector infection. The relative HTT mRNA expression was obtained by normalizing the HTT mRNA level to the housekeeping gene mRNA level; this normalized HTT mRNA level was then expressed relative to the normalized HTT mRNA level in mCherry-treated and/or untreated cells, as determined by qRT-PCR. The results are shown in Tables 15-18. The infection of HeLa cells was at a MOI of 1E5 vg/cell (Tables 15-17) or at a MOI of 1E4 vg/cell (Table 18).

The relative expression of HTT was determined in HEK293T cells at 24 hours after AAV-miRNA expression vector infection. The relative HTT mRNA expression was obtained by normalizing the HTT mRNA level to the housekeeping gene mRNA level; this normalized HTT mRNA level was then expressed relative to the normalized HTT mRNA level in mCherry-treated and/or untreated cells, as determined by qRT-PCR. The results are shown in Tables 15, 17 and 18. The infection of HEK293T cells was at a MOI of 1E5 vg/cell (Tables 15 and 17) or at a MOI of 1E4 vg/cell (Table 18).

TABLE 15

HTT mRNA Suppression in HEK293T and HeLa Cells after Infection of AAV2-miRNA Expression Vectors at MOI of 1E5/Cell

| Name | Duplex ID | Expression Cassette | Relative HTT mRNA Level HEK293T Cells | HeLa Cells |
|---|---|---|---|---|
| VOYHTmiR-102.219.n | D-3513 | 288 | 0.8 | 0.79 |
| VOYHTmiR-102.894 | D-3520 | 299 | 0.7 | 0.71 |
| VOYHTmiR-102.579 | D-3548 | 341 | 0.49 | 0.7 |
| VOYHTmiR-104.219.n | D-3514 | 289 | 0.9 | 0.81 |
| VOYHTmiR-104.894 | D-3521 | 300 | 0.8 | 0.71 |
| VOYHTmiR-104.579 | D-3549 | 342 | 0.4 | 0.48 |
| VOYHTmiR-109.219.n | D-3513 | 290 | 0.79 | 0.8 |
| VOYHTmiR-109.894 | D-3520 | 301 | 0.6 | 0.71 |
| VOYHTmiR-109.579 | D-3548 | 343 | 0.58 | 0.61 |
| VOYHTmiR-116.219.n | D-3515 | 291 | 0.95 | 0.81 |
| VOYHTmiR-116.894 | D-3523 | 303 | 0.75 | 0.75 |
| VOYHTmiR-116.579 | D-3551 | 345 | 0.5 | 0.7 |
| VOYHTmiR-114.219 | D-3511 | 285 | 0.74 | 0.81 |
| VOYHTmiR-114.894 | D-3522 | 302 | 0.6 | 0.75 |
| VOYHTmiR-114.579 | D-3550 | 344 | 0.43 | 0.61 |
| VOYHTmiR-127.219.n | D-3513 | 292 | 0.93 | 0.9 |
| VOYHTmiR-127.894 | D-3520 | 304 | 0.5 | 0.6 |
| VOYHTmiR-127.579 | D-3548 | 346 | 0.31 | 0.4 |
| mCherry | N/A | — | 1.0 | 1.0 |
| Untreated | N/A | — | 0.9 | 0.9 |

TABLE 16

HTT mRNA Suppression in HeLa Cells after Infection of AAV2-miRNA Expression Vectors at MOI of 1E5/Cell

| Name | Duplex ID | Expression Cassette | Relative HTT mRNA Level HeLa Cells |
|---|---|---|---|
| VOYHTmiR-102.016 | D-3544 | 335 | 0.52 |
| VOYHTmiR-102.214 | D-3500 | 270 | 0.9 |
| VOYHTmiR-102.218 | D-3505 | 276 | 0.88 |
| VOYHTmiR-102.372 | D-3528 | 311 | 0.89 |
| VOYHTmiR-102.425 | D-3532 | 317 | 0.8 |
| VOYHTmiR-102.907 | D-3524 | 305 | 0.74 |
| VOYHTmiR-102.257 | D-3516 | 293 | 0.79 |
| VOYHTmiR-104.016 | D-3545 | 336 | 0.57 |
| VOYHTmiR-104.218 | D-3506 | 277 | 0.79 |
| VOYHTmiR-104.372 | D-3529 | 312 | 0.79 |
| VOYHTmiR-104.425 | D-3533 | 318 | 0.67 |
| VOYHTmiR-104.907 | D-3525 | 306 | 0.71 |
| VOYHTmiR-104.257 | D-3517 | 294 | 0.72 |
| VOYHTmiR-109.016 | D-3546 | 337 | 0.6 |
| VOYHTmiR-109.218 | D-3507 | 278 | 0.83 |
| VOYHTmiR-109.372 | D-3530 | 313 | 0.85 |
| VOYHTmiR-109.425 | D-3534 | 319 | 0.75 |
| VOYHTmiR-109.907 | D-3526 | 307 | 0.8 |
| VOYHTmiR-109.257 | D-3518 | 295 | 0.9 |
| VOYHTmiR-114.016 | D-3547 | 338 | 0.68 |
| VOYHTmiR-114.214 | D-3503 | 273 | 0.99 |
| VOYHTmiR-114.372 | D-3531 | 314 | 0.85 |
| VOYHTmiR-116.016 | D-3546 | 339 | 0.59 |
| VOYHTmiR-116.218 | D-3507 | 280 | 0.81 |
| VOYHTmiR-127.016 | D-3546 | 340 | 0.3 |
| VOYHTmiR-127.214 | D-3504 | 275 | 1.0 |
| VOYHTmiR-127.218 | D-3507 | 281 | 0.4 |
| VOYHTmiR-127.372 | D-3530 | 316 | 0.48 |
| VOYHTmiR-127.425 | D-3534 | 322 | 0.5 |

TABLE 16-continued

HTT mRNA Suppression in HeLa Cells after Infection of AAV2-miRNA Expression Vectors at MOI of 1E5/Cell

| Name | Duplex ID | Expression Cassette | Relative HTT mRNA Level HeLa Cells |
|---|---|---|---|
| VOYHTmiR-127.907 | D-3526 | 310 | 0.55 |
| VOYHTmiR-127.257 | D-3518 | 298 | 0.42 |
| mCherry | N/A | — | 1.0 |
| Untreated | N/A | — | 0.93 |

TABLE 17

HTT mRNA Suppression in HEK293T and HeLa Cells after Infection of AAV2-miRNA Expression Vectors at MOI of 1E5/Cell

| Name | Duplex ID | Expression Cassette | Relative HTT mRNA Level HEK293T Cells | HeLa Cells |
|---|---|---|---|---|
| VOYHTmiR-104.579 | D-3549 | 342 | 0.4 | 0.5 |
| VOYHTmiR-104.579.1 | D-3566 | 347 | 0.38 | 0.51 |
| VOYHTmiR-104.579.3 | D-3566 | 349 | 0.35 | 0.3 |
| VOYHTmiR-104.579.5 | D-3569 | 367 | 0.7 | 0.75 |
| VOYHTmiR-104.579.7 | D-3567 | 352 | 0.35 | 0.45 |
| VOYHTmiR-104.579.9 | D-3566 | 354 | 0.35 | 0.48 |
| VOYHTmiR-104.579.10 | D-3570 | 368 | 0.31 | 0.3 |
| mCherry | N/A | — | 1.0 | 1.0 |

TABLE 18

HTT mRNA Suppression in HEK293T and HeLa Cells after Infection of AAV2-miRNA Expression Vectors at MOI of 1E4/Cell

| Name | Duplex ID | Expression Cassette | Relative HTT mRNA Level HEK293T Cells | HeLa Cells |
|---|---|---|---|---|
| VOYHTmiR-102.016 | D-3544 | 335 | 0.5 | 0.51 |
| VOYHTmiR-102.214 | D-3500 | 270 | 1.08 | 0.9 |
| VOYHTmiR-102.218 | D-3505 | 276 | 0.82 | 0.9 |
| VOYHTmiR-102.372 | D-3528 | 311 | 0.9 | 0.9 |
| VOYHTmiR-102.425 | D-3532 | 317 | 0.7 | 0.8 |
| VOYHTmiR-102.907 | D-3524 | 305 | 0.7 | 0.71 |
| VOYHTmiR-102.257 | D-3516 | 293 | 0.7 | 0.8 |
| VOYHTmiR-104.016 | D-3545 | 336 | 0.51 | 0.59 |
| VOYHTmiR-104.218 | D-3506 | 277 | 0.8 | 0.8 |
| VOYHTmiR-104.372 | D-3529 | 312 | 0.8 | 0.8 |
| VOYHTmiR-104.425 | D-3533 | 318 | 0.6 | 0.65 |
| VOYHTmiR-104.907 | D-3525 | 306 | 0.7 | 0.7 |
| VOYHTmiR-104.257 | D-3517 | 294 | 0.85 | 0.71 |
| VOYHTmiR-109.016 | D-3546 | 337 | 0.5 | 0.6 |
| VOYHTmiR-109.218 | D-3507 | 278 | 0.8 | 0.81 |
| VOYHTmiR-109.372 | D-3530 | 313 | 0.91 | 0.88 |
| VOYHTmiR-109.425 | D-3534 | 319 | 0.7 | 0.71 |
| VOYHTmiR-109.907 | D-3526 | 307 | 0.85 | 0.8 |
| VOYHTmiR-109.257 | D-3518 | 295 | 0.85 | 0.91 |
| VOYHTmiR-114.016 | D-3547 | 338 | 0.6 | 0.68 |
| VOYHTmiR-114.214 | D-3503 | 273 | 1.1 | 0.98 |
| VOYHTmiR-114.372 | D-3531 | 314 | 0.82 | 0.88 |
| VOYHTmiR-116.016 | D-3546 | 339 | 0.69 | 0.59 |
| VOYHTmiR-116.218 | D-3507 | 280 | 0.91 | 0.81 |
| VOYHTmiR-127.016 | D-3546 | 340 | 0.39 | 0.3 |
| VOYHTmiR-127.214 | D-3504 | 275 | 1.2 | 1.0 |
| VOYHTmiR-127.218 | D-3507 | 281 | 0.41 | 0.41 |
| VOYHTmiR-127.372 | D-3530 | 316 | 0.5 | 0.5 |
| VOYHTmiR-127.425 | D-3534 | 322 | 0.58 | 0.57 |
| VOYHTmiR-127.907 | D-3526 | 310 | 0.6 | 0.59 |
| VOYHTmiR-127.257 | D-3518 | 298 | 0.5 | 0.41 |
| mCherry | N/A | — | 1.0 | 1.1 |
| Untreated | N/A | — | 1.08 | 0.98 |

In HEK293T cells, VOYHTmiR-127.016 provided a relative HTT mRNA level of 0.3-0.4; VOYHTmiR-127.218, VOYHTmiR-102.016, VOYHTmiR-109.016, VOYHTmiR-127.372, and VOYHTmiR-127.257 provided a relative HTT mRNA level of 0.41-0.5; VOYHTmiR-104.016, VOYHTmiR-127.425, VOYHTmiR-104.425, VOYHTmiR-114.016, and VOYHTmiR-127.907 provided a relative HTT mRNA level of 0.51-0.6; VOYHTmiR-116.016, VOYHTmiR-102.425, VOYHTmiR-102.907, VOYHTmiR-102.257, VOYHTmiR-104.907, and VOYHTmiR-109.425 provided a relative HTT mRNA level of 0.61-0.7; VOYHTmiR-104.218, VOYHTmiR-104.372, and VOYHTmiR-109.218 provided a relative HTT mRNA level of 0.71-0.8; VOYHTmiR-102.218, VOYHTmiR-114.372, VOYHTmiR-104.257, VOYHTmiR-109.907, VOYHTmiR-109.257, and VOYHTmiR-102.372 provided a relative HTT mRNA level of 0.81-0.9; VOYHTmiR-109.372, and VOYHTmiR-116.218 provided a relative HTT mRNA level of 0.91 24 hours after infection at a MOI of 1E4 vg/cell.

In HEK293T cells, VOYHTmiR-127.579, VOYHTmiR-104.579.10, VOYHTmiR-104.579.3, VOYHTmiR-104.579.7, VOYHTmiR-104.579.9, VOYHTmiR-104.579.1, and VOYHTmiR-104.579 provided a relative HTT mRNA level of 0.3-0.4; VOYHTmiR-114.579, VOYHTmiR-102.579, VOYHTmiR-116.579, and VOYHTmiR-127.894 provided a relative HTT mRNA level of 0.41-0.5; VOYHTmiR-109.579, VOYHTmiR-109.894, and VOYHTmiR-114.894 provided a relative HTT mRNA level of 0.51-0.6; VOYHTmiR-102.894, and VOYHTmiR-104.579.5 provided a relative HTT mRNA level of 0.61-0.7; VOYHTmiR-114.219, VOYHTmiR-116.894, VOYHTmiR-109.219.n, VOYHTmiR-102.219.n, and VOYHTmiR-104.894 provided a relative HTT mRNA level of 0.71-0.8; VOYHTmiR-104.219.n provided a relative HTT mRNA level of 0.81-0.9; VOYHTmiR-127.219.n, and VOYHTmiR-116.219.n provided a relative HTT mRNA level of 0.91-0.95 24 hours after infection at a MOI of 1E5 vg/cell.

In HeLa cells, VOYHTmiR-127.016 provided a relative HTT mRNA level of 0.3-0.4; VOYHTmiR-127.218, VOYHTmiR-127.257, and VOYHTmiR-127.372 provided a relative HTT mRNA level of 0.41-0.5; VOYHTmiR-102.016, VOYHTmiR-127.425, VOYHTmiR-104.016, VOYHTmiR-127.907, VOYHTmiR-116.016, and VOYHTmiR-109.016 provided a relative HTT mRNA level of 0.51-0.6; VOYHTmiR-104.425, VOYHTmiR-114.016, and VOYHTmiR-104.907 provided a relative HTT mRNA level of 0.61-0.7; VOYHTmiR-102.907, VOYHTmiR-109.425, VOYHTmiR-104.257, VOYHTmiR-102.425, VOYHTmiR-102.257, VOYHTmiR-104.218, VOYHTmiR-104.372, and VOYHTmiR-109.907 provided a relative HTT mRNA level of 0.71-0.8; VOYHTmiR-109.218, VOYHTmiR-116.218, VOYHTmiR-114.372, VOYHTmiR-109.372, VOYHTmiR-102.218, VOYHTmiR-102.372, and VOYHTmiR-102.214 provided a relative HTT mRNA level of 0.81-0.9; VOYHTmiR-109.257, VOYHTmiR-114.214, and VOYHTmiR-127.214 provided a relative HTT mRNA level of 0.91-1 24 hours after infection at a MOI of 1E4 vg/cell.

In HeLa cells, VOYHTmiR-127.016, VOYHTmiR-104.579.3, VOYHTmiR-104.579.10, VOYHTmiR-127.218, and VOYHTmiR-127.579 provided a relative HTT mRNA level of 0.3-0.4; VOYHTmiR-127.257, VOYHTmiR-104.579.7, VOYHTmiR-127.372, VOYHTmiR-104.579, VOYHTmiR-104.579.9, and VOYHTmiR-127.425 provided a relative HTT mRNA level of 0.41-0.5; VOYHTmiR-104.579.1, VOYHTmiR-102.016, VOYHTmiR-127.907, VOYHTmiR-104.016, VOYHTmiR-116.016, VOYHTmiR-109.016, and VOYHTmiR-127.894 provided a relative HTT mRNA level of 0.51-0.6; VOYHTmiR-109.579, VOYHTmiR-114.579, VOYHTmiR-104.425, VOYHTmiR-114.016, VOYHTmiR-102.579, and VOYHTmiR-116.579 provided a relative HTT mRNA level of 0.61-0.7; VOYHTmiR-104.907, VOYHTmiR-102.894, VOYHTmiR-104.894, VOYHTmiR-109.894, VOYHTmiR-104.257, VOYHTmiR-102.907, VOYHTmiR-109.425, VOYHTmiR-116.894, VOYHTmiR-114.894, VOYHTmiR-104.579.5, VOYHTmiR-102.257, VOYHTmiR-104.218, VOYHTmiR-104.372, VOYHTmiR-102.219.n, VOYHTmiR-102.425, VOYHTmiR-109.907, and VOYHTmiR-109.219.n provided a relative HTT mRNA level of 0.71-0.8; VOYHTmiR-116.218, VOYHTmiR-104.219.n, VOYHTmiR-116.219.n, VOYHTmiR-114.219, VOYHTmiR-109.218, VOYHTmiR-109.372, VOYHTmiR-114.372, VOYHTmiR-102.218, VOYHTmiR-102.372, VOYHTmiR-102.214, VOYHTmiR-109.257, and VOYHTmiR-127.219.n provided a relative HTT mRNA level of 0.81-0.9; VOYHTmiR-114.214 and VOYHTmiR-127.214 provided a relative HTT mRNA level of 0.91-1 24 hours after infection at a MOI of 1E5 vg/cell.

Example 2. Activity of Constructs in Human Normal Primary Astrocytes, U251MG Cells, Neuronally Differentiated SH—SY5Y Cells, and Human HD Fibroblasts The AAV-miRNA expression vectors were packaged in AAV2, and infected into human normal primary astrocytes NHA (Lonza) (cultured in AGM™ Astrocyte Growth Medium, Lonza Cat #CC-3186), human astrocyte cell line U251MG (Sigma Cat #09063001-1VL) (cultured in DMEM/F-12 containing 2 mM GLUAMAX™ supplement, 1×MEM Non-Essential Amino Acids Solution, 10 mM HEPES and 10% FBS, 2 ng/ml human FGF-2 and 5 ug/ml human insulin, all reagents from Life Technologies), neuronally differentiated SH—SY5Y cells (Sigma Cat #94030304) (cultured in DMEM/F-12 containing 2 mM GLUAMAX™ supplement, 1×MEM Non-Essential Amino Acids Solution, 10 mM HEPES and 10% FBS, 2 ng/ml human FGF-2 and 5 ug/ml human insulin, all reagents from Life Technologies) and/or human HD primary fibroblasts (Coriell Institute Cat #GM21756) (cultured in DMEM/F-12 containing 2 mM GLUAMAX™ supplement, 1×MEM Non-Essential Amino Acids Solution, 10 mM HEPES and 10% FBS, 2 ng/ml human FGF-2 and 5 ug/ml human insulin, all reagents from Life Technologies). A control of mCherry was also evaluated. For NHA, fibroblasts and U251MG the cells were plated into 96-well plates (1-2E4 cells/well in 200 ul cell culture medium) and infected in triplicate with AAV-miRNA expression vectors or the control mCherry vector packaged in AAV2. The SH—SY5Y cells were plated into 96-well plates (1E4 cells/well in 200 ul cell culture medium) that were double coated with 0.1 ug/ml Poly-D-lysine and 15 ug/ml laminin, induced for neuronal differentiation in differentiation medium for 4 days, and then infected in triplicate with AAV2-miRNA expression vectors. The AAV2-miRNA expression vectors were infected at a MOT of 1E5 or 1E6 vg/cell. 24-48 hours after infection, the cells were harvested for immediate cell lysis and qRT-PCR.

A. HTT Suppression at 24 Hours after Infection at MOI of 1E5 vg/Cell

The relative expression of HTT mRNA 24 hours after infection at a MOT of 1E5 vg/cell was determined by qRT-PCR for the normal human primary astrocytes, human astrocyte cell line U251MG, SH—SY5Y differentiated neurons, and human HD primary fibroblasts. The relative HTT mRNA expression was obtained by normalizing the HTT mRNA level to the housekeeping gene mRNA level as determined by qRT-PCR; this normalized HTT mRNA level was then expressed relative to the normalized HTT mRNA level in mCherry-treated cells. The results are shown in Table 19.

TABLE 19

HTT mRNA Suppression in Normal Primary Human Astrocytes, U251MG Cells, Neuronally Differentiated SH-SY5Y Cells and Human HD Fibroblasts at 24 hours after Infection of AAV2-miRNA Expression Vectors at a MOI of 1E5 vg/cell

| Name | Duplex ID | Expression Cassette | Relative HTT mRNA Level (%) (normalized to mCherry) | | | |
| --- | --- | --- | --- | --- | --- | --- |
| | | | Human Primary Astrocytes (NHA) | U251MG | SH-SY5Y | HD Fibroblast |
| VOYHTmiR-102.219.n | D-3513 | 288 | 103 | 119 | 91 | 102 |
| VOYHTmiR-102.894 | D-3520 | 299 | 102 | 102 | 82 | 100 |
| VOYHTmiR-102.579 | D-3548 | 341 | 105 | 102 | 101 | 86 |
| VOYHTmiR-104.219.n | D-3514 | 289 | 91 | 111 | 90 | 121 |
| VOYHTmiR-104.894 | D-3521 | 300 | 98 | 112 | 103 | 104 |
| VOYHTmiR-104.579 | D-3549 | 342 | 102 | 79 | 79 | 88 |
| VOYHTmiR-109.219.n | D-3513 | 290 | 89 | 96 | 89 | 78 |
| VOYHTmiR-109.894 | D-3520 | 301 | 89 | 102 | 77 | 91 |
| VOYHTmiR-109.579 | D-3548 | 343 | 82 | 82 | 71 | 78 |
| VOYHTmiR-116.219.n | D-3515 | 291 | 81 | 90 | 95 | 79 |
| VOYHTmiR-116.894 | D-3523 | 303 | 94 | 86 | 80 | 70 |
| VOYHTmiR-116.579 | D-3551 | 345 | 108 | 95 | 98 | 100 |
| VOYHTmiR-114.219 | D-3511 | 285 | 91 | 105 | 95 | 106 |
| VOYHTmiR-114.894 | D-3522 | 302 | 100 | 85 | 82 | 81 |
| VOYHTmiR-114.579 | D-3550 | 344 | 100 | 77 | 70 | 80 |

TABLE 19-continued

HTT mRNA Suppression in Normal Primary Human Astrocytes, U251MG Cells, Neuronally Differentiated SH-SY5Y Cells and Human HD Fibroblasts at 24 hours after Infection of AAV2-miRNA Expression Vectors at a MOI of 1E5 vg/cell

| Name | Duplex ID | Expression Cassette | Human Primary Astrocytes (NHA) | U251MG | SH-SY5Y | HD Fibroblast |
|---|---|---|---|---|---|---|
| VOYHTmiR-127.219.n | D-3513 | 292 | 89 | 90 | 86 | 81 |
| VOYHTmiR-127.894 | D-3520 | 304 | 80 | 79 | 69 | 80 |
| VOYHTmiR-127.579 | D-3548 | 346 | 79 | 61 | 54 | 73 |
| VOYHTmiR-102.214 | D-3500 | 270 | 78 | 80 | 91 | 81 |
| VOYHTmiR-102.016 | D-3544 | 335 | 70 | 51 | 51 | 77 |
| VOYHTmiR-102.218 | D-3505 | 276 | 92 | 100 | 92 | 115 |
| VOYHTmiR-102.372 | D-3528 | 311 | 90 | 99 | 118 | 120 |
| VOYHTmiR-102.425 | D-3532 | 317 | 95 | 85 | 103 | 114 |
| VOYHTmiR-102.907 | D-3524 | 305 | 84 | 69 | 85 | 84 |
| VOYHTmiR-102.257 | D-3516 | 293 | 124 | 72 | 73 | 90 |
| VOYHTmiR-104.016 | D-3545 | 336 | 115 | 75 | 65 | 85 |
| VOYHTmiR-104.218 | D-3506 | 277 | 119 | 78 | 85 | 88 |
| VOYHTmiR-104.372 | D-3529 | 312 | 101 | 95 | 96 | 90 |
| VOYHTmiR-104.425 | D-3533 | 318 | 126 | 81 | 76 | 95 |
| VOYHTmiR-104.907 | D-3525 | 306 | 121 | 75 | 79 | 110 |
| VOYHTmiR-104.257 | D-3517 | 294 | 110 | 77 | 81 | 90 |
| VOYHTmiR-109.016 | D-3546 | 337 | 81 | 67 | 70 | 79 |
| VOYHTmiR-109.218 | D-3507 | 278 | 96 | 68 | 73 | 80 |
| VOYHTmiR-109.372 | D-3530 | 313 | 102 | 81 | 73 | 77 |
| VOYHTmiR-109.425 | D-3534 | 319 | 98 | 74 | 71 | 82 |
| VOYHTmiR-109.907 | D-3526 | 307 | 88 | 80 | 80 | 82 |
| VOYHTmiR-109.257 | D-3518 | 295 | 120 | 89 | 94 | 95 |
| VOYHTmiR-114.016 | D-3547 | 338 | 100 | 73 | 65 | 95 |
| VOYHTmiR-114.214 | D-3501 | 273 | 114 | 97 | 100 | 88 |
| VOYHTmiR-114.372 | D-3531 | 314 | 90 | 83 | 77 | 79 |
| VOYHTmiR-116.016 | D-3546 | 339 | 87 | 57 | 51 | 79 |
| VOYHTmiR-116.218 | D-3508 | 280 | 100 | 77 | 74 | 75 |
| VOYHTmiR-127.016 | D-3546 | 340 | 62 | 30 | 40 | 61 |
| VOYHTmiR-127.214 | D-3504 | 275 | 92 | 97 | 100 | 69 |
| VOYHTmiR-127.218 | D-3507 | 281 | 81 | 42 | 49 | 72 |
| VOYHTmiR-127.372 | D-3530 | 316 | 90 | 50 | 64 | 83 |
| VOYHTmiR-127.425 | D-3534 | 322 | 97 | 68 | 69 | 81 |
| VOYHTmiR-127.907 | D-3526 | 310 | 79 | 57 | 62 | 70 |
| VOYHTmiR-127.257 | D-3518 | 298 | 78 | 63 | 52 | 61 |
| mCherry | N/A | — | 100 | 100 | 100 | 100 |

In normal human primary astrocytes, VOYHTmiR-102.016 and VOYHTmiR-127.016 caused about 30-40% silencing of HTT mRNA 24 hours after infection at a MOI of 1E5 vg/cell.

In the human astrocyte cell line U251MG, VOYHTmiR-127.579, VOYHTmiR-102.907, VOYHTmiR-102.257, VOYHTmiR-109.016, VOYHTmiR-109.218, VOYHT-miR-114.016, VOYHTmiR-127.425 and VOYHTmiR-127.257 cause about 30-40% silencing; VOYHTmiR-102.016, VOYHTmiR-127.372, VOYHTmiR-116.016 and VOYHTmiR-127.907 cause 41-50% silencing; VOYHTmiR-127.218 causes 51-60% silencing; and VOYHTmiR-127.016 causes 61-70% silencing of HTT mRNA 24 hours after infection at a MOI of 1E5 vg/cell.

In SH—SY5Y differentiated neurons, VOYHTmiR-109.579, VOYHTmiR-114.579, VOYHTmiR-127.894, VOYHTmiR-102.257, VOYHTmiR-104.016, VOYHT-miR-109.016, VOYHTmiR-109.218, VOYHTmiR-109.372, VOYHTmiR-109.425, VOYHTmiR-114.016, VOYHTmiR-127.372, VOYHTmiR-127.425 and VOYHT-miR-127.907 cause about 30-40% silencing; VOYHTmiR-127.579, VOYHTmiR-102.016, VOYHTmiR-116.016 and VOYHTmiR-127.257 cause 41-50% silencing; and VOYHTmiR-127.016 and VOYHTmiR-127.218 cause about 51-60% silencing of Htt mRNA 24 hours after infection at a MOI of 1E5 vg/cell.

In human HD fibroblasts, VOYHTmiR-116.894, VOYHT-miR-127.579, VOYHTmiR-127.016, VOYHT-miR-127.214, VOYHTmiR-127.218, VOYHTmiR-127.907 and VOYHTmiR-127.257 cause about 30-40% silencing of Htt mRNA 24 hours after infection at a MOI of 1E5 vg/cell.

B. HTT Suppression at 24 Hours after Infection at MOI of 1E6 vg/Cell

The relative expression of HTT mRNA 24 hours after infection at a MOI of 1E6, was determined by qRT-PCR for the human astrocyte cell line U251MG and neuronally differentiated SH—SY5Y cells. The relative HTT mRNA expression was obtained by normalizing the HTT mRNA level to the housekeeping gene mRNA level as determined by qRT-PCR; this normalized HTT mRNA level was then expressed relative to the normalized HTT mRNA level in mCherry-treated cells. The results are shown in Table 20.

TABLE 20

HTT mRNA Suppression in U251MG Cells and Neuronally Differentiated SH-SY5Y Cells at 24 hours after infection with a MOI of 1E6 vg/cell

| Name | Duplex ID | Expression Cassette | Relative HTT mRNA Level (%) (normalized to XPNPEP1) | |
|---|---|---|---|---|
| | | | U251MG | SH-SY5Y |
| VOYHTmiR-102.219.n | D-3513 | 288 | 113 | 69 |
| VOYHTmiR-102.894 | D-3520 | 299 | 113 | 58 |

TABLE 20-continued

HTT mRNA Suppression in U251MG Cells and Neuronally Differentiated SH-SY5Y Cells at 24 hours after infection with a MOI of 1E6 vg/cell

| Name | Duplex ID | Expression Cassette | Relative HTT mRNA Level (%) (normalized to XPNPEP1) | |
|---|---|---|---|---|
| | | | U251MG | SH-SY5Y |
| VOYHTmiR-102.579 | D-3548 | 341 | 79 | 56 |
| VOYHTmiR-104.219.n | D-3514 | 289 | 119 | 80 |
| VOYHTmiR-104.894 | D-3521 | 300 | 125 | 69 |
| VOYHTmiR-104.579 | D-3549 | 342 | 69 | 46 |
| VOYHTmiR-109.219.n | D-3513 | 290 | 111 | 70 |
| VOYHTmiR-109.894 | D-3520 | 301 | 80 | 57 |
| VOYHTmiR-109.579 | D-3548 | 343 | 65 | 50 |
| VOYHTmiR-116.219.n | D-3515 | 291 | 92 | 70 |
| VOYHTmiR-116.894 | D-3523 | 303 | 86 | 60 |
| VOYHTmiR-116.579 | D-3551 | 345 | 90 | 60 |
| VOYHTmiR-114.219 | D-3511 | 285 | 108 | 68 |
| VOYHTmiR-114.894 | D-3522 | 302 | 83 | 57 |
| VOYHTmiR-114.579 | D-3550 | 344 | 60 | 42 |
| VOYHTmiR-127.219.n | D-3513 | 292 | 102 | 87 |
| VOYHTmiR-127.894 | D-3520 | 304 | 61 | 47 |
| VOYHTmiR-127.579 | D-3548 | 346 | 48 | 42 |
| VOYHTmiR-102.214 | D-3500 | 270 | 78 | 115 |
| VOYHTmiR-102.016 | D-3544 | 335 | 48 | 45 |
| VOYHTmiR-102.218 | D-3505 | 276 | 100 | 90 |
| VOYHTmiR-102.372 | D3528 | 311 | 78 | 97 |
| VOYHTmiR-102.425 | D-3532 | 317 | 69 | 90 |
| VOYHTmiR-102.907 | D-3524 | 305 | 58 | 108 |
| VOYHTmiR-102.257 | D-3516 | 293 | 68 | 69 |
| VOYHTmiR-104.016 | D-3545 | 336 | 51 | 45 |
| VOYHTmiR-104.218 | D-3506 | 277 | 60 | 63 |
| VOYHTmiR-104.372 | D-3529 | 312 | 78 | 79 |
| VOYHTmiR-104.425 | D-3533 | 318 | 60 | 58 |
| VOYHTmiR-104.907 | D-3525 | 306 | 68 | 67 |
| VOYHTmiR-104.257 | D-3517 | 294 | 70 | 57 |
| VOYHTmiR-109.016 | D-3546 | 337 | 49 | 55 |
| VOYHTmiR-109.218 | D-3507 | 278 | 65 | 61 |
| VOYHTmiR-109.372 | D-3530 | 313 | 82 | 58 |
| VOYHTmiR-109.425 | D-3534 | 319 | 70 | 59 |
| VOYHTmiR-109.907 | D-3526 | 307 | 69 | 65 |
| VOYHTmiR-109.257 | D-3518 | 295 | 75 | 61 |
| VOYHTmiR-114.016 | D-3547 | 338 | 63 | 48 |
| VOYHTmiR-114.214 | D-3501 | 273 | 81 | 90 |
| VOYHTmiR-114.372 | D-3531 | 314 | 66 | 56 |
| VOYHTmiR-116.016 | D-3546 | 339 | 45 | 45 |
| VOYHTmiR-116.218 | D-3508 | 280 | 80 | 65 |
| VOYHTmiR-127.016 | D-3546 | 340 | 30 | 26 |
| VOYHTmiR-127.214 | D-3504 | 275 | 102 | 80 |
| VOYHTmiR-127.218 | D-3507 | 281 | 35 | 33 |
| VOYHTmiR-127.372 | D-3530 | 316 | 45 | 42 |
| VOYHTmiR-127.425 | D-3534 | 322 | 50 | 51 |
| VOYHTmiR-127.907 | D-3526 | 310 | 42 | 42 |
| VOYHTmiR-127.257 | D-3518 | 298 | 38 | 39 |
| mCherry | N/A | — | 100 | 100 |

In the human astrocyte cell line U251MG, VOYHTmiR-104.579, VOYHTmiR-109.579, VOYHTmiR-114.579, VOYHTmiR-127.894, VOYHTmiR-102.425, VOYHTmiR-102.257, VOYHTmiR-104.218, VOYHTmiR-104.425, VOYHTmiR-104.907, VOYHTmiR-104.257, VOYHTmiR-109.218, VOYHTmiR-109.425, VOYHTmiR-109.907, VOYHTmiR-114.016 and VOYHTmiR-114.372 cause about 30-40% silencing; VOYHTmiR-102.907, VOYHTmiR-104.016, VOYHTmiR-127.425 cause about 41-50% silencing; VOYHTmiR-127.579, VOYHTmiR-102.016, VOYHTmiR-109.016, VOYHTmiR-116.016, VOYHTmiR-127.372 and VOYHTmiR-127.907 cause about 51-60% silencing; and VOYHTmiR-127.016, VOYHTmiR-127.218 and VOYHTmiR-127.257 cause about 61-70% silencing of HTT mRNA 24 hours after infection at a MOI of 1E6 vg/cell.

In neuronally differentiated SH—SY5Y cells, VOYHTmiR-102.219.n, VOYHTmiR-104.894, VOYHTmiR-109.219.n, VOYHTmiR-116.219.n, VOYHTmiR-116.894, VOYHTmiR-116.579, VOYHTmiR-114.219, VOYHTmiR-102.257, VOYHTmiR-104.218, VOYHTmiR-104.907, VOYHTmiR-109.218, VOYHTmiR-109.907, VOYHTmiR-109.257, VOYHTmiR-116.218 cause about 30-40% silencing; VOYHTmiR-102.894, VOYHTmiR-102.579, VOYHTmiR-109.894, VOYHTmiR-109.579, VOYHTmiR-114.894, VOYHTmiR-104.425, VOYHTmiR-104.257, VOYHTmiR-109.016, VOYHTmiR-109.372, VOYHTmiR-109.425, VOYHTmiR-114.372, VOYHTmiR-127.425 cause about 41-50% silencing; VOYHTmiR-104.579, VOYHTmiR-114.579, VOYHTmiR-127.894, VOYHTmiR-127.579, VOYHTmiR-102.016, VOYHTmiR-104.016, VOYHTmiR-114.016, VOYHTmiR-116.016, VOYHTmiR-127.372, VOYHTmiR-127.907 cause about 51-60% silencing; and VOYHTmiR-127.016, VOYHTmiR-127.218 and VOYHTmiR-127.257 cause about 61-75% silencing of HTT mRNA 24 hours after infection at a MOI of 1E6 vg/cell.

C. HTT Suppression at 36 Hours after Infection with MOI of 1E5 vg/Cell 36 hours after infection, the relative expression of HTT mRNA was determined by qRT-PCR for the human astrocyte cell line U251MG, and neuronally differentiated SH—SY5Y cells at a MOI of 1E5 vg/cell. Relative HTT mRNA expression was determined by normalization of HTT mRNA to a housekeeping mRNA, and further normalization to the mCherry-treated cells; the results are shown in Table 21.

TABLE 21

HTT mRNA Suppression in U251MG Cells and Neuronally Differentiated SH-SY5Y Cells at MOI 1E5 vg/cell - 36 hours after infection

| Name | Duplex ID | Expression Cassette | Relative HTT mRNA Level (%) (normalized to XPNPEP1) | |
|---|---|---|---|---|
| | | | U251MG | SH-SY5Y |
| VOYHTmiR-104.579.5 | D-3569 | 367 | 75 | 70 |
| VOYHTmiR-104.579.2 | D-3566 | 348 | 70 | 88 |
| VOYHTmiR-104.579.1 | D-3566 | 347 | 45 | 53 |
| VOYHTmiR-104.579.9 | D-3566 | 354 | 40 | 60 |
| VOYHTmiR-104.579 | D-3549 | 342 | 37 | 50 |
| VOYHTmiR-104.579.7 | D-3567 | 352 | 35 | 44 |
| VOYHTmiR-104.579.3 | D-3566 | 349 | 25 | 35 |
| VOYHTmiR-104.579.10 | D-3570 | 368 | 25 | 38 |
| mCherry | N/A | — | 100 | 100 |

In the human astrocyte cell line U251MG, VOYHTmiR-104.579.2 causes about 30-40% silencing; VOYHTmiR-104.579.1 and VOYHTmiR-104.579.9 cause about 51-60% silencing; VOYHTmiR-104.579, and VOYHTmiR-104.579.7 cause about 61-70% silencing; and VOYHTmiR-104.579.3, and VOYHTmiR-104.579.10 cause about 71-80% silencing of Htt mRNA 36 hours after infection at a MOI of 1E5 vg/cell.

In neuronally differentiated SH—SY5Y, VOYHTmiR-104.579.5 and VOYHTmiR-104.579.9 cause about 30-40% silencing; VOYHTmiR-104.579.1 and VOYHTmiR-104.579 cause about 41-50% silencing; and VOYHTmiR-104.579.7, VOYHTmiR-104.579.3 and VOYHTmiR-104.579.10 cause about 51-65% silencing of Htt mRNA 36 hours after infection at a MOI of 1E5 vg/cell.

D. HTT Suppression at 36 Hours after Infection with MOI of 1E6 vg/Cell 36 hours after infection, the relative expression of HTT mRNA was determined by qRT-PCR in neuronally differentiated SH—SY5Y cells at a MOI of 1E6 vg/cell. Relative HTT mRNA expression was determined by normalization of HTT mRNA to a housekeeping mRNA, and further normalization to the mCherry-treated cells; the results are shown in Table 22.

TABLE 22

HTT mRNA Suppression in Neuronally Differentiated SH-SY5Y Cells with MOI 1E6 - 36 hours after infection

| Name | Duplex ID | Expression Cassette | Relative HTT mRNA Level (%) (normalized to XPNPEP1) SH-SY5Y |
|---|---|---|---|
| VOYHTmiR-104.579.5 | D-3569 | 367 | 73 |
| VOYHTmiR-104.579.2 | D-3566 | 348 | 68 |
| VOYHTmiR-104.579.1 | D-3566 | 347 | 58 |
| VOYHTmiR-104.579.9 | D-3566 | 354 | 61 |
| VOYHTmiR-104.579 | D-3549 | 342 | 62 |
| VOYHTmiR-104.579.7 | D-3567 | 352 | 43 |
| VOYHTmiR-104.579.3 | D-3566 | 349 | 38 |
| VOYHTmiR-104.579.10 | D-3570 | 368 | 38 |
| mCherry | N/A | — | 100 |

In neuronally differentiated SH—SY5Y cells, VOYHTmiR-104.579.5, VOYHTmiR-104.579.2, VOYHTmiR-104.579.9, VOYHTmiR-104.579 cause about 30-40% silencing; VOYHTmiR-104.579.1 cause about 41-50% silencing; and VOYHTmiR-104.579.7, VOYHTmiR-104.579.3, and VOYHTmiR-104.579.10 cause about 51-65% silencing of Htt mRNA 36 hours after infection at a MOI of 1E6/cell.

E. HTT Suppression at 40 Hours after Infection—MOI of 1E6

40 hours after infection, the relative expression of HTT mRNA was determined by qRT-PCR in the human astrocyte cell line U251MG, and neuronally differentiated SH—SY5Y cells at a MOI of 1E6 vg/cell. Relative HTT mRNA expression was determined by normalization of HTT mRNA to a housekeeping mRNA, and further normalization to the mCherry-treated cells; the results are shown in Table 23.

TABLE 23

HTT mRNA Suppression in U251MG Cells and Neuronally Differentiated SH-SY5Y Cells 40 hours after infection with a MOI of 1E6 vg/cell

| Name | Duplex ID | Expression Cassette | Relative HTT mRNA Level (%) (normalized to XPNPEP1) U251MG | SH-SY5Y |
|---|---|---|---|---|
| VOYHTmiR-102.219.n | D-3513 | 288 | 111 | 84 |
| VOYHTmiR-102.894 | D-3520 | 299 | 94 | 79 |
| VOYHTmiR-102.579 | D-3548 | 341 | 97 | 78 |
| VOYHTmiR-104.219.n | D-3514 | 289 | 98 | 85 |
| VOYHTmiR-104.894 | D-3521 | 300 | 97 | 78 |
| VOYHTmiR-104.579 | D-3549 | 342 | 78 | 64 |
| VOYHTmiR-109.219.n | D-3513 | 290 | 106 | 88 |
| VOYHTmiR-109.894 | D-3520 | 301 | 90 | 74 |
| VOYHTmiR-109.579 | D-3548 | 343 | 87 | 69 |
| VOYHTmiR-116.219.n | D-3515 | 291 | 94 | 85 |
| VOYHTmiR-116.894 | D-3523 | 303 | 97 | 84 |
| VOYHTmiR-116.579 | D-3551 | 345 | 95 | 76 |
| VOYHTmiR-114.219 | D-3511 | 285 | 97 | 76 |
| VOYHTmiR-114.894 | D-3522 | 302 | 92 | 74 |
| VOYHTmiR-114.579 | D-3550 | 344 | 83 | 71 |
| VOYHTmiR-127.219.n | D-3513 | 292 | 105 | 85 |
| VOYHTmiR-127.894 | D-3520 | 304 | 85 | 67 |
| VOYHTmiR-127.579 | D-3548 | 346 | 74 | 59 |
| VOYHTmiR-102.214 | D-3500 | 270 | 66 | 70 |
| VOYHTmiR-102.016 | D-3544 | 335 | 94 | 96 |
| VOYHTmiR-102.218 | D-3505 | 276 | 95 | 90 |
| VOYHTmiR-102.372 | D-3528 | 311 | 91 | 91 |
| VOYHTmiR-102.425 | D-3532 | 317 | 86 | 91 |
| VOYHTmiR-102.907 | D-3524 | 305 | 87 | 94 |
| VOYHTmiR-102.257 | D-3516 | 293 | 92 | 88 |
| VOYHTmiR-104.016 | D-3545 | 336 | 71 | 66 |
| VOYHTmiR-104.218 | D-3506 | 277 | 85 | 81 |
| VOYHTmiR-104.372 | D-3529 | 312 | 95 | 93 |
| VOYHTmiR-104.425 | D-3533 | 318 | 80 | 78 |
| VOYHTmiR-104.907 | D-3525 | 306 | 77 | 71 |
| VOYHTmiR-104.257 | D-3517 | 294 | 76 | 69 |
| VOYHTmiR-109.016 | D-3546 | 337 | 76 | 75 |
| VOYHTmiR-109.218 | D-3507 | 278 | 88 | 74 |
| VOYHTmiR-109.372 | D-3530 | 313 | 89 | 76 |
| VOYHTmiR-109.425 | D-3534 | 319 | 84 | 77 |
| VOYHTmiR-109.907 | D-3526 | 307 | 84 | 83 |
| VOYHTmiR-109.257 | D-3518 | 295 | 92 | 75 |
| VOYHTmiR-114.016 | D-3547 | 338 | 72 | 60 |
| VOYHTmiR-114.214 | D-3501 | 273 | 93 | 88 |
| VOYHTmiR-114.372 | D-3531 | 314 | 90 | 81 |
| VOYHTmiR-116.016 | D-3546 | 339 | 75 | 66 |
| VOYHTmiR-116.218 | D-3508 | 280 | 91 | 76 |
| VOYHTmiR-127.016 | D-3546 | 340 | 55 | 48 |
| VOYHTmiR-127.214 | D-3504 | 275 | 99 | 86 |
| VOYHTmiR-127.218 | D-3507 | 281 | 59 | 60 |
| VOYHTmiR-127.372 | D-3530 | 316 | 63 | 62 |
| VOYHTmiR-127.425 | D-3534 | 322 | 71 | 66 |
| VOYHTmiR-127.907 | D-3526 | 310 | 74 | 70 |
| VOYHTmiR-127.257 | D-3518 | 298 | 62 | 63 |
| mCherry | N/A | — | 102 | 102 |

In the human astrocyte cell line U251MG, VOYHTmiR-102.214, VOYHTmiR-104.016, VOYHTmiR-114.016, VOYHTmiR-127.372, VOYHTmiR-127.425 and VOYHTmiR-127.257 caused about 30-40% silencing; and VOYHTmiR-127.016 and VOYHTmiR-127.218 caused about 41-50% silencing of HTT mRNA 40 hours after infection at a MOI of 1E6 vg/cell.

In neuronally differentiated SH—SY5Y cells, VOYHTmiR-104.579, VOYHTmiR-109.579, VOYHTmiR-114.579, VOYHTmiR-127.894, VOYHTmiR-102.214, VOYHTmiR-104.016, VOYHTmiR-104.907, VOYHTmiR-104.257, VOYHTmiR-114.016, VOYHTmiR-116.016, VOYHTmiR-127.218, VOYHTmiR-127.372, VOYHTmiR-127.425, VOYHTmiR-127.907 and VOYHTmiR-127.257 caused about 30-40% silencing; VOYHTmiR-127.579 caused about 41-50% silencing; and VOYHTmiR-127.016 caused about 51-60% silencing of HTT mRNA 40 hours after infection at a MOI of 1E6 vg/cell.

Example 3. In Vivo YAC128 Mouse Study of HTT Suppression, Guide to Passenger Ratio and Precision of 5' End Processing after Treatment with AAV-miRNA Vectors Produced in Mammalian Cells Based on in vitro suppression of HTT with plasmid transfection and with infection of AAV packaged AAV-miRNA expression vectors, selected AAV-miRNA expression vectors were packaged in AAV1 and evaluated in vivo in YAC128 mice, to quantify HTT mRNA suppression, and to assess guide to passenger ratio and the precision of 5' end processing by deep sequencing. The AAV-miRNA transgene genomes were packaged in AAV1 with a CBA promoter (AAV1.CBA.iHtt), and then the vectors were produced by triple transfection in HEK293 or HEK293T cells, purified and formulated in phosphate buffered saline (PBS) with 0.001% F-68. Vectors were administered to YAC128 mice 7-12 weeks of age via bilateral intrastriatal infusion at a dose of approximately 1E10 to 3E10 vg in 5 uL over 10 minutes per hemisphere. A control group was treated with vehicle (PBS with 0.001% F-68). Each group comprised 4 females and 4 males. Approximately 28 days following test article administration, striatum tissue punches were collected and snap-frozen for later analysis.

Striatum tissue samples were then homogenized and total RNAs were purified. The relative expression of HTT was determined by qRT-PCR. Housekeeping genes for normalization included mouse XPNPEP1 (X-Prolyl Aminopeptidase 1) and mouse HPRT (hypoxanthine-guanine phosphoribosyltransferase). HTT mRNA was normalized to housekeeping gene expression, and then further normalized to the vehicle group. The results are shown in Tables 24 and 25.

TABLE 24

HTT mRNA Suppression in YAC128 Mouse Striatum after Intrastriatal Infusion

| Name | Duplex ID | Expression Cassette | Relative HTT mRNA Level (%) (normalized to XPNPEP1) - mean ± standard deviation | Relative HTT mRNA Level (%) (normalized to HPRT) - mean ± standard deviation |
|---|---|---|---|---|
| VOYHTmiR-127.016 | D-3546 | 340 | 63 ± 8 | 68 ± 9 |
| VOYHTmiR-127.218 | D-3507 | 281 | 85 ± 19 | 86 ± 22 |
| VOYHTmiR-127.257 | D-3518 | 298 | 76 ± 13 | 78 ± 8 |
| VOYHTmiR-116.016 | D-3546 | 339 | 99 ± 11 | 106 ± 18 |
| VOYHTmiR-127.579 | D-3548 | 346 | 74 ± 6 | 77 ± 10 |
| VOYHTmiR-104.425 | D-3533 | 318 | 83 ± 4 | 86 ± 7 |
| VOYHTmiR-104.257 | D-3517 | 294 | 91 ± 7 | 96 ± 10 |
| VOYHTmiR-104.907 | D-3525 | 306 | 103 ± 18 | 102 ± 14 |
| Vehicle | N/A | — | 100 ± 15 | 100 ± 14 |

TABLE 25

HTT mRNA Suppression in YAC128 Mouse Striatum after Intrastriatal Infusion

| Name | Duplex ID | Expression Cassette | Relative HTT mRNA Level (%) (normalized to XPNPEP1) - mean ± standard deviation | Relative HTT mRNA Level (%) (normalized to HPRT) - mean ± standard deviation |
|---|---|---|---|---|
| VOYHTmiR-104.579.3 | D-3566 | 349 | 67 + 19 | 63 ± 18 |
| VOYHTmiR-104.579.10 | D-3570 | 368 | 70 + 10 | 69 ± 10 |
| VOYHTmiR-102.016 | D-3544 | 335 | 92 + 12 | 91 ± 12 |
| VOYHTmiR-104.016 | D-3545 | 336 | 73 + 10 | 68 ± 7 |
| VOYHTmiR-114.016 | D-3547 | 338 | 93 + 9 | 88 ± 16 |
| VOYHTmiR-127.907 | D-3526 | 310 | 87 + 14 | 83 ± 10 |
| VOYHTmiR-109.016 | D-3546 | 337 | 79 + 7 | 76 ± 6 |
| VOYHTmiR-104.579 | D-3549 | 342 | 94 + 16 | 96 ± 13 |
| Vehicle | N/A | — | 100 ± 6 | 100 ± 8 |

In YAC128 mouse striatum, VOYHTmiR-127.016, VOYHTmiR-127.257, VOYHTmiR-127.579, VOYHTmiR-104.579.3, VOYHTmiR-104.579.10, VOYHTmiR-104.016 and VOYHTmiR-109.016 caused about 20-40% silencing of HTT mRNA at about 28 days after intrastriatal infusion of 1E10 to 3E10 vg per striatum.

Striatum tissue samples were also evaluated for pri-miRNA processing by deep sequencing to assess guide: passenger ratio, abundance of guide and passenger strands relative to the total endogenous pool of miRNAs, and precision of processing at the 5'-end of the guide strand. The results are shown in Table 26.

TABLE 26

Deep Sequencing of YAC128 Mouse Striatal Samples after Intrastriatal Infusion

| Name | Duplex ID | Expression Cassette | Abundance Relative to Endogenous miRNA Pool (%) | Guide/Passenger Ratio | % N (Guide) |
|---|---|---|---|---|---|
| VOYHTmiR-127.016 | D-3546 | 340 | 58.13 | 422.9 | 91.5 |
| VOYHTmiR-127.218 | D-3507 | 281 | 1.49 | 2.44 | 96.2 |
| VOYHTmiR-127.257 | D-3518 | 298 | 9.66 | 0.04 | 85.7 |
| VOYHTmiR-116.016 | D-3546 | 339 | 3.09 | 207.8 | 95.9 |
| VOYHTmiR-127.579 | D-3548 | 346 | 0.05 | 24.28 | 83.2 |
| VOYHTmiR-104.425 | D-3533 | 318 | 0.12 | 0.32 | 92.7 |
| VOYHTmiR-104.257 | D-3517 | 294 | 0.07 | 0.38 | 97.1 |
| VOYHTmiR-104.907 | D-3525 | 306 | 6.45 | 2384 | 96.4 |
| VOYHTmiR-104.579.3 | D-3566 | 349 | 0.21 | 40 | 86.8 |
| VOYHTmiR-104.579.10 | D-3570 | 368 | 0.76 | 83 | 89.8 |
| VOYHTmiR-102.016 | D-3544 | 335 | 3.06 | 494 | 86.4 |
| VOYHTmiR-104.016 | D-3545 | 336 | 5.41 | 629 | 86.8 |
| VOYHTmiR-114.016 | D-3547 | 338 | 1.7 | 256 | 85.8 |
| VOYHTmiR-127.907 | D-3526 | 310 | 51.29 | 163 | 82.9 |
| VOYHTmiR-109.016 | D-3546 | 337 | 1.75 | 135 | 87.1 |
| VOYHTmiR-104.579 | D-3549 | 342 | 0.01 | 19 | 84.9 |

Example 4. HTT Sequences

HTT derived oligonucleotides are synthesized and formed into duplexes as described in Table 3. The siRNA duplexes are then tested for in vitro inhibitory activity on endogenous HTT gene expression.

Example 5. In Vitro Evaluation of AAV-miRNA Expression Vectors Containing Guide Strands Targeting HTT and Passenger Strands Based on predicted selectivity of the antisense strand for human HTT genes, some of the guide and passenger strands of duplexes of the HTT siRNA listed in Table 3 are engineered into AAV-miRNA expression vectors and transfected into cells of the central nervous system, neuronal cell lines or non-neuronal cell lines. Even though overhang utilized in the siRNA knockdown study is a canonical dTdT for siRNA, the overhang in the constructs may comprise any dinucleotide overhang.

The cells used may be primary cells, cell lines, or cells derived from induced pluripotent stem cells (iPS cells).

HTT knockdown is then measured and deep sequencing performed to quantify the exact passenger and guide strands processed from each construct administered in the expression vector.

A guide to passenger strand ratio is calculated.

The 5'-terminus of the guide strand is sequenced to determine the precision of cleavage and to determine the percent expected guide strand resulting from precise cleavage.

AAV-miRNA expression vectors were packaged in AAV2, and then used to infect cells of the central nervous system, neuronal cell lines or non-neuronal cell lines to analyze in vitro knockdown of HTT. A mCherry construct or vehicle group is used as a negative control.

Deep sequencing is again performed.

Example 6. Pri-miRNA Cassettes Containing Guide Sequences Targeting HTT and Passenger Sequences According to the present invention, constructs comprising the pri-miRNA cassette and HTT siRNAs were designed and are given in Table 27. The passenger and guide strands are described in the tables as well as the 5' and 3' Flanking Regions and the Loop region (also referred to as the linker region). In Table 27, the "miR" component of the name of the sequence does not necessarily correspond to the sequence numbering of miRNA genes (e.g., VOYHTmiR-102 is the name of the sequence and does not necessarily mean that miR-102 is part of the sequence).

TABLE 27

Pri-miRNA Cassettes Containing Passenger and Guide Sequences (5'-3')

| Name | 5' Flanking to 3' Flanking SEQ ID NO | 5' Flanking SEQ ID NO | Passenger SEQ ID NO | Loop (Linker) SEQ ID NO | Guide SEQ ID NO | 3' Flanking SEQ ID NO |
|---|---|---|---|---|---|---|
| VOYHTmiR-102.016 | 335 | 251 | 119 | 257 | 9 | 266 |
| VOYHTmiR-102.214 | 270 | 251 | 120 | 257 | 11 | 266 |
| VOYHTmiR-102.218 | 276 | 251 | 121 | 257 | 13 | 266 |
| VOYHTmiR-102.219.n | 288 | 251 | 116 | 257 | 3 | 266 |
| VOYHTmiR-102.257 | 293 | 251 | 122 | 257 | 15 | 266 |
| VOYHTmiR-102.372 | 311 | 251 | 123 | 257 | 17 | 266 |
| VOYHTmiR-102.425 | 317 | 251 | 124 | 257 | 19 | 266 |
| VOYHTmiR-102.579 | 341 | 251 | 105 | 257 | 7 | 266 |
| VOYHTmiR-102.894 | 299 | 251 | 104 | 257 | 5 | 266 |
| VOYHTmiR-102.907 | 305 | 251 | 125 | 257 | 21 | 266 |
| VOYHTmiR-104.016 | 336 | 251 | 126 | 257 | 9 | 266 |
| VOYHTmiR-104.214 | 271 | 251 | 127 | 257 | 11 | 266 |
| VOYHTmiR-104.218 | 277 | 251 | 128 | 257 | 13 | 266 |

TABLE 27-continued

Pri-miRNA Cassettes Containing Passenger and Guide Sequences (5'-3')

| Name | 5' Flanking to 3' Flanking SEQ ID NO | 5' Flanking SEQ ID NO | Passenger SEQ ID NO | Loop (Linker) SEQ ID NO | Guide SEQ ID NO | 3' Flanking SEQ ID NO |
|---|---|---|---|---|---|---|
| VOYHTmiR-104.219.n | 289 | 251 | 117 | 257 | 3 | 266 |
| VOYHTmiR-104.257 | 294 | 251 | 129 | 257 | 15 | 266 |
| VOYHTmiR-104.372 | 312 | 251 | 130 | 257 | 17 | 266 |
| VOYHTmiR-104.425 | 318 | 251 | 131 | 257 | 19 | 266 |
| VOYHTmiR-104.579 | 342 | 251 | 108 | 257 | 7 | 266 |
| VOYHTmiR-104.579.1 | 347 | 250 | 168 | 260 | 7 | 265 |
| VOYHTmiR-104.579.10 | 368 | 256 | 171 | 264 | 7 | 269 |
| VOYHTmiR-104.579.2 | 348 | 252 | 168 | 260 | 7 | 265 |
| VOYHTmiR-104.579.3 | 349 | 252 | 168 | 261 | 7 | 265 |
| VOYHTmiR-104.579.4 | 350 | 253 | 168 | 260 | 7 | 268 |
| VOYHTmiR-104.579.5 | 367 | 252 | 170 | 263 | 30 | 265 |
| VOYHTmiR-104.579.6 | 351 | 254 | 168 | 260 | 7 | 268 |
| VOYHTmiR-104.579.7 | 352 | 255 | 168 | 260 | 29 | 265 |
| VOYHTmiR-104.579.8 | 353 | 252 | 169 | 262 | 7 | 265 |
| VOYHTmiR-104.579.9 | 354 | 256 | 168 | 260 | 7 | 269 |
| VOYHTmiR-104.894 | 300 | 251 | 107 | 257 | 5 | 266 |
| VOYHTmiR-104.907 | 306 | 251 | 132 | 257 | 21 | 266 |
| VOYHTmiR-109.016 | 337 | 251 | 133 | 258 | 9 | 266 |
| VOYHTmiR-109.214 | 272 | 251 | 135 | 258 | 11 | 266 |
| VOYHTmiR-109.218 | 278 | 251 | 137 | 258 | 13 | 266 |
| VOYHTmiR-109.219.n | 290 | 251 | 116 | 258 | 3 | 266 |
| VOYHTmiR-109.257 | 295 | 251 | 138 | 258 | 15 | 266 |
| VOYHTmiR-109.372 | 313 | 251 | 139 | 258 | 17 | 266 |
| VOYHTmiR-109.425 | 319 | 251 | 140 | 258 | 19 | 266 |
| VOYHTmiR-109.579 | 343 | 251 | 105 | 258 | 7 | 266 |
| VOYHTmiR-109.894 | 301 | 251 | 104 | 258 | 5 | 266 |
| VOYHTmiR-109.907 | 307 | 251 | 142 | 258 | 21 | 266 |
| VOYHTmiR-114.016 | 338 | 251 | 144 | 257 | 9 | 267 |
| VOYHTmiR-114.214 | 273 | 251 | 145 | 257 | 11 | 267 |
| VOYHTmiR-114.218 | 279 | 251 | 146 | 257 | 13 | 267 |
| VOYHTmiR-114.219 | 285 | 251 | 109 | 257 | 3 | 267 |
| VOYHTmiR-114.257 | 296 | 251 | 147 | 257 | 15 | 267 |
| VOYHTmiR-114.372 | 314 | 251 | 148 | 257 | 17 | 267 |
| VOYHTmiR-114.425 | 320 | 251 | 149 | 257 | 19 | 267 |
| VOYHTmiR-114.579 | 344 | 251 | 111 | 257 | 7 | 267 |
| VOYHTmiR-114.894 | 302 | 251 | 110 | 257 | 5 | 267 |
| VOYHTmiR-114.907 | 308 | 251 | 150 | 257 | 21 | 267 |
| VOYHTmiR-116.016 | 339 | 251 | 133 | 257 | 9 | 267 |
| VOYHTmiR-116.214 | 274 | 251 | 135 | 257 | 11 | 267 |
| VOYHTmiR-116.218 | 280 | 251 | 137 | 257 | 13 | 267 |
| VOYHTmiR-116.219.n | 291 | 251 | 118 | 257 | 3 | 267 |
| VOYHTmiR-116.257 | 297 | 251 | 138 | 257 | 15 | 267 |
| VOYHTmiR-116.372 | 315 | 251 | 139 | 257 | 17 | 267 |
| VOYHTmiR-116.425 | 321 | 251 | 140 | 257 | 19 | 267 |
| VOYHTmiR-116.579 | 345 | 251 | 114 | 257 | 7 | 267 |
| VOYHTmiR-116.894 | 303 | 251 | 113 | 257 | 5 | 267 |
| VOYHTmiR-116.907 | 309 | 251 | 142 | 257 | 21 | 267 |
| VOYHTmiR-127.016 | 340 | 252 | 133 | 261 | 9 | 268 |
| VOYHTmiR-127.214 | 275 | 252 | 135 | 261 | 5 | 268 |
| VOYHTmiR-127.218 | 281 | 252 | 137 | 261 | 13 | 268 |
| VOYHTmiR-127.219.n | 292 | 252 | 116 | 261 | 3 | 268 |
| VOYHTmiR-127.257 | 298 | 252 | 138 | 261 | 15 | 268 |
| VOYHTmiR-127.372 | 316 | 252 | 139 | 261 | 17 | 268 |
| VOYHTmiR-127.425 | 322 | 252 | 140 | 261 | 19 | 268 |
| VOYHTmiR-127.579 | 346 | 252 | 105 | 261 | 7 | 268 |
| VOYHTmiR-127.894 | 304 | 252 | 104 | 261 | 5 | 268 |
| VOYHTmiR-127.907 | 310 | 252 | 142 | 261 | 21 | 268 |

Example 7. AAV-miRNA Expression Vectors

The constructs comprising the pri-miRNA cassettes containing guide strands targeting HTT and passenger strands were engineered into AAV-miRNA expression vectors (either ss or sc). The AAV-miRNA expression vector construct from ITR to ITR, recited 5' to 3', comprises a mutant or wild type ITR, a promoter (either a CMV (which includes an SV40 intron), U6, H1, CBA (which includes a CMVie enhancer, a CB promoter and an SV40 intron), the pri-miRNA cassette containing guide sequence targeting HTT and passenger sequence (from Table 3), a rabbit globin polyA and wild type ITR. In vitro and in vivo studies are performed to evaluate the pharmacological activity of the AAV-miRNA expression vectors.

Example 8. In Vivo Studies of AAV-miRNA Expression Vectors

A. In Vivo Studies of Efficacy

Based on HTT suppression in YAC128 mice, guide to passenger ratio, and precision of 5' end processing, selected AAV-miRNA expression vectors are packaged in AAV1 (either as ss or sc) with a CBA promoter (AAV1.CBA.iHtt), formulated in phosphate buffered saline (PBS) with 0.001% F-68 and administered to YAC128 mice to assess efficacy. AAV1 vectors are administered to YAC128 mice 7-12 weeks of age via bilateral intrastriatal infusion at a dose of approximately 1E10 to 3E10 vg in 5 uL over 10 minutes per hemisphere. A control group is treated with vehicle (PBS with 0.001% F-68). Following test article administration, behavioral tests including rotarod and Porsolt swim tests are performed at pre-determined time intervals, to assess efficacy. At a pre-determined day post-dosing, animals are euthanized, and striatum tissue punches are collected and snap-frozen. Tissue samples are homogenized and the total RNA is purified. The relative expression of HTT is determined by qRT-PCR. Housekeeping genes for normalization included mouse XPNPEP1. HTT is normalized to housekeeping gene expression, and then further normalized to the vehicle group. Samples are also used to quantify HTT protein.

B. In Vivo Study in NHP of HTT Suppression, Guide to Passenger Ratio and 5' End Precision of Processing Based on HTT suppression in YAC128 mice, guide to passenger ratio, and precision of 5' end processing, selected AAV-miRNA expression vectors are packaged in AAV1 with a CBA promoter (AAV1.CBA.iHtt), formulated in phosphate buffered saline (PBS) with 0.001% F-68 and administered to non-human primates by intraparenchymal brain infusion. A control group is treated with vehicle (PBS with 0.001% F-68). The relative expression of HTT mRNA, guide to passenger ratio, and the precision of 5' end processing is determined in various tissue samples at a pre-determined time post-dosing.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

SEQUENCE LISTING

The patent contains a lengthy sequence listing. A copy of the sequence listing is available in electronic form from the USPTO web site (https://seqdata.uspto.gov/?pageRequest=docDetail&DocID=US11951121B2). An electronic copy of the sequence listing will also be available from the USPTO upon request and payment of the fee set forth in 37 CFR 1.19(b)(3).

We claim:

1. A modulatory polynucleotide comprising the nucleotide sequence of SEQ ID NO: 349.

2. An adeno-associated viral (AAV) vector genome comprising a nucleic acid sequence positioned between two inverted terminal repeats (ITRs), wherein the nucleic acid sequence encodes a modulatory polynucleotide comprising the nucleotide sequence of SEQ ID NO: 349.

3. The AAV vector genome of claim 2, which further comprises:
   (i) a promoter operably linked to the nucleic acid sequence encoding the modulatory polynucleotide;
   (ii) an enhancer;
   (iii) an intron region; and/or
   (iii) a poly A signal region.

4. The AAV vector genome of claim 3, wherein:
   (i) the promoter comprises a CBA promoter, a CMV promoter, a PGK promoter, an H1 promoter, a UBC promoter, a GUSB promoter, an NSE promoter, a synapsin promoter, a MeCP2 promoter, or a GFAP promoter;
   (ii) the enhancer comprises a CMV enhancer; and/or
   (iii) the intron comprises an SV40 intron.

5. A recombinant AAV (rAAV) viral particle comprising the AAV vector genome of claim 2, and a capsid protein.

6. The rAAV viral particle of claim 5, wherein the capsid protein comprises an AAV1 capsid protein or a variant thereof, an AAV5 capsid protein or a variant thereof, or an AAV9 capsid protein or a variant thereof.

7. A vector comprising the AAV vector genome of claim 2.

8. An isolated cell comprising the AAV vector genome of claim 2, which is a mammalian cell, a medium spiny neuron, a cortical neuron, or an astrocyte.

9. A pharmaceutical composition comprising the AAV vector genome of claim 2, and a pharmaceutically acceptable excipient.

10. A pharmaceutical composition comprising the rAAV viral particle of claim 5, and a pharmaceutically acceptable excipient.

11. A method of inhibiting a huntingtin (HTT) gene, mRNA, and/or protein expression in a cell, comprising contacting the cell with an AAV vector genome comprising a nucleic acid sequence positioned between two inverted terminal repeats (ITRs), wherein the nucleic acid sequence encodes a modulatory polynucleotide comprising the nucleotide sequence of SEQ ID NO: 349,
   thereby inhibiting expression of the HTT gene, mRNA, and/or protein in the cell.

12. The method of claim 11, wherein the AAV vector genome is present in an rAAV viral particle.

13. The method of claim 12, wherein the rAAV viral particle further comprises a capsid protein, wherein the capsid protein comprises an AAV1 capsid protein or variant thereof, an AAV5 capsid or variant thereof, or an AAV9 capsid or variant thereof.

14. The method of claim 11, wherein the cell comprises a medium spiny neuron, a cortical neuron, or an astrocyte.

15. The method of claim 11, wherein the cell is in a subject, wherein the subject has Huntingtin's disease (HD).

16. The method of claim 11, wherein expression of the HTT mRNA is inhibited by at least 45%, 50%, 55%, 60%, 65%, 70%, 75%, or 80%.

17. A method of treating Huntington's Disease (HD) in a subject, comprising administering to the subject an effective amount of an AAV vector genome comprising a nucleic acid sequence positioned between two inverted terminal repeats (ITRs), wherein the nucleic acid sequence encodes a modulatory polynucleotide comprising the nucleotide sequence of SEQ ID NO: 349, thereby treating HD in the subject.

18. The method of claim 17, wherein the AAV vector genome is present in an rAAV viral particle.

19. The method of claim 18, wherein the rAAV viral particle further comprises a capsid protein, wherein the capsid protein comprises an AAV1 capsid protein or variant thereof, an AAV5 capsid or variant thereof, or an AAV9 capsid or variant thereof.

20. The method of claim 18, wherein the AAV vector genome or the rAAV viral particle is present in a pharmaceutical composition, which further comprises a pharmaceutically acceptable excipient.

21. The method of claim 17, wherein the expression of an HTT gene, mRNA, and/or protein is inhibited in a CNS cell or a CNS region, wherein:
(i) the CNS cell comprises a neuron, a medium spiny neuron, an astrocyte, or a combination thereof;
(ii) the CNS region is a forebrain region, a midbrain region, a putamen region, a striatum region, a cortex region, a motor cortex region, a somatosensory cortex region, a temporal cortex region, or a combination thereof; or
(iii) the CNS region is a putamen region.

22. The method of claim 21, wherein the HTT gene, mRNA, and/or protein comprises:
an HTT gene, mRNA, and/or protein comprising a CAG repeat.

23. The method of claim 22, wherein the HTT gene, mRNA, and/or protein comprising a CAG repeat is a CAG-expanded HTT, comprising at least 36-40 CAG repeats.

24. The method of claim 17, wherein the HD is:
(i) a juvenile form HD, wherein a subject having HD is 2 to 20 years of age;
(ii) an early stage HD;
(iii) a late stage HD;
(iv) a fully penetrant HD, wherein an HTT gene has least 41 or more CAG repeats;
(v) an incomplete penetrance HD, wherein an HTT gene has 36-40 CAG repeats; and/or
(vi) an asymptomatic HD.

25. The method of claim 17, wherein treatment comprises amelioration of a symptom of HD in the subject, wherein the symptom comprises apathy or lack of initiative, dysphoria, irritability, agitation or anxiety, poor self-care, poor judgment, inflexibility, disinhibition, depression, suicidal ideation euphoria, aggression, delusions, compulsions, hypersexuality, hallucinations, dystonia, speech deterioration, slurred speech, difficulty swallowing, weight loss, bradykinesia, incoordination, cognitive dysfunction, unsteady gait and involuntary movements, or CNS deterioration.

26. The method of claim 17, wherein the AAV vector genome is administered via intravenous administration, intracisternal administration, or both.

27. The method of claim 17, wherein the AAV vector genome is administered to the subject in combination with an additional therapeutic agent suitable for treatment of HD, wherein the additional therapeutic agent comprises a neuroprotective agent, a dopamine-depleting agent, a benzodiazepine, an anticonvulsant, an amino acid precursor of dopamine, a skeletal muscle relaxant, an inhibitor for acetylcholine release at the neuromuscular junction, an atypical neuroleptic, an agent to increase ATP/cellular energetics, a selective serotonin reuptake inhibitor (SSRI), a mood stabilizer, or a combination thereof.

28. The method of claim 27, wherein the additional therapeutic agent comprises tetrabenazine, clonazepam, sodium valproate, levetiracetam, levodopa, baclofen, tizanidine, botulinum toxin, olanzapine, quetiapine, risperidone, sulpiride, haloperidol, clozapine, aripiprazole, creatine, citalopram, fluoxetine, paroxetine, sertraline, mirtazapine, venlafaxine, xopiclone and/or zolpidem, odium valproate, carbamazepine, IGF-I, GDNF, BDNF, CTNF, VEGF, Colivelin, Xaliproden, Thyrotrophin-releasing hormone and ADNF, or a combination thereof.

29. A method of making the rAAV particle of claim 5, comprising:
(i) providing a cell comprising the AAV vector genome and a nucleic acid encoding a capsid protein; and
(ii) purifying the rAAV viral particle from the cell; thereby making the rAAV viral particle.

* * * * *